US011420963B2

(12) United States Patent
Cho et al.

(10) Patent No.: US 11,420,963 B2
(45) Date of Patent: Aug. 23, 2022

(54) REBAMIPIDE PRODRUGS, PREPARATION METHOD AND USE THEREOF

(71) Applicants: SAMJIN PHARMACEUTICAL CO., LTD., Seoul (KR); ASTECH. CO., LTD., Gyeonggi-do (KR)

(72) Inventors: Eui Hwan Cho, Seoul (KR); Sung Ju Choi, Seoul (KR); Sung Woo Lee, Seoul (KR); Hee Jong Shin, Gyeonggi-do (KR); Ho Seok Kwon, Gyeonggi-do (KR); Jae Woong Lee, Gyeonggi-do (KR); Jeong Ho Joo, Gyeonggi-do (KR); Hyun Tae Kim, Gyeonggi-do (KR); Woo Heon Song, Gyeonggi-do (KR); Jong Bae Yoon, Gyeonggi-do (KR); Ki Seok Park, Gyeonggi-do (KR); Ho Joon Park, Gyeonggi-do (KR); Ho Tae Nam, Gyeonggi-do (KR)

(73) Assignees: SAMJIN PHARMACEUTICAL CO., LTD., Seoul (KR); ASTECH. CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/411,390

(22) PCT Filed: Jun. 26, 2013

(86) PCT No.: PCT/KR2013/005622
§ 371 (c)(1),
(2) Date: Dec. 25, 2014

(87) PCT Pub. No.: WO2014/003424
PCT Pub. Date: Jan. 3, 2014

(65) Prior Publication Data
US 2015/0141409 A1 May 21, 2015

(30) Foreign Application Priority Data

Jun. 26, 2012 (KR) .................. 10-2012-0068394

(51) Int. Cl.
C07D 417/12 (2006.01)
C07D 215/227 (2006.01)
C07D 413/12 (2006.01)
A61K 31/4704 (2006.01)
C07D 401/12 (2006.01)
C07D 405/12 (2006.01)
C07D 409/12 (2006.01)

(52) U.S. Cl.
CPC ........ *C07D 417/12* (2013.01); *A61K 31/4704* (2013.01); *C07D 215/227* (2013.01); *C07D 401/12* (2013.01); *C07D 405/12* (2013.01); *C07D 409/12* (2013.01); *C07D 413/12* (2013.01)

(58) Field of Classification Search
None
See application file for complete search history.

(56) References Cited

U.S. PATENT DOCUMENTS

| 4,578,381 A * | 3/1986 | Uchida ................. C07C 205/57 |
| | | 514/235.2 |
| 9,301,954 B2 | 4/2016 | Min et al. |
| 2003/0087930 A1 | 5/2003 | Lee et al. |

FOREIGN PATENT DOCUMENTS

| CA | 2791526 | 9/2011 |
| CN | 102174015 | 9/2011 |
| ER | 1 336 602 A1 | 8/2003 |
| JP | 60019767 | 1/1985 |
| JP | H08295673 | 11/1996 |
| JP | 2004518737 | 6/2004 |
| JP | 2007503476 | 2/2007 |
| JP | 2008105970 | 5/2008 |
| KR | 101032600 | 5/2011 |
| KR | 10-2011-0100700 A | 9/2011 |
| WO | WO02066436 A1 | 8/2002 |
| WO | 10-2004-0104020 A | 12/2004 |
| WO | WO2006059781 A1 | 6/2006 |
| WO | WO2008074853 A1 | 6/2008 |
| WO | 2011108882 | 9/2011 |

OTHER PUBLICATIONS

CAPLUS 1986:497287.*
Lewis, R., ed., "Hawley's Condensed Chemical Dictionary," 15th ed., New York, Wiley, 2007, p. 711.*
CAPLUS Accession No. 1987:50063.*
CAPLUS Accession No. 1997:48743.*
International Search Report for PCT/KR2013/005622.
Kikuchi et al., "Peptide derivation of poorly absorbable drug allows intestinal absorption via peptide transporter", Journal of Pharmaceutical Sciences, vol. 98, No. 5, May 2009.
Australian Examination Report—Australian Application No. 2013281442 dated May 13, 2016, citing Uchida, et al., U.S. Pat. No. 4,578,381, Chemical Abstracts Accession No. 2008:548103 & JP 2008-105970, Yamasaki, et al., WO 2006/059781, and Huttunen, et al.
CAS Registry No. 1030023-91-6.
CAS Registry No. 1046529-92-3.

(Continued)

Primary Examiner — Heidi Reese
(74) Attorney, Agent, or Firm — Cantor Colburn LLP

(57) ABSTRACT

Disclosed are a novel rebamipide prodrug, a method for preparing the same, and use thereof. Also, a pharmaceutical composition comprising the novel rebamipide prodrug as an active ingredient is provided. The rebamipide prodrug is increased 25-fold in absorption rate compared to rebamipide itself, and can be applied to the prophylaxis or therapy of gastric ulcer, acute gastritis, chronic gastritis, xerophthalmia, cancer, osteoarthritis, rheumatoid arthritis, or obesity.

12 Claims, 1 Drawing Sheet

(56) References Cited

OTHER PUBLICATIONS

CAS Registry No. 1046779-56-9.
CAS Registry No. 1047978-94-8.
Chemical Abstracts Accession No. 2008:548103.
Chinese Office Action—Chinese Application No. 201380034373.4 dated Sep. 21, 2015, citing CN 102174015, WO 2006/059781, WO 2008/074853, WO 02/066436, and KR 10-2011-0100700.
European Search Report—European Application No. 13809037.8 dated Nov. 2, 2015, citing Uchida, et al., CA 2791526, Shin, et al., US 2003/0087930, Yamasaki, et al., WO 2006/059781, and Huttunen, et al.
Huttunen, et al., Prodrugs-from Serendipity to Rational Design, Pharmacological Reviews, 2011, vol. 63, No. 3, pp. 750-771.
Indian Examination Report—Indian Application No. 500/CHENP/2015 dated May 21, 2018, citing CA 2791526, US 2003/0087930, WO 2006/059781, Uchida, et al., Shin, et al., Yamasaki, et al., and Huttunen, et al.
Japanese Office Action—Japanese Application No. 2015-520012 dated Jan. 20, 2016, citing Uchida, et al., JP 60-019767, JP 08-295673, JP 2008-105970, Kikuchi, et al., CAS Registry Numbers 1047978-94-8, 1046779-56-9, 1046529-92-3, and 1030023-91-6, WO 2011/108882, JP 2004-518737, JP 2007-503476, and WO 2008/074853.
New Zealand Examination Report—New Zealand Application No. 704023 dated Mar. 27, 2015, citing U.S. Pat. No. 4,578,381, Kikuchi, et al., and ER 1336602.
Russian Office Action—Russian Application No. 2015102043 dated Apr. 5, 2016, citing Uchida, et al., CA 2791526, Shin, et al., US 2003/0087930, Yamasaki, et al., WO 2006/059781, and Huttunen, et al.
Shin, et al., Oral Absorption and Pharmacokinetics of Rebamipide and Rebamipide Lysinate in Rats, Drug Development and Industrial Pharmacy, 2004, vol. 30, No. 8, pp. 869-876.
Taiwanese Office Action—Taiwanese Application No. 102122678 dated Apr. 29, 2014, citing Kikuchi, et al.
Uchida, et al., Studies on 2(1H)-Quinolinone Derivatives as Gastric Antiulcer Active Agents. 2-(4-Chlorobenzoylamino)-3-[2(1H)-quinolinon-4-yl]propionic Acid and Related Compounds, Chemical and Pharmaceutical Bulletin, 1985, vol. 33, No. 9, pp. 3775-3786.
Yamasaki, et al., Effect of OPC-12759, a Novel Antiulcer Agent, on Chronic and Acute Experimental Gastric Ulcer, and Gastric Secretion in Rats, Japanese Journal of Pharmacology, 1989, vol. 49, pp. 441-448.

* cited by examiner

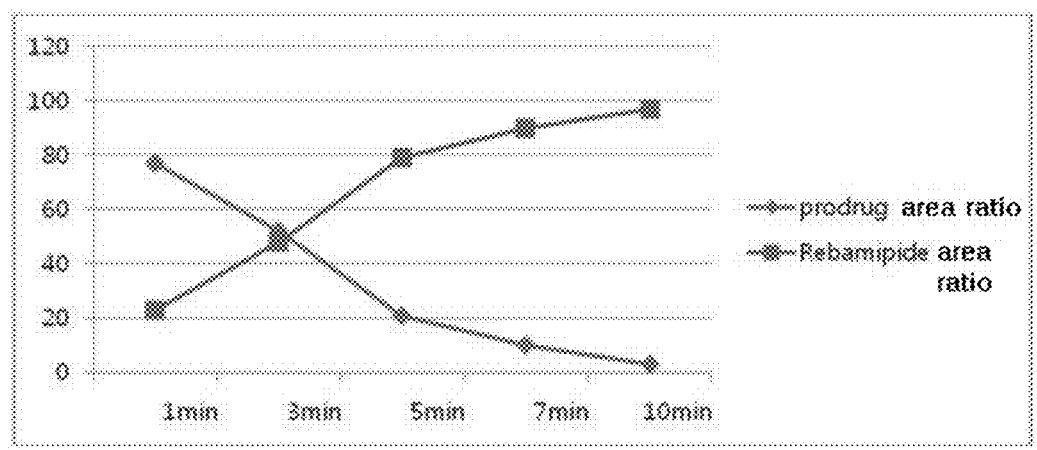

REBAMIPIDE PRODRUGS, PREPARATION METHOD AND USE THEREOF

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/005622, filed 26 Jun. 2013, which claims priority to Korean Patent Application No. 10-2012-0068394, filed 26 Jun. 2012, entire contents of which are incorporated herein by reference.

TECHNICAL FIELD

The present invention relates to a novel rebamipide prodrug, a method for preparing the same, and the use thereof. More particularly, the present invention relates to a novel rebamipide prodrug which retains the same pharmaceutical efficacy as rebamipide, but is improved in bioavailability, and a method for preparing the same, which is a simple method.

BACKGROUND ART

Rebamipide, systemically named 2-(4-chlorobenzoylamino)-3-[2(1H)-quinolon-4-yl]propionic acid, is an excellent therapeutic for digestive ulcer, including gastric ulcer, acute gastritis, and gastric mucosal lesion induced by the acute exacerbation of chronic gastritis. This drug performs a gastroprotective function by stimulating the biosynthesis of PGE2 in gastric mucosa and by promoting the proliferation of endothelial cells. Particularly, the drug is prescribed to patients with *Helicobacter pyroli*-induced gastritis because it prevents the bacteria from adhering to and penetrating gastric mucosal cells.

As for the gastroprotective mechanism of rebamipide, it is based on the dual action of defensive factor enhancement and inflammation suppression. Rebamipide stimulates the biosynthesis of the biosynthesis of prostaglandin to enhance defensive factors, and, among defensive factor enhancers, acts as the only antioxidant to protect against *Helicobacter*-induced inflammation. Therefore, rebamipide is very effectively applied to patients with ulcer or gastritis with a great reduction in relapse rate and treatment duration. A previous experiment in rats with acetic acid-induced gastric ulcers demonstrated that rebamipide reduces sizes and relapse rates of the ulcer while improving the cure rate.

There are many methods that are disclosed as for synthesizing rebamipide or producing rebamipid at high purity. For example, Korean Patent No. 10-0669823 discloses a process for preparing 2-(4-chlorobenzoylamino)-3-[2(1h)-quinolinon-4-yl]propionic acid and an intermediate thereof, and Korean Patent No. 10-1032600 provides a process for preparing highly pure rebamipide in which purification is performed while carrying out reactions so that rebamipide can be produced at high yield and low production cost with a purity of 99.95%.

In addition to gastric ulcer, acute gastritis and chronic gastritis, rebamipide is known to have prophylactic and therapeutic effects on xerophthalmia, cancer, osteoarthritis, and rheumatoid arthritis. Moreover, rebamipide has aroused keen interest as an anti-obesity agent as recent studies have revealed the suppressive effect of rebamipide on obesity. Like this, various pharmaceutical compositions based on rebamipide have been developed.

Rebamipide is freely soluble in dimethylformamide, slightly soluble in methanol and ethanol, but almost insoluble in ether and water. The aqueous solubility of rebamipide is reported to be approximately 0.0001% (w/v) at pH 3 and approximately 0.013% (w/v) at pH 7. According to the Biopharmaceutics Classification System (BCS), rebamipide is classified as Class IV due to its low solubility and low intestinal permeability. With extremely poor absorption to the circulation system, rebamipide is reported to have a bioavailability of around 5%. Due to such poor absorption and bioavailability, pharmaceutical compositions having, as described above, various efficacies contain a relatively great amount of rebamipide, thus causing the patients to suffer from inconvenience upon administration, and lowering the relative efficiency to the dose. A variety of attempts have been made to increase the oral bioavailability, particularly attempts directed toward the use of absorption enhancers and auxiliary agents, or toward preparation into various salt forms. Korean Patent Laid-Opent Publication No. 10-2004-0104020 suggests rebamipide lysinate, rebamipide argininate and pharmaceutical preparations containing the same active substances as a pharmaceutical formulation, but their absorption in the body is still in doubt. Other techniques for effectively increasing the bioavailability of rebamipide have not yet been noticeably detected.

In the present invention, rebamipide, which is very poor in absorption rate despite being therapeutically effective in the treatment of various above-mentioned symptoms, is provided as a rebamipide prodrug which is increased 25-fold in absorption rate compared to rebamipide itself, and a method for preparing the same, and the uses of the rebamipide prodrug are also disclosed.

SUMMARY

It is an object of the present invention to provide a novel rebamipid prodrug which is improved in absorption rate.

It is another object of the present invention to provide a method for preparing a rebamipide prodrug improved in absorption rate, and the use of the rebamipide prodrug.

In accordance with an aspect thereof, the present invention provides a compound represented by the following Chemical Formula 1, or a pharmaceutically acceptable salt, isomer, hydrate or solvate thereof:

[Chemical Formula I]

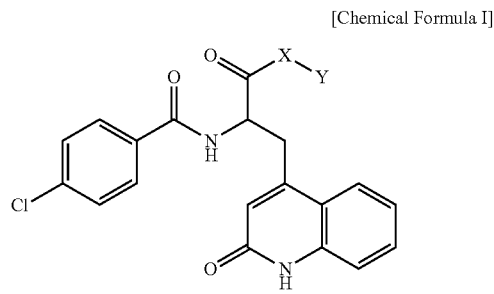

wherein, X and Y are as defined below.

In accordance with another aspect thereof, the present invention provides a method for preparing the compound of Chemical Formula 1, comprising reacting a compound of the following Chemical Formula II with a compound of the following Chemical Formula III:

[Chemical Formula II]

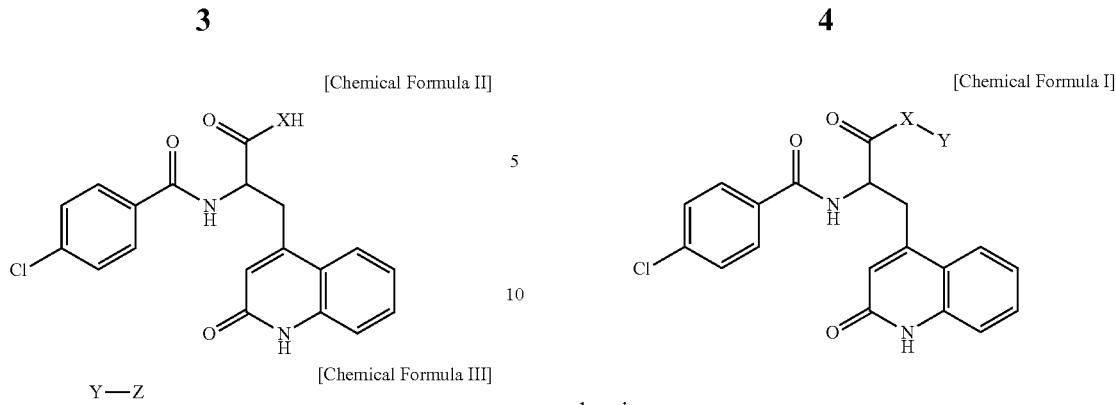

[Chemical Formula I]

[Chemical Formula III]

Y—Z wherein,

X and Y are as defined below, and Z is a hydroxy group, an amino group, an amine group, a halogen atom, or a leaving group.

In accordance with a further aspect thereof, the present invention provides a pharmaceutical composition for the prophylaxis or therapy of gastric ulcer, acute gastritis, chronic gastritis, xerophthalmia, cancer, osteoarthritis, rheumatoid arthritis, hyperlipidemia, hypertriglyceridemia, diabetes, irritable bowel syndrome, and obesity, comprising the rebamipide prodrug as an active ingredient, comprising the rebamipide prodrug as an active ingredient.

As descried hitherto, novel rebamipide prodrugs according to the present invention are greatly improved in body absorption performance. Also, the present invention provides a method for the preparation of the novel rebamipide prodrugs, and the use of the novel rebamipide prodrugs.

Particularly, when in the form of salts, the novel rebamipide prodrugs of the present invention are remarkably increased in body absorption performance, compared to free acid forms. Thus, even a small amount of salts of the novel rebamipide prodrugs are effective for preventing or treating various diseases including gastric ulcer, acute gastritis, chronic gastritis, xerophthalmia, cancer, osteoarthritis, rheumatoid arthritis, obesity, hyperlipidemia, hypertriglyceridemia, diabetes, and irritable bowel syndrome.

DESCRIPTION OF DRAWINGS

FIG. 1 is a graph in which conversion of the rebamipide prodrug of Example 47 into rebamipide (acting drug) in whole rat blood is monitored with time.

DETAILED DESCRIPTION

A detailed description will be given of the present invention, below.

In accordance with an aspect thereof, the present invention addresses a prodrug of rebamipide, which is known as a therapeutic for gastric ulcer, acute gastritis, chronic gastritis, xerophthalmia, cancer, osteoarthritis, and rheumatoid arthritis.

In one embodiment thereof, the present invention provides a compound represented by the following Chemical Formula 1, or a pharmaceutically acceptable salt, isomer, hydrate, or solvate thereof:

wherein,

X is an oxygen atom, a nitrogen atom, or a sulfur atom; and

Y is a radical selected from the group consisting of $C_1$-$C_6$ alkyl, $C_1$-$C_6$ haloalkyl, ($C_1$-$C_3$ alkyloxy)$C_1$-$C_6$ alkyl, ($C_2$-$C_6$ alkenyloxy)$C_1$-$C_6$ alkyl, ($C_1$-$C_6$ alkylcarbonyloxy)$C_1$-$C_6$ alkyl, ($C_1$-$C_6$ alkylsufanyl)$C_1$-$C_6$ alkyl, (arylsufanyl)$C_1$-$C_6$ alkyl, (arylsulfonyl)$C_1$-$C_6$ alkyl, ($C_1$-$C_6$ alkylamino)$C_1$-$C_6$ alkyl, [($C_1$-$C_6$ alkyl)($C_1$-$C_6$ alkyl)amino]$C_1$-$C_6$ alkyl, [($C_1$-$C_3$ alkyl)(aryl)amino]$C_1$-$C_6$ alkyl, {[($C_1$-$C_3$ alkyl)(aryl)$C_1$-$C_3$ alkyl]amino}$C_1$-$C_6$ alkyl, [($C_1$-$C_3$ alkyl)(heteroaryl)amino]$C_1$-$C_6$ alkyl, (arylcarbonylamino)$C_1$-$C_6$ alkyl, $C_2$-$C_6$ alkenyl, $C_2$-$C_6$ alkynyl, $C_2$-$C_6$ oxoalkyl, $C_3$-$C_8$ cycloalkyl, ($C_3$-$C_8$ cycloalkyl)$C_1$-$C_6$ alkyl, ($C_3$-$C_8$ cycloalkenyl)$C_1$-$C_6$ alkyl, ($C_3$-$C_8$ heterocycloalkyl)$C_1$-$C_6$ alkyl, [($C_1$-$C_3$ alkyl)$C_3$-$C_8$ heterocycloalkyl]$C_1$-$C_6$ alkyl, {[(aryl)$C_1$-$C_3$ alkyl]$C_3$-$C_8$ heterocycloalkyl}$C_1$-$C_6$ alkyl, [($C_1$-$C_6$ alkyloxycarbonyl)$C_3$-$C_8$ heterocycloalkyl]$C_1$-$C_6$ alkyl, [($C_1$-$C_3$ alkyloxycarbonyl)$C_3$-$C_8$ heterocycloalkyl]$C_1$-$C_6$ alkyl, ($C_3$-$C_8$ heterocycloalkyl)$C_1$-$C_6$ alkenyl, [($C_1$-$C_3$ alkyl)$C_3$-$C_8$ heterocycloalkenyl]$C_1$-$C_6$ alkyl, (aryl)$C_1$-$C_6$ alkyl, [($C_1$-$C_3$ alkyl)aryl]$C_1$-$C_6$ alkyl, [($C_1$-$C_3$ alkyloxy)aryl]$C_1$-$C_6$ alkyl, [(aryloxy)aryl]$C_1$-$C_6$ alkyl, [($C_1$-$C_3$ alkylsufanyl)aryl]$C_1$-$C_6$ alkyl, [($C_1$-$C_3$ alkyloxycarbonyl)aryl]$C_1$-$C_6$ alkyl, [(aryloxycarbonyl)aryl]$C_1$-$C_6$ alkyl, (aryl)$C_3$-$C_6$ alkenyl, (heteroaryl)$C_1$-$C_6$ alkyl, [(alkyloxycarbonyl)heteroaryl]$C_1$-$C_6$ alkyl, [($C_1$-$C_3$ alkyl)$C_3$-$C_8$ heteroaryl]$C_1$-$C_6$ alkyl, [($C_3$-$C_8$ cycloalkyl)heteroaryl]$C_1$-$C_6$ alkyl, [(aryl)heteroaryl]$C_1$-$C_6$ alkyl, [($C_1$-$C_3$ alkyl)heteroaryl]$C_1$-$C_6$ alkyl, { [(aryl)$C_1$-$C_3$ alkyl]heteroaryl}$C_1$-$C_6$ alkyl, ($C_1$-$C_6$ alkyloxycarbonyl)$C_1$-$C_6$ alkyl, [($C_3$-$C_8$ heterocycloalkyl)$C_1$-$C_6$ alkyloxycarbonyl]$C_1$-$C_6$ alkyl, ($C_3$-$C_5$ heterocycloalkylcarbonyl)$C_1$-$C_6$ alkyl, [($C_1$-$C_3$ alkyl)$C_3$-$C_8$ heterocycloalkylcarbonyl]$C_1$-$C_6$ alkyl, [($C_1$-$C_3$ alkyl)$C_3$-$C_8$ heterocycloalkylcarbonyl]$C_1$-$C_6$ alkyl, [($C_3$-$C_8$ cycloalkyl)oxycarbonyloxy]$C_1$-$C_6$ alkyl, [($C_3$-$C_8$ heterocycloalkyl)oxycarbonyloxy]$C_1$-$C_6$ alkyl, (ureido)$C_1$-$C_6$ alkyl, (arylureido)$C_1$-$C_6$ alkyl, [(aryl)($C_1$-$C_3$ alkylureido]$C_1$-$C_6$ alkyl, ($C_1$-$C_6$ alkylaminocarbonyl)$C_1$-$C_6$ alkyl, [($C_3$-$C_5$ heterocycloalkyl)aminocarbonyl]$C_1$-$C_6$ alkyl, {[($C_1$-$C_3$ alkyl)$C_3$-$C_8$ heterocycloalkyl]aminocarbonyl}$C_1$-$C_6$ alkyl, [($C_1$-$C_3$ alkyl)($C_1$-$C_3$ alkyloxy)aminocarbonyl]$C_1$-$C_6$ alkyl and (oxo$C_3$-$C_8$ heterocycloalkyl)$C_1$-$C_6$ alkyl, with a proviso that the $C_1$-$C_6$ alkyl radical, the $C_2$-$C_6$ alkenyl radical, the $C_2$-$C_6$ alkynyl radical, the $C_2$-$C_6$ oxoalkyl radical, the $C_3$-$C_8$ cycloalkyl radical, the $C_3$-$C_8$ cycloalkenyl radical, the $C_3$-$C_8$ heterocycloalkenyl radical, the aryl radical or the heteroaryl radical may be substituted with at least one substituent selected from the group consisting of $C_1$-$C_3$ alkyl, fluoro, chloro, bromo, hydroxy, oxo, nitro, and cyano.

As used herein, the term "heterocycloalkyl" refers to a non-aromatic, cyclic moiety having one or more heteroatoms, such as N, O and S, as constituent elements of the ring(s) at one, two or three sequential or discontinuous positions in the ring(s). As used herein, the term "heterocycloalkenyl" refers to a non-aromatic, cyclic moiety having one or more heateroatoms, such as N, O and S, as constitutent elements of the ring(s) at one, two or three sequential or discontinuous positions in the ring(s), and having at least one double bond in the ring(s). Examples of heterocycloalkyl or heterocycloalkenyl radicals include aziridine, oxirane, azetidine, oxetane, pyrrolidine, pyrroline, pyrazolidine, pyrazoline, imidazolidine, imidazoline, triazolidine, oxazolidine, tetrahydrofuran, tetrahydrothiophene, thiazolidine, dioxolane, dioxole, oxathiolane, morpholine, thiomorpholine, dithiane, piperidine, piperazine, pyran, dioxane, and azepane, but are not limited thereto.

The term "aryl," as used in the context of the present invention, is intended to encompass benzene, naphthalene, anthracene, or phenanthrene, but is not limited thereto.

As used herein, the term "heteroaryl" refers to a moiety having at least one aromatic ring in which at least one heteroatom, such as N, O and S, as an element atom, is present at one, two or three sequential or discontinuous positions. Examples of heteroaryl moieties include pyrrole, imidazole, pyrazole, triazole, furan, thiophene, oxazole, isoxazole, thiazole, isothiazole, oxadiazole, thiadiazole, pyridine, pyrimidine, pyrazine, pyridazine, triazine, azepine, indole, benzimidazole, indazole, benzoxazole, benzoisoxazole, benzothiazole, benzotriazole, benzofuran, benzothiophene, quinoline, isoquinoline, quinoxaline, quinazoline, cinnoline, naphthyridine, phthalazine, benzopyran, benzoxazine, benzotriazine, chromane, chromene, benzodioxane, atridine, phenothiazine, phenoxazine, and carbazole, but are not limited thereto.

In the present invention, X—Y represents an amino acid or an amino acid ($C_1$-$C_3$ alkyl)ester. The amino acid includes glycine, leucine, methionine, valine, alanine, isoleucine, proline, tryptophan, phenylalanine, serine, threonine, asparagine, glutamic acid, lysine, histidine, and tyrosine.

Illustrative, non-limiting, concrete examples of the compound of Chemical Formula 1 include:
1) methyl 2-(4-chlorobenzoylamino)-3-(2-oxo-1,2-dihydroquinolin-4-yl)propionate;
2) ethyl 2-(4-chlorobenzoylamino)-3-(2-oxo-1,2-dihydroquinolin-4-yl)propionate;
3) 3-methylbutyl 2-(4-chlorobenzoylamino)-3-(2-oxo-1,2-dihydroquinolin-4-yl)propionate;
4) hexyl 2-(4-chlorobenzoylamino)-3-(2-oxo-1,2-dihydroquinolin-4-yl)propionate;
5) 2-bromoethyl 2-(4-chlorobenzoylamino)-3-(2-oxo-1,2-dihydroquinolin-4-yl)propionate;
6) 2-hydroxyethyl 2-(4-chlorobenzoylamino)-3-(2-oxo-1,2-dihydroquinolin-4-yl)propionate;
7) methoxymethyl 2-(4-chlorobenzoylamino)-3-(2-oxo-1,2-dihydroquinolin-4-yl)propionate;
8) 2-methoxyethyl 2-(4-chlorobenzoylamino)-3-(2-oxo-1,2-dihydroquinolin-4-yl)propionate;
9) 2-vinyloxyethyl 2-(4-chlorobenzoylamino)-3-(2-oxo-1,2-dihydroquinolin-4-yl)propionate;
10) 2-acetoxyethyl 2-(4-chlorobenzoylamino)-3-(2-oxo-1,2-dihydroquinolin-4-yl)propionate;
11) 2-methylsulfanylethyl 2-(4-chlorobenzoylamino)-3-(2-oxo-1,2-dihydroquinolin-4-yl)propionate;
12) 2-phenylsulfanylethyl 2-(4-chlorobenzoylamino)-3-(2-oxo-1,2-dihydroquinolin-4-yl)propionate;
13) 2-methylaminoethyl 2-(4-chlorobenzoylamino)-3-(2-oxo-1,2-dihydroquinolin-4-yl)propionate;
14) 2-dimethylaminoethyl 2-(4-chlorobenzoylamino)-3-(2-oxo-1,2-dihydroquinolin-4-yl)propionate;
15) 2-dimethylamino-1-methyl-ethyl 2-(4-chlorobenzoylamino)-3-(2-oxo-1,2-dihydroquinolin-4-yl)propionate;
16) 2-diethylaminoethyl 2-(4-chlorobenzoylamino)-3-(2-oxo-1,2-dihydroquinolin-4-yl)propionate;
17) 2-diisopropylaminoethyl 2-(4-chlorobenzoylamino)-3-(2-oxo-1,2-dihydroquinolin-4-yl)propionate;
18) 3-dimethylaminopropyl 2-(4-chlorobenzoylamino)-3-(2-oxo-1,2-dihydroquinolin-4-yl)propionate;
19) 2-(methyl phenyl amino)ethyl 2-(4-chlorobenzoylamino)-3-(2-oxo-1,2-dihydroquinolin-4-yl)propionate;
20) 2-(benzyl ethyl amino)ethyl 2-(4-chlorobenzoylamino)-3-(2-oxo-1,2-dihydroquinolin-4-yl)propionate;
21) 2-(benzoxazol-2-ylmethyl amino)ethyl 2-(4-chlorobenzoylamino)-3-(2-oxo-1,2-dihydroquinolin-4-yl)propionate;
22) 2-benzoylaminoethyl 2-(4-chlorobenzoylamino)-3-(2-oxo-1,2-dihydroquinolin-4-yl)propionate;
23) allyl 2-(4-chlorobenzoylamino)-3-(2-oxo-1,2-dihydroquinolin-4-yl)propionate;
24) but-2-enyl 2-(4-chlorobenzoylamino)-3-(2-oxo-1,2-dihydroquinolin-4-yl)propionate;
25) 3-methylbut-2-enyl 2-(4-chlorobenzoylamino)-3-(2-oxo-1,2-dihydroquinolin-4-yl)propionate;
26) 3-prop-2-ynyl 2-(4-chlorobenzoylamino)-3-(2-oxo-1,2-dihydroquinolin-4-yl)propionate 27) 2-oxopropyl 2-(4-chlorobenzoylamino)-3-(2-oxo-1,2-dihydroquinolin-4-yl)propionate;
28) 2-oxobutyl 2-(4-chlorobenzoylamino)-3-(2-oxo-1,2-dihydroquinolin-4-yl)propionate;
29) cyclopentyl 2-(4-chlorobenzoylamino)-3-(2-oxo-1,2-dihydroquinolin-4-yl)propionate;
30) cyclohexyl 2-(4-chlorobenzoylamino)-3-(2-oxo-1,2-dihydroquinolin-4-yl)propionate;
31) cyclopropylmethyl 2-(4-chlorobenzoylamino)-3-(2-oxo-1,2-dihydroquinolin-4-yl)propionate;
32) cyclobutylmethyl 2-(4-chlorobenzoylamino)-3-(2-oxo-1,2-dihydroquinolin-4-yl)propionate;
33) cyclohexylmethyl 2-(4-chlorobenzoylamino)-3-(2-oxo-1,2-dihydroquinolin-4-yl)propionate;
34) cyclopent-3-enylmethyl 2-(4-chlorobenzoylamino)-3-(2-oxo-1,2-dihydroquinolin-4-yl)propionate;
35) oxiranylmethyl 2-(4-chlorobenzoylamino)-3-(2-oxo-1,2-dihydroquinolin-4-yl)propionate;
36) 3-methyloxetan-3-ylmethyl 2-(4-chlorobenzoylamino)-3-(2-oxo-1,2-dihydroquinolin-4-yl)propionate;
37) 2-(1-methylpyrrolidin-2-yl)ethyl 2-(4-chlorobenzoylamino)-3-(2-oxo-1,2-dihydroquinolin-4-yl)propionate;
38) 2-pyrrolidin-1-yl-ethyl 2-(4-chlorobenzoylamino)-3-(2-oxo-1,2-dihydroquinolin-4-yl)propionate;
39) tetrahydrofuran-2-ylmethyl 2-(4-chlorobenzoylamino)-3-(2-oxo-1,2-dihydroquinolin-4-yl)propionate;
40) [1,3]dioxolan-2-ylmethyl 2-(4-chlorobenzoylamino)-3-(2-oxo-1,2-dihydroquinolin-4-yl)propionate;
41) 2-[1,3]-dioxolan-2-ylethyl 2-(4-chlorobenzoylamino)-3-(2-oxo-1,2-dihydroquinolin-4-yl)propionate;
42) 1-methylpiperidin-2-ylmethyl 2-(4-chlorobenzoylamino)-3-(2-oxo-1,2-dihydroquinolin-4-yl)propionate;
43) 1-methylpiperidin-3-ylmethyl 2-(4-chlorobenzoylamino)-3-(2-oxo-1,2-dihydroquinolin-4-yl)propionate;
44) 2-piperidin-1-ylethyl 2-(4-chlorobenzoylamino)-3-(2-oxo-1,2-dihydroquinolin-4-yl)propionate;
45) tetrahydropyran 2 ylmethyl 2-(4-chlorobenzoylamino)-3-(2-oxo-1,2-dihydroquinolin-4-yl)propionate;
46) 2-[1,3]dioxan-2-ylethyl 2-(4-chlorobenzoylamino)-3-(2-oxo-1,2-dihydroquinolin-4-yl)propionate;
47) 2-morpholin-4-ylethyl 2-(4-chlorobenzoylamino)-3-(2-oxo-1,2-dihydroquinolin-4-yl)propionate;

48) 3-morpholin-4-ylpropyl 2-(4-chlorobenzoylamino)-3-(2-oxo-1,2-dihydroquinolin-4-yl)propionate;
49) 4-morpholin-4-ylbutyl 2-(4-chlorobenzoylamino)-3-(2-oxo-1,2-dihydroquinolin-4-yl)propionate;
50) 6-morpholin-4-ylhexyl 2-(4-chlorobenzoylamino)-3-(2-oxo-1,2-dihydroquinolin-4-yl)propionate;
51) (4-methylpiperazin-1-yl)methyl 2-(4-chlorobenzoylamino)-3-(2-oxo-1,2-dihydroquinolin-4-yl)propionate;
52) 2-(4-benzylpiperazin-1-yl)ethyl 2-(4-chlorobenzoylamino)-3-(2-oxo-1,2-dihydroquinolin-4-yl)propionate;
53) 4-[4-(3-chlorophenyl)piperazin-1-yl]butyl 2-(4-chlorobenzoylamino)-3-(2-oxo-1,2-dihydroquinolin-4-yl)propionate;
54) (4-tert-butyloxycarbonylpiperazin-1-yl)ethyl 2-(4-chlorobenzoylamino)-3-(2-oxo-1,2-dihydroquinolin-4-yl)propionate;
55) 2-azepan-1-ylethyl 2-(4-chlorobenzoylamino)-3-(2-oxo-1,2-dihydroquinolin-4-yl)propionate;
56) 2-(2-oxopyrrolidin-1-yl)ethyl 2-(4-chlorobenzoylamino)-3-(2-oxo-1,2-dihydroquinolin-4-yl)propionate;
57) (2-oxooxazolidin-5-yl)methyl 2-(4-chlorobenzoylamino)-3-(2-oxo-1,2-dihydroquinolin-4-yl)propionate;
58) 4-morpholin-4-yl-cis-but-2-enyl 2-(4-chlorobenzoylamino)-3-(2-oxo-1,2-dihydroquinolin-4-yl)propionate;
59) 4-morpholin-4-yl-trans-but-2-enyl 2-(4-chlorobenzoylamino)-3-(2-oxo-1,2-dihydroquinolin-4-yl)propionate;
60) 5-methyl-2-oxo-[1,3]dioxol-4-ylmethyl 2-(4-chlorobenzoylamino)-3-(2-oxo-1,2-dihydroquinolin-4-yl)propionate;
61) benzyl 2-(4-chlorobenzoylamino)-3-(2-oxo-1,2-dihydroquinolin-4-yl)propionate;
62) phenethyl 2-(4-chlorobenzoylamino)-3-(2-oxo-1,2-dihydroquinolin-4-yl)propionate;
63) 2-methylbenzyl 2-(4-chlorobenzoylamino)-3-(oxo-1,2-dihydroquinolin-4-yl)propionate;
64) 3-methylbenzyl 2-(4-chlorobenzoylamino)-3-(oxo-1,2-dihydroquinolin-4-yl)propionate;
65) 3,4-dimethylbenzyl 2-(4-chlorobenzoylamino)-3-(2-oxo-1,2-dihydroquinolin-4-yl)propionate;
66) 3,5-dimethylbenzyl 2-(4-chlorobenzoylamino)-3-(2-oxo-1,2-dihydroquinolin-4-yl)propionate;
67) 3-fluorobenzyl 2-(4-chlorobenzoylamino)-3-(2-oxo-1,2-dihydroquinolin-4-yl)propionate;
68) 2,5-difluorobenzyl 2-(4-chlorobenzoylamino)-3-(2-oxo-1,2-dihydroquinolin-4-yl)propionate;
69) 3-cyanobenzyl 2-(4-chlorobenzoylamino)-3-(2-oxo-1,2-dihydroquinolin-4-yl)propionate;
70) 3-nitrobenzyl 2-(4-chlorobenzoylamino)-3-(2-oxo-1,2-dihydroquinolin-4-yl)propionate;
71) 4-methoxybenzyl 2-(4-chlorobenzoylamino)-3-(2-oxo-1,2-dihydroquinolin-4-yl)propionate;
72) 3-phenoxybenzyl 2-(4-chlorobenzoylamino)-3-(2-oxo-1,2-dihydroquinolin-4-yl)propionate;
73) 4-methylsulfanylbenzyl 2-(4-chlorobenzoylamino)-3-(2-oxo-1,2-dihydroquinolin-4-yl)propionate;
74) (4-methyloxycarbonyl)benzyl 4-[2-(4-chlorobenzoylamino)-3-(2-oxo-1,2-dihydroquinolin-4-yl)propionate;
75) (3-phenyloxycarbonyl)benzyl 2-(4-chlorobenzoylamino)-3-(2-oxo-1,2-dihydroquinolin-4-yl)propionate;
76) naphthalen-2-ylmethyl 2-(4-chlorobenzoylamino)-3-(2-oxo-1,2-dihydroquinolin-4-yl)propionate;
77) anthracen-9-ylmethyl 2-(4-chlorobenzoylamino)-3-(2-oxo-1,2-dihydroquinolin-4-yl)propionate;
78) 2-pyrrol-1-ylethyl 2-(4-chlorobenzoylamino)-3-(2-oxo-1,2-dihydroquinolin-4-yl)propionate;
79) (2-ethoxycarbonyl)furan-4-ylmethyl 2-(4-chlorobenzoylamino)-3-(2-oxo-1,2-dihydroquinolin-4-yl)propionate;
80) 2-thiophen-2-ylethyl 2-(4-chlorobenzoylamino)-3-(2-oxo-1,2-dihydroquinolin-4-yl)propionate;
81) 2-thiophen-3-ylethyl 2-(4-chlorobenzoylamino)-3-(2-oxo-1,2-dihydroquinolin-4-yl)propionate;
82) 2-imidazol-1-ylethyl 2-(4-chlorobenzoylamino)-3-(2-oxo-1,2-dihydroquinolin-4-yl)propionate;
83) 5-cyclopropyl-2-methyl-2H-pyrazol-3-ylmethyl 2-(4-chlorobenzoylamino)-3-(2-oxo-1,2-dihydroquinolin-4-yl)propionate;
84) 3,5-dimethylisoxazol-4-ylmethyl 2-(4-chlorobenzoylamino)-3-(2-oxo-1,2-dihydroquinolin-4-yl)propionate;
85) 2-(5-methyl-4-phenyloxazol-2-yl)ethyl 2-(4-chlorobenzoylamino)-3-(2-oxo-1,2-dihydroquinolin-4-yl)propionate;
86) 2-methylthiazol-4-ylmethyl 2-(4-chlorobenzoylamino)-3-(2-oxo-1,2-dihydroquinolin-4-yl)propionate;
87) 2-(4-methylthiazol-5-yl)ethyl 2-(4-chlorobenzoylamino)-3-(2-oxo-1,2-dihydroquinolin-4-yl)propionate;
88) pyrimidin-2-ylmethyl 2-(4-chlorobenzoylamino)-3-(2-oxo-1,2-dihydroquinolin-4-yl)propionate;
89) pyrimidin-3-ylmethyl 2-(4-chlorobenzoylamino)-3-(2-oxo-1,2-dihydroquinolin-4-yl)propionate;
90) pyrimidin-4-ylmethyl 2-(4-chlorobenzoylamino)-3-(2-oxo-1,2-dihydroquinolin-4-yl)propionate;
91) 2-(pyrimidin-2-yl)ethyl 2-(4-chlorobenzoylamino)-3-(2-oxo-1,2-dihydroquinolin-4-yl)propionate;
92) quinolin-2-ylmethyl 2-(4-chlorobenzoylamino)-3-(2-oxo-1,2-dihydroquinolin-4-yl)propionate;
93) quinolin-3-ylmethyl 2-(4-chlorobenzoylamino)-3-(2-oxo-1,2-dihydroquinolin-4-yl)propionate;
94) 2-(1-methyl-1H-indol-3-yl)ethyl 2-(4-chlorobenzoylamino)-3-(2-oxo-1,2-dihydroquinolin-4-yl)propionate;
95) benzothiazol-2-ylmethyl 2-(4-chlorobenzoylamino)-3-(2-oxo-1,2-dihydroquinolin-4-yl)propionate;
96) 2,3-dihydrobenzo[1,4]dioxin-2-ylmethyl 2-(4-chlorobenzoylamino)-3-(2-oxo-1,2-dihydroquinolin-4-yl)propionate;
97) carbazol-9-ylmethyl 2-(4-chlorobenzoylamino)-3-(2-oxo-1,2-dihydroquinolin-4-yl)propionate;
98) methylcarbamoylmethyl 2-(4-chlorobenzoylamino)-3-(2-oxo-1,2-dihydroquinolin-4-yl)propionate;
99) 2-(4-methylpiperazin-1-yl)-2-oxoethyl 2-(4-chlorobenzoylamino)-3-(2-oxo-1,2-dihydroquinolin-4-yl)propionate;
100) 1-(4-methylpiperazine-1-carbonyl)propyl 2-(4-chlorobenzoylamino)-3-(2-oxo-1,2-dihydroquinolin-4-yl)propionate;
101) 2-morpholin-4-yl-2-oxoethyl 2-(4-chlorobenzoylamino)-3-(2-oxo-1,2-dihydroquinolin-4-yl)propionate;
102) (methoxymethylcarbamoyl)methyl 2-(4-chlorobenzoylamino)-3-(2-oxo-1,2-dihydroquinolin-4-yl)propionate;
103) 2-ethoxycarbonylethyl 2-(4-chlorobenzoylamino)-3-(2-oxo-1,2-dihydroquinolin-4-yl)propionate;
104) 2-ethoxycarbonylethyl 2-(4-chlorobenzoylamino)-3-(2-oxo-1,2-dihydroquinolin-4-yl)propionate;
105) 2-morpholin-4-yl-ethoxycarbonylmethyl 2-(4-chlorobenzoylamino)-3-(2-oxo-1,2-dihydroquinolin-4-yl)propionate;
106) 2-morpholin-4-ylethyl 2-[2-(4-chlorobenzoylamino)-3-(2-oxo-1,2-dihydroquinolin-4-yl)propionyloxy]butyrate;
107) 2-(1,3-dioxo-1,3-dihydroisoindol-2-yl)ethyl 2-(4-chlorobenzoylamino)-3-(2-oxo-1,2-dihydroquinolin-4-yl)propionate;

108) cyclohexyloxycarbonyloxymethyl 2-(4-chlorobenzoylamino)-3-(2-oxo-1,2-dihydroquinolin-4-yl)propionate;
109) 2-morpholin-4-yl-ethoxycarbonyloxymethyl 2-(4-chlorobenzoylamino)-3-(2-oxo-1,2-dihydroquinolin-4-yl)propionate;
110) 2-ureidoethyl 2-(4-chlorobenzoylamino)-3-(2-oxo-1,2-dihydroquinolin-4-yl)propionate;
111) 2-(3-phenyl-ureido)ethyl 2-(4-chlorobenzoylamino)-3-(2-oxo-1,2-dihydroquinolin-4-yl)propionate;
112) 2-(3-benzyl-ureido)ethyl 2-(4-chlorobenzoylamino)-3-(2-oxo-1,2-dihydroquinolin-4-yl)propionate;
113) 2-(4-chlorobenzoylamino)-3-(2-oxo-1,2-dihydroquinolin-4-yl)thiopropionic acid;
114) S-methyl 2-(4-chlorobenzoylamino)-3-(2-oxo-1,2-dihydroquinolin-4-yl)thiopropionate;
115) S-ethyl 2-(4-chlorobenzoylamino)-3-(2-oxo-1,2-dihydroquinolin-4-yl)thiopropionate;
116) S-propyl 2-(4-chlorobenzoylamino)-3-(2-oxo-1,2-dihydroquinolin-4-yl)thiopropionate;
117) S-butyl 2-(4-chlorobenzoylamino)-3-(2-oxo-1,2-dihydroquinolin-4-yl)thiopropionate;
118) S-(3-methylbutyl)2-(4-chlorobenzoylamino)-3-(2-oxo-1,2-dihydroquinolin-4-yl)thiopropionate;
119) S-hexyl 2-(4-chlorobenzoylamino)-3-(2-oxo-1,2-dihydroquinolin-4-yl)thiopropionate;
120) S-(2-dimethylamino)ethyl 2-(4-chlorobenzoylamino)-3-(2-oxo-1,2-dihydroquinolin-4-yl)thiopropionate;
121) S-(2-diethylamino)ethyl 2-(4-chlorobenzoylamino)-3-(2-oxo-1,2-dihydroquinolin-4-yl)thiopropionate;
122) S-(2-diisopropylamino)ethyl 2-(4-chlorobenzoylamino)-3-(2-oxo-1,2-dihydroquinolin-4-yl)thiopropionate;
123) S-(2-dimethylamino)propyl 2-(4-chlorobenzoylamino)-3-(2-oxo-1,2-dihydroquinolin-4-yl)thiopropionate;
124) S-(2-benzoylamino)ethyl 2-(4-chlorobenzoylamino)-3-(2-oxo-1,2-dihydroquinolin-4-yl)propionate oxalate;
125) S-methoxymethyl 2-(4-chlorobenzoylamino)-3-(2-oxo-1,2-dihydroquinolin-4-yl)thiopropionate;
126) S-(2-benzoyloxy)ethyl 2-(4-chlorobenzoylamino)-3-(2-oxo-1,2-dihydroquinolin-4-yl)thiopropionate;
127) S-(2-methylsufanyl)ethyl 2-(4-chlorobenzoylamino)-3-(2-oxo-1,2-dihydroquinolin-4-yl)thiopropionate;
128) S-(2-phenylsufanyl)ethyl 2-(4-chlorobenzoylamino)-3-(2-oxo-1,2-dihydroquinolin-4-yl)propionate;
129) S-(2-benzenesulfonyl)ethyl 2-(4-chlorobenzoylamino)-3-(2-oxo-1,2-dihydroquinolin-4-yl)propionate;
130) S-(2-oxobutyl) 2-(4-chlorobenzoylamino)-3-(2-oxo-1,2-dihydroquinolin-4-yl)thiopropionate;
131) S-(2-ureido)ethyl 2-(4-chlorobenzoylamino)-3-(2-oxo-1,2-dihydroquinolin-4-yl)thiopropionate;
132) N,N-dimethyl S-[2-(4-chlorobenzoylamino)-3-(2-oxo-1,2-dihydroquinolin-4-yl)]thiocarbamate;
133) S-allyl 2-(4-chlorobenzoylamino)-3-(2-oxo-1,2-dihydroquinolin-4-yl)thiopropionate;
134) S-but-2-enyl 2-(4-chlorobenzoylamino)-3-(2-oxo-1,2-dihydroquinolin-4-yl)thiopropionate;
135) S-prop-2-ynyl 2-(4-chlorobenzoylamino)-3-(2-oxo-1,2-dihydroquinolin-4-yl)thiopropionate;
136) S-cyclopentyl 2-(4-chlorobenzoylamino)-3-(2-oxo-1,2-dihydroquinolin-4-yl)thiopropionate;
137) S-cyclohexyl 2-(4-chlorobenzoylamino)-3-(2-oxo-1,2-dihydroquinolin-4-yl)thiopropionate;
138) S-cyclopropylmethyl 2-(4-chlorobenzoylamino)-3-(2-oxo-1,2-dihydroquinolin-4-yl)thiopropionate;
139) S-cyclobutylmethyl 2-(4-chlorobenzoylamino)-3-(2-oxo-1,2-dihydroquinolin-4-yl)thiopropionate;
140) S-cyclohexylmethyl 2-(4-chlorobenzoylamino)-3-(2-oxo-1,2-dihydroquinolin-4-yl)thiopropionate;
141) S-(cyclopent-3-enyl)methyl 2-(4-chlorobenzoylamino)-3-(2-oxo-1,2-dihydroquinolin-4-yl)thiopropionate;
142) S-oxiranylmethyl 2-(4-chlorobenzoylamino)-3-(2-oxo-1,2-dihydroquinolin-4-yl)thiopropionate;
143) S-(tetrahydrofuran-2-yl)methyl 2-(4-chlorobenzoylamino)-3-(2-oxo-1,2-dihydroquinolin-4-yl)thiopropionate;
144) S-(2-pyrrolidin-1-yl)ethyl 2-(4-chlorobenzoylamino)-3-(2-oxo-1,2-dihydroquinolin-4-yl)thiopropionate;
145) S-[2-(1-methylpyrrolidin-2-yl)]ethyl 2-(4-chlorobenzoylamino)-3-(2-oxo-1,2-dihydroquinolin-4-yl)thiopropionate;
146) S-([1,3]dioxolan-2-yl)methyl 2-(4-chlorobenzoylamino)-3-(2-oxo-1,2-dihydroquinolin-4-yl)thiopropionate;
147) S-(2-[1,3]dioxolan-2-yl)ethyl 2-(4-chlorobenzoylamino)-3-(2-oxo-1,2-dihydroquinolin-4-yl)thiopropionate;
148) S-(2-piperidin-1-yl)ethyl 2-(4-chlorobenzoylamino)-3-(2-oxo-1,2-dihydroquinolin-4-yl)thiopropionate;
149) S-(1-methylpiperidin-2-yl)methyl 2-(4-chlorobenzoylamino)-3-(2-oxo-1,2-dihydroquinolin-4-yl)thiopropionate;
150) S-{4-[4-(4-chlorophenyl)piperazin-1-yl]-butyl}2-(4-chlorobenzoylamino)-3-(2-oxo-1,2-dihydroquinolin-4-yl)propionate;
151) S-(2-morpholin-4-yl)ethyl 2-(4-chlorobenzoylamino)-3-(2-oxo-1,2-dihydroquinolin-4-yl)propionate;
152) S-(tetrahydropyran 2 yl)methyl 2-(4-chlorobenzoylamino)-3-(2-oxo-1,2-dihydroquinolin-4-yl)thiopropionate;
153) S-(2-[1,3]-dioxan-2-yl)ethyl 2-(4-chlorobenzoylamino)-3-(2-oxo-1,2-dihydroquinolin-4-yl)thiopropionate;
154) S-(2-azepan-1-yl)ethyl 2-(4-chlorobenzoylamino)-3-(2-oxo-1,2-dihydroquinolin-4-yl)thiopropionate;
155) S-(5-methyl-2-oxo-[1,3]dioxol-4-yl)methyl 2-(4-chlorobenzoylamino)-3-(2-oxo-1,2-dihydroquinolin-4-yl)thiopropionate;
156) S-benzyl 2-(4-chlorobenzoylamino)-3-(2-oxo-1,2-dihydroquinolin-4-yl)thiopropionate;
157) S-phenethyl 2-(4-chlorobenzoylamino)-3-(2-oxo-1,2-dihydroquinolin-4-yl)thiopropionate;
158) S-(2-methylbenzyl) 2-(4-chlorobenzoylamino)-3-(2-oxo-1,2-dihydroquinolin-4-yl)thiopropionate;
159) S-(3-methylbenzyl) 2-(4-chlorobenzoylamino)-3-(2-oxo-1,2-dihydroquinolin-4-yl)thiopropionate;
160) S-(3,4-dimethylbenzyl) 2-(4-chlorobenzoylamino)-3-(2-oxo-1,2-dihydroquinolin-4-yl)thiopropionate;
161) S-(4-fluorobenzyl) 2-(4-chlorobenzoylamino)-3-(2-oxo-1,2-dihydroquinolin-4-yl)thiopropionate;
162) S-(2,5-difluorobenzyl) 2-(4-chlorobenzoylamino)-3-(2-oxo-1,2-dihydroquinolin-4-yl)thiopropionate;
163) S-(3-chlorobenzyl) 2-(4-chlorobenzoylamino)-3-(2-oxo-1,2-dihydroquinolin-4-yl)thiopropionate;
164) S-(3,5-dibromobenzyl) 2-(4-chlorobenzoylamino)-3-(2-oxo-1,2-dihydroquinolin-4-yl)thiopropionate;
165) S-(3-cyanobenzyl) 2-(4-chlorobenzoylamino)-3-(2-oxo-1,2-dihydroquinolin-4-yl)thiopropionate;
166) S-(4-cyanobenzyl) 2-(4-chlorobenzoylamino)-3-(2-oxo-1,2-dihydroquinolin-4-yl)thiopropionate;
167) S-(3-methoxybenzyl) 2-(4-chlorobenzoylamino)-3-(2-oxo-1,2-dihydroquinolin-4-yl)thiopropionate;

168) S-(4-methoxybenzyl) 2-(4-chlorobenzoylamino)-3-(2-oxo-1,2-dihydroquinolin-4-yl)thiopropionate;
169) S-(3-phenoxybenzyl) 2-(4-chlorobenzoylamino)-3-(2-oxo-1,2-dihydroquinolin-4-yl)thiopropionate;
170) S-(3-methoxycarbonyl)benzyl 2-(4-chlorobenzoylamino)-3-(2-oxo-1,2-dihydroquinolin-4-yl)thiopropionate;
171) S-(3-phenyloxycarbonyl)benzyl 2-(4-chlorobenzoylamino)-3-(2-oxo-1,2-dihydroquinolin-4-yl)propionate;
172) S-[2-(4-methylthiazol-5yl)ethyl]2-(4-chlorobenzoylamino)-3-(2-oxo-1,2-dihydroquinolin-4-yl)thiopropionate;
173) S-(pyrimidin-2-yl)methyl 2-(4-chlorobenzoylamino)-3-(2-oxo-1,2-dihydroquinolin-4-yl)thiopropionate;
174) S-(pyrimidin-3-yl)methyl 2-(4-chlorobenzoylamino)-3-(2-oxo-1,2-dihydroquinolin-4-yl)thiopropionate;
175) S-(3-phenylallyl)2-(4-chlorobenzoylamino)-3-(2-oxo-1,2-dihydroquinolin-4-yl)thiopropionate;
176) S-ethoxy-3-oxopropyl 2-(4-chlorobenzoylamino)-3-(2-oxo-1,2-dihydroquinolin-4-yl)thiopropionate;
177) ethyl[2-(4-chlorobenzoylamino)-3-(2-oxo-1,2-dihydroquinolin-4-yl)propionylamino]acetate;
178) [2-(4-chlorobenzoylamino)-3-(2-oxo-1,2-dihydroquinolin-4-yl)propionylamino]acetic acid;
179) ethyl 4-[2-(4-chlorobenzoylamino)-3-(2-oxo-1,2-dihydroquinolin-4-yl)propionylamino]butyrate;
180) ethyl 2-[2-(4-chlorobenzoylamino)-3-(2-oxo-1,2-dihydroquinolin-4-yl)propionylamino]-4-methyl pentanoate;
181) ethyl 2-[2-(4-chlorobenzoylamino)-3-(2-oxo-1,2-dihydroquinolin-4-yl)propionylamino]-3-phenyl propionate;
182) ethyl 2-[2-(4-chlorobenzoylamino)-3-(2-oxo-1,2-dihydroquinolin-4-yl)propionylamino]-3-(1H-indol-3-yl)propionate;
183) diethyl 2-[2-(4-chlorobenzoylamino)-3-(2-oxo-1,2-dihydroquinolin-4-yl)propionylamino]pentane-1,5-dioate;
184) diethyl 2-[2-(4-chlorobenzoylamino)-3-(2-oxo-1,2-dihydroquinolin-4-yl)propionylamino]pentane-1,5-dioic acid;
185) 4-chloro-N-[1-[2-(3H-imidazol-4-yl)ethylcarbamoyl]-2-(2-oxo-1,2-dihydroquinolin-4-yl)ethyl]benzamide;
186) 4-chloro-N-[2-(2-oxo-1,2-dihydroquinolin-4-yl)-1-(2-pyrrolidin-1-yl-ethylcarbamoyl)ethyl]benzamide; and
187) 4-chloro-N-[1-(2-morpholin-4-yl-ethylcarbamoyl)-2-(2-oxo-1,2-dihydroquinolin-4-yl)ethyl]benzamide.

The rebamipide prodrugs according to the present invention may be in the form of salts, and preferably, pharmaceutically acceptable salts. The salt most useful in the present invention is an acid addition salt formed with a pharmaceutically acceptable free acid. The free acid may be an inorganic acid or an organic acid. Examples of the organic acids include, but are not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, camphorsulfonic acid, glutamic acid, aspartic acid, salicylic acid, malonic acid, malic acid, and benzosulfonic acid. Among the inorganic acids may be hydrochloric acid, bromic acid, sulfuric acid and phosphoric acid, without limitation thereto.

Also, isomers of the compounds of Chemical Formula 1 fall within the scope of the present invention. For example, the compounds of Chemical Formula 1 may have an asymmetric carbon atom (chiral center), and thus may exist as enantiomers taking R or S configuration, racemates, diastereomers, diastereomic racemates, or meso-forms. These and other optical isomers, and mixtures thereof, fall within the scope of the present invention.

In addition, the compound of Chemical Formula 1 may take a form of a solvate or a hydrate, which is also within the scope of the present invention.

In accordance with another aspect thereof, the present invention addresses a method for preparing the compound of Chemical Formula 1, comprising reacting a compound represented by the following Chemical Formula II with a compound represented by the following Chemical Formula III:

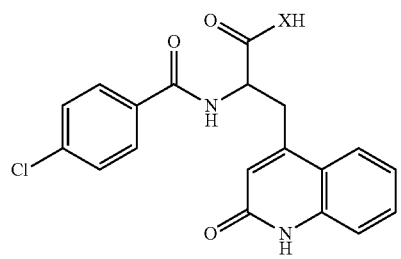

[Chemical Formula II]

Y—Z   [Chemical Formula III]

wherein,

X and Y are as defined above, and Z is a hydroxy group, an amino group, an amine group, a halogen atom, or a leaving group.

In one embodiment of the present invention, Z is hydroxy, —NH₂, Cl, Br, alkylsulfonyl or arylsulfonyl.

In detail, the compound of the present invention may be prepared as illustrated by the following Reaction Scheme 1, but without limitation thereto.

[Reaction Scheme 1]

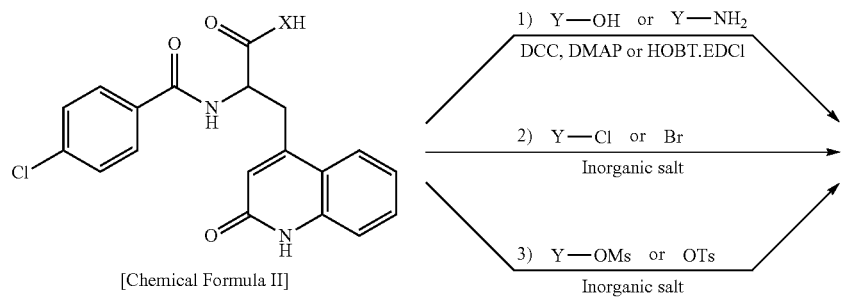

[Chemical Formula II]

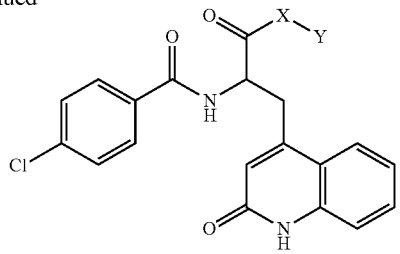

[Chemical Formula I]

(wherein, X is an oxygen atom, a nitrogen atom, or a sulfur atom)

The compound of Chemical Formula II, serving as the starting material in Reaction Scheme 1, may be synthesized using the method disclosed in U.S. Pat. No. 4,578,381. The inorganic salt employed in Reaction Scheme 1 may be an inorganic base such as sodium bicarbonate, sodium carbonate, potassium bicarbonate, potassium carbonate, or cesium carbonate. The reaction may be performed at 10 to 100° C. for 1 to 24 hrs in a solvent, such as acetone, dimethylformamide, dimethylsulfoxide, or acetonitrile. In Reactopm Scheme 1, DCC stands for dicyclohexylcarbodiimide; DMAP for 4-dimethylaminopyridine; HOBT for 1-hydroxybenzotriazole; and EDCl for 1-ethyl-3-(3-dimethylaminopropyl)carbodiimide HCl. Y-OMs or Y-OTs is a sulfonyl group such as an alkylsulfonyl group, e.g., methanesulfonyl; or an arylsulfonyl group, such as paratoluene sulfonyl, benzene sulfonyl or 4-nitrobenzene sulfonyl.

In Reaction Scheme 1, when X is sulfur, the compound of Chemical Formula II may be synthesized according to the following Reaction Scheme 2:

[Reaction Scheme 2]

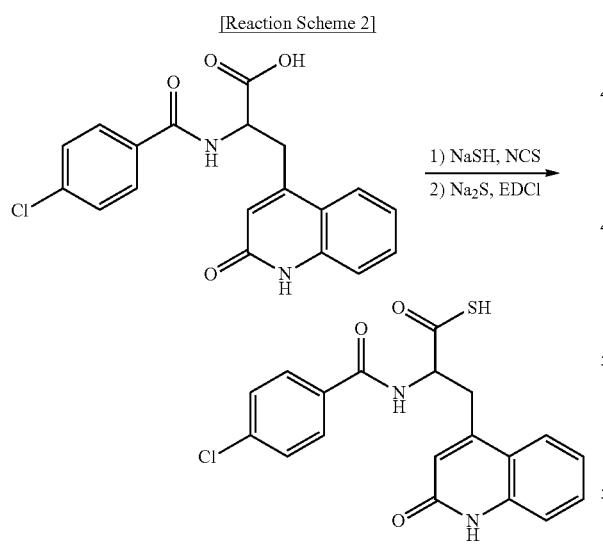

In Reaction Scheme 2, sodium hydrosulfide is used in an amount of from 1 to 10 equivalents, and preferably in an amount of from 4 to 5 equivalents, while sodium sulfide is used in an amount of from 1 to 5 equivalents and preferably in an amount of 2 to 5 equivalents. This reaction may be carried out at 10 to 100° C. for 1 to 24 hrs, with dimethylformamide, dimethylsulfoxide or acetonitrile serving as a solvent. In the reaction scheme, NCS stands for N-chlorosuccinimide.

In detail, the compound of the present invention may be prepared according to the general experiment protocols set forth below.

Experimental Protocol A

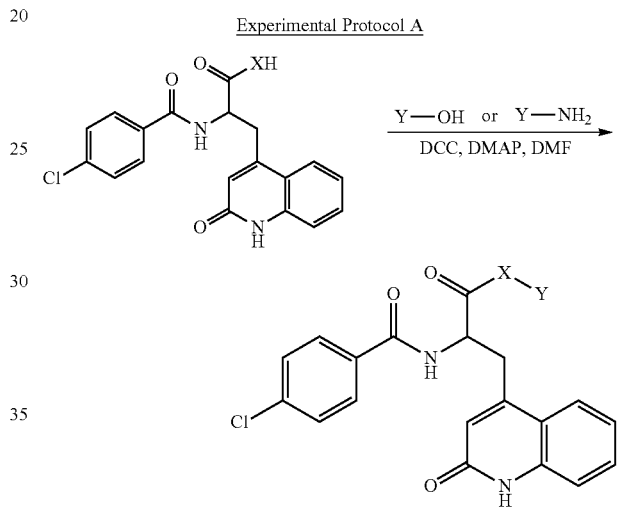

A compound of Chemical Formula II is dissolved at an elevated temperature in DMF (dimethylformamide, 8~10 volumes of the compound of Chemical Formula II), and quenched to 0° C. To this mixture are added DCC (dicyclohexylcarbodiimide, 1~1.5 equivalents) and DMAP (dimethylaminopyridine, 0.1~0.3 equivalents). When the internal temperature becomes stable, an alcohol or amine (1~1.2 equivalents) is slowly added. The resulting mixture is stirred at room temperature for 4 to 24 hrs. The product thus formed is obtained by filtration, followed by removing DMF in a vacuum. Subsequently, the residue is subjected to column chromatography using methylene chloride:methanol (9:1, v/v) to afford the compound of Chemical Formula I as a solid. If necessary, recrystallization is carried out.

Experimental Protocol B

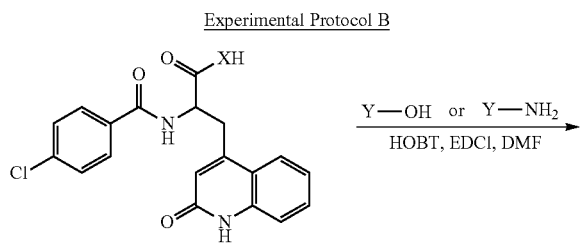

-continued

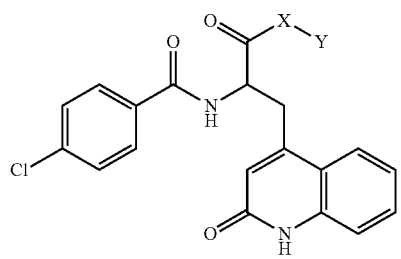

The compound of Chemical Formula II is dissolved at an elevated temperature in DMF (dimethylformamide, 8~10 volumes of the compound of Chemical Formula II), and quenched to 0° C. To this mixture are added EDCl (1-ethyl-3-(3-dimethylaminopropyl)carbodiimide HCl, 1~3 equivalents) and HOBT (1-hydroxybenzotriazole, 1~3 equivalents). When the internal temperature becomes stable, an alcohol or amine (1~1.5 equivalents) is slowly added. The resulting mixture is stirred at room temperature for 4 to 24 hrs. The product thus formed is obtained by filtration, followed by removing DMF in a vacuum. Subsequently, the residue is subjected to column chromatography using methylene chloride:methanol (9:1, v/v) to afford the compound of Chemical Formula I as a solid. If necessary, recrystallization is carried out Experimental Protocol C

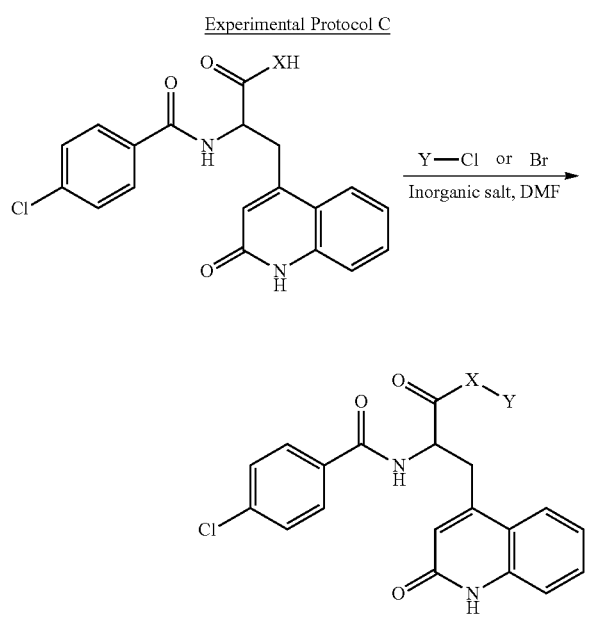

To a compound of Chemical Formula II are sequentially added DMF (dimethylformamide, 8~10 volumes of the compound of Chemical Formula II), a halogen compound (1~1.5 equivalents), and an inorganic salt (1~2 equivalents), and the resulting mixture is allowed to react at 20~80° C. for 1~24 hrs. After completion of the reaction, the product is obtained by filtration, followed by removing DMF in a vacuum. The residue is subjected to column chromatography using methylene chloride:methanol (9:1, v/v) to afford the compound of Chemical Formula 1 as a solid. If necessary, recrystallization is carried out.

Experimental Protocol D

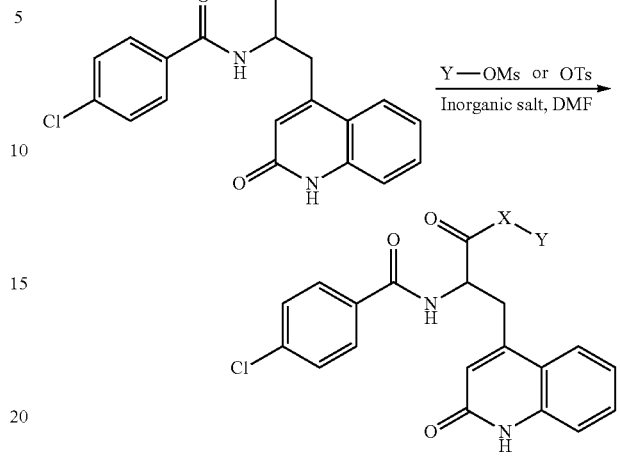

To a compound of Chemical Formula II are sequentially added DMF (dimethylformamide, 8~10 volumes of the compound of Chemical Formula II), a sulfonate compound (1~1.5 equivalents), and an inorganic salt (1~2 equivalents), and the resulting mixture is allowed to react at 20~80° C. for 1~24 hrs. After completion of the reaction, the product is obtained by filtration, followed by removing DMF in a vacuum. The residue is subjected to column chromatography using methylene chloride:methanol (9:1, v/v) to afford the compound of Chemical Formula 1 as a solid. If necessary, recrystallization is carried out.

In greater detail, the compound of Example 113, 2-(4-chlorobenzoylamino)-3-(2-oxo-1,2-dihydroquinolin-4-yl)-thiopropionic acid, can be prepared according to Experiment Protocol A or B as follows:

Experiment Protocol A

In 400 mL of DMF (dimethylformamide) is dissolved 50 g (134.8 mmol) of rebamipide at an elevated temperature, and the solution is quenched to room temperature. The solution is stirred, together with 28.1 g (1.0 eq, 134.8 mmol) of DCC (dicyclohexylcarbodiimide) for 30 min, and then, together with 16.0 g (1.0 eq, 134.8 mmol) of NaSH (sodium hydrosulfide) at room temperature for 15 hrs. After the reaction is completed, the reaction mixture is added with 800 mL of water, and then extracted three times with 800 mL of ethyl acetate. The organic phase is dried over anhydrous magnesium sulfate, filtered, and concentrated. To the residue is added 800 mL of ethyl acetate, followed by stirring at room temperature. The precipitate thus formed is filtered, and dried to obtain the title compound as a yellowish solid (42.0 g).

Experiment Protocol B

In 80 mL of DMF (dimethylformamide) is dissolved 10 g (26.97 mmol) of rebamipide at an elevated temperature, and the solution is quenched to 0° C. The solution is mixed with 5.69 g (1.1 eq, 29.67 mmol) of EDCl (1-ethyl-3-(3-dimethylaminopropyl)carbodiimide HCl) and 13.6 g (3.0 eq, 80.9 mmol) of Na$_2$S (sodium sulfide), after which the ice bath is removed before stirring at room temperature for 3 hrs. When the reaction is completed, the reaction mixture is added with 160 mL of water, and then extracted three times with 160 mL of ethyl acetate. The organic phase is dried over anhydrous magnesium sulfate, filtered, and concentrated. To the residue is added 200 mL of ethyl acetate, followed by stirring at room temperature. The precipitate thus formed is filtered, and dried to obtain the title compound as a yellowish solid (6.5 g).

Meanwhile, a salt of the rebamipide prodrug according to the present invention may be prepared according to Experiment Protocol E as set forth below, but without limitation thereto.

Experiment Protocol E

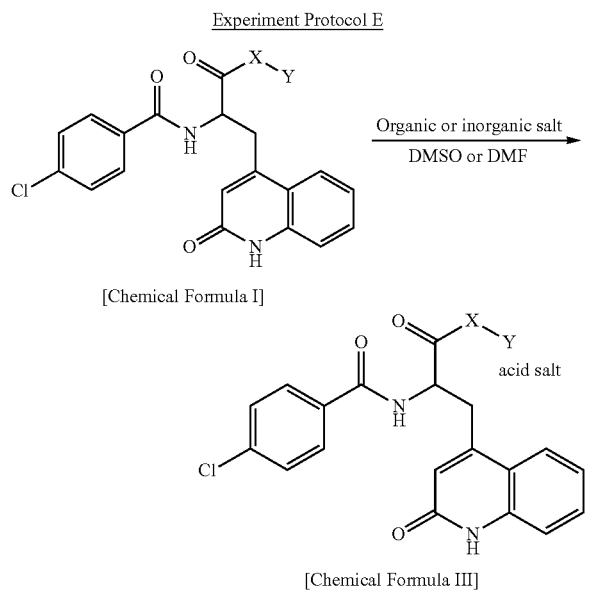

[Chemical Formula I]

[Chemical Formula III]

In the compound of Chemical Formula I is dissolved dimethylsulfoxide or dimethylformamide (3~10 volumes of the weight of the compound of Chemical Formula I). An organic acid or inorganic acid (1 eq) is added to the solution, and stirred to afford the compound of Chemical Formula III as a solid.

Being superior in body absorption rate to rebamipide in the free acid state, the compound of Chemical Formula I according to the present invention can be usefully applied, instead of rebamipide, to the prophylaxis or therapy of gastric ulcer, acute gastritis, chronic gastritis, xerophthalmia, cancer, osteoarthritis, rheumatoid arthritis, or obesity. Because these diseases are known or are regarded as being treatable or curable with rebamipide, the rebamipide prodrugs of the present invention are more likely to effectively treat the diseases. Thus, according to a further aspect thereof, the present invention envisages a pharmaceutical composition for the prophylaxis or therapy of gastric ulcer, acute gastritis, chronic gastritis, xerophthalmia, cancer, osteoarthritis, rheumatoid arthritis, or obesity, comprising the compound of Chemical Formula I or a pharmaceutically acceptable salt thereof as an active ingredient.

The pharmaceutically effective daily dosage is about 0.5 mg/kg body weight to 100 mg/kg body, and preferably about 1 mg/kg body weight to 30 mg/kg body weight of the rebamipide or its pharmaceutically acceptable salt thereof. However, the pharmaceutically effective dose may vary depending on various factors including the severity of disease, the patient's age, weight, health condition, and sex, the route of administration, and the time of administration.

In addition, the pharmaceutical composition of the present invention may further comprise a pharmaceutically acceptable additive. The term "pharmaceutically acceptable," as used herein, refers to pertaining to being physiologically compatible and not causing a gastrointestinal disorder, an allergic response such as dizziness, or analogous responses after administration to humans. The additive may be any one of a carrier, an excipient, and a diluent, as typified by lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil. A filler, an anti-coagulant, a lubricant, a humectants, a flavoring agent, an emulsifier, and a preservative may be used in the pharmaceutical composition of the present invention.

Moreover, the pharmaceutical composition of the present invention may be formulated into a preparation suitable for use in releasing the active ingredient in an immediate, sustained or delayed manner. The preparation may be in such a form as a powder, a granule, a tablet, an emulsion, a syrup, an aerosol, a soft or hard gelatin capsule, a sterile injection, or a sterile powder.

The pharmaceutical composition according to the present invention can be administered via various routes including oral, transdermal, subcutaneous, intravenous, and intramuscular routes. The dose of the active ingredient may be determined depending on various factors such as the route of administration, the patient's age, sex, and weight, the severity of disease to be treated, etc. The pharmaceutical composition may be administered in combination with a compound known to be prophylactic or therapeutic of the disease of interest.

Also, contemplated in accordance with still another aspect of the present invention is a method for preventing or treating a disease, comprising administering the compound of Chemical Formula I to a subject in need thereof, said disease being selected from the group consisting of gastric ulcer, acute gastritis, chronic gastritis, xerophthalmia, cancer, osteoarthritis, rheumatoid arthritis, andr obesity.

In accordance with a still further aspect thereof, the present invention addresses the use of the compound of Chemical Formula I in preventing or treating gastric ulcer, acute gastritis, chronic gastritis, xerophthalmia, cancer, osteoarthritis, rheumatoid arthritis, or obesity.

A better understanding of the present invention may be obtained through the following examples which are set forth to illustrate, but are not to be construed as limiting the present invention.

Example 1

Preparation of Methyl 2-(4-chlorobenzoylamino)-3-(2-oxo-1,2-dihydroquinolin-4-yl)propionate

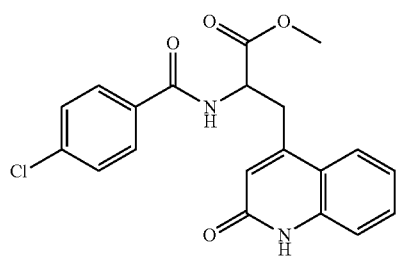

According to Experiment Prototocol C, 1.0 g (2.69 mmol) of rebamipide and 0.36 g (1.5 eq, 0.40 mmol) of methyl iodide were reacted to afford the title compound as a white solid (0.8 g).

¹H NMR (400 MHz, DMSO-d₆): δ 11.69 (s, 1H), 9.06 (d, 1H), 7.83 (t, 3H), 7.55 (d, 2H), 7.31 (d, 1H), 7.24 (dd, 1H), 6.44 (s, 1H), 4.79 (m, 1H), 3.69 (s, 3H), 3.47 (dd, 1H), 3.27 (q, 1H)

Example 2

Preparation of Ethyl 2-(4-chlorobenzoylamino)-3-(2-oxo-1,2-dihydroquinolin-4-yl)propionate

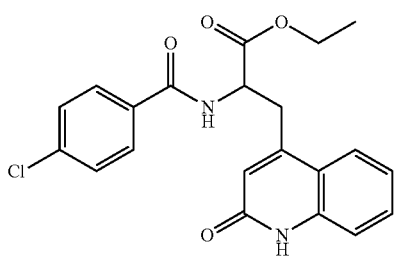 [SMILES: CCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.62 g (1.5 eq, 4.03 mmol) of iodoethane were reacted to afford the title compound as a white solid (1.0 g).

¹H NMR (400 MHz, DMSO-d₆): δ 11.70 (s, 1H), 9.04 (d, 1H), 7.82 (m, 3H), 7.55 (d, 2H), 7.52 (t, 1H), 7.31 (d, 1H), 7.24 (t, 1H), 6.45 (s, 1H), 4.76 (m, 1H), 4.12 (q, 2H), 3.44 (dd, 1H), 3.28 (q, 1H), 1.17 (t, ³H)\

Example 3

Preparation of 3-Methylbutyl 2-(4-chlorobenzoylamino)-3-(2-oxo-1,2-dihydroquinolin-4-yl)propionate

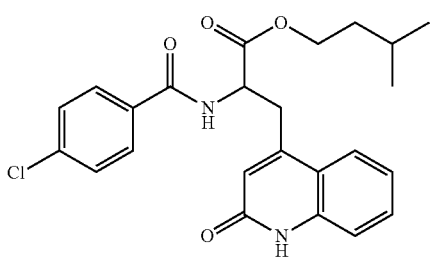

According to Experiment Prototocol C, 1.0 g (2.69 mmol) of rebamipide and 0.60 g (1.5 eq, 4.03 mmol) of 1-bromo-3-methylbutane were reacted to afford the title compound as a white solid (0.7 g).

¹H NMR (700 MHz, DMSO-d₆): δ 11.70 (s, 1H), 9.04 (d, 1H), 7.84-7.80 (m, 3H), 7.58-7.50 (m, 2H), 7.50 (t, 1H), 7.32 (dd, 1H), 7.24-7.21 (m, 1H), 6.44 (s, 1H), 4.77-4.74 (m, 1H), 4.09 (t, 2H), 3.43 (dd, 1H), 3.29 (q, 1H), 1.57-1.53 (m, 1H), 1.43-1.40 (m, 2H), 0.83 (q, 6H)

Example 4

Preparation of Hexyl 2-(4-chlorobenzoylamino)-3-(2-oxo-1,2-dihydroquinolin-4-yl)propionate

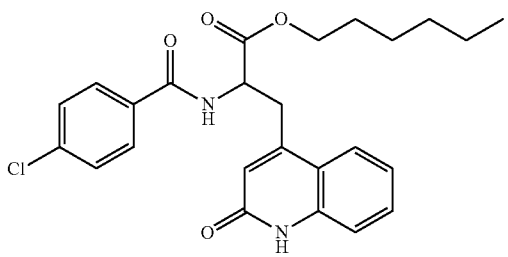

According to Experiment Prototocol C, 1.0 g (2.69 mmol) of rebamipide and 0.66 g (1.5 eq, 4.03 mmol) of 1-bromohexane were reacted to afford the title compound as a white solid (1.1 g).

¹H NMR (400 MHz, DMSO-d₆): δ 11.70 (s, 1H), 9.07 (d, 1H), 7.82 (q, 3H), 7.56 (d, 2H), 7.52 (t, 1H), 7.31 (d, 1H), 7.23 (t, 1H), 6.44 (s, 1H), 4.75 (m, 1H), 4.06 (t, 2H), 3.43 (dd, 1H), 3.29 (q, 1H), 1.51 (t, 3H), 1.19 (br-s, 6H), 0.81 (t, 3H)

Example 5

Preparation of 2-Bromoethyl 2-(4-chlorobenzoylamino)-3-(2-oxo-1,2-dihydroquinolin-4-yl)propionate

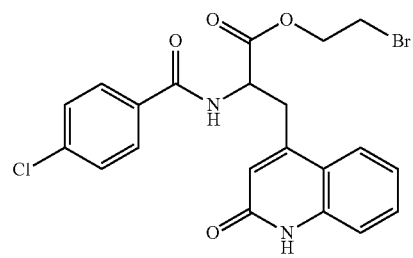 [SMILES: O=C(NC(Cc1cc(=O)[nH]c2ccccc12)C(=O)OCCBr)c1ccc(Cl)cc1]

According to Experiment Prototocol A, 1.0 g (2.69 mmol) of rebamipide and 0.33 g (1.0 eq, 2.69 mmol) of 2-bromoethanol were reacted to afford the title compound as a white solid (0.4 g).

¹H NMR (400 MHz, DMSO-d₆): δ 11.67 (s, 1H), 9.11 (d, 1H), 8.03 (d, 1H), 7.85 (m, 3H), 7.74 (d, 1H), 7.55 (m, 4H), 7.44 (m, 1H), 7.31 (d, 1H), 7.24 (t, 1H), 6.47 (s, 1H), 4.83 (m, 3H), 4.52 (m, 2H), 3.43 (dd, 1H), 3.33 (m, 1H)

Example 6

Preparation of 2-Hydroxyethyl 2-(4-chlorobenzoylamino)-3-(2-oxo-1,2-dihydroquinolin-4-yl)propionate

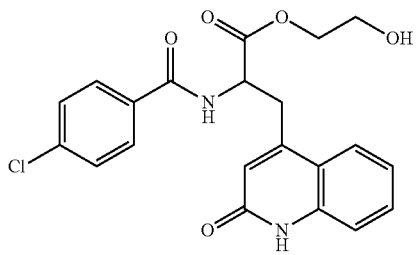 [SMILES: O=C(NC(Cc1cc(=O)[nH]c2ccccc12)C(=O)OCCO)c1ccc(Cl)cc1]

According to Experiment Prototocol C, 1.0 g (2.69 mmol) of rebamipide and 0.50 g (1.5 eq, 4.03 mmol) of 2-bromoethanol were reacted to afford the title compound as a white solid (0.7 g).

$^1$H NMR (700 MHz, DMSO-$d_6$): δ 11.68 (s, 1H), 9.03 (d, 1H), 7.85-7.82 (m, 3H), 7.57 (s, 1H), 7.56 (s, 1H), 7.52 (t, 1H), 7.31 (d, 1H), 7.24 (t, 1H), 6.45 (s, 1H), 4.88 (t, 1H), 4.16-4.11 (m, 2H), 3.61-3.58 (m, 2H), 3.51 (dd, 1H), 3.26 (q, 1H)

Example 7

Preparation of Methoxymethyl 2-(4-chlorobenzoylamino)-3-(2-oxo-1,2-dihydroquinolin-4-yl)propionate

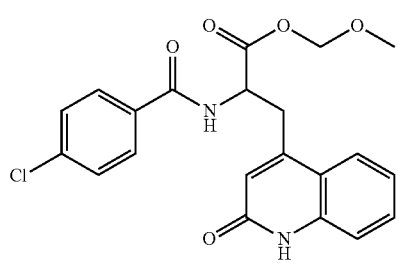 [SMILES: COCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.32 g (1.5 eq, 4.03 mmol) of chloromethyl methyl ether were reacted to afford the title compound as a white solid (0.6 g).

$^1$H NMR (400 MHz, DMSO-$d_6$): δ 11.70 (s, 1H), 9.11 (d, 1H), 7.83 (br-s, 3H), 7.59-7.51 (m, 3H), 7.32 (d, 1H), 7.25 (t, 1H), 6.47 (s, 1H), 5.29 (s, 2H), 4.80 (m, 1H), 3.56-3.49 (m, 5H)

Example 8

Preparation of 2-Methoxyethyl 2-(4-chlorobenzoylamino)-3-(2-oxo-1,2-dihydroquinolin-4-yl)propionate

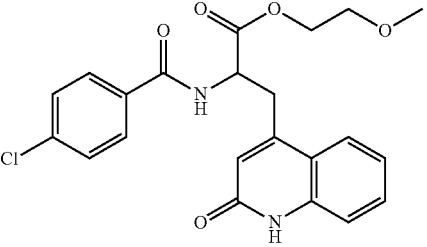

According to Experiment Prototocol C, 1.0 g (2.69 mmol) of rebamipide and 0.38 g (1.5 eq, 4.03 mmol) of 2-chloroethyl methyl ether were reacted to afford the title compound as a white solid (1.0 g).

$^1$H NMR (400 MHz, DMSO-$d_6$): δ 11.70 (s, 1H), 9.07 (d, 1H), 7.82 (t, 3H), 7.56 (d, 2H), 7.52 (t, 1H), 7.32 (d, 1H), 7.24 (t, 1H), 6.45 (s, 1H), 4.76 (m, 1H), 4.21 (m, 2H), 3.56-3.49 (m, 2H), 3.43 (dd, 1H), 3.29 (q, 1H), 3.24 (s, 3H)

Example 9

Preparation of 2-Vinyloxyethyl 2-(4-chlorobenzoylamino)-3-(2-oxo-1,2-dihydroquinolin-4-yl)propionate

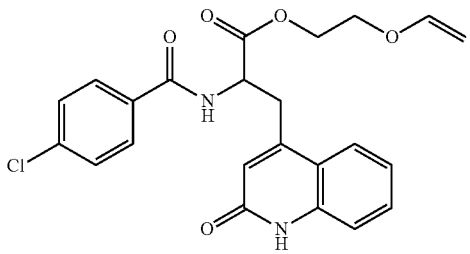 [SMILES: C=COCCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.43 g (1.5 eq, 4.03 mmol) of 2-chloroethyl vinyl ether were reacted to afford the title compound as a white solid (0.7 g).

$^1$H NMR (400 MHz, DMSO-$d_6$): δ 11.69 (s, 1H), 9.07 (d, 1H), 7.84-7.81 (m, 3H), 7.57 (t, 1H), 7.56 (t, 1H), 7.52 (m, 1H), 7.31 (dd, 1H), 7.21 (m, 1H), 6.49 (q, 1H), 6.45 (s, 1H), 4.78 (m, 1H), 4.36-4.27 (m, 2H), 4.19 (dd, 1H), 3.97 (dd, 1H), 3.94-3.84 (m, 2H), 3.45 (dd, 1H), 3.28 (q, 1H)

Example 10

Preparation of 2-Acetoxyethyl 2-(4-chlorobenzoylamino)-3-(2-oxo-1,2-dihydroquinolin-4-yl)propionate

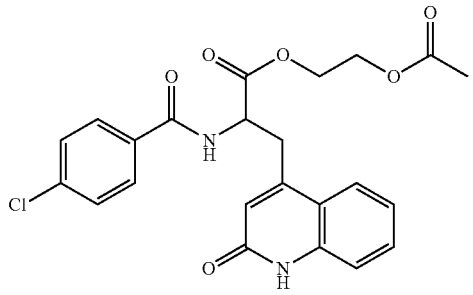 [SMILES: CC(=O)OCCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.49 g (1.5 eq, 4.03 mmol) of 2-chloroethyl acetate were reacted to afford the title compound as a white solid (0.8 g).

$^1$H NMR (400 MHz, DMSO-$d_6$): δ 11.70 (s, 1H), 9.07 (d, 1H), 7.82 (t, 3H), 7.56 (d, 2H), 7.52 (t, 1H), 7.32 (d, 1H), 7.24 (t, 1H), 6.46 (s, 1H), 4.76 (m, 1H), 4.36-4.29 (m, 2H), 4.22-4.18 (m, 2H), 3.45 (dd, 1H), 3.28 (q, 1H), 1.99 (s, 3H)

Example 11

Preparation of 2-Methylsulfanylethyl 2-(4-chlorobenzoylamino)-3-(2-oxo-1,2-dihydroquinolin-4-yl) propionate

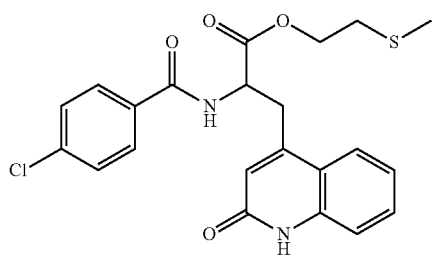

According to Experiment Prototocol C, 1.0 g (2.69 mmol) of rebamipide and 0.44 g (1.5 eq, 4.03 mmol) of 2-chloroethyl methyl sulfide were reacted to afford the title compound as a white solid (0.7 g).

$^1$H NMR (400 MHz, DMSO-$d_6$): δ 11.70 (s, 1H), 9.06 (d, 1H), 7.84 (t, 3H), 7.56 (d, 2H), 7.52 (t, 1H), 7.31 (d, 1H), 7.24 (t, 1H), 6.46 (s, 1H), 4.78 (m, 1H), 4.25 (m, 2H), 3.48 (dd, 1H), 3.29 (q, 1H), 2.72 (t, 2H), 2.07 (s, 3H)

Example 12

Preparation of 2-Phenylsulfanylethyl 2-(4-chlorobenzoylamino)-3-(2-oxo-1,2-dihydroquinolin-4-yl) propionate

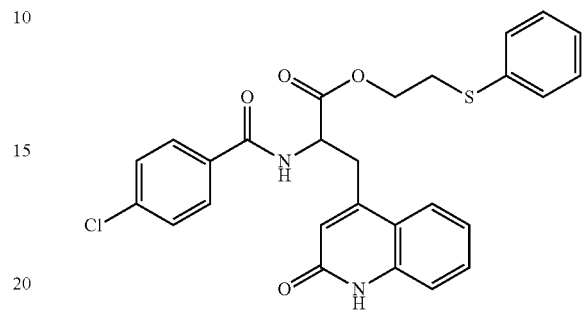

According to Experiment Prototocol C, 1.0 g (2.69 mmol) of rebamipide and 0.69 g (1.5 eq, 4.03 mmol) of 2-chloroethyl phenyl sulfide were reacted to afford the title compound as a white solid (0.9 g).

$^1$H NMR (400 MHz, DMSO-$d_6$): δ 11.71 (s, 1H), 9.06 (d, 1H), 7.82 (t, 3H), 7.58 (d, 2H), 7.52 (t, 1H), 7.39-7.30 (m, 5H), 7.25-7.18 (m, 2H), 6.45 (s, 1H), 4.75 (m, 1H), 4.25 (m, 2H), 3.43 (dd, 1H), 3.29-3.22 (m, 3H)

Example 13

Preparation of 2-Methylaminoethyl 2-(4-chlorobenzoylamino)-3-(2-oxo-1,2-dihydroquinolin-4-yl)propionate

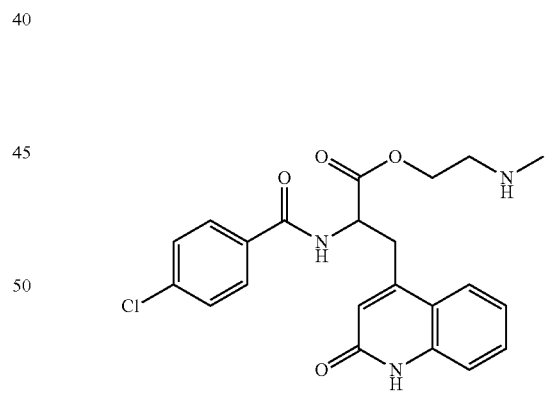

According to Experiment Prototocol B, 1.0 g (2.69 mmol) of rebamipide and 0.24 g (1.2 eq, 3.23 mmol) of (2-methylamino)ethanol were reacted to afford the title compound as a white solid (0.4 g).

$^1$H NMR (400 MHz, DMSO-$d_6$): δ 11.61 (s, 1H), 8.84 (d, 1H), 8.17 (q, 1H), 7.91 (d, 1H), 7.86 (d, 2H), 7.55 (d, 2H), 7.48 (t, 1H), 7.30 (d, 1H), 7.23 (m, 1H), 6.46 (s, 1H), 4.79 (m, 1H), 3.44 (dd, 1H), 3.14 (q, 1H), 2.90 (d, 3H)

Example 14

Preparation of 2-Dimethylaminoethyl 2-(4-chlorobenzoylamino)-3-(2-oxo-1,2-dihydroquinolin-4-yl)propionate

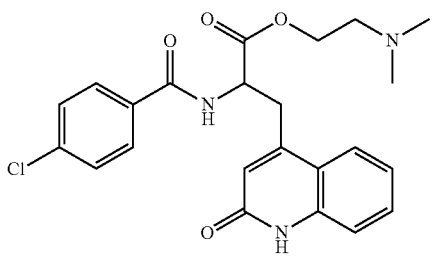 [SMILES: CN(C)CCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.57 g (1.5 eq, 4.03 mmol) of (2-dimethylamino)ethylchloride HCl were reacted to afford the title compound as a white solid (0.7 g).

$^1$H NMR (400 MHz, DMSO-$d_6$): δ 11.61 (s, 1H), 9.06 (d, 1H), 7.83 (m, 3H), 7.56 (d, 2H), 7.52 (t, 1H), 7.32 (d, 1H), 7.23 (t, 1H), 6.46 (s, 1H), 4.76 (m, 1H), 4.15 (m, 2H), 3.45 (dd, 1H), 3.28 (q, 1H), 2.43 (m, 2H), 2.13 (s, 6H)

Example 15

Preparation of 2-Dimethylamino-1-methyl-ethyl 2-(4-chlorobenzoylamino)-3-(2-oxo-1,2-dihydroquinolin-4-yl)propionate

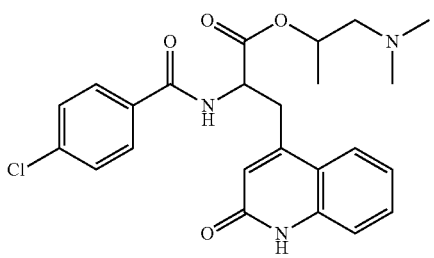

According to Experiment Prototocol B, 1.0 g (2.69 mmol) of rebamipide and 0.33 g (1.2 eq, 3.23 mmol) of 1-dimethylamino-2-propanol were reacted to afford the title compound as a white solid (0.7 g).

$^1$H NMR (400 MHz, DMSO-$d_6$): δ 11.69 (s, 1H), 9.05 (d, 1H), 7.83 (m, 3H), 7.56 (m, 2H), 7.52 (t, 1H), 7.32 (d, 1H), 7.22 (m, 1H), 6.46 (t, 1H), 4.77 (m, 1H), 4.18 (m, 1H), 3.94 (m, 1H), 3.46 (dd, 1H), 3.30 (m, 1H), 2.75 (m, 1H), 2.15 (dd, 6H), 1.16 (m, 1H), 0.89 (q, 2H)

Example 16

Preparation of 2-Diethylaminoethyl 2-(4-chlorobenzoylamino)-3-(2-oxo-1,2-dihydroquinolin-4-yl)propionate

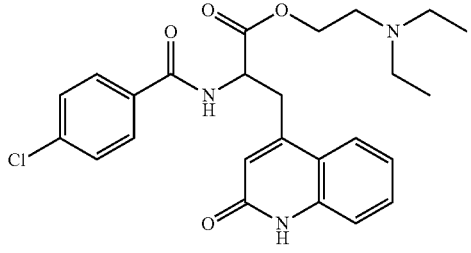 [SMILES: CCN(CC)CCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.69 g (1.5 eq, 4.03 mmol) of 2-(diethylamino)ethyl chloride HCl were reacted to afford the title compound as a white solid (0.6 g).

$^1$H NMR (400 MHz, DMSO-$d_6$): δ 11.68 (s, 1H), 9.03 (d, 1H), 7.83 (t, 3H), 7.56 (d, 2H), 7.50 (t, 1H), 7.32 (d, 1H), 7.23 (t, 1H), 6.46 (s, 1H), 4.78 (m, 1H), 4.11 (m, 2H), 3.49 (dd, 1H), 3.28 (m, 1H), 2.60 (m, 2H), 2.48 (q, 4H), 0.90 (t, 6H)

Example 17

Preparation of 2-Diisopropylaminoethyl 2-(4-chlorobenzoylamino)-3-(2-oxo-1,2-dihydroquinolin-4-yl)propionate

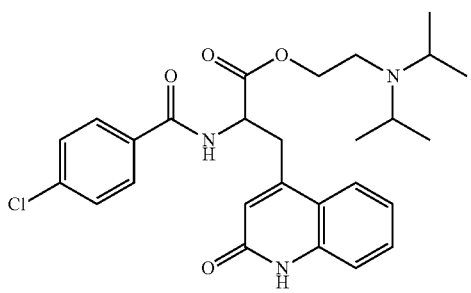 [SMILES: CC(C)N(CCOC(=O)C(Cc1cc(=O)[nH]c2ccccc12)NC(=O)c1ccc(Cl)cc1)C(C)C]

According to Experiment Prototocol C, 1.0 g (2.69 mmol) of rebamipide and 0.80 g (1.5 eq, 4.03 mmol) of 2-(diisopropylamino)ethyl chloride HCl were reacted to afford the title compound as a white solid (0.6 g).

$^1$H NMR (400 MHz, DMSO-$d_6$): δ 11.69 (s, 1H), 9.02 (d, 1H), 7.83 (t, 3H), 7.56 (d, 2H), 7.51 (t, 1H), 7.32 (d, 1H), 7.23 (t, 1H), 6.45 (s, 1H), 4.80 (m, 1H), 3.98 (m, 2H), 3.46 (dd, 1H), 3.27 (m, 1H), 2.93 (m, 2H), 2.55 (t, 2H), 0.93 (s, 6H), 0.91 (s, 6H)

Example 18

Preparation of 3-dimethylaminopropyl 2-(4-chlorobenzoylamino)-3-(2-oxo-1,2-dihydroquinolin-4-yl)propionate

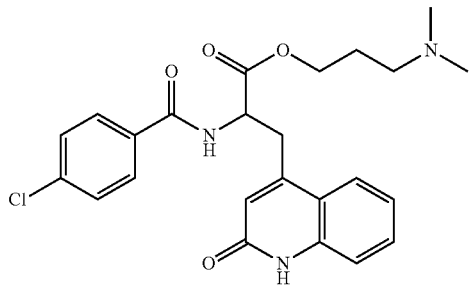 [SMILES: CN(C)CCCOC(=O)C(Cc1cc(=O)[nH]c2ccccc12)NC(=O)c1ccc(Cl)cc1]

According to Experiment Prototocol B, 1.0 g (2.69 mmol) of rebamipide and 0.33 g (1.2 eq, 3.23 mmol) of 3-dimethylamino-1-propanol were reacted to afford the title compound as a white solid (0.5 g).

$^1$H NMR (400 MHz, DMSO-$d_6$): δ 11.69 (s, 1H), 9.03 (d, 1H), 7.83 (m, 3H), 7.54 (m, 3H), 7.32 (d, 1H), 7.23 (m, 1H), 6.45 (s, 1H), 4.76 (m, 1H), 4.09 (m, 1H), 3.46 (dd, 1H), 3.30 (m, 1H), 2.16 (t, 2H), 2.06 (s, 6H), 1.66 (m, 2H)

Example 19

Preparation of 2-(Methyl phenyl amino)ethyl 2-(4-chlorobenzoylamino)-3-(2-oxo-1,2-dihydroquinolin-4-yl)propionate

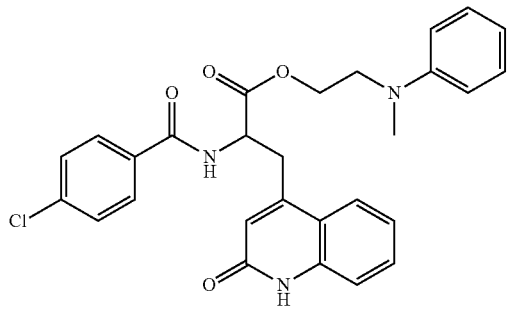 [SMILES: CN(CCOC(=O)C(Cc1cc(=O)[nH]c2ccccc12)NC(=O)c1ccc(Cl)cc1)c1ccccc1]

According to Experiment Prototocol B, 1.0 g (2.69 mmol) of rebamipide and 0.49 g (1.2 eq, 3.23 mmol) of 2-(methylphenylamino)ethanol were reacted to afford the title compound as a white solid (0.5 g).

$^1$H NMR (400 MHz, DMSO-$d_6$): δ 11.70 (s, 1H), 9.03 (d, 1H), 7.80 (d, 2H), 7.73 (d, 1H), 7.55 (d, 2H), 7.51 (t, 1H), 7.30 (d, 1H), 7.21 (t, 1H), 7.13 (t, 2H), 6.70 (d, 2H), 6.59 (t, 1H), 6.43 (s, 1H), 4.76 (m, 1H), 4.25 (m, 2H), 3.66-3.54 (m, 2H), 3.38 (dd, 1H), 3.20 (q, 1H), 2.87 (s, 3H)

Example 20

Preparation of 2-(Benzyl ethyl amino)ethyl 2-(4-chlorobenzoylamino)-3-(2-oxo-1,2-dihydroquinolin-4-yl)propionate

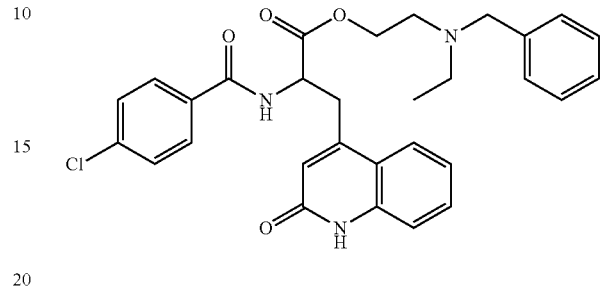

According to Experiment Prototocol C, 1.0 g (2.69 mmol) of rebamipide and 0.61 g (1.5 eq, 4.03 mmol) of 2-(benzyl ethylamino)ethyl chloride HCl were reacted to afford the title compound as a white solid (0.5 g).

$^1$H NMR (700 MHz, DMSO-$d_6$): δ 11.71 (s, 1H), 9.05 (d, 1H), 7.83 (d, 2H), 7.79 (d, 1H), 7.55 (d, 2H), 7.51 (t, 1H), 7.33 (d, 1H), 7.27-7.24 (m, 4H), 7.20 (q, 2H), 6.47 (s, 1H), 4.83-4.79 (m, 1H), 4.22-4.14 (m, 2H), 3.56 (s, 2H), 3.46 (dd, 1H), 3.28 (q, 1H), 2.69-2.64 (m, 2H), 2.51-2.43 (m, 2H), 0.92 (t, 3H)

Example 21

Preparation of 2-(Benzoxazol-2-ylmethyl amino)ethyl 2-(4-chlorobenzoylamino)-3-(2-oxo-1,2-dihydroquinolin-4-yl)propionate

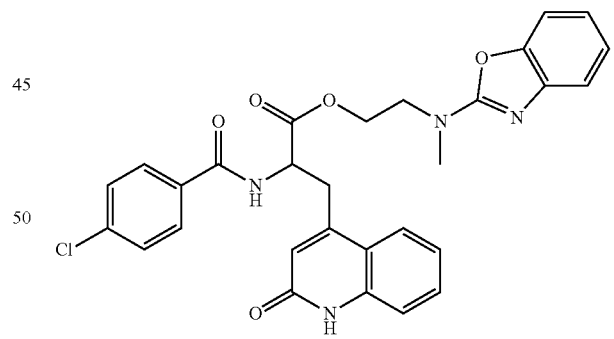

According to Experiment Prototocol C, 1.0 g (2.69 mmol) of rebamipide and 0.85 g (1.5 eq, 4.03 mmol) of benzoxazol-2-yl-(2-chloroethyl)methyl amine were reacted to afford the title compound as a white solid (0.5 g).

$^1$H NMR (400 MHz, DMSO-$d_6$): δ 11.64 (s, 1H), 8.99 (d, 1H), 7.96 (s, 1H), 7.75 (d, 2H), 7.63 (d, 1H), 7.50 (d, 2H), 7.46 (t, 1H), 7.33 (d, 1H), 7.27 (d, 1H), 7.22 (d, 1H), 7.09 (t, 1H), 6.95 (t, 1H), 6.38 (s, 1H), 4.75 (m, 1H), 4.41 (m, 2H), 3.83 (m, 2H), 3.38 (dd, 1H), 3.17 (dd, 1H), 3.14 (s, 3H)

Example 22

Preparation of 2-Benzoylaminoethyl 2-(4-chlorobenzoylamino)-3-(2-oxo-1,2-dihydroquinolin-4-yl)propionate

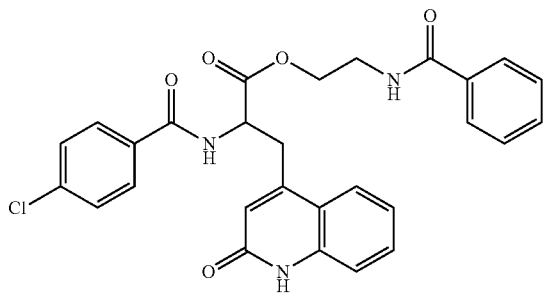

According to Experiment Prototocol C, 1.0 g (2.69 mmol) of rebamipide and 0.74 g (1.5 eq, 4.03 mmol) of 2-chloroethyl benzamide were reacted to afford the title compound as a white solid (0.4 g).

$^1$H NMR (400 MHz, DMSO-$d_6$): δ 11.68 (s, 1H), 8.67 (d, 1H), 8.64 (t, 1H), 7.84-7.77 (m, 5H), 7.54-7.43 (m, 6H), 7.29 (d, 1H), 7.13 (t, 1H), 6.43 (s, 1H), 4.80 (m, 1H), 4.38 (m, 1H), 4.23 (m, 1H), 3.61-3.50 (m, 3H), 3.21 (q, 1H)

Example 23

Preparation of Allyl 2-(4-chlorobenzoylamino)-3-(2-oxo-1,2-dihydroquinolin-4-yl)propionate

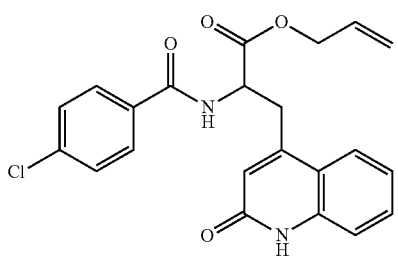

According to Experiment Prototocol C, 1.0 g (2.69 mmol) of rebamipide and 0.48 g (1.5 eq, 4.03 mmol) of allylbromide were reacted to afford the title compound as a white solid (0.7 g).

$^1$H NMR (400 MHz, DMSO-$d_6$): δ 11.68 (s, 1H), 9.06 (d, 1H), 7.84-7.81 (m, 3H), 7.55 (d, 2H), 7.51 (t, 1H), 7.31 (d, 1H), 7.23 (t, 1H), 6.45 (s, 1H), 5.94-5.84 (m, 1H), 5.32-5.27 (m, 1H), 5.22-5.19 (dd, 1H), 4.85-4.80 (m, 1H), 4.63-4.62 (m, 2H), 3.47 (dd, 1H), 3.30 (q, 1H)

Example 24

Preparation of But-2-enyl 2-(4-chlorobenzoylamino)-3-(2-oxo-1,2-dihydroquinolin-4-yl)propionate

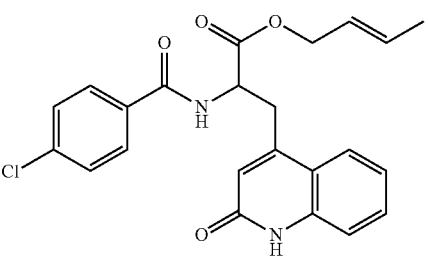 [SMILES: C/C=C/COC(=O)C(Cc1cc(=O)[nH]c2ccccc12)NC(=O)c1ccc(Cl)cc1]

According to Experiment Prototocol C, 1.0 g (2.69 mmol) of rebamipide and 0.36 g (1.5 eq, 4.03 mmol) of 1-chloro-2-butene were reacted to afford the title compound as a white solid (0.6 g).

$^1$H NMR (400 MHz, DMSO-$d_6$): δ 11.66 (s, 1H), 9.02 (d, 1H), 7.84-7.80 (m, 3H), 7.57 (t, 1H), 7.55 (t, 1H), 7.53-7.49 (m, 1H), 7.31 (dd, 1H), 7.25-7.21 (m, 1H), 6.43 (s, 1H), 5.78-5.71 (m, 1H), 5.55-5.48 (m, 1H), 4.83-4.66 (m, 1H), 4.54 (d, 2H), 3.43 (dd, 1H), 3.29 (q, 1H), 1.65 (t, 3H)

Example 25

Preparation of 3-Methylbut-2-enyl 2-(4-chlorobenzoylamino)-3-(2-oxo-1,2-dihydroquinolin-4-yl)propionate

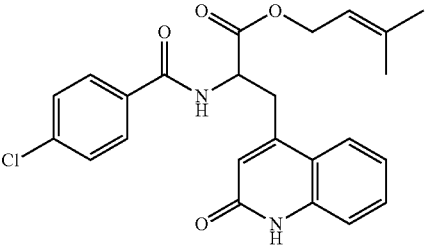 [SMILES: CC(C)=CCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.42 g (1.5 eq, 4.03 mmol) of 1-chloro-3-methyl-2-butene were reacted to afford the title compound as a white solid (0.7 g).

$^1$H NMR (700 MHz, DMSO-$d_6$): δ 11.66 (s, 1H), 9.00 (d, 1H), 7.84-7.82 (m, 2H), 7.79 (d, 1H), 7.52-7.50 (m, 2H), 7.49-7.46 (m, 1H), 7.31 (dd, 1H), 7.22-7.20 (m, 1H), 6.44 (s, 1H), 5.26-5.25 (m, 1H), 4.80-4.77 (m, 1H), 4.60-4.59 (m, 2H), 3.42 (dd, 1H), 3.27 (q, 1H), 1.71 (s, 3H), 1.65 (s, 3H)

Example 26

Preparation of 3-Prop-2-ynyl 2-(4-chlorobenzoylamino)-3-(2-oxo-1,2-dihydroquinolin-4-yl)propionate

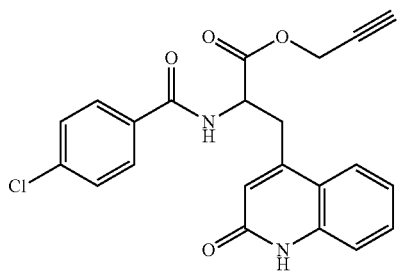

According to Experiment Prototocol D, 1.0 g (2.69 mmol) of rebamipide and 0.84 g (1.5 eq, 4.03 mmol) of propargyl tosylate were reacted to afford the title compound as a white solid (0.7 g).

$^1$H NMR (700 MHz, DMSO-$d_6$): δ 11.66 (s, 1H), 9.07 (d, 1H), 7.84-7.80 (m, 3H), 7.57 (s, 1H), 7.55 (s, 1H), 7.51 (t, 1H), 7.31 (d, 1H), 7.23 (t, 1H), 6.45 (s, 1H), 4.81-4.76 (m, 2H), 3.50-43 (m, 1H), 3.32-3.26 (m, 3H)

Example 27

Preparation of 2-Oxopropyl 2-(4-chlorobenzoylamino)-3-(2-oxo-1,2-dihydroquinolin-4-yl)propionate

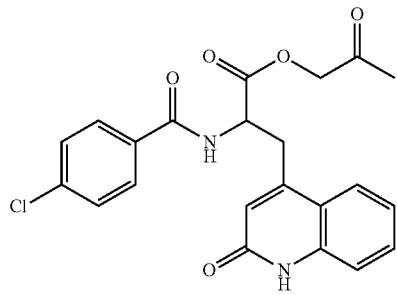 [SMILES: CC(=O)COC(=O)C(Cc1cc(=O)[nH]c2ccccc12)NC(=O)c1ccc(Cl)cc1]

According to Experiment Prototocol C, 1.0 g (2.69 mmol) of rebamipide and 0.37 g (1.5 eq, 4.03 mmol) of chloroacetone were reacted to afford the title compound as a white solid (1.0 g).

$^1$H NMR (700 MHz, DMSO-$d_6$): δ 11.69 (s, 1H), 9.11 (d, 1H), 7.84 (t, 1H), 7.83 (t, 1H), 7.81 (d, 1H), 7.57 (t, 1H), 7.56 (t, 1H), 7.53-7.51 (m, 1H), 7.32 (dd, 1H), 7.26-7.24 (m, 1H), 6.50 (s, 1H), 4.95-4.86 (m, 3H), 3.58 (dd, 1H), 3.31 (q, 1H), 2.15 (s, 3H)

Example 28

Preparation of 2-oxobutyl 2-(4-chlorobenzoylamino)-3-(2-oxo-1,2-dihydroquinolin-4-yl)propionate

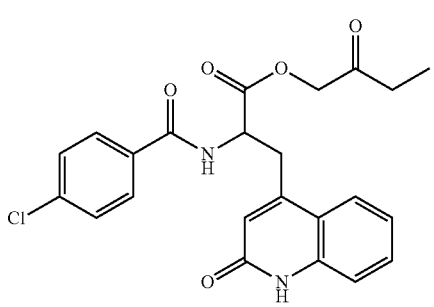 [SMILES: CCC(=O)COC(=O)C(Cc1cc(=O)[nH]c2ccccc12)NC(=O)c1ccc(Cl)cc1]

According to Experiment Prototocol C, 1.0 g (2.69 mmol) of rebamipide and 0.43 g (1.5 eq, 4.03 mmol) of 1-chloro-2-butanone were reacted to afford the title compound as a white solid (1.0 g).

$^1$H NMR (400 MHz, DMSO-$d_6$): δ 11.68 (s, 1H), 9.08 (d, 1H), 7.82 (t, 3H), 7.57 (s, 1H), 7.55 (s, 1H), 7.52 (t, 1H), 7.32 (d, 1H), 7.25 (t, 1H), 6.50 (s, 1H), 4.97-4.85 (m, 3H), 3.58 (dd, 1H), 3.31 (q, 1H), 2.47 (q, 2H), 0.96 (t, 3H)

Example 29

Preparation of Cyclopentyl 2-(4-chlorobenzoylamino)-3-(2-oxo-1,2-dihydroquinolin-4-yl)propionate

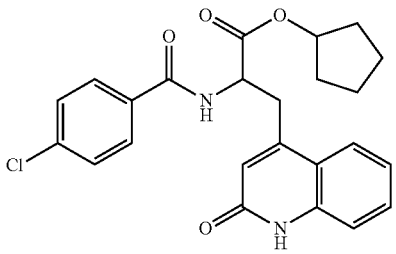 [SMILES: O=C(NC(Cc1cc(=O)[nH]c2ccccc12)C(=O)OC1CCCC1)c1ccc(Cl)cc1]

According to Experiment Prototocol C, 1.0 g (2.69 mmol) of rebamipide and 0.42 g (1.5 eq, 4.03 mmol) of chlorocyclopentane were reacted to afford the title compound as a white solid (0.8 g).

$^1$H NMR (700 MHz, DMSO-$d_6$): δ 11.70 (s, 1H), 9.02 (d, 1H), 7.83 (d, 2H), 7.81 (d, 1H), 7.57 (d, 2H), 7.52 (t, 1H), 7.32 (d, 1H), 7.24 (t, 1H), 6.44 (s, 1H), 5.11-5.10 (m, 1H), 4.71-4.68 (m, 1H), 3.40 (dd, 1H), 3.29 (q, 1H), 1.81-1.74 (m, 2H), 1.65-1.62 (m, 1H), 1.58-1.55 (m, 5H)

Example 30

Preparation of Cyclohexyl 2-(4-chlorobenzoylamino)-3-(2-oxo-1,2-dihydroquinolin-4-yl)propionate

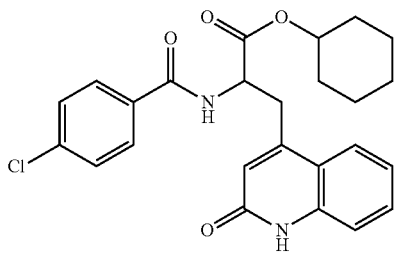 [SMILES: O=C(NC(Cc1cc(=O)[nH]c2ccccc12)C(=O)OC1CCCCC1)c1ccc(Cl)cc1]

According to Experiment Prototocol C, 1.0 g (2.69 mmol) of rebamipide and 0.47 g (1.5 eq, 4.03 mmol) of chlorocyclohexane were reacted to afford the title compound as a white solid (0.9 g).

$^1$H NMR (400 MHz, DMSO-$d_6$): δ 11.68 (s, 1H), 9.01 (d, 1H), 7.85-7.81 (m, 3H), 7.58 (t, 1H), 7.55 (t, 1H), 7.53-7.49 (m, 1H), 7.31 (dd, 1H), 7.25-7.21 (m, 1H), 6.44 (s, 1H), 4.75-4.70 (m, 1H), 3.45-3.37 (m, 2H), 3.28 (q, 1H), 1.75-1.56 (m, 4H), 1.44-1.27 (m, 6H)

Example 31

Preparation of Cyclopropylmethyl 2-(4-chlorobenzoylamino)-3-(2-oxo-1,2-dihydroquinolin-4-yl)propionate

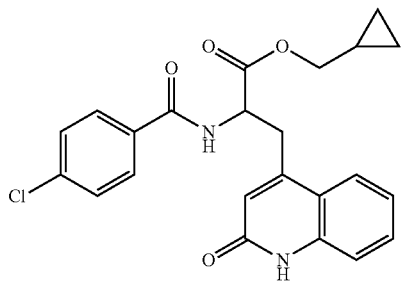 [SMILES: O=C(NC(Cc1cc(=O)[nH]c2ccccc12)C(=O)OCC1CC1)c1ccc(Cl)cc1]

According to Experiment Prototocol C, 1.0 g (2.69 mmol) of rebamipide and 0.36 g (1.5 eq, 4.03 mmol) of (chloromethyl)cyclopropane were reacted to afford the title compound as a white solid (0.8 g).

$^1$H NMR (400 MHz, DMSO-$d_6$): δ 11.70 (s, 1H), 9.06 (d, 1H), 7.86-7.80 (m, 3H), 7.58 (s, 1H), 7.56 (s, 1H), 7.52 (t, 1H), 7.32 (d, 1H), 7.24 (t, 1H), 6.45 (s, 1H), 4.78 (m, 1H), 3.93 (d, 2H), 3.44 (dd, 1H), 3.28 (q, 1H), 1.10-1.01 (m, 1H), 0.51-0.45 (m, 2H), 0.29-0.23 (m, 2H)

Example 32

Preparation of Cyclobutylmethyl 2-(4-chlorobenzoylamino)-3-(2-oxo-1,2-dihydroquinolin-4-yl)propionate

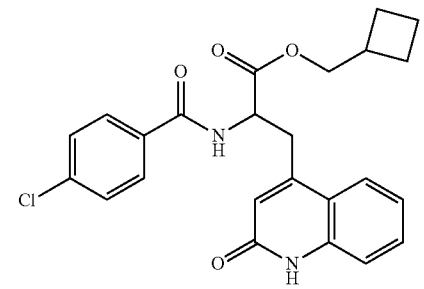 [SMILES: O=C(NC(Cc1cc(=O)[nH]c2ccccc12)C(=O)OCC1CCC1)c1ccc(Cl)cc1]

According to Experiment Prototocol A, 1.0 g (2.69 mmol) of rebamipide and 0.28 g (1.2 eq, 3.23 mmol) of cyclobutanemethanol were reacted to afford the title compound as a white solid (0.5 g).

$^1$H NMR (700 MHz, DMSO-$d_6$): δ 11.70 (s, 1H), 9.06 (d, 1H), 7.84 (t, 1H), 7.82 (t, 1H), 7.81 (d, 1H), 7.57 (t, 1H), 7.56 (t, 1H), 7.53-7.50 (m, 1H), 7.321 (dd, 1H), 7.24-7.22 (m, 1H), 6.45 (s, 1H), 4.77-4.75 (m, 1H), 4.05-4.02 (m, 2H), 3.44 (dd, 1H), 3.30 (q, 1H), 2.55-2.51 (m, 1H), 1.94-1.90 (m, 2H), 1.83-1.79 (m, 1H), 1.75-1.69 (m, 3H)

Example 33

Preparation of Cyclohexylmethyl 2-(4-chlorobenzoylamino)-3-(2-oxo-1,2-dihydroquinolin-4-yl)propionate

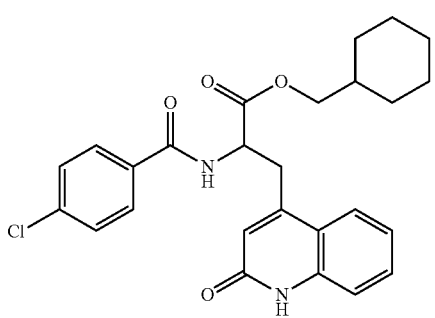 [SMILES: O=C(NC(Cc1cc(=O)[nH]c2ccccc12)C(=O)OCC1CCCCC1)c1ccc(Cl)cc1]

According to Experiment Prototocol C, 1.0 g (2.69 mmol) of rebamipide and 0.37 g (1.2 eq, 3.23 mmol) of cyclohexanemethanol were reacted to afford the title compound as a white solid (0.7 g).

$^1$H NMR (700 MHz, DMSO-$d_6$): δ 11.70 (s, 1H), 9.05 (d, 1H), 7.84 (t, 1H), 7.83 (t, 1H), 7.81 (d, 1H), 7.58 (t, 1H), 7.56 (t, 1H), 7.53-7.50 (m, 1H), 7.32 (dd, 1H), 7.24-7.22 (m, 1H), 6.44 (s, 1H), 4.79-4.76 (m, 1H), 3.87 (d, 2H), 3.42 (dd, 1H), 3.31 (q, 1H), 1.63-1.55 (m, 5H), 1.50-1.49 (m, 1H), 1.18-1.12 (m, 2H), 1.07-1.03 (m, 1H), 0.89-0.85 (m, 2H)

Example 34

Preparation of Cyclopent-3-enylmethyl 2-(4-chlorobenzoylamino)-3-(2-oxo-1,2-dihydroquinolin-4-yl)propionate

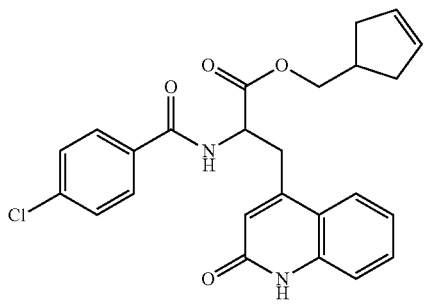 [SMILES: O=C(NC(Cc1cc(=O)[nH]c2ccccc12)C(=O)OCC1CC=CC1)c1ccc(Cl)cc1]

According to Experiment Prototocol D, 1.0 g (2.69 mmol) of rebamipide and 1.02 g (1.5 eq, 4.03 mmol) of (cyclopent-3-enyl)methyl tosylate were reacted to afford the title compound as a white solid (0.8 g).

$^1$H NMR (700 MHz, DMSO-d$_6$): δ 11.70 (s, 1H), 9.05 (d, 1H), 7.84 (t, 1H), 7.82 (t, 1H), 7.80 (d, 1H), 7.58 (t, 1H), 7.56 (t, 1H), 7.53-7.50 (m, 1H), 7.32 (dd, 1H), 7.25-7.22 (m, 1H), 6.44 (s, 1H), 5.64 (s, 2H), 4.77-4.73 (m, 1H), 4.02-3.97 (m, 2H), 3.44 (dd, 1H), 3.29 (q, 1H), 2.53-2.51 (m, 1H), 2.39-2.35 (m, 2H), 2.05-2.01 (m, 2H)

Example 35

Preparation of Oxiranylmethyl 2-(4-chlorobenzoylamino)-3-(2-oxo-1,2-dihydroquinolin-4-yl)propionate

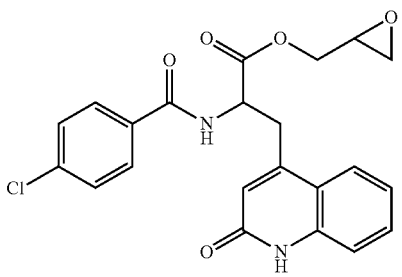

According to Experiment Prototocol C, 1.0 g (2.69 mmol) of rebamipide and 0.37 g (1.5 eq, 4.03 mmol) of 2-(chloromethyl)oxirane were reacted to afford the title compound as a white solid (0.5 g).

$^1$H NMR (400 MHz, DMSO-d$_6$): δ 11.70 (s, 1H), 9.09 (d, 1H), 7.81 (m, 3H), 7.57 (s, 1H), 7.56 (d, 1H), 7.52 (t, 1H), 7.31 (d, 1H), 7.22 (t, 1H), 6.44 (s, 1H), 5.09 (m, 1H), 4.80 (m, 1H), 4.60 (t, 1H), 4.47-4.31 (m, 3H), 4.22-4.18 (m, 2H), 3.47 (dd, 1H), 3.28 (q, 1H)

Example 36

Preparation of 3-Methyloxetan-3-ylmethyl 2-(4-chlorobenzoylamino)-3-(2-oxo-1,2-dihydroquinolin-4-yl)propionate

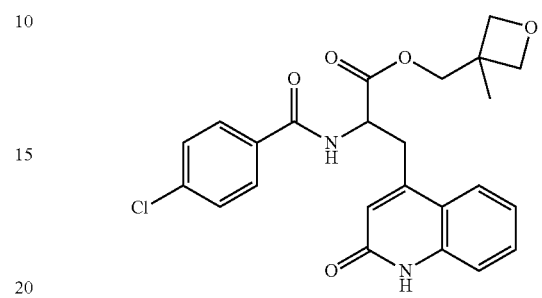

According to Experiment Prototocol D, 1.0 g (2.69 mmol) of rebamipide and 0.72 g (1.5 eq, 4.03 mmol) of 3-methyl-3-oxetanemethyl methanesulfonate were reacted to afford the title compound as a white solid (0.5 g).

$^1$H NMR (400 MHz, DMSO-d$_6$): δ 11.70 (s, 1H), 9.08 (d, 1H), 7.82 (d, 3H), 7.58-7.50 (m, 3H), 7.32 (d, 1H), 7.23 (t, 1H), 6.45 (s, 1H), 4.78 (m, 1H), 4.36 (t, 2H), 4.21 (t, 4H), 3.48 (dd, 1H), 3.36-3.30 (m, 1H)

Example 37

Preparation of 2-(1-Methylpyrrolidin-2-yl)ethyl 2-(4-chlorobenzoylamino)-3-(2-oxo-1,2-dihydroquinolin-4-yl)propionate

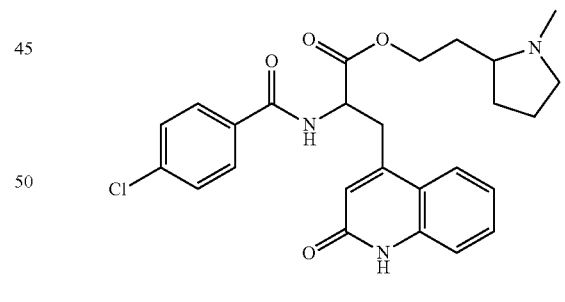

According to Experiment Prototocol D, rebamipide 1.0 g (2.69 mmol) and 0.83 g (1.5 eq, 4.03 mmol) of 1-methyl-2-pyrrolidine ethylmethanesulfonate were reacted to afford the title compound as a white solid (0.7 g).

$^1$H NMR (400 MHz, DMSO-d$_6$): δ 11.69 (s, 1H), 9.04 (d, 1H), 7.83 (t, 3H), 7.58 (s, 1H), 7.56 (s, 1H), 7.52 (t, 1H), 7.32 (d, 1H), 7.24 (m, 1H), 6.44 (s, 1H), 4.95 (m, 1H), 4.70 (m, 1H), 3.41 (dd, 1H), 3.30 (m, 2H), 2.51-2.36 (m, 3H), 2.20 (s, 3H), 1.99-1.81 (m, 2H), 1.70-1.51 (m, 4H)

Example 38

Preparation of 2-Pyrrolidin-1-yl-ethyl 2-(4-chlorobenzoylamino)-3-(2-oxo-1,2-dihydroquinolin-4-yl)propionate

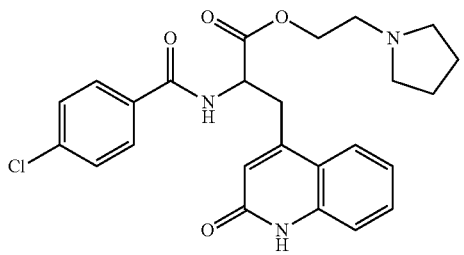 [SMILES: O=C(NC(Cc1cc(=O)[nH]c2ccccc12)C(=O)OCCN1CCCC1)c1ccc(Cl)cc1]

According to Experiment Prototocol D, 1.0 g (2.69 mmol) of rebamipide and 0.78 g (1.5 eq, 4.03 mmol) of 2-pyrrolidine ethylmethanesulfonate were reacted to afford the title compound as a white solid (0.7 g).

$^1$H NMR (400 MHz, DMSO-$d_6$): δ 11.69 (s, 1H), 9.04 (d, 1H), 7.83 (t, 3H), 7.57 (s, 1H), 7.55 (s, 1H), 7.50 (t, 1H), 7.32 (d, 1H), 7.23 (m, 1H), 6.46 (s, 1H), 4.78 (m, 1H), 4.18 (m, 2H), 3.46 (dd, 1H), 3.30 (m, 2H), 2.60 (m, 1H), 2.41 (d, 4H), 1.59 (m, 4H)

Example 39

Preparation of Tetrahydrofuran-2-ylmethyl 2-(4-chlorobenzoylamino)-3-(2-oxo-1,2-dihydroquinolin-4-yl)propionate

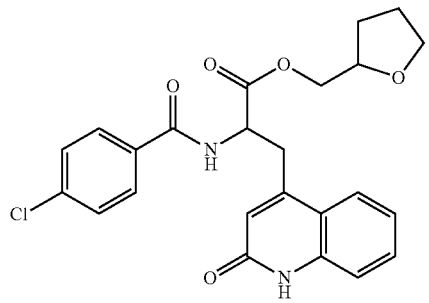

According to Experiment Prototocol C, 1.0 g (2.69 mmol) of rebamipide and 0.48 g (1.5 eq, 4.03 mmol) of 2-(chloromethyl)tetrahydrofuran were reacted to afford the title compound as a white solid (0.8 g).

$^1$H NMR (400 MHz, DMSO-$d_6$): δ 11.70 (s, 1H), 9.06 (d, 1H), 7.85-7.81 (m, 3H), 7.58 (s, 1H), 7.56 (s, 1H), 7.52 (t, 1H), 7.32 (d, 1H), 7.23 (t, 1H), 6.46 (s, 1H), 4.79 (m, 1H), 4.12-3.98 (m, 32H), 3.72-3.58 (m, 2H), 3.45 (dd, 1H), 3.32 (q, 1H), 1.93-1.78 (m, 1H), 1.77-1.72 (m, 2H), 1.61-1.49 (m, 1H)

Example 40

Preparation of [1,3]Dioxolan-2-ylmethyl 2-(4-chlorobenzoylamino)-3-(2-oxo-1,2-dihydroquinolin-4-yl)propionate

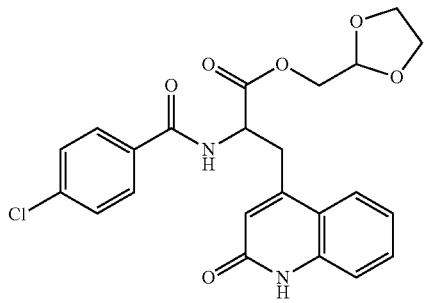

According to Experiment Prototocol C, 1.0 g (2.69 mmol) of rebamipide and 0.49 g (1.5 eq, 4.03 mmol) of 2-chloromethyl-1,3-dioxolane were reacted to afford the title compound as a white solid (0.5 g).

$^1$H NMR (700 MHz, DMSO-$d_6$): δ 11.68 (s, 1H), 9.06 (d, 1H), 7.84-7.82 (m, 2H), 7.79 (d, 1H), 7.53-7.51 (m, 2H), 7.50-7.47 (m, 1H), 7.32 (d, 1H), 7.23-7.21 (m, 1H), 6.46 (s, 1H), 5.07 (t, 1H), 4.83-4.80 (m, 1H), 4.17-4.10 (m, 2H), 3.90-3.87 (m, 2H), 3.84-3.80 (m, 2H), 3.44 (dd, 1H), 3.29 (q, 1H)

Example 41

Preparation of 2-[1,3]-Dioxolan-2-ylethyl 2-(4-chlorobenzoylamino)-3-(2-oxo-1,2-dihydroquinolin-4-yl)propionate

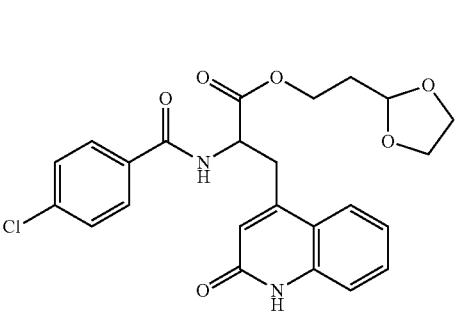

According to Experiment Prototocol C, 1.0 g (2.69 mmol) of rebamipide and 0.73 g (1.5 eq, 4.03 mmol) of 2-(2-bromoethyl)-1,3-dioxolane were reacted to afford the title compound as a white solid (0.6 g).

$^1$H NMR (400 MHz, DMSO-$d_6$): δ 11.70 (s, 1H), 9.04 (d, 1H), 7.82 (d, 3H), 7.56 (d, 2H), 7.52 (t, 1H), 7.31 (d, 1H), 7.24 (t, 1H), 6.45 (s, 1H), 4.83 (t, 1H), 4.76 (m, 1H), 4.19 (m, 2H), 3.89-3.86 (m, 2H), 3.76-3.72 (m, 2H), 3.47 (dd, 1H), 3.26 (q, 1H), 1.88 (q, 2H)

Example 42

Preparation of 1-Methylpiperidin-2-ylmethyl 2-(4-chlorobenzoylamino)-3-(2-oxo-1,2-dihydroquinolin-4-yl)propionate

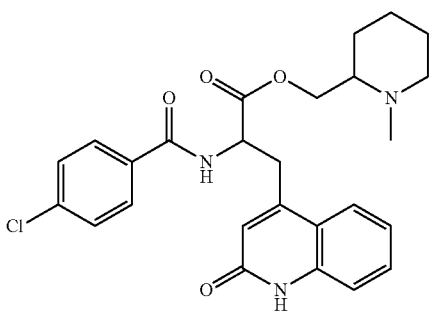 [SMILES: CN1CCCCC1COC(=O)C(Cc1cc(=O)[nH]c2ccccc12)NC(=O)c1ccc(Cl)cc1]

According to Experiment Prototocol D, 1.0 g (2.69 mmol) of rebamipide and 0.83 g (1.5 eq, 4.03 mmol) of 1-methyl-2-piperidinemethyl methanesulfonate were reacted to afford the title compound as a white solid (0.4 g).

$^1$H NMR (400 MHz, DMSO-$d_6$): δ 11.68 (s, 1H), 9.04 (d, 1H), 7.85-7.81 (m, 3H), 7.57 (s, 1H), 7.55 (s, 1H), 7.51 (t, 1H), 7.32 (d, 1H), 7.22 (t, 1H), 6.44 (s, 1H), 4.77-4.69 (m, 1H), 4.09-4.05 (m, 1H), 3.45-3.40 (m, 1H), 3.33-3.27 (m, 4H), 2.73-2.67 (m, 1H), 2.47-2.44 (m, 2H), 1.99-1.91 (m, 1H), 1.62-1.47 (m, 4H), 1.41-1.38 (m, 1H), 1.20-1.15 (m, 1H)

Example 43

Preparation of 1-Methylpiperidin-3-ylmethyl 2-(4-chlorobenzoylamino)-3-(2-oxo-1,2-dihydroquinolin-4-yl)propionate

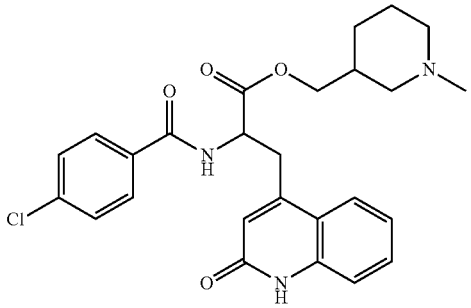 [SMILES: CN1CCCC(COC(=O)C(Cc2cc(=O)[nH]c3ccccc23)NC(=O)c2ccc(Cl)cc2)C1]

According to Experiment Prototocol C, 1.0 g (2.69 mmol) of rebamipide and 0.74 g (1.5 eq, 4.03 mmol) of 3-chloromethyl-1-methylpiperidine HCl were reacted to afford the title compound as a white solid (0.3 g).

$^1$H NMR (400 MHz, DMSO-$d_6$): δ 11.71 (s, 1H), 9.07 (dd, 1H), 7.86-7.81 (m, 3H), 7.59 (s, 1H), 7.57 (s, 1H), 7.52 (t, 1H), 7.32 (d, 1H), 7.23 (m, 1H), 6.44 (s, 1H), 4.75 (m, 1H), 4.00-3.82 (m, 2H), 3.47-3.40 (m, 1H), 3.35-3.28 (m, 1H), 2.58-2.50 (m, 2H), 2.05 (s, 3H), 1.77-1.72 (m, 2H), 1.63-1.39 (m, 4H), 0.92-0.84 (m, 1H)

Example 44

Preparation of 2-Piperidin-1-ylethyl 2-(4-chlorobenzoylamino)-3-(2-oxo-1,2-dihydroquinolin-4-yl)propionate

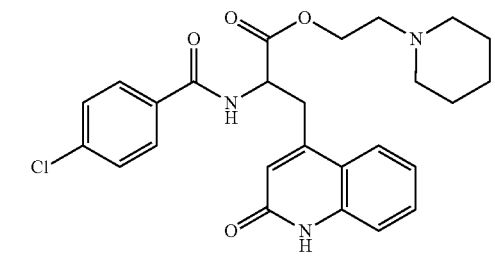

According to Experiment Prototocol C, 1.0 g (2.69 mmol) of rebamipide and 0.74 g (1.5 eq, 4.03 mmol) of 1-(2-chloroethyl)piperidine HCl were reacted to afford the title compound as a white solid (0.7 g).

$^1$H NMR (400 MHz, DMSO-$d_6$): δ 11.69 (s, 1H), 9.04 (d, 1H), 7.83 (m, 3H), 7.58 (t, 1H), 7.56 (t, 1H), 7.50 (m, 1H), 7.32 (dd, 1H), 7.23 (m, 1H), 6.47 (s, 1H), 4.76 (m, 1H), 4.24 (m, 1H), 4.12 (m, 1H), 3.47 (dd, 1H), 3.31 (m, 2H), 2.48 (m, 1H), 2.33 (br-s, 4H), 1.40 (m, 4H), 1.32 (m, 2H)

Example 45

Preparation of Tetrahydropyran 2 ylmethyl 2-(4-chlorobenzoylamino)-3-(2-oxo-1,2-dihydroquinolin-4-yl)propionate

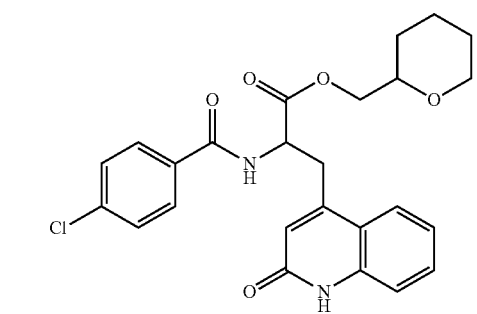

According to Experiment Prototocol C, 1.0 g (2.69 mmol) of rebamipide and 0.54 g (1.5 eq, 4.03 mmol) of 2-(chloromethyl)tetrahydro-2H-pyran were reacted to afford the title compound as a white solid (0.9 g).

$^1$H NMR (400 MHz, DMSO-$d_6$): δ 11.70 (s, 1H), 9.07 (dd, 1H), 7.85-7.82 (m, 3H), 7.58 (t, 1H), 7.56 (t, 1H), 7.52 (m, 1H), 7.32 (dd, 1H), 7.24 (t, 1H), 6.45 (s, 1H), 4.76 (m, 1H), 4.09-3.98 (m, 2H), 3.89-3.86 (m, 2H), 3.82 (d, 1H), 3.47-3.39 (m, 2H), 3.34-3.27 (m, 2H), 1.74 (br-s, 1H), 1.50-1.36 (m, 4H), 1.21-1.17 (m, 1H)

Example 46

Preparation of 2-[1,3]Dioxan-2-ylethyl 2-(4-chlorobenzoylamino)-3-(2-oxo-1,2-dihydroquinolin-4-yl)propionate

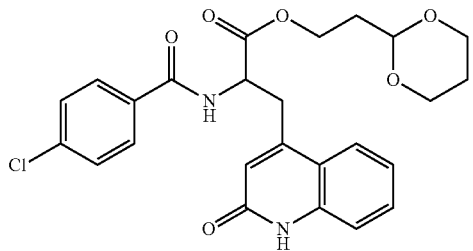

According to Experiment Prototocol C, 1.0 g (2.69 mmol) of rebamipide and 0.78 g (1.5 eq, 4.03 mmol) of 2-(2-bromoethyl)-1,3-dioxane were reacted to afford the title compound as a white solid (0.8 g).

$^1$H NMR (400 MHz, DMSO-$d_6$): δ 11.71 (s, 1H), 9.05 (d, 1H), 7.83 (t, 3H), 7.57 (d, 2H), 7.52 (t, 1H), 7.32 (d, 1H), 7.24 (t, 1H), 6.45 (s, 1H), 4.75 (m, 1H), 4.54 (t, 1H), 4.12 (m, 2H), 3.95 (dd, 2H), 3.62-3.56 (m, 2H), 3.43 (dd, 1H), 3.28 (q, 1H), 1.89-1.74 (m, 3H), 1.28 (d, 1H)

Example 47

Preparation of 2-Morpholin-4-ylethyl 2-(4-chlorobenzoylamino)-3-(2-oxo-1,2-dihydroquinolin-4-yl)propionate

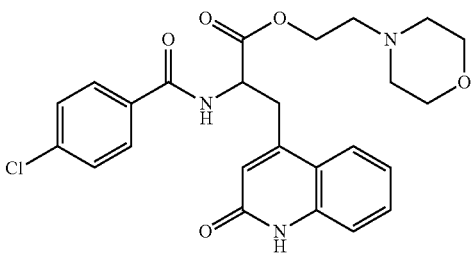

According to Experiment Prototocol C, 1.0 g (2.69 mmol) of rebamipide and 0.75 g (1.5 eq, 4.03 mmol) of 4-(2-chloroethyl)morpholine HCl were reacted to afford the title compound as a white solid (0.8 g).

$^1$H NMR (DMSO-$d_6$): δ 9.0 (d, 1H), 7.82 (t, 3H), 7.53 (m, 4H), 7.31 (d, 1H), 7.23 (t, 1H), 6.44 (s, 1H), 4.78-4.72 (m, 1H), 4.26-4.14 (m, 2H), 3.74 (t, 1H), 3.66 (t, 1H), 3.46 (t, 6H), 3.30-3.24 (m, 2H), 3.01-2.95 (m, 2H)

Example 48

Preparation of 3-Morpholin-4-ylpropyl 2-(4-chlorobenzoylamino)-3-(2-oxo-1,2-dihydroquinolin-4-yl)propionate

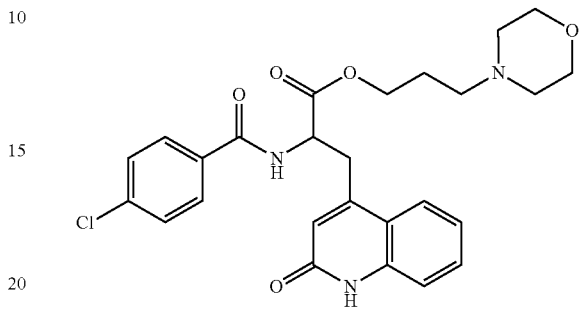

According to Experiment Prototocol D, 1.0 g (2.69 mmol) of rebamipide and 0.90 g (1.5 eq, 4.03 mmol) of 3-(morpholin-4-yl)propyl HCl methanesulfonate were reacted to afford the title compound as a white solid (0.7 g).

$^1$H NMR (400 MHz, DMSO-$d_6$): δ 11.68 (s, 1H), 9.04 (d, 1H), 7.81 (d, 3H), 7.57 (s, 1H), 7.55 (s, 1H), 7.52 (t, 1H), 7.31 (d, 1H), 7.23 (t, 1H), 6.44 (s, 1H), 4.77 (m, 1H), 4.17 (t, 2H), 4.05 (t, 2H), 3.53 (t, 4H), 3.46 (dd, 1H), 3.38-3.26 (m, 6H), 1.89 (m, 2H)

Example 49

Preparation of 4-Morpholin-4-ylbutyl 2-(4-chlorobenzoylamino)-3-(2-oxo-1,2-dihydroquinolin-4-yl)propionate

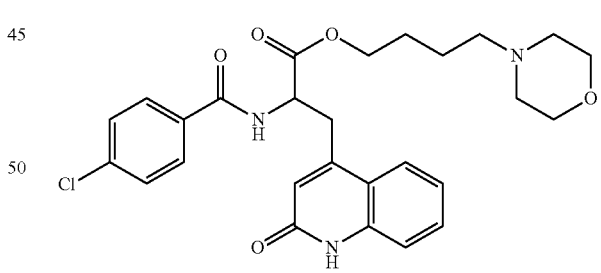

According to Experiment Prototocol C, 1.0 g (2.69 mmol) of rebamipide and 0.89 g (1.5 eq, 4.03 mmol) of 4-(4-bromobutyl)morpholine were reacted to afford the title compound as a white solid (0.7 g).

$^1$H NMR (400 MHz, DMSO-$d_6$): δ 11.71 (s, 1H), 9.06 (d, 1H), 7.83 (d, 3H), 7.57 (s, 1H), 7.55 (s, 1H), 7.52 (t, 1H), 7.31 (d, 1H), 7.23 (t, 1H), 6.44 (s, 1H), 4.75 (m, 1H), 4.13-4.08 (m, 2H), 3.98 (t, 2H), 3.52 (m, 5H), 3.36-3.26 (m, 5H), 1.61-1.54 (m, 4H)

Example 50

Preparation of 6-Morpholin-4-ylhexyl 2-(4-chlorobenzoylamino)-3-(2-oxo-1,2-dihydroquinolin-4-yl)propionate

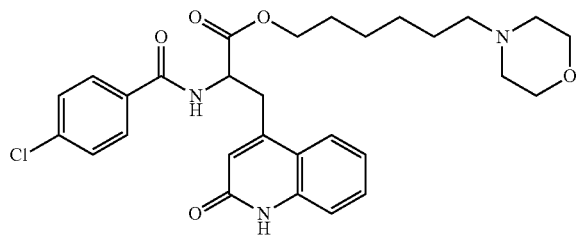 [SMILES: O=C(NC(Cc1cc(=O)[nH]c2ccccc12)C(=O)OCCCCCCN1CCOCC1)c1ccc(Cl)cc1]

According to Experiment Prototocol C, 1.0 g (2.69 mmol) of rebamipide and 1.01 g (1.5 eq, 4.03 mmol) of 4-(6-bromohexyl)morpholine were reacted to afford the title compound as a white solid (0.6 g).

$^1$H NMR (400 MHz, DMSO-$d_6$): δ 11.71 (s, 1H), 9.05 (d, 1H), 7.82 (m, 3H), 7.58 (s, 1H), 7.56 (s, 1H), 7.52 (t, 1H), 7.31 (d, 1H), 7.23 (t, 1H), 6.44 (s, 1H), 4.75 (m, 1H), 4.06 (m, 2H), 3.54 (t, 4H), 3.43 (dd, 1H), 3.35-3.27 (m, 2H), 2.27 (br-s, 4H), 2.16 (t, 2H), 1.52 (m, 2H), 1.31 (m, 2H), 1.21 (s, 4H)

Example 51

Preparation of (4-Methylpiperazin-1-yl)methyl 2-(4-chlorobenzoylamino)-3-(2-oxo-1,2-dihydroquinolin-4-yl)propionate

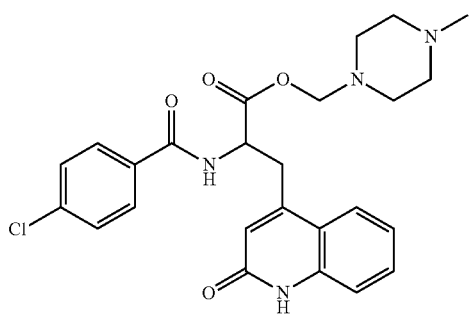 [SMILES: CN1CCN(COC(=O)C(Cc2cc(=O)[nH]c3ccccc23)NC(=O)c2ccc(Cl)cc2)CC1]

According to Experiment Prototocol C, 1.0 g (2.69 mmol) of rebamipide and 0.60 g (1.5 eq, 4.03 mmol) of 1-chloromethyl-4-methylpiperazine were reacted to afford the title compound as a white solid (0.4 g).

$^1$H NMR (700 MHz, DMSO-$d_6$): δ 11.70 (s, 1H), 9.03 (d, 1H), 7.85-7.82 (m, 3H), 7.58-7.56 (m, 2H), 7.52 (t, 1H), 7.33 (d, 1H), 7.24 (t, 1H), 6.44 (s, 1H), 4.75-4.72 (m, 1H), 3.42 (dd, 1H), 3.30 (q, 1H), 1.76-1.57 (m, 4H), 1.45-1.31 (m, 6H)

Example 52

Preparation of 2-(4-Benzylpiperazin-1-yl)ethyl 2-(4-chlorobenzoylamino)-3-(2-oxo-1,2-dihydroquinolin-4-yl)propionate

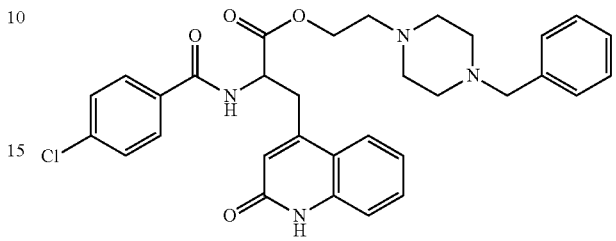

According to Experiment Prototocol C, 1.0 g (2.69 mmol) of rebamipide and 0.96 g (1.5 eq, 4.03 mmol) of 1-benzyl-4-(2-chloroethyl)piperazine were reacted to afford the title compound as a white solid (0.6 g).

$^1$H NMR (700 MHz, DMSO-$d_6$): δ 11.70 (s, 1H), 9.06 (d, 1H), 7.83-7.81 (m, 3H), 7.55-7.53 (m, 2H), 7.51 (t, 1H), 7.33-7.30 (m, 3H), 7.26-7.24 (m, 3H), 7.21 (t, 1H), 6.46 (s, 1H), 4.77-4.74 (m, 1H), 4.25-4.22 (m, 1H), 4.17-4.13 (m, 1H), 3.47 (dd, 1H), 3.38 (s, 2H), 3.28 (q, 1H), 2.57-2.48 (m, 4H), 2.41-2.26 (m, 6H)

Example 53

Preparation of 4-[4-(3-Chlorophenyl)piperazin-1-yl]butyl 2-(4-chlorobenzoylamino)-3-(2-oxo-1,2-dihydroquinolin-4-yl)propionate

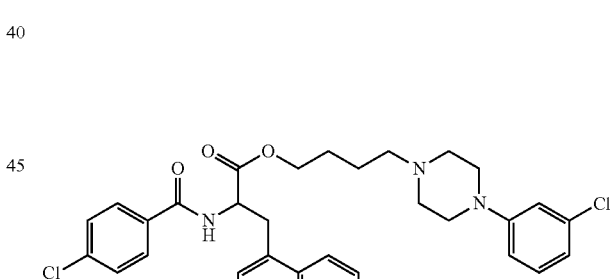

According to Experiment Prototocol D, 1.0 g (2.69 mmol) of rebamipide and 1.70 g (1.5 eq, 4.03 mmol) of 4-[4-(3-chlorophenyl)piperazin-1-yl]butyl toluenesulfonate were reacted to afford the title compound as a white solid (0.6 g).

$^1$H NMR (400 MHz, DMSO-$d_6$): δ 11.71 (s, 1H), 9.06 (d, 1H), 7.84 (m, 3H), 7.56 (d, 2H), 7.52 (t, 1H), 7.32 (d, 1H), 7.22 (m, 2H), 6.91 (br-s, 1H), 6.86 (dd, 1H), 6.77 (dd, 1H), 6.46 (s, 1H), 4.77 (m, 1H), 4.11 (m, 2H), 3.45 (dd, 1H), 3.56-3.28 (m, 3H), 3.12 (t, 4H), 2.40 (t, 4H), 2.28 (t, 2H), 1.72 (m, 2H)

Example 54

Preparation of (4-tert-Butyloxycarbonylpiperazin-1-yl)ethyl 2-(4-chlorobenzoylamino)-3-(2-oxo-1,2-dihydroquinolin-4-yl)propionate

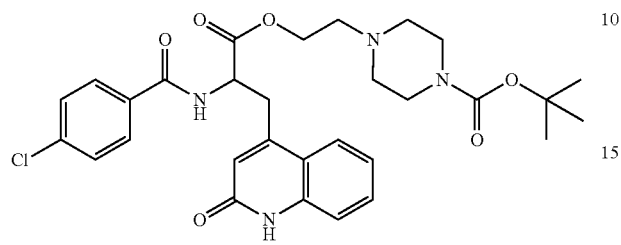

According to Experiment Prototocol C, 1.0 g (2.69 mmol) of rebamipide and 1.18 g (1.5 eq, 4.03 mmol) of tert-butyl 4-(2-bromoethyl)piperazine-1-carboxylate were reacted to afford the title compound as a white solid (0.6 g).

$^1$H NMR (700 MHz, DMSO-$d_6$): δ 11.70 (s, 1H), 9.05 (d, 1H), 7.85-7.81 (m, 3H), 7.58-7.56 (m, 2H), 7.52 (t, 1H), 7.32 (d, 1H), 7.22 (t, 1H), 6.46 (s, 1H), 4.77-4.74 (m, 1H), 4.25-4.16 (m, 2H), 3.47 (dd, 1H), 3.29 (q, 1H), 3.19 (t, 4H), 2.74-2.50 (m, 2H), 2.32 (m, 4H), 1.38 (s, 9H)

Example 55

Preparation of 2-Azepan-1-ylethyl 2-(4-chlorobenzoylamino)-3-(2-oxo-1,2-dihydroquinolin-4-yl)propionate

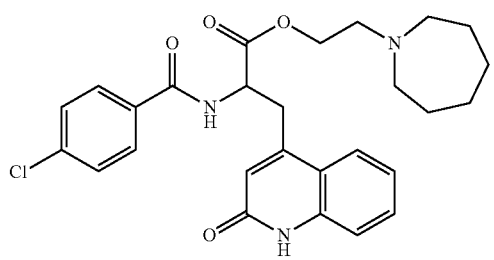 [SMILES: O=C(NC(Cc1cc(=O)[nH]c2ccccc12)C(=O)OCCN1CCCCCC1)c1ccc(Cl)cc1]

According to Experiment Prototocol C, 1.0 g (2.69 mmol) of rebamipide and 0.80 g (1.5 eq, 4.03 mmol) of 2-(hexamethyleneimino)ethyl chloride HCl was reacted to afford the title compound as a white solid (0.8 g).

$^1$H NMR (400 MHz, DMSO-$d_6$): δ 11.69 (s, 1H), 9.03 (d, 1H), 7.84 (t, 3H), 7.58 (s, 1H), 7.55 (s, 1H), 7.52 (t, 1H), 7.32 (d, 1H), 7.23 (m, 1H), 6.47 (s, 1H), 4.77 (m, 1H), 4.19 (m, 1H), 4.11 (m, 1H), 3.47 (dd, 1H), 3.32 (m, 1H), 2.57 (m, 4H), 1.47 (s, 8H)

Example 56

Preparation of 2-(2-Oxopyrrolidin-1-yl)ethyl 2-(4-chlorobenzoylamino)-3-(2-oxo-1,2-dihydroquinolin-4-yl)propionate

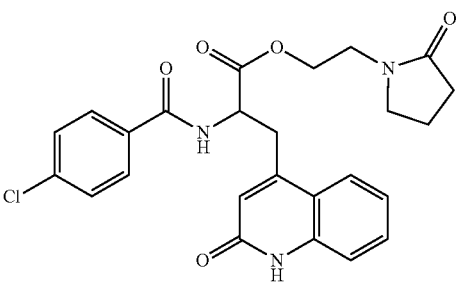 [SMILES: O=C(NC(Cc1cc(=O)[nH]c2ccccc12)C(=O)OCCN1CCCC1=O)c1ccc(Cl)cc1]

According to Experiment Prototocol C, 1.0 g (2.69 mmol) of rebamipide and 0.77 g (1.5 eq, 4.03 mmol) of 1-(2-bromoethyl)pyrrolidin-2-one were reacted to afford the title compound as a white solid (0.3 g).

$^1$H NMR (400 MHz, DMSO-$d_6$): δ 11.70 (s, 1H), 9.04 (d, 1H), 7.82 (t, 3H), 7.56 (d, 2H), 7.52 (t, 1H), 7.31 (d, 1H), 7.24 (m, 1H), 6.45 (s, 1H), 4.75 (m, 1H), 4.30-4.17 (m, 2H), 3.50-3.45 (m, 3H), 3.32 (t, 2H), 3.24 (q, 1H), 2.17-2.09 (m, 2H), 1.86-1.78 (m, 2H)

Example 57

Preparation of (2-oxooxazolidin-5-yl)methyl 2-(4-chlorobenzoylamino)-3-(2-oxo-1,2-dihydroquinolin-4-yl)propionate

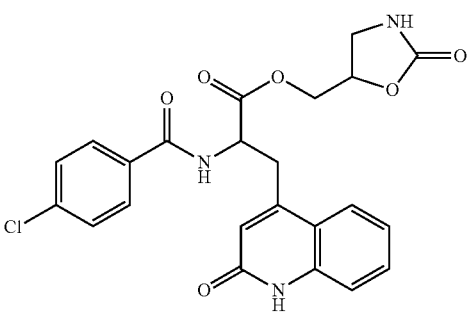 [SMILES: O=C1NCC(COC(=O)C(Cc2cc(=O)[nH]c3ccccc23)NC(=O)c2ccc(Cl)cc2)O1]

According to Experiment Prototocol C, 1.0 g (2.69 mmol) of rebamipide and 0.54 g (1.5 eq, 4.03 mmol) of 5-chloromethyl-2-oxazolidinone were reacted to afford the title compound as a white solid (0.4 g).

$^1$H NMR (400 MHz, DMSO-$d_6$): δ 11.66 (s, 1H), 9.07 (d, 1H), 7.82 (d, 3H), 7.59-7.49 (m, 4H), 7.31 (d, 1H), 7.27-7.23 (m, 1H), 6.46 (s, 1H), 4.84-4.79 (m, 2H), 4.31 (d, 1H), 4.27 (q, 1H), 3.62-3.53 (m, 1H), 3.52 (−3.47 (m, 1H), 3.30-3.25 (m, 2H)

Example 58

Preparation of 4-Morpholin-4-yl-cis-but-2-enyl 2-(4-chlorobenzoylamino)-3-(2-oxo-1,2-dihydroquinolin-4-yl)propionate

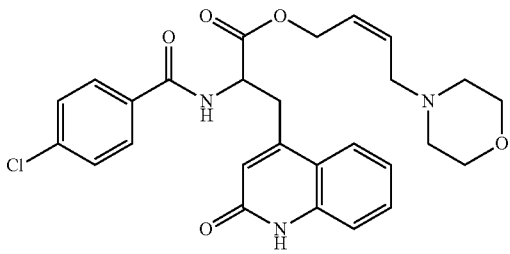 [SMILES: O=C(NC(Cc1cc(=O)[nH]c2ccccc12)C(=O)OC/C=C\CN1CCOCC1)c1ccc(Cl)cc1]

According to Experiment Prototocol C, 1.0 g (2.69 mmol) of rebamipide and 0.88 g (1.5 eq, 4.03 mmol) of 4-(4-bromo-cis-but-2-enyl)morpholine were reacted to afford the title compound as a white solid (0.6 g).

$^1$H NMR (400 MHz, DMSO-$d_6$): δ 11.70 (s, 1H), 9.08 (d, 1H), 7.82 (t, 3H), 7.56 (d, 2H), 7.52 (t, 1H), 7.31 (d, 1H), 7.23 (t, 1H), 6.44 (s, 1H), 5.76-5.62 (m, 2H), 4.78 (m, 1H), 4.60 (m, 2H), 3.52 (t, 4H), 3.44 (dd, 1H), 3.30 (m, 2H), 2.89 (d, 2H), 2.28 (s, 4H)

Example 59

Preparation of 4-Morpholines-yl-trans-but-2-enyl 2-(4-chlorobenzoylamino)-3-(2-oxo-1,2-dihydroquinolin-4-yl)propionate

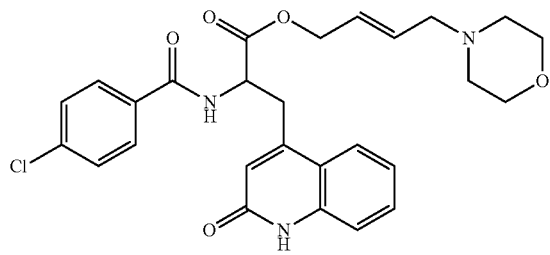 [SMILES: O=C(NC(Cc1cc(=O)[nH]c2ccccc12)C(=O)OC/C=C/CN1CCOCC1)c1ccc(Cl)cc1]

According to Experiment Prototocol C, 1.0 g (2.69 mmol) of rebamipide and 0.88 g (1.5 eq, 4.03 mmol) of 4-(4-bromo-trans-but-2-enyl)morpholine were reacted to afford the title compound as a white solid (0.7 g).

$^1$H NMR (400 MHz, DMSO-$d_6$): δ 11.70 (s, 1H), 9.07 (d, 1H), 7.82 (t, 3H), 7.56 (d, 2H), 7.50 (t, 1H), 7.31 (d, 1H), 7.23 (t, 1H), 6.44 (s, 1H), 5.75-5.63 (m, 2H), 4.60 (m, 2H), 3.52 (t, 3H), 3.44 (dd, 1H), 3.39-3.27 (m, 2H), 2.89 (d, 2H), 2.28 (s, 3H)

Example 60

Preparation of 5-Methyl-2-oxo-[1,3]dioxol-4-ylmethyl 2-(4-chlorobenzoylamino)-3-(2-oxo-1,2-dihydroquinolin-4-yl)propionate

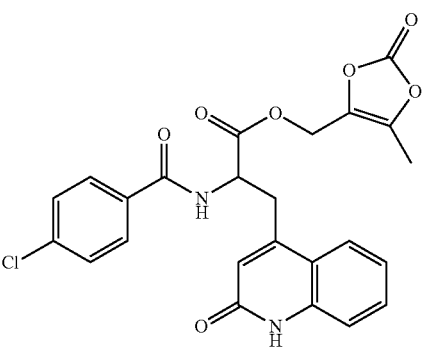 [SMILES: Cc1oc(=O)oc1COC(=O)C(Cc1cc(=O)[nH]c2ccccc12)NC(=O)c1ccc(Cl)cc1]

According to Experiment Prototocol C, 1.0 g (2.69 mmol) of rebamipide and 0.60 g (1.5 eq, 4.03 mmol) of 4-chloromethyl-5-methyl-1,3-dioxol-2-one were reacted to afford the title compound as a white solid (0.5 g).

$^1$H NMR (400 MHz, DMSO-$d_6$): δ 11.68 (s, 1H), 9.10 (d, 1H), 7.82 (m, 3H), 7.56 (m, 2H), 7.51 (t, 1H), 7.33 (d, 1H), 7.20 (t, 1H), 6.51 (s, 1H), 5.05 (s, 2H), 4.80 (m, 1H), 3.47 (dd, 1H), 3.32 (m, 1H), 2.16 (s, 3H)

Example 61

Preparation of Benzyl 2-(4-chlorobenzoylamino)-3-(2-oxo-1,2-dihydroquinolin-4-yl)propionate

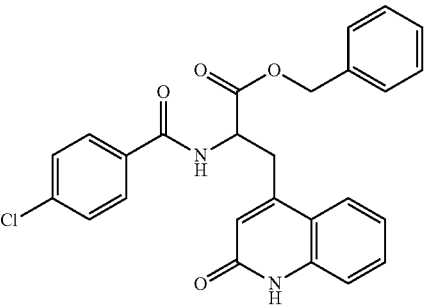

According to Experiment Prototocol C, 1.0 g (2.69 mmol) of rebamipide and 0.69 g (1.5 eq, 4.03 mmol) of benzyl bromide were reacted to afford the title compound as a white solid (1.0 g).

$^1$H NMR (700 MHz, DMSO-$d_6$): δ 11.70 (s, 1H), 9.10 (d, 1H), 7.84-7.82 (m, 3H), 7.58-7.56 (m, 2H), 7.51 (t, 1H), 7.37-7.32 (m, 6H), 7.21 (t, 1H), 6.47 (s, 1H), 5.16 (q, 2H), 4.87-4.84 (m, 1H), 3.50 (dd, 1H), 3.33 (q, 1H)

Example 62

Preparation of Phenethyl 2-(4-chlorobenzoylamino)-3-(2-oxo-1,2-dihydroquinolin-4-yl)propionate

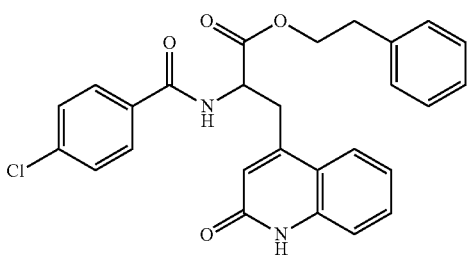 [SMILES: O=C(NC(Cc1cc(=O)[nH]c2ccccc12)C(=O)OCCc1ccccc1)c1ccc(Cl)cc1]

According to Experiment Prototocol C, 1.0 g (2.69 mmol) of rebamipide and 0.74 g (1.5 eq, 4.03 mmol) of (1-bromoethyl)benzene were reacted to afford the title compound as a white solid (0.9 g).

$^1$H NMR (400 MHz, DMSO-$d_6$): δ 11.69 (s, 1H), 9.01 (d, 1H), 7.83 (t, 1H), 7.81 (t, 1H), 7.72 (d, 1H), 7.58 (t, 1H), 7.56 (t, 1H), 7.52 (m, 1H), 7.31 (dd, 1H), 7.25-7.19 (m, 6H), 6.43 (s, 1H), 4.72 (m, 1H), 4.39-4.02 (m, 2H), 3.44 (dd, 1H), 3.20 (q, 1H), 2.89 (t, 2H)

Example 63

Preparation of 2-Methylbenzyl 2-(4-chlorobenzoylamino)-3-(2-oxo-1,2-dihydroquinolin-4-yl)propionate

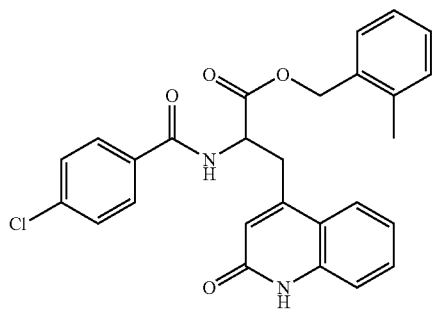 [SMILES: Cc1ccccc1COC(=O)C(Cc1cc(=O)[nH]c2ccccc12)NC(=O)c1ccc(Cl)cc1]

According to Experiment Prototocol C, 1.0 g (2.69 mmol) of rebamipide and 0.56 g (1.5 eq, 4.03 mmol) of 2-methylbenzyl chloride were reacted to afford the title compound as a white solid (0.9 g).

$^1$H NMR (700 MHz, DMSO-$d_6$): δ 11.69 (s, 1H), 9.09 (d, 1H), 7.81 (d, 2H), 7.80 (s, 1H), 7.57-7.55 (m, 2H), 7.51 (t, 1H), 7.31 (d, 1H), 7.27 (d, 1H), 7.25-7.19 (m, 3H), 7.16 (t, 1H), 6.45 (s, 1H), 5.21-5.12 (q, 2H), 4.84-4.82 (m, 1H), 3.48 (dd, 1H), 3.32 (q, 1H), 2.24 (s, 3H)

Example 64

Preparation of 3-Methylbenzyl 2-(4-chlorobenzoylamino)-3-(2-oxo-1,2-dihydroquinolin-4-yl)propionate

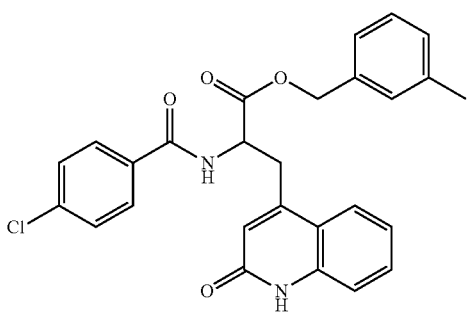 [SMILES: Cc1cccc(COC(=O)C(Cc2cc(=O)[nH]c3ccccc23)NC(=O)c2ccc(Cl)cc2)c1]

According to Experiment Prototocol C, 1.0 g (2.69 mmol) of rebamipide and 0.56 g (1.5 eq, 4.03 mmol) of 3-methylbenzyl chloride were reacted to afford the title compound as a white solid (0.9 g).

$^1$H NMR (700 MHz, DMSO-$d_6$): δ 11.69 (s, 1H), 9.10 (d, 1H), 7.84-7.81 (m, 3H), 7.58-7.56 (m, 2H), 7.51 (t, 1H), 7.32 (d, 1H), 7.24-7.20 (q, 2H), 7.13-7.09 (m, 3H), 6.45 (s, 1H), 5.15-5.07 (q, 2H), 4.85-4.81 (m, 1H), 3.48 (dd, 1H), 3.32 (q, 1H), 2.25 (s, 3H)

Example 65

Preparation of 3,4-Dimethylbenzyl 2-(4-chlorobenzoylamino)-3-(2-oxo-1,2-dihydroquinolin-4-yl)propionate

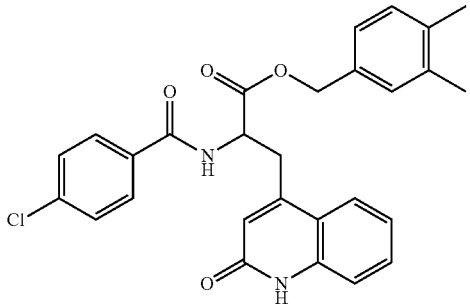 [SMILES: Cc1ccc(COC(=O)C(Cc2cc(=O)[nH]c3ccccc23)NC(=O)c2ccc(Cl)cc2)cc1C]

According to Experiment Prototocol C, 1.0 g (2.69 mmol) of rebamipide and 0.62 g (1.5 eq, 4.03 mmol) of 3,4-dimethylbenzyl chloride were reacted to afford the title compound as a white solid (0.9 g).

$^1$H NMR (700 MHz, DMSO-$d_6$): δ 11.70 (s, 1H), 9.09 (d, 1H), 7.84-7.79 (m, 3H), 7.58-7.56 (m, 2H), 7.52-7.51 (m, 1H), 7.32 (d, 1H), 7.23-7.20 (m, 1H), 7.14 (t, 1H), 7.09 (d, 1H), 7.06-7.03 (m, 2H), 6.44 (d, 1H), 5.11-5.03 (q, 2H), 4.82 (br-s, 1H), 3.48 (dd, 1H), 3.32 (q, 1H), 2.19 (s, 3H), 2.16 (s, 3H)

Example 66

Preparation of 3,5-Dimethylbenzyl 2-(4-chlorobenzoylamino)-3-(2-oxo-1,2-dihydroquinolin-4-yl)propionate

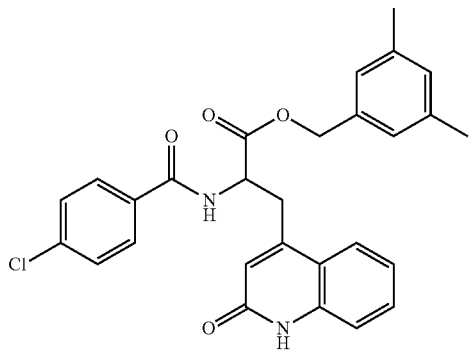 [SMILES: Cc1cc(C)cc(COC(=O)C(Cc2cc(=O)[nH]c3ccccc23)NC(=O)c2ccc(Cl)cc2)c1]

According to Experiment Prototocol C, 1.0 g (2.69 mmol) of rebamipide and 0.62 g (1.5 eq, 4.03 mmol) of 3,5-dimethylbenzyl chloride were reacted to afford the title compound as a white solid (0.9 g).

$^1$H NMR (700 MHz, DMSO-$d_6$): δ 11.70 (s, 1H), 9.11 (d, 1H), 7.84 (d, 2H), 7.81 (d, 1H), 7.57 (d, 2H), 7.52 (t, 1H), 7.32 (d, 1H), 7.22 (t, 1H), 6.93 (s, 1H), 6.89 (d, 1H), 6.46 (s, 1H), 5.11-5.01 (q, 2H), 4.83-4.82 (m, 1H), 3.48 (dd, 1H), 3.33 (q, 1H), 2.21 (s, 6H)

Example 67

Preparation of 3-Fluorobenzyl 2-(4-chlorobenzoylamino)-3-(2-oxo-1,2-dihydroquinolin-4-yl)propionate

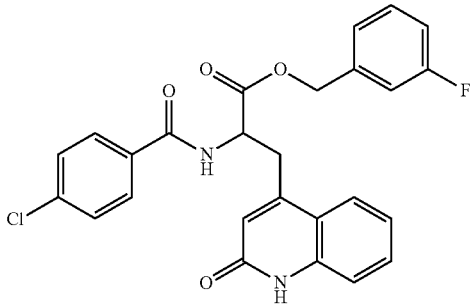 [SMILES: O=C(NC(Cc1cc(=O)[nH]c2ccccc12)C(=O)OCc1cccc(F)c1)c1ccc(Cl)cc1]

According to Experiment Prototocol C, 1.0 g (2.69 mmol) of rebamipide and 0.58 g (1.5 eq, 4.03 mmol) of 3-fluorobenzyl chloride were reacted to afford the title compound as a white solid (0.9 g).

$^1$H NMR (700 MHz, DMSO-$d_6$): δ 11.69 (s, 1H), 9.11 (d, 1H), 7.83-7.81 (m, 3H), 7.57-7.55 (m, 2H), 7.51 (t, 1H), 7.39 (q, 1H), 7.31 (d, 1H), 7.21 (t, 1H), 7.18-7.14 (m, 3H), 6.45 (s, 1H), 5.23-5.15 (q, 2H), 4.88-4.84 (m, 1H), 3.51 (dd, 1H), 3.33 (q, 1H)

Example 68

Preparation of 2,5-Difluorobenzyl 2-(4-chlorobenzoylamino)-3-(2-oxo-1,2-dihydroquinolin-4-yl)propionate

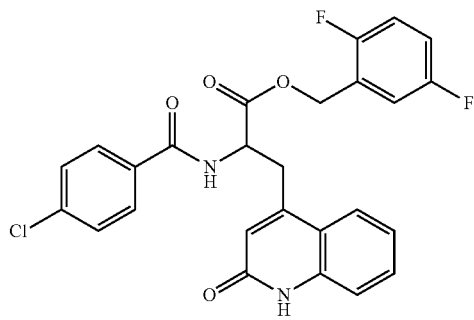 [SMILES: O=C(NC(Cc1cc(=O)[nH]c2ccccc12)C(=O)OCc1cc(F)ccc1F)c1ccc(Cl)cc1]

According to Experiment Prototocol C, 1.0 g (2.69 mmol) of rebamipide and 0.83 g (1.5 eq, 4.03 mmol) of 2,5-difluorobenzyl bromide were reacted to afford the title compound as a white solid (0.8 g).

$^1$H NMR (400 MHz, DMSO-$d_6$): δ 11.65 (s, 1H), 9.08 (d, 1H), 7.79 (d, 3H), 7.57 (s, 1H), 7.55 (s, 1H), 7.50 (t, 1H), 7.32-7.18 (m, 5H), 6.44 (s, 1H), 5.20 (q, 2H), 4.86-4.83 (m, 1H), 3.48 (dd, 1H), 3.29 (q, 1H)

Example 69

Preparation of 3-Cyanobenzyl 2-(4-chlorobenzoylamino)-3-(2-oxo-1,2-dihydroquinolin-4-yl)propionate

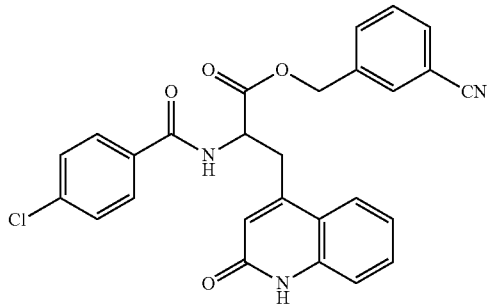 [SMILES: N#Cc1cccc(COC(=O)C(Cc2cc(=O)[nH]c3ccccc23)NC(=O)c2ccc(Cl)cc2)c1]

According to Experiment Prototocol C, 1.0 g (2.69 mmol) of rebamipide and 0.79 g (1.5 eq, 4.03 mmol) of 2-methylbenzyl chloride3-(bromomethyl)benzonitrile were reacted to afford the title compound as a white solid (0.7 g).

$^1$H NMR (400 MHz, DMSO-$d_6$): δ 11.68 (s, 1H), 9.11 (d, 1H), 7.84-7.80 (m, 5H), 7.67 (d, 1H), 7.60-7.55 (m, 3H), 7.53-7.49 (m, 1H), 7.31 (dd, 1H), 7.24-7.20 (m, 1H), 6.45 (s, 1H), 5.18 (q, 2H), 4.87 (m, 1H), 3.52 (dd, 1H), 3.33 (q, 1H)

Example 70

Preparation of 3-Nitrobenzyl 2-(4-chlorobenzoylamino)-3-(2-oxo-1,2-dihydroquinolin-4-yl)propionate

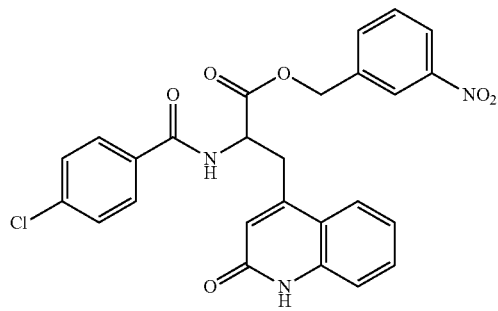 [SMILES: O=C(NC(Cc1cc(=O)[nH]c2ccccc12)C(=O)OCc1cccc([N+](=O)[O-])c1)c1ccc(Cl)cc1]

According to Experiment Prototocol C, 1.0 g (2.69 mmol) of rebamipide and 3-nitrobenzyl 클로라 bromide 0.87 g (1.5 eq, 4.03 mmol) were reacted to afford the title compound as a white solid (0.9 g).

$^1$H NMR (700 MHz, DMSO-$d_6$): δ 11.67 (s, 1H), 9.13 (d, 1H), 8.23 (d, 1H), 8.18 ((dd, 1H), 7.83-7.80 (m, 3H), 7.79 (d, 1H), 7.66 (t, 1H), 7.57-7.55 (m, 2H), 7.51-7.49 (m, 1H), 7.30 (dd, 1H), 7.21 (t, 1H), 6.43 (s, 1H), 5.35-5.28 (q, 2H), 4.88-4.85 (m, 1H), 3.51 (dd, 1H), 3.33 (q, 1H)

Example 71

Preparation of 4-Methoxybenzyl 2-(4-chlorobenzoylamino)-3-(2-oxo-1,2-dihydroquinolin-4-yl)propionate

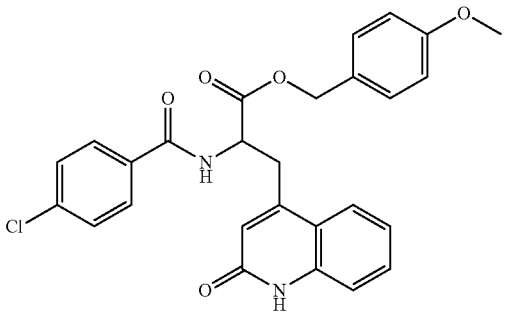 [SMILES: COc1ccc(COC(=O)C(Cc2cc(=O)[nH]c3ccccc23)NC(=O)c2ccc(Cl)cc2)cc1]

According to Experiment Prototocol C, rebamipide 1.0 g (2.69 mmol) and 4-methoxybenzyl chloride 0.63 g (1.5 eq, 4.03 mmol) were reacted to afford the title compound as a white solid (0.9 g).

$^1$H NMR (700 MHz, DMSO-$d_6$): δ 11.68 (s, 1H), 9.06 (d, 1H), 7.82-7.79 (m, 3H), 7.57-7.55 (m, 2H), 7.50 (t, 1H), 7.31 (d, 1H), 7.26 (d, 2H), 7.21 (t, 1H), 6.91-6.89 (m, 2H), 6.44 (s, 1H), 5.12-5.06 (q, 2H), 4.81-4.79 (m, 1H), 3.75 (s, 3H), 3.46 (dd, 1H), 3.28 (q, 1H)

Example 72

Preparation of 3-phenoxybenzyl 2-(4-chlorobenzoylamino)-3-(2-oxo-1,2-dihydroquinolin-4-yl)propionate

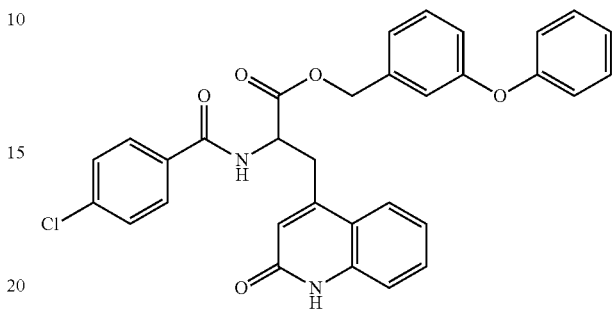

According to Experiment Prototocol C, 1.0 g (2.69 mmol) of rebamipide and 0.88 g (1.5 eq, 4.03 mmol) of 3-phenoxybenzyl chloride were reacted to afford the title compound as a white solid (1.1 g).

$^1$H NMR (400 MHz, DMSO-$d_6$): δ 11.67 (s, 1H), 9.07 (d, 1H), 7.81-7.78 (m, 3H), 7.52 (d, 2H), 7.50 (t, 1H), 7.38-7.30 (m, 4H), 7.19 (t, 1H), 7.121 (t, 2H), 7.03 (s, 1H), 6.95 (d, 2H), 6.93 (dd, 1H), 6.44 (s, 1H), 5.22-5.13 (q, 2H), 4.83 (m, 1H), 3.46 (dd, 1H), 3.29 (q, 1H)

Example 73

Preparation of 4-Methylsulfanylbenzyl 2-(4-chlorobenzoylamino)-3-(2-oxo-1,2-dihydroquinolin-4-yl)propionate

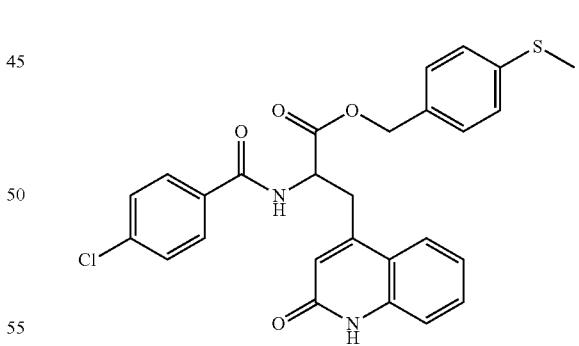

According to Experiment Prototocol C, 1.0 g (2.69 mmol) of rebamipide and 4-(methylthio)benzyl chloride 0.69 g (1.5 eq, 4.03 mmol) were reacted to afford the title compound as a white solid (0.7 g).

$^1$H NMR (400 MHz, DMSO-$d_6$): δ 11.68 (s, 1H), 9.06 (d, 1H), 7.82-7.80 (m, 3H), 7.55 (d, 2H), 7.51 (t, 1H), 7.31 (d, 1H), 7.28-7.19 (m, 5H), 6.45 (s, 1H), 5.11 (q, 2H), 4.86-4.80 (m, 1H), 3.47 (dd, 1H), 3.30 (q, 1H), 2.47 (s, 3H)

Example 74

Preparation of (4-methyloxycarbonyl)benzyl 4-[2-(4-chlorobenzoylamino)-3-(2-oxo-1,2-dihydroquinolin-4-yl)propionate

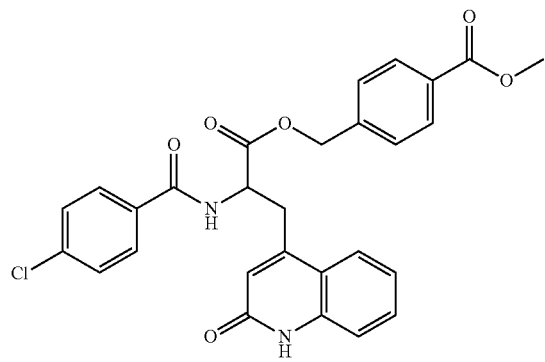 [SMILES: COC(=O)c1ccc(COC(=O)C(Cc2cc(=O)[nH]c3ccccc23)NC(=O)c2ccc(Cl)cc2)cc1]

According to Experiment Prototocol C, rebamipide 1.0 g (2.69 mmol) and methyl(4-bromomethyl)benzoate 0.92 g (1.5 eq, 4.03 mmol) were reacted to afford the title compound as a white solid (0.9 g).

$^1$H NMR (400 MHz, DMSO-$d_6$): δ 11.66 (s, 1H), 9.09 (d, 1H), 7.96 (d, 1H), 7.93-7.90 (m, 1H), 7.83-7.79 (m, 3H), 7.60 (d, 1H), 7.57-7.48 (m, 4H), 7.32 (dd, 1H), 7.23-7.19 (m, 1H), 6.44 (s, 1H), 5.30-5.21 (q, 2H), 4.88-4.82 (m, 1H), 3.84 (s, 3H), 3.50 (dd, 1H), 3.31 (q, 1H)

Example 75

Preparation of (3-phenyloxycarbonyl)benzyl 2-(4-chlorobenzoylamino)-3-(2-oxo-1,2-dihydroquinolin-4-yl)propionate

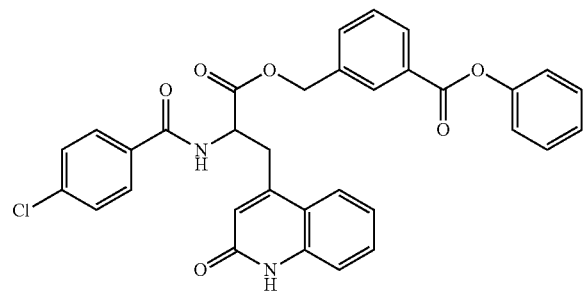 [SMILES: O=C(NC(Cc1cc(=O)[nH]c2ccccc12)C(=O)OCc1cccc(C(=O)Oc2ccccc2)c1)c1ccc(Cl)cc1]

According to Experiment Prototocol D, 1.0 g (2.69 mmol) of rebamipide and 1.11 g (1.5 eq, 4.03 mmol) of (3-phenyloxycarbonyl)benzyl mesylate were reacted to afford the title compound as a white solid (0.9 g).

$^1$H NMR (400 MHz, DMSO-$d_6$): δ 11.66 (s, 1H), 9.10 (d, 1H), 8.15 (s, 1H), 8.08 (d, 1H), 7.83-7.79 (m, 3H), 7.69 (d, 1H), 7.58 (t, 1H), 7.58-7.46 (m, 5H), 7.35-7.26 (m, 4H), 7.21-7.17 (m, 1H), 6.45 (s, 1H), 5.30 (q, 2H), 4.90-4.84 (m, 1H), 3.51 (dd, 1H), 3.30 (q, 1H)

Example 76

Preparation of Naphthalen-2-ylmethyl 2-(4-chlorobenzoylamino)-3-(2-oxo-1,2-dihydroquinolin-4-yl)propionate

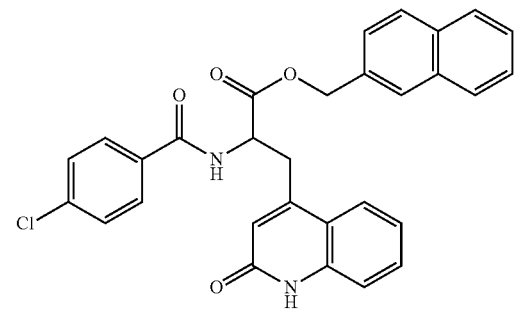 [SMILES: O=C(NC(Cc1cc(=O)[nH]c2ccccc12)C(=O)OCc1ccc2ccccc2c1)c1ccc(Cl)cc1]

According to Experiment Prototocol C, 1.0 g (2.69 mmol) of rebamipide and 0.71 g (1.5 eq, 4.03 mmol) of (1-chloromethyl)naphthalene were reacted to afford the title compound as a white solid (0.8 g).

$^1$H NMR (400 MHz, DMSO-$d_6$): δ 11.71 (s, 1H), 9.12 (d, 1H), 7.93-7.82 (m, 7H), 7.58-7.45 (m, 6H), 7.31 (d, 1H), 7.21 (t, 1H), 6.48 (s, 1H), 5.29 (q, 2H), 4.88 (m, 1H), 3.53 (dd, 1H), 3.32 (q, 1H)

Example 77

Preparation of Anthracen-9-ylmethyl 2-(4-chlorobenzoylamino)-3-(2-oxo-1,2-dihydroquinolin-4-yl)propionate

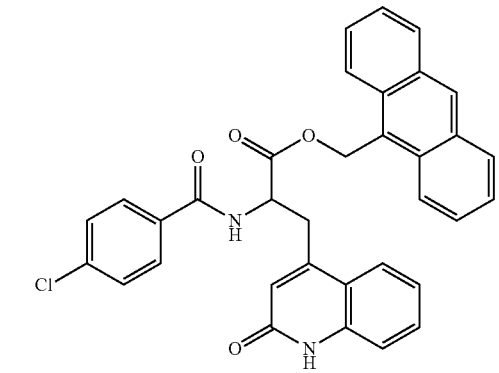 [SMILES: O=C(NC(Cc1cc(=O)[nH]c2ccccc12)C(=O)OCc1c2ccccc2cc2ccccc12)c1ccc(Cl)cc1]

According to Experiment Prototocol C, 1.0 g (2.69 mmol) of rebamipide and 0.91 g (1.5 eq, 4.03 mmol) of (9-chloromethyl)anthracene were reacted to afford the title compound as a white solid (0.8 g).

$^1$H NMR (400 MHz, DMSO-$d_6$): δ 11.67 (s, 1H), 9.01 (d, 1H), 8.71 (s, 1H), 8.32 (d, 2H), 8.12 (d, 2H), 7.70 (t, 3H), 7.68-7.45 (m, 7H), 7.28 (d, 1H), 7.08 (t, 1H), 6.40 (s, 1H), 6.15 (dd, 2H), 4.69 (m, 1H), 3.40 (dd, 1H), 3.22 (q, 1H)

Example 78

Preparation of 2-Pyrrol-1-ylethyl 2-(4-chlorobenzoylamino)-3-(2-oxo-1,2-dihydroquinolin-4-yl)propionate

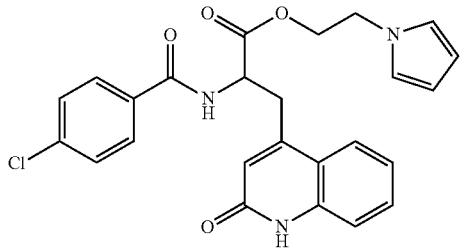 [SMILES: O=C(NC(Cc1cc(=O)[nH]c2ccccc12)C(=O)OCCn1cccc1)c1ccc(Cl)cc1]

According to Experiment Prototocol C, 1.0 g (2.69 mmol) of rebamipide and 0.70 g (1.5 eq, 4.03 mmol) of 1-(2-bromoethyl)pyrrole were reacted to afford the title compound as a white solid (0.5 g).

$^1$H NMR (400 MHz, DMSO-$d_6$): δ 11.69 (s, 1H), 9.03 (d, 1H), 7.83 (t, 1H), 7.57 (t, 1H), 7.73 (d, 1H), 7.52 (m, 1H), 7.31 (dd, 1H), 7.24 (m, 1H), 6.76 (t, 2H), 6.44 (s, 1H), 5.93 (t, 2H), 4.74-4.73 (m, 1H), 4.40-4.35 (m, 1H), 4.33-4.27 (m, 1H), 4.17-4.13 (m, 2H), 3.37 (dd, 1H), 3.20 (q, 1H)

Example 79

Preparation of (2-Ethoxycarbonyl)furan-4-ylmethyl 2-(4-chlorobenzoylamino)-3-(2-oxo-1,2-dihydroquinolin-4-yl)propionate

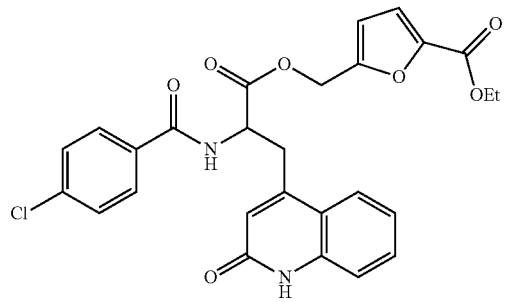 [SMILES: CCOC(=O)c1ccc(COC(=O)C(Cc2cc(=O)[nH]c3ccccc23)NC(=O)c2ccc(Cl)cc2)o1]

According to Experiment Prototocol C, 1.0 g (2.69 mmol) of rebamipide and 0.76 g (1.5 eq, 4.03 mmol) of ethyl 5-(chloromethyl)-2-furancarboxylate were reacted to afford the title compound as a white solid (0.8 g).

$^1$H NMR (700 MHz, DMSO-$d_6$): δ 11.67 (s, 1H), 9.10 (d, 1H), 7.79 (d, 3H), 7.56 (t, 2H), 7.50 (t, 1H), 7.31-7.26 (m, 2H), 7.21 (t, 1H), 6.71 (d, 1H), 6.43 (s, 1H), 5.26-5.21 (m, 2H), 4.82 (br-s, 1H), 4.27 (q, 2H), 3.45 (dd, 1H), 3.30 (q, 1H), 1.27 (t, 3H)

Example 80

Preparation of 2-Thiophen-2-ylethyl 2-(4-chlorobenzoylamino)-3-(2-oxo-1,2-dihydroquinolin-4-yl)propionate

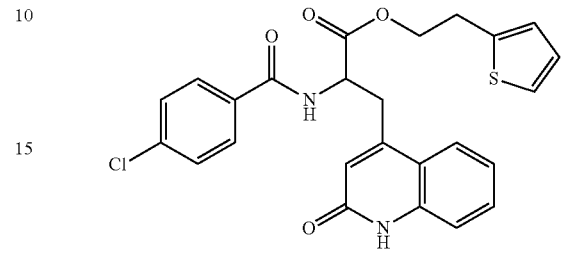

According to Experiment Prototocol D, 1.0 g (2.69 mmol) of rebamipide and 0.83 g (1.5 eq, 4.03 mmol) of 2-thiophenethyl methanesulfonate were reacted to afford the title compound as a white solid (0.6 g).

$^1$H NMR (400 MHz, DMSO-$d_6$): δ 11.70 (s, 1H), 9.04 (d, 1H), 7.83 (t, 1H), 7.83 (s, 1H), 7.81 (s, 1H), 7.76 (d, 1H), 7.58 (s, 1H), 7.56 (s, 1H), 7.52 (t, 1H), 7.34-7.32 (m, 2H), 7.25 (t, 1H), 6.92-6.90 (m, 2H), 6.45 (s, 1H), 4.77 (m, 1H), 4.37-4.26 (m, 2H), 3.41 (dd, 1H), 3.21 (q, 1H), 3.14 (t, 2H)

Example 81

Preparation of 2-Thiophen-3-ylethyl 2-(4-chlorobenzoylamino)-3-(2-oxo-1,2-dihydroquinolin-4-yl)propionate

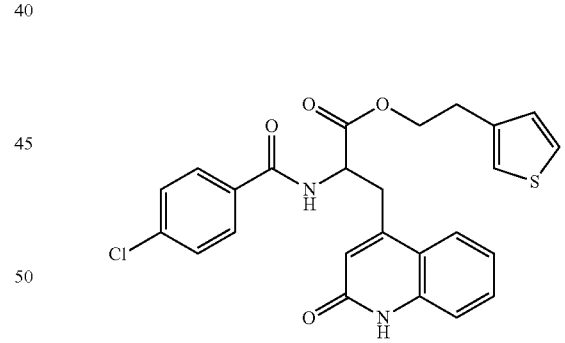

According to Experiment Prototocol D, 1.0 g (2.69 mmol) of rebamipide and 0.83 g (1.5 eq, 4.03 mmol) of 3-thiophenethyl methanesulfonate were reacted to afford the title compound as a white solid (0.6 g).

$^1$H NMR (400 MHz, DMSO-$d_6$): δ 11.70 (s, 1H), 9.04 (d, 1H), 7.83 (t, 1H), 7.84 (s, 1H), 7.82 (s, 1H), 7.73 (d, 1H), 7.58 (s, 1H), 7.56 (s, 1H), 7.52 (t, 1H), 7.42 (q, 1H), 7.32 (d, 1H), 7.24-7.21 (m, 2H), 7.03 (dd, 2H), 6.45 (s, 1H), 4.75 (m, 1H), 4.38-4.26 (m, 2H), 3.37 (dd, 1H), 3.23 (q, 1H), 2.90 (t, 2H)

Example 82

Preparation of 2-Imidazol-1-ylethyl 2-(4-chlorobenzoylamino)-3-(2-oxo-1,2-dihydroquinolin-4-yl)propionate

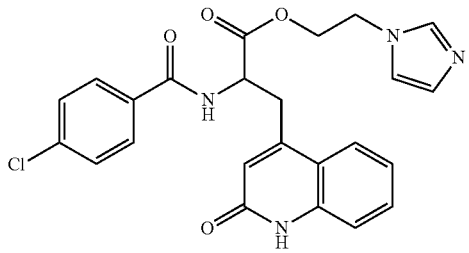 [SMILES: O=C(NC(Cc1cc(=O)[nH]c2ccccc12)C(=O)OCCn1ccnc1)c1ccc(Cl)cc1]

According to Experiment Prototocol A, 1.0 g (2.69 mmol) of rebamipide and 0.45 g (1.2 eq, 3.23 mmol) of 1-(2-hydroxyethyl)imidazole were reacted to afford the title compound as a white solid (0.3 g).

$^1$H NMR (400 MHz, DMSO-$d_6$): δ 11.69 (s, 1H), 9.04 (d, 1H), 7.80 (d, 2H), 7.73 (d, 1H), 7.66 (s, 1H), 7.56 (d, 2H), 7.52 (t, 1H), 7.31 (d, 1H), 7.25 (t, 1H), 7.18 (s, 1H), 6.85 (s, 1H), 6.43 (s, 1H), 4.76 (m, 1H), 4.40 (m, 2H), 4.28 (m, 2H), 3.42 (dd, 1H), 3.21 (q, 1H)

Example 83

Preparation of 5-Cyclopropyl-2-methyl-2H-pyrazol-3-ylmethyl 2-(4-chlorobenzoylamino)-3-(2-oxo-1,2-dihydroquinolin-4-yl)propionate

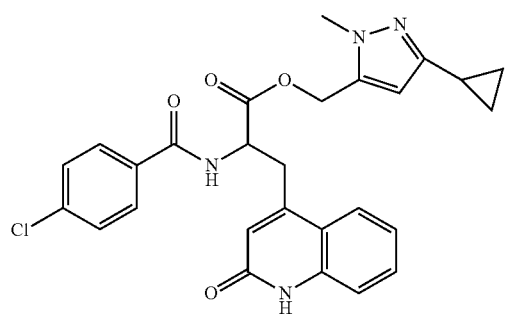 [SMILES: Cn1nc(C2CC2)cc1COC(=O)C(Cc1cc(=O)[nH]c2ccccc12)NC(=O)c1ccc(Cl)cc1]

According to Experiment Prototocol C, 1.0 g (2.69 mmol) of rebamipide and 0.68 g (1.5 eq, 4.03 mmol) of 5-chloromethyl-3-cyclopropyl-1-methyl-1H-pyrazole were reacted to afford the title compound as a white solid (0.5 g).

$^1$H NMR (400 MHz, DMSO-$d_6$): δ 11.69 (s, 1H), 9.08 (d, 1H), 7.79 (d, 3H), 7.55 (d, 2H), 7.49 (t, 1H), 7.31 (d, 1H), 7.21 (t, 1H), 6.44 (s, 1H), 5.99 (s, 1H), 5.12 (q, 2H), 4.80 (m, 1H), 3.63 (s, 3H), 3.46 (dd, 1H), 3.30 (q, 1H), 1.80 (m, 1H), 0.81 (m, 2H), 0.57 (m, 2H)

Example 84

Preparation of 3,5-Dimethylisoxazol-4-ylmethyl 2-(4-chlorobenzoylamino)-3-(2-oxo-1,2-dihydroquinolin-4-yl)propionate

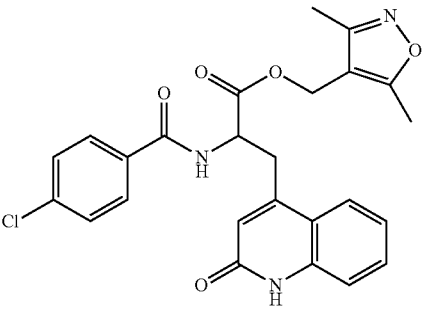 [SMILES: Cc1noc(C)c1COC(=O)C(Cc1cc(=O)[nH]c2ccccc12)NC(=O)c1ccc(Cl)cc1]

According to Experiment Prototocol C, 1.0 g (2.69 mmol) of rebamipide and 0.58 g (1.5 eq, 4.03 mmol) of 4-chloromethyl-3,5-dimethylisoxazole were reacted to afford the title compound as a white solid (0.8 g).

$^1$H NMR (400 MHz, DMSO-$d_6$): δ 11.67 (s, 1H), 9.05 (d, 1H), 7.78 (m, 3H), 7.57 (t, 1H), 7.52 (t, 1H), 7.50 (m, 1H), 7.30 (d, 1H), 7.21 (t, 1H), 6.42 (s, 1H), 4.99 (q, 2H), 4.78 (m, 1H), 3.43 (dd, 1H), 3.27 (q, 1H), 2.36 (s, 3H), 2.13 (s, 3H)

Example 85

Preparation of 2-(5-Methyl-4-phenyloxazol-2-yl)ethyl 2-(4-chlorobenzoylamino)-3-(2-oxo-1,2-dihydroquinolin-4-yl)propionate

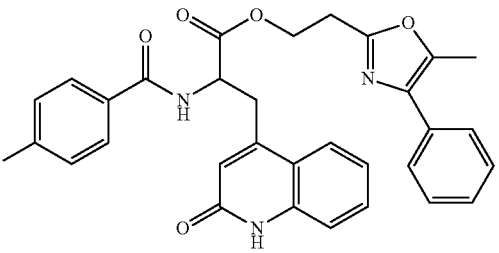

According to Experiment Prototocol C, 1.0 g (2.69 mmol) of rebamipide and 1.07 g (1.5 eq, 4.03 mmol) of 2-(2-bromoethyl)-5-methyl-4-phenyloxazole were reacted to afford the title compound as a white solid (0.6 g).

$^1$H NMR (400 MHz, DMSO-$d_6$): δ 11.67 (s, 1H), 8.98 (d, 1H), 7.87 (m, 2H), 7.79 (s, 1H), 7.77 (s, 1H), 7.73 (d, 1H), 7.52-7.46 (m, 6H), 7.30 (d, 1H), 7.16 (t, 1H), 6.43 (s, 1H), 4.76 (m, 1H), 4.38 (m, 1H), 4.36 (m, 1H), 3.43 (dd, 1H), 3.22 (dd, 1H), 2.80 (t, 2H), 2.25 (s, 3H)

Example 86

Preparation of 2-Methylthiazol-4-ylmethyl 2-(4-chlorobenzoylamino)-3-(2-oxo-1,2-dihydroquinolin-4-yl)propionate

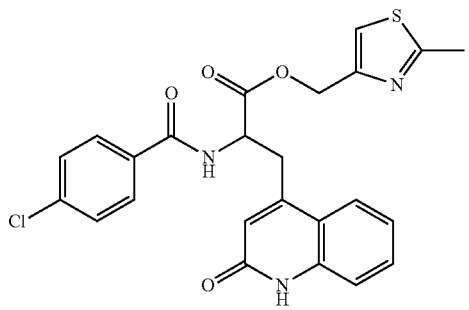 [SMILES: Cc1nc(COC(=O)C(Cc2cc(=O)[nH]c3ccccc23)NC(=O)c2ccc(Cl)cc2)cs1]

According to Experiment Prototocol A, 1.0 g (2.69 mmol) of rebamipide and 0.42 g (1.2 eq, 3.23 mmol) of 2-methyl-4-thiazolemethanol were reacted to afford the title compound as a white solid (0.4 g).

$^1$H NMR (400 MHz, DMSO-d$_6$): δ 11.68 (s, 1H), 9.09 (d, 1H), 7.81 (d, 3H), 7.55 (d, 2H), 7.51 (t, 1H), 7.46 (s, 1H), 7.36 (d, 1H), 7.30 (d, 1H), 7.22 (t, 1H), 6.44 (s, 1H), 5.19 (s, 2H), 4.84 (m, 1H), 3.48 (dd, 1H), 3.30 (q, 1H), 2.64 (s, 3H)

Example 87

Preparation of 2-(4-Methylthiazol-5-yl)ethyl 2-(4-chlorobenzoylamino)-3-(2-oxo-1,2-dihydroquinolin-4-yl)propionate

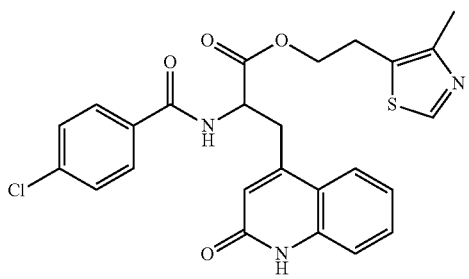 [SMILES: Cc1ncsc1CCOC(=O)C(Cc1cc(=O)[nH]c2ccccc12)NC(=O)c1ccc(Cl)cc1]

According to Experiment Prototocol A, 1.0 g (2.69 mmol) of rebamipide and 0.46 g (1.2 eq, 3.23 mmol) of 4-methyl-5-thiazole ethanol were reacted to afford the title compound as a white solid (0.4 g).

$^1$H NMR (700 MHz, DMSO-d$_6$): δ 11.70 (s, 1H), 9.04 (d, 1H), 8.82 (s, 1H), 7.81 (d, 3H), 7.76 (d, 1H), 7.56 (d, 2H), 7.52 (t, 1H), 7.32 (d, 1H), 7.23 (t, 1H), 6.45 (s, 1H), 4.80-4.77 (m, 1H), 4.30-4.24 (m, 2H), 3.42 (dd, 1H), 3.24 (q, 1H), 3.13-3.08 (m, 2H), 2.30 (s, 3H)

Example 88

Preparation of Pyrimidin-2-ylmethyl 2-(4-chlorobenzoylamino)-3-(2-oxo-1,2-dihydroquinolin-4-yl)propionate

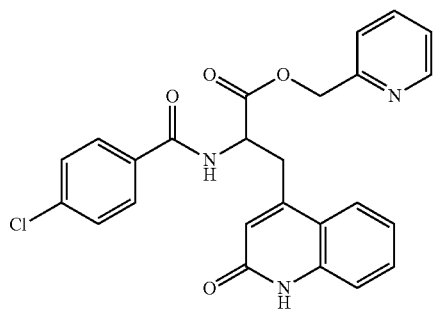 [SMILES: O=C(NC(Cc1cc(=O)[nH]c2ccccc12)C(=O)OCc1ccccn1)c1ccc(Cl)cc1]

According to Experiment Prototocol C, 1.0 g (2.69 mmol) of rebamipide and 0.66 g (1.5 eq, 4.03 mmol) of 2-(Chloromethyl)pyridine HCl were reacted to afford the title compound as a white solid (0.9 g).

$^1$H NMR (400 MHz, DMSO-d$_6$): δ 11.68 (s, 1H), 9.13 (d, 1H), 8.55 (d, 1H), 7.86-7.78 (m, 4H), 7.58 (s, 1H), 7.56 (s, 1H), 7.51 (t, 1H), 7.36 (d, 1H), 7.34 (m, 1H), 7.22 (t, 1H), 6.48 (s, 1H), 5.26 (s, 2H), 4.92 (m, 1H), 3.56 (dd, 1H), 3.32-3.41 (m, 1H)

Example 89

Preparation of Pyrimidin-3-ylmethyl 2-(4-chlorobenzoylamino)-3-(2-oxo-1,2-dihydroquinolin-4-yl)propionate

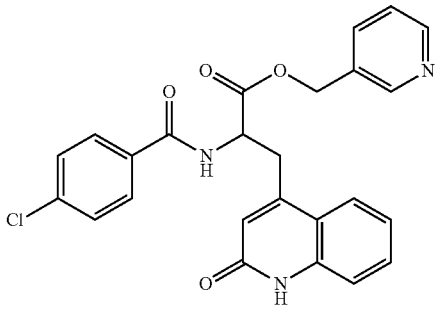

According to Experiment Prototocol C, 1.0 g (2.69 mmol) of rebamipide and 0.66 g (1.5 eq, 4.03 mmol) of 23-(chloromethyl)pyridine HCl were reacted to afford the title compound as a white solid (0.9 g).

$^1$H NMR (400 MHz, DMSO-d$_6$): δ 11.68 (s, 1H), 9.09 (d, 1H), 8.58 (d, 1H), 8.54 (dd, 1H), 7.83 (t, 3H), 7.74 (m, 1H), 7.57 (m, 2H), 7.48 (m, 1H), 7.39 (m, 1H), 7.31 (dd, 1H), 7.21 (m, 1H), 6.45 (s, 1H), 5.21 (q, 2H), 4.86 (m, 1H), 3.50 (dd, 1H), 3.33 (m, 1H)

Example 90

Preparation of Pyrimidin-4-ylmethyl 2-(4-chlorobenzoylamino)-3-(2-oxo-1,2-dihydroquinolin-4-yl)propionate

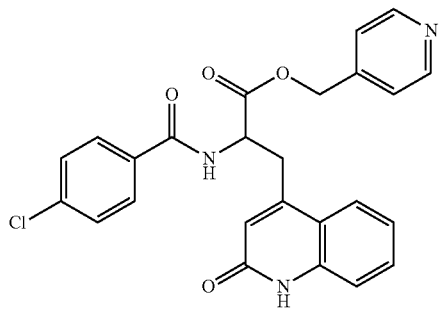 [SMILES: O=C(NC(Cc1cc(=O)[nH]c2ccccc12)C(=O)OCc1ccncc1)c1ccc(Cl)cc1]

According to Experiment Prototocol C, 1.0 g (2.69 mmol) of rebamipide and 0.66 g (1.5 eq, 4.03 mmol) of 4-(chloromethyl)pyridine HCl were reacted to afford the title compound as a white solid (0.7 g).

$^1$H NMR (400 MHz, DMSO-$d_6$): δ 11.70 (s, 1H), 9.14 (d, 1H), 8.55 (d, 2H), 8.54 (d, 1H), 7.85 (t, 3H), 7.58 (s, 1H), 7.56 (s, 1H), 7.32 (m, 3H), 7.21 (t, 1H), 6.48 (s, 1H), 5.23 (q, 2H), 4.93 (m, 1H), 3.54 (dd, 1H), 3.38 (m, 1H)

Example 91

Preparation of 2-(Pyrimidin-2-yl)ethyl 2-(4-chlorobenzoylamino)-3-(2-oxo-1,2-dihydroquinolin-4-yl)propionate

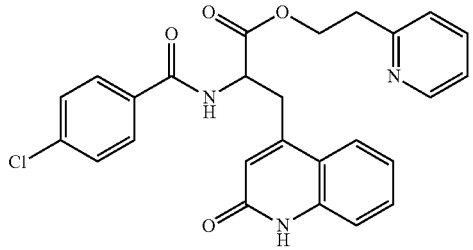

According to Experiment Prototocol D, 1.0 g (2.69 mmol) of rebamipide and 0.81 g (1.5 eq, 4.03 mmol) of 2-pyridineethyl methanesulfonate were reacted to afford the title compound as a white solid (0.7 g).

$^1$H NMR (700 MHz, DMSO-$d_6$): δ 11.68 (s, 1H), 8.99 (d, 1H), 8.55 (d, 2H), 8.48 (s, 1H), 7.78 (d, 2H), 7.66-7.51 (m, 5H), 7.32-7.20 (m, 4H), 6.42 (s, 1H), 4.69 (br-s, 1H), 4.54-4.45 (m, 2H), 3.34 (d, 1H), 3.18 (d, 1H), 3.06 (d, 2H)

Example 92

Preparation of Quinolin-2-ylmethyl 2-(4-chlorobenzoylamino)-3-(2-oxo-1,2-dihydroquinolin-4-yl)propionate

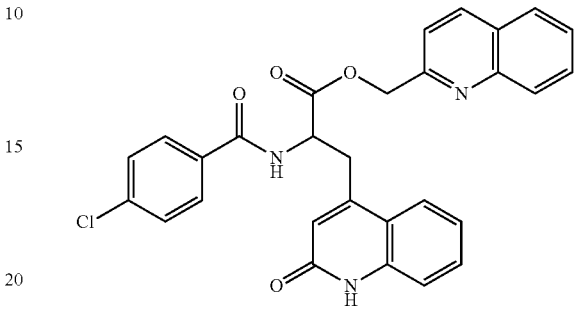

According to Experiment Prototocol C, 1.0 g (2.69 mmol) of rebamipide and 0.86 g (1.5 eq, 4.03 mmol) of 2-(chloromethyl)quinoline HCl were reacted to afford the title compound as a white solid (0.9 g).

$^1$H NMR (400 MHz, DMSO-$d_6$): δ 11.70 (s, 1H), 9.16 (d, 1H), 8.38 (d, 2H), 7.99 (t, 2H), 7.88 (t, 1H), 7.86 (s, 1H), 7.84 (s, 1H), 7.78 (m, 1H), 7.62 (m, 1H), 7.58 (s, 1H), 7.56 (s, 1H), 7.52 (t, 2H), 7.32 (d, 1H), 7.21 (t, 1H), 6.52 (s, 1H), 5.47 (s, 2H), 4.97 (m, 1H), 3.67 (dd, 1H), 3.39 (m, 1H)

Example 93

Preparation of Quinolin-3-ylmethyl 2-(4-chlorobenzoylamino)-3-(2-oxo-1,2-dihydroquinolin-4-yl)propionate

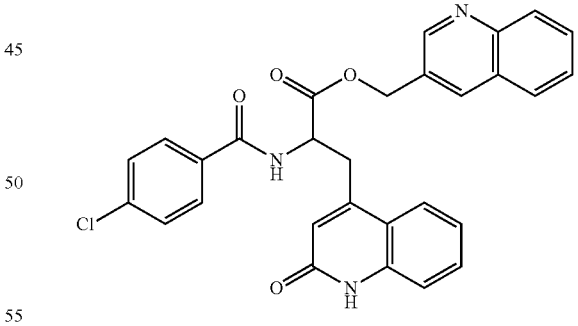

According to Experiment Prototocol C, 1.0 g (2.69 mmol) of rebamipide and 0.66 g (1.5 eq, 4.03 mmol) of 3-(chloromethyl)pyridine HCl were reacted to afford the title compound as a white solid (0.8 g).

$^1$H NMR (400 MHz, DMSO-$d_6$): δ 11.68 (s, 1H), 9.31 (s, 1H), 9.15 (d, 1H), 8.13 (d, 2H), 7.87-7.84 (m, 4H), 7.81-7.78 (m, 1H), 7.75 (s, 1H), 7.72-7.68 (m, 1H), 7.58-7.77 (m, 2H), 7.52-7.48 (m, 1H), 7.23 (q, 1H), 7.21-7.20 (m, 1H), 6.50 (s, 1H), 5.39 (q, 2H), 4.97-4.91 (m, 1H), 3.57 (dd, 1H), 3.37 (m, 1H)

Example 94

Preparation of 2-(1-Methyl-1H-indol-3-yl)ethyl 2-(4-chlorobenzoylamino)-3-(2-oxo-1,2-dihydroquinolin-4-yl)propionate

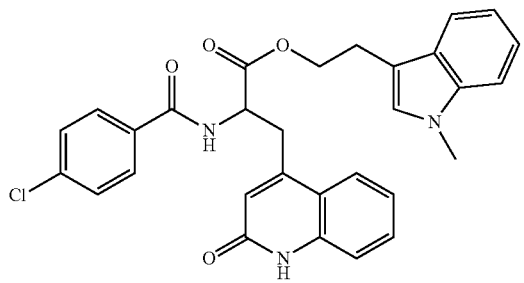 [SMILES: Cn1cc(CCOC(=O)C(Cc2cc(=O)[nH]c3ccccc23)NC(=O)c2ccc(Cl)cc2)c2ccccc21]

According to Experiment Prototocol B, 1.0 g (2.69 mmol) of rebamipide and 0.56 g (1.2 eq, 3.23 mmol) of 3-(2-hydroxyethyl)-1-methylindole were reacted to afford the title compound as a white solid (0.3 g).

$^1$H NMR (400 MHz, DMSO-d$_6$): δ 11.69 (s, 1H), 9.03 (d, 1H), 7.84 (s, 1H), 7.82 (s, 1H), 7.73 (d, 1H), 7.57 (s, 1H), 7.55 (s, 1H), 7.34 (q, 2H), 7.19 (t, 1H), 7.13 (t, 1H), 7.11 (s, 1H), 6.99 (t, 1H), 6.45 (s, 1H), 4.78 (m, 1H), 4.40-4.27 (m, 2H), 3.65 (s, 3H), 3.39 (dd, 1H), 3.24 (m, 1H), 2.98 (t, 2H)

Example 95

Preparation of Benzothiazol-2-ylmethyl 2-(4-chlorobenzoylamino)-3-(2-oxo-1,2-dihydroquinolin-4-yl)propionate

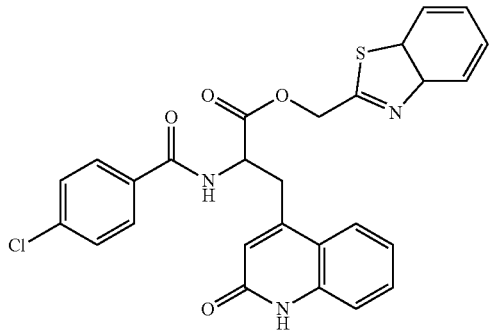 [SMILES: O=C(NC(Cc1cc(=O)[nH]c2ccccc12)C(=O)OCC1=NC2C=CC=CC2S1)c1ccc(Cl)cc1]

According to Experiment Prototocol C, 1.0 g (2.69 mmol) of rebamipide and 0.74 g (1.5 eq, 4.03 mmol) of 2-(chloromethyl)benzothiazole were reacted to afford the title compound as a white solid (0.8 g).

$^1$H NMR (400 MHz, DMSO-d$_6$): δ 11.70 (s, 1H), 9.17 (d, 1H), 8.12 (d, 2H), 8.01 (d, 1H), 7.88-7.82 (m, 3H), 7.56 (d, 2H), 7.53-7.46 (m, 3H), 7.31 (d, 1H), 7.20 (t, 1H), 6.50 (s, 1H), 5.59 (s, 2H), 4.93 (m, 1H), 3.59 (dd, 1H), 3.35 (q, 1H)

Example 96

Preparation of 2,3-Dihydrobenzo[1,4]dioxin-2-ylmethyl 2-(4-chlorobenzoylamino)-3-(2-oxo-1,2-dihydroquinolin-4-yl)propionate

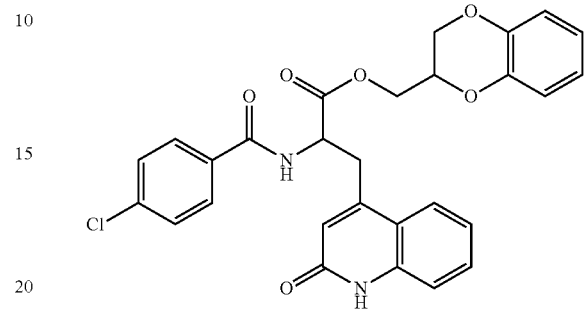

According to Experiment Prototocol C, 1.0 g (2.69 mmol) of rebamipide and 0.92 g (1.5 eq, 4.03 mmol) of 2-(bromomethyl)-1,4-benzodioxane were reacted to afford the title compound as a white solid (1.0 g).

$^1$H NMR (400 MHz, DMSO-d$_6$): δ 11.70 (d, 1H), 9.09 (dd, 1H), 7.81 (t, 3H), 7.55-7.50 (m, 3H), 7.86 (s, 1H), 7.84 (s, 1H), 7.78 (m, 1H), 7.62 (m, 1H), 7.58 (s, 1H), 7.56 (s, 1H), 7.52 (t, 2H), 7.32 (q, 1H), 7.18 (q, 1H), 6.88-6.81 (m, 4H), 6.46 (d, 1H), 4.81 (m, 1H), 4.46-4.29 (m, 4H), 4.06-3.98 (m, 1H), 3.51-3.47 (m, 1H), 3.36-3.30 (m, 1H)

Example 97

Preparation of Carbazol-9-ylmethyl 2-(4-chlorobenzoylamino)-3-(2-oxo-1,2-dihydroquinolin-4-yl)propionate

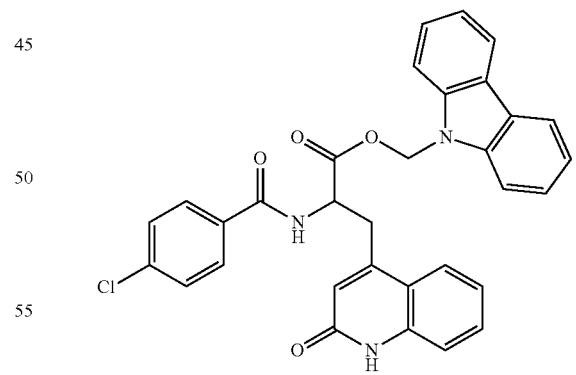

According to Experiment Prototocol B, 1.0 g (2.69 mmol) of rebamipide and 0.64 g (1.2 eq, 3.23 mmol) of 9H-carbazole 9-methanol were reacted to afford the title compound as a white solid (0.6 g).

$^1$H NMR (400 MHz, DMSO-d$_6$): δ 11.64 (s, 1H), 8.85 (d, 1H), 8.13 (d, 2H), 7.71 (d, 2H), 7.65 (d, 1H), 7.53-7.46 (m, 4H), 7.36 (t, 2H), 7.29 (d, 1H), 7.18-7.12 (m, 3H), 6.33 (s, 1H), 4.64 (m, 2H), 3.09 (dd, 1H), 2.95 (dd, 1H)

Example 98

Preparation of Methylcarbamoylmethyl 2-(4-chlorobenzoylamino)-3-(2-oxo-1,2-dihydroquinolin-4-yl)propionate

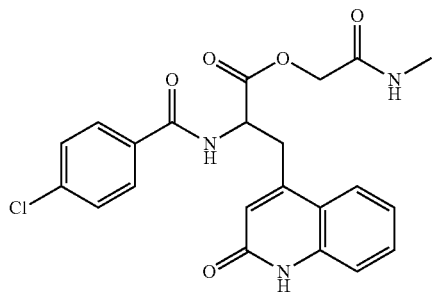 [SMILES: CNC(=O)COC(=O)C(Cc1cc(=O)[nH]c2ccccc12)NC(=O)c1ccc(Cl)cc1]

According to Experiment Prototocol C, 1.0 g (2.69 mmol) of rebamipide and 0.43 g (1.5 eq, 4.03 mmol) of 2-chloro-N-methylacetamide were reacted to afford the title compound as a white solid (0.4 g).

$^1$H NMR (400 MHz, DMSO-d$_6$): δ 11.68 (s, 1H), 9.09 (d, 1H), 7.95 (m, 1H), 7.84-7.81 (m, 3H), 7.55 (d, 2H), 7.51 (t, 1H), 7.31 (d, 1H), 7.23 (t, 1H), 6.47 (s, 1H), 4.96-4.90 (m, 1H), 4.59 (s, 2H), 3.58 (dd, 1H), 3.29 (q, 1H), 2.64 (d, 3H)

Example 99

Preparation of 2-(4-Methylpiperazin-1-yl)-2-oxoethyl 2-(4-chlorobenzoylamino)-3-(2-oxo-1,2-dihydroquinolin-4-yl)propionate

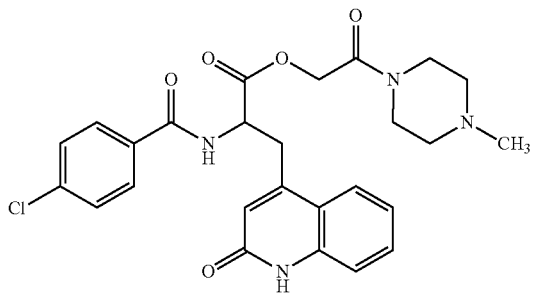 [SMILES: CN1CCN(C(=O)COC(=O)C(Cc2cc(=O)[nH]c3ccccc23)NC(=O)c2ccc(Cl)cc2)CC1]

According to Experiment Prototocol C, 2.0 g (5.38 mmol) of rebamipide and 1.40 g (1.2 eq, 6.48 mmol) of 1-(2-bromoacetyl)-4-methylpiperazin-1-ium bromide were reacted to afford the title compound as a white solid (0.1 g).

$^1$H NMR (400 MHz, DMSO-d$_6$): δ 9.10 (d, 1H), 7.81 (t, 3H), 7.53 (m, 4H), 7.31 (d, 1H), 7.23 (t, 1H), 6.48 (s, 1H), 4.93-4.90 (m, 2H), 4.23 (t, 1H), 3.45-3.42 (m, 4H), 2.71-2.50 (m, 2H), 2.29-2.25 (m, 4H), 2.12 (s, 3H)

Example 100

Preparation of 1-(4-Methylpiperazine-1-carbonyl)propyl 2-(4-chlorobenzoylamino)-3-(2-oxo-1,2-dihydroquinolin-4-yl)propionate

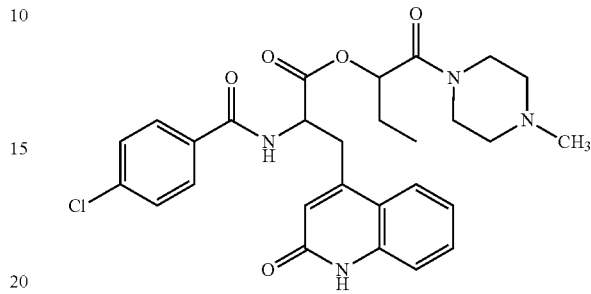

According to Experiment Prototocol C, 2.0 g (5.38 mmol) of rebamipide and 1.60 g (1.2 eq, 6.48 mmol) of 1-(2-bromobutanoyl)-4-methylpiperazin-1-ium bromide were reacted to afford the title compound as a white solid (0.1 g).

$^1$H NMR (400 MHz, DMSO-d$_6$): δ 9.09 (d, 1H), 7.81 (t, 3H), 7.53 (m, 4H), 7.31 (d, 1H), 7.23 (t, 1H), 7.25-7.23 (m, 1H), 6.48 (d, 1H), 5.06-4.78 (m, 1H), 4.52-4.50 (m, 1H), 3.33-3.30 (m, 4H), 2.60-2.51 (m, 6H), 2.16-2.10 (m, 5H), 1.10 (t, 3H)

Example 101

Preparation of 2-Morpholin-4-yl-2-oxoethyl 2-(4-chlorobenzoylamino)-3-(2-oxo-1,2-dihydroquinolin-4-yl)propionate

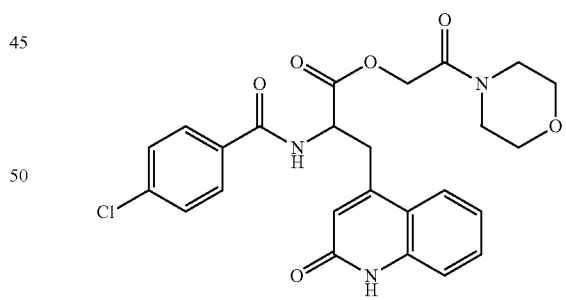

According to Experiment Prototocol C, 1.0 g (2.69 mmol) of rebamipide and 0.66 g (1.5 eq, 4.03 mmol) of 1-(2-chloroacetyl)morpholine were reacted to afford the title compound as a white solid (0.5 g).

$^1$H NMR (400 MHz, DMSO-d$_6$): δ 11.68 (s, 1H), 9.08 (d, 1H), 7.83 (t, 3H), 7.58 (s, 1H), 7.56 (s, 1H), 7.53 (t, 1H), 7.32 (d, 1H), 7.26 (t, 1H), 6.52 (s, 1H), 4.93 (dd, 2H), 4.87 (m, 1H), 3.65 (dd, 1H), 3.58 (br-s, 4H), 3.44 (m, 4H), 3.29 (m, 1H)

Example 102

Preparation of (Methoxymethylcarbamoyl)methyl 2-(4-chlorobenzoylamino)-3-(2-oxo-1,2-dihydroquinolin-4-yl)propionate

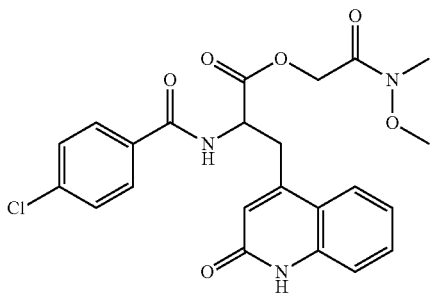 [SMILES: CON(C)C(=O)COC(=O)C(Cc1cc(=O)[nH]c2ccccc12)NC(=O)c1ccc(Cl)cc1]

According to Experiment Prototocol C, 1.0 g (2.69 mmol) of rebamipide and 0.55 g (1.5 eq, 4.03 mmol) of 2-chloro-N-methoxy-N-methylacetamide were reacted to afford the title compound as a white solid (0.7 g).

$^1$H NMR (400 MHz, DMSO-d$_6$): δ 11.70 (s, 1H), 9.10 (d, 1H), 7.86-7.81 (m, 3H), 7.59-7.51 (m, 3H), 7.33 (dd, 1H), 7.26 (m, 1H), 6.52 (s, 1H), 5.09-4.89 (m, 3H), 3.74 (s, 3H), 3.63 (dd, 1H), 3.29 (q, 1H), 3.14 (s, 3H)

Example 103

Preparation of 2-Ethoxycarbonylmethyl 2-(4-chlorobenzoylamino)-3-(2-oxo-1,2-dihydroquinolin-4-yl)propionate

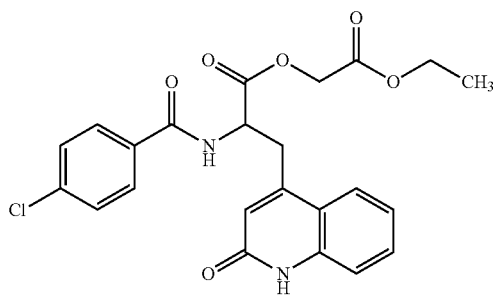 [SMILES: CCOC(=O)COC(=O)C(Cc1cc(=O)[nH]c2ccccc12)NC(=O)c1ccc(Cl)cc1]

According to Experiment Prototocol C, 1.0 g (2.69 mmol) of rebamipide and 0.49 g (1.5 eq, 4.03 mmol) of ethyl chloroacetate were reacted to afford the title compound as a white solid (0.8 g).

$^1$H NMR (400 MHz, DMSO-d$_6$): δ 11.69 (s, 1H), 9.10 (d, 1H), 7.85 (t, 1H), 7.83-7.80 (m, 2H), 7.77 (d, 1H), 7.57 (t, 1H), 7.55 (t, 1H), 7.54-7.50 (m, 1H), 7.32 (dd, 1H), 7.27-7.23 (m, 1H), 6.51 (s, 1H), 4.95-4.89 (m, 1H), 4.81 (q, 2H), 4.16 (q, 2H), 3.55 (dd, 1H), 3.30 (q, 1H), 1.21 (t, 3H)

Example 104

Preparation of 2-Ethoxycarbonylethyl 2-(4-chlorobenzoylamino)-3-(2-oxo-1,2-dihydroquinolin-4-yl)propionate

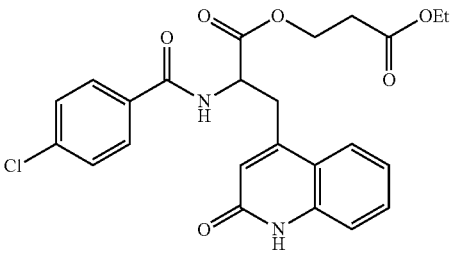 [SMILES: CCOC(=O)CCOC(=O)C(Cc1cc(=O)[nH]c2ccccc12)NC(=O)c1ccc(Cl)cc1]

According to Experiment Prototocol C, 1.0 g (2.69 mmol) of rebamipide and 0.55 g (1.5 eq, 4.03 mmol) of ethyl 3-chloropropionate were reacted to afford the title compound as a white solid (0.8 g).

$^1$H NMR (700 MHz, DMSO-d$_6$): δ 11.69 (s, 1H), 9.03 (d, 1H), 7.82 (t, 1H), 7.81 (t, 1H), 7.77 (d, 1H), 7.57 (t, 1H), 7.56 (t, 1H), 7.52-7.50 (m, 1H), 7.32 (dd, 1H), 7.23-7.21 (m, 1H), 6.45 (s, 1H), 4.77-4.73 (m, 1H), 4.34-4.30 (m, 2H), 4.01 (q, 2H), 3.43 (dd, 1H), 3.26 (q, 1H), 2.69-2.66 (m, 2H), 1.13 (t, 3H)

Example 105

Preparation of 2-Morpholin-4-yl-ethoxycarbonylmethyl 2-(4-chlorobenzoylamino)-3-(2-oxo-1,2-dihydroquinolin-4-yl)propionate

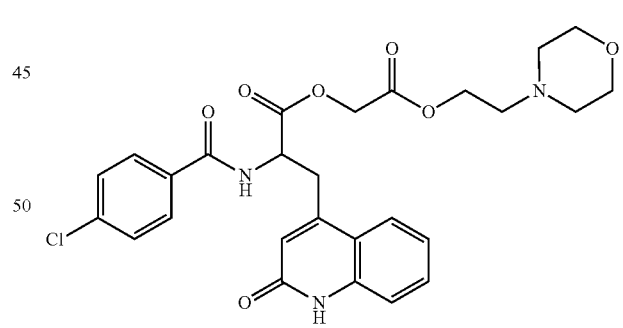

According to Experiment Prototocol C, 1.0 g (2.69 mmol) of rebamipide and 1.07 g (1.2 eq, 3.23 mmol) of 4-[2-(2-bromoacetoxyl)ethyl]morpholin-4-ium bromide were reacted to afford the title compound as a white solid (0.1 g).

$^1$H NMR (DMSO-d$_6$): δ 9.09 (d, 1H), 7.81 (t, 3H), 7.53 (m, 3H), 7.31 (d, 1H), 7.23 (t, 1H), 6.48 (s, 1H), 4.87-4.80 (m, 2H), 4.23 (t, 1H), 3.57-3.52 (m, 4H), 3.31-3.25 (m, 2H), 3.14 (t, 4H), 2.62 (t, 4H)

Example 106

Preparation of 2-Morpholin-4-ylethyl 2-[2-(4-chlorobenzoylamino)-3-(2-oxo-1,2-dihydroquinolin-4-yl)propionyloxy]butyrate

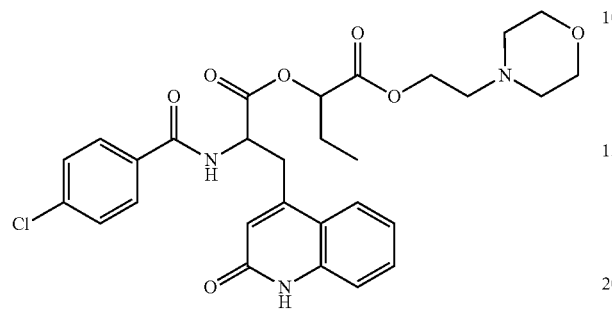

According to Experiment Prototocol C, 2.0 g (5.38 mmol) of rebamipide and 1.8 g (1.2 eq, 6.47 mmol) of ethyl chloroacetate were reacted to afford the title compound as a white solid (1.0 g).

$^1$H NMR (DMSO-d$_6$): δ 9.09 (d, 1H), 7.81 (t, 3H), 7.53 (m, 3H), 7.31 (d, 1H), 7.25-7.23 (m, 1H), 6.48 (d, 1H), 5.06-4.78 (m, 1H), 4.30-4.11 (m, 1H), 3.61-3.24 (m, 8H), 3.35-3.25 (m, 4H), 2.54-2.35 (m, 2H), 1.90-1.75 (m, 2H), 0.95 (t, 3H)

Example 107

Preparation of 2-(1,3-Dioxo-1,3-dihydroisoindol-2-yl)ethyl 2-(4-chlorobenzoylamino)-3-(2-oxo-1,2-dihydroquinolin-4-yl)propionate

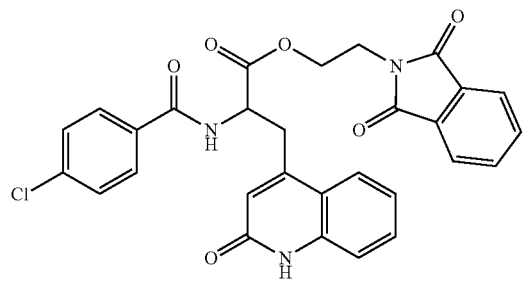 [SMILES: O=C(NC(Cc1cc(=O)[nH]c2ccccc12)C(=O)OCCN1C(=O)c2ccccc2C1=O)c1ccc(Cl)cc1]

According to Experiment Prototocol C, 1.0 g (2.69 mmol) of rebamipide and 0.79 g (1.5 eq, 4.03 mmol) of N-(chloromethyl)phthalimide were reacted to afford the title compound as a white solid (0.6 g).

$^1$H NMR (400 MHz, DMSO-d$_6$): δ 11.65 (s, 1H), 8.94 (d, 1H), 7.82 (s, 4H), 7.76-7.70 (m, 3H), 7.52-7.48 (m, 3H), 7.29 (dd, 1H), 7.21 (m, 1H), 6.41 (s, 1H), 4.71 (m, 1H), 4.48-4.42 (m, 1H), 4.36-4.31 (m, 1H), 3.92 (t, 2H), 3.43 (dd, 1H), 3.15 (dd, 1H)

Example 108

Preparation of Cyclohexyloxycarbonyloxymethyl 2-(4-chlorobenzoylamino)-3-(2-oxo-1,2-dihydroquinolin-4-yl)propionate

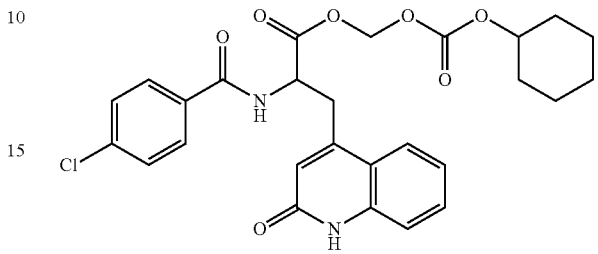

According to Experiment Prototocol C, 1.0 g (2.69 mmol) of rebamipide and 0.77 g (1.5 eq, 4.03 mmol) of ethyl chloromethyl cyclohexyl carbonate were reacted to afford the title compound as a white solid (0.4 g).

$^1$H NMR (400 MHz, DMSO-d$_6$): δ 11.66 (s, 1H), 9.09 (d, 1H), 7.81 (m, 3H), 7.52 (m, 3H), 7.33 (d, 1H), 7.21 (m, 1H), 6.45 (s, 1H), 5.77 (s, 2H), 4.81 (m, 1H), 4.53 (m, 1H), 3.28-3.49 (m, 2H), 1.80 (m, 2H), 1.63 (m, 2H), 1.14-1.51 (m, 6H)

Example 109

Preparation of 2-Morpholin-4-yl-ethoxycarbonyloxymethyl 2-(4-chlorobenzoylamino)-3-(2-oxo-1,2-dihydroquinolin-4-yl)propionate

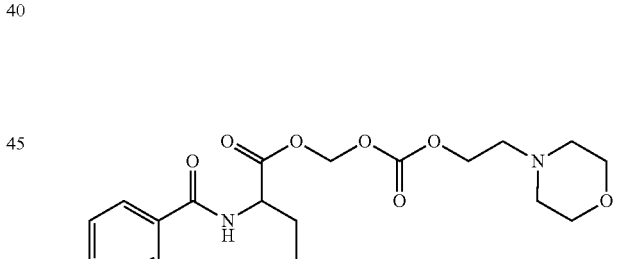

According to Experiment Prototocol C, 2.0 g (5.38 mmol) of rebamipide and 1.68 g (1.2 eq, 6.47 mmol) of chloromethyl(2-morpholin-4-yl)ethyl carbonate HCl were reacted to afford the title compound as a white solid (0.1 g).

$^1$H NMR (DMSO-d$_6$): δ 9.09 (d, 1H), 7.81 (t, 3H), 7.53 (m, 4H), 7.31 (d, 1H), 7.23 (t, 1H), 7.26-6.95 (m, 3H), 6.48 (s, 1H), 4.23 (t, 1H), 3.57-3.52 (m, 4H), 3.31-3.25 (m, 2H), 3.14 (t, 4H), 2.62 (t, 4H)

Example 110

Preparation of 2-ureidoethyl 2-(4-chlorobenzoylamino)-3-(2-oxo-1,2-dihydroquinolin-4-yl)propionate

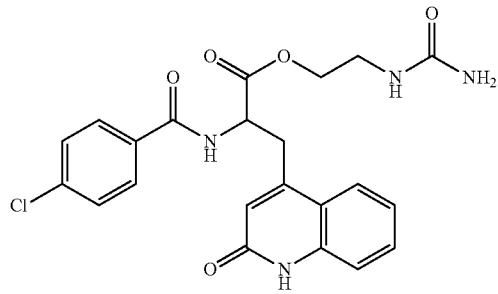

According to Experiment Prototocol C, 1.0 g (2.69 mmol) of rebamipide and 0.67 g (1.5 eq, 4.03 mmol) of (2-bromoethyl)urea were reacted to afford the title compound as a white solid (0.2 g).

$^1$H NMR (400 MHz, DMSO-d$_6$): δ 11.68 (s, 1H), 9.01 (d, 1H), 8.64 (t, 1H), 7.87-7.82 (m, 3H), 7.57 (t, 1H), 7.55 (t, 1H), 7.52 (m, 1H), 7.31 (d, 1H), 7.26 (m, 1H), 6.46 (s, 1H), 6.12 (t, 1H), 5.57 (s, 2H), 4.81 (m, 1H), 4.13 (m, 1H), 4.06 (m, 1H), 3.53 (dd, 1H), 3.28-3.22 (m, 3H)

Example 111

Preparation of 2-(3-Phenyl-ureido)ethyl 2-(4-chlorobenzoylamino)-3-(2-oxo-1,2-dihydroquinolin-4-yl) propionate

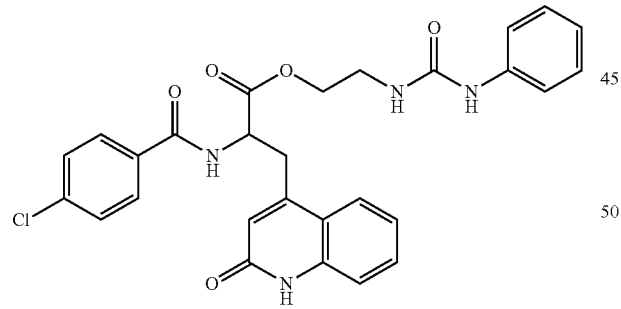

According to Experiment Prototocol C, 1.0 g (2.69 mmol) of rebamipide and 0.98 g (1.5 eq, 4.03 mmol) of 1-(2-bromoethyl)-3-phenyl urea were reacted to afford the title compound as a white solid (0.3 g).

$^1$H NMR (400 MHz, DMSO-d$_6$): δ 11.68 (s, 1H), 9.02 (d, 1H), 8.60 (s, 1H), 7.83 (t, 3H), 7.54 (s, 1H), 7.52 (s, 1H), 7.49 (t, 1H), 7.40 (s, 1H), 7.38 (s, 1H), 7.30 (d, 1H), 7.21-7.15 (m, 3H), 6.88 (t, 1H), 6.45 (s, 1H), 6.30 (t, 1H), 4.83 (m, 1H), 4.25 (m, 1H), 4.13 (m, 1H), 3.56 (dd, 1H), 3.41 (t, 2H), 3.27 (m, 1H)

Example 112

Preparation of 2-(3-Benzyl-ureido)ethyl 2-(4-chlorobenzoylamino)-3-(2-oxo-1,2-dihydroquinolin-4-yl) propionate

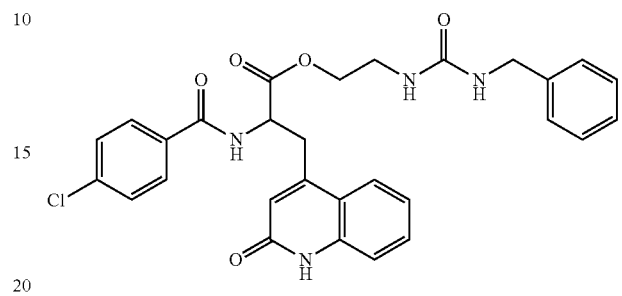

According to Experiment Prototocol C, 1.0 g (2.69 mmol) of rebamipide and 1.04 g (1.5 eq, 4.03 mmol) of 1-(2-bromoethyl)-3-benzyl urea were reacted to afford the title compound as a white solid (0.3 g).

$^1$H NMR (400 MHz, DMSO-d$_6$): δ 11.69 (s, 1H), 9.03 (d, 1H), 7.87-7.82 (m, 3H), 7.55 (d, 2H), 7.51 (t, 1H), 7.33-7.17 (m, 6H), 6.52 (t, 1H), 6.46 (s, 1H), 6.15 (t, 1H), 4.82 (m, 1H), 4.23-4.17 (m, 3H), 4.07 (m, 1H), 3.52 (dd, 1H), 3.33 (m, 2H), 3.24 (dd, 1H)

Example 113

Preparation of 2-(4-Chlorobenzoylamino)-3-(2-oxo-1,2-dihydroquinolin-4-yl)thiopropionic acid

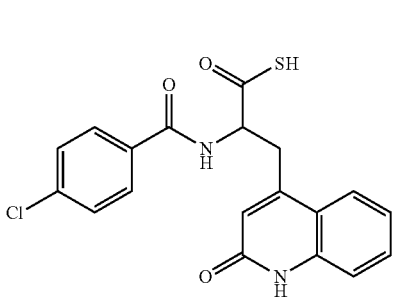 [SMILES: O=C(NC(Cc1cc(=O)[nH]c2ccccc12)C(=O)S)c1ccc(Cl)cc1]

According to Experiment Prototocol A or B, the title compound was prepared as a pale yellow solid (200 g).

$^1$H NMR (700 MHz, DMSO-d$_6$): δ 11.52 (s, 1H), 8.40 (d, 1H), 8.22 (d, 1H), 7.81 (dd, 2H), 7.54 (d, 1H), 7.52 (d, 1H), 7.48 (m, 1H), 7.28 (d, 1H), 7.22 (m, 1H), 6.37 (s, 1H), 4.65-4.60 (m, 1H), 4.11 (q, 1H), 3.72 (dd, 1H), 2.93 (q, 1H)

Example 114

Preparation of S-Methyl 2-(4-chlorobenzoylamino)-3-(2-oxo-1,2-dihydroquinolin-4-yl)thiopropionate

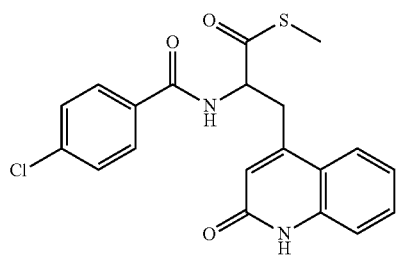 [SMILES: CSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.10 g (1.5 eq, 7.76 mmol) of iodomethane were reacted to afford the title compound as a white solid (1.2 g).

$^1$H NMR (400 MHz, DMSO-$d_6$): δ 11.65 (s, 1H), 9.24 (d, 1H), 7.86 (s, 1H), 7.84 (s, 1H), 7.79 (d, 1H), 7.60 (s, 1H), 7.58 (s, 2H), 7.51 (t, 1H), 7.30 (d, 1H), 7.23 (t, 1H), 6.43 (s, 1H), 4.97-4.92 (m, 1H), 3.54 (dd, 1H), 3.21 (q, 1H), 2.28 (s, 3H)

Example 115

Preparation of S-Ethyl 2-(4-chlorobenzoylamino)-3-(2-oxo-1,2-dihydroquinolin-4-yl)thiopropionate

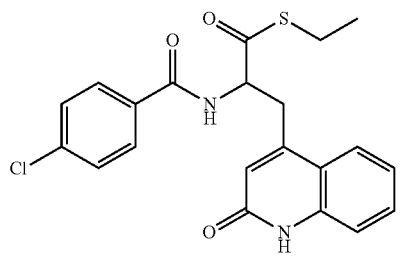 [SMILES: CCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.21 g (1.5 eq, 7.76 mmol) of iodoethane were reacted to afford the title compound as a white solid (1.2 g).

$^1$H NMR (700 MHz, DMSO-$d_6$): δ 11.68 (s, 1H), 9.28 (d, 1H), 7.88 (t, 1H), 7.85 (t, 1H), 7.82 (t, 1H), 7.60 (t, 1H), 7.58 (t, 1H), 7.53-7.49 (m, 1H), 7.34-7.31 (m, 1H), 7.26-7.22 (m, 1H), 6.44 (s, 1H), 4.95-4.90 (m, 1H), 3.53 (dd, 1H), 3.21 (q, 1H), 2.86 (q, 2H), 1.19 (t, 3H)

Example 116

Preparation of S-Propyl 2-(4-chlorobenzoylamino)-3-(2-oxo-1,2-dihydroquinolin-4-yl)thiopropionate

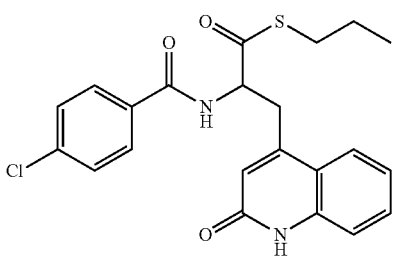

According to Experiment Prototocol C, 2.0 g (5.17 mmol) of 2-(4-chlorobenzoylamino)-3-(2-oxo-1,2-dihydroquinolin-4-yl)thiopropionic acid and 0.95 g (1.5 eq, 7.76 mmol) of 1-bromopropane were reacted to afford the title compound as a white solid (1.0 g).

$^1$H NMR (700 MHz, DMSO-$d_6$): δ 11.65 (s, 1H), 9.22 (d, 1H), 7.86-7.79 (m, 3H), 7.64 (s, 1H), 7.62 (s, 1H), 7.49 (d, 1H), 7.26-7.22 (m, 1H), 7.26-7.22 (m, 1H), 6.43 (s, 1H), 4.93-4.90 (m, 1H), 3.52 (dd, 1H), 3.20 (q, 1H), 2.85 (t, 2H), 1.51 (q, 2H), 0.91 (t, 3H)

Example 117

Preparation of S-Butyl 2-(4-chlorobenzoylamino)-3-(2-oxo-1,2-dihydroquinolin-4-yl)thiopropionate

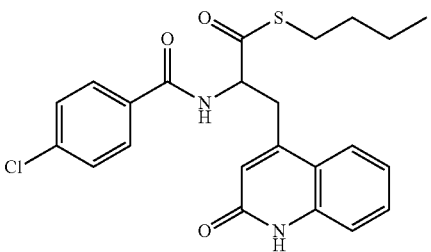 [SMILES: CCCCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.06 g (1.5 eq, 7.76 mmol) of 1-bromobutane were reacted to afford the title compound as a white solid (0.8 g).

$^1$H NMR (400 MHz, DMSO-$d_6$): δ 11.64 (s, 1H), 9.21 (d, 1H), 7.87-7.79 (m, 3H), 7.58 (t, 1H), 7.55 (t, 1H), 7.52-7.49 (m, 1H), 7.30 (dd, 1H), 7.25-7.20 (m, 1H), 6.43 (s, 1H), 4.96-4.90 (m, 1H), 3.52 (dd, 1H), 3.20 (q, 1H), 2.87 (t, 2H), 1.53-1.46 (m, 2H), 1.35-1.24 (m, 2H), 0.87 (t, 3H)

Example 118

Preparation of S-(3-Methylbutyl)2-(4-chlorobenzoylamino)-3-(2-oxo-1,2-dihydroquinolin-4-yl)thiopropionate

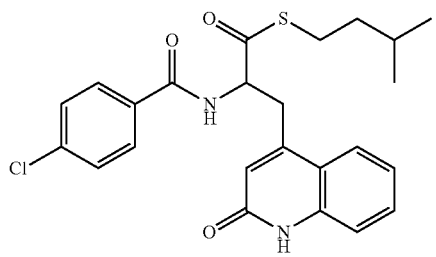 [SMILES: CC(C)CCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.17 g (1.5 eq, 7.76 mmol) of 1-bromo-3-methylbutane were reacted to afford the title compound as a white solid (0.7 g).

$^1$H NMR (400 MHz, DMSO-$d_6$): δ 11.65 (s, 1H), 9.22 (d, 1H), 7.86-7.79 (m, 3H), 7.60 (t, 1H), 7.58 (t, 1H), 7.53-7.49 (m, 1H), 7.30 (dd, 1H), 7.26-7.22 (m, 1H), 6.43 (s, 1H), 4.92 (m, 1H), 3.52 (dd, 1H), 3.20 (q, 1H), 2.89-2.85 (m, 2H), 1.60-1.55 (m, 1H), 1.42-1.37 (m, 2H), 0.87 (dd, 6H)

Example 119

Preparation of S-Hexyl 2-(4-chlorobenzoylamino)-3-(2-oxo-1,2-dihydroquinolin-4-yl)thiopropionate

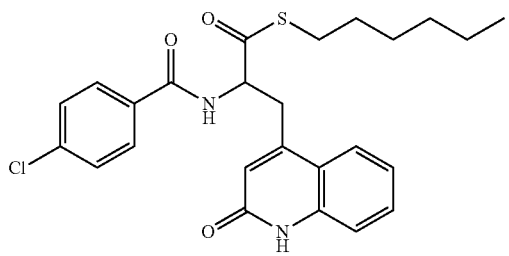 [SMILES: CCCCCCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.28 g (1.5 eq, 7.76 mmol) of 1-bromohexane were reacted to afford the title compound as a white solid (0.6 g).

$^1$H NMR (400 MHz, DMSO-$d_6$): δ 11.64 (s, 1H), 9.21 (d, 1H), 7.86-7.79 (m, 3H), 7.58 (t, 1H), 7.55 (t, 1H), 7.53-7.49 (m, 1H), 7.30 (dd, 1H), 7.25-7.16 (m, 1H), 6.43 (s, 1H), 4.95-4.90 (m, 1H), 3.52 (dd, 1H), 3.20 (q, 1H), 2.86 (t, 2H), 1.54-1.47 (m, 2H), 1.34-1.8 (m, 6H), 0.85 (t, 3H)

Example 120

Preparation of S-(2-Dimethylamino)ethyl 2-(4-chlorobenzoylamino)-3-(2-oxo-1,2-dihydroquinolin-4-yl)thiopropionate

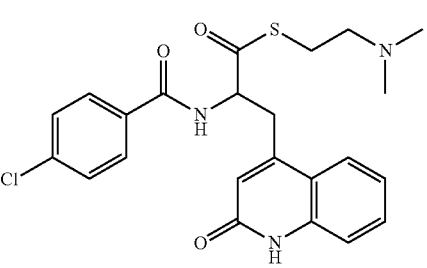

According to Experiment Prototocol C, 2.0 g (5.17 mmol) of 2-(4-chlorobenzoylamino)-3-(2-oxo-1,2-dihydroquinolin-4-yl)thiopropionic acid and 1.12 g (1.5 eq, 7.76 mmol) of 2-(dimethylamino)ethyl chloride HCl were reacted to afford the title compound as a white solid (0.7 g).

$^1$H NMR (400 MHz, DMSO-$d_6$): δ 11.64 (s, 1H), 9.23 (d, 1H), 7.87-7.84 (m, 2H), 7.79 (d, 1H), 7.58 (d, 2H), 7.51 (t, 1H), 7.30 (d, 1H), 7.24 (t, 1H), 6.43 (s, 1H), 4.95-4.92 (m, 1H), 3.53 (dd, 1H), 3.20 (q, 1H), 2.99 (t, 2H), 2.40 (t, 2H), 2.16 (s, 6H)

Example 121

Preparation of S-(2-Diethylamino)ethyl 2-(4-chlorobenzoylamino)-3-(2-oxo-1,2-dihydroquinolin-4-yl)thiopropionate

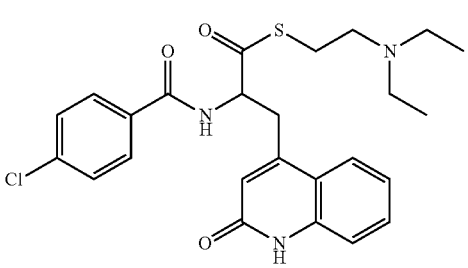

According to Experiment Prototocol C, 2.0 g (5.17 mmol) of 2-(4-chlorobenzoylamino)-3-(2-oxo-1,2-dihydroquinolin-4-yl)thiopropionic acid and 1.33 g (1.5 eq, 7.76 mmol) of 2-(diethylamino)ethyl chloride HCl were reacted to afford the title compound as a white solid (0.7 g).

$^1$H NMR (400 MHz, DMSO-$d_6$): δ 11.65 (s, 1H), 9.25 (d, 1H), 7.87 (t, 1H), 7.84 (t, 1H), 7.79 (d, 1H), 7.60 (t, 1H), 7.58 (t, 1H), 7.53-7.49 (m, 1H), 7.31 (d, 1H), 7.25-7.21 (m, 1H), 6.43 (s, 1H), 4.93-4.90 (m, 1H), 3.52 (dd, 1H), 3.22 (q, 1H), 2.97 (t, 2H), 2.62-2.58 (m, 6H), 0.98 (t, 6H)

Example 122

Preparation of S-(2-Diisopropylamino)ethyl 2-(4-chlorobenzoylamino)-3-(2-oxo-1,2-dihydroquinolin-4-yl)thiopropionate

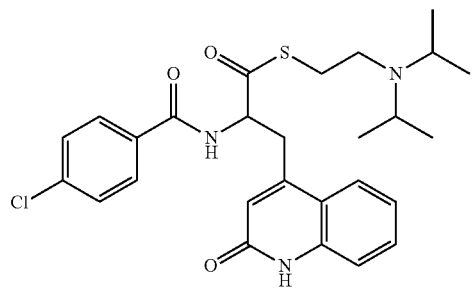

According to Experiment Prototocol C, 2.0 g (5.17 mmol) of 2-(4-chlorobenzoylamino)-3-(2-oxo-1,2-dihydroquinolin-4-yl)thiopropionic acid and 1.55 g (1.5 eq, 7.76 mmol) of 2-(diisopropylamino)ethyl chloride HCl were reacted to afford the title compound as a white solid (0.8 g).

$^1$H NMR (400 MHz, DMSO-$d_6$): δ 11.65 (s, 1H), 9.23 (d, 1H), 7.86 (s, 1H), 7.84 (s, 1H), 7.80 (d, 1H), 7.64 (s, 1H), 7.62 (s, 1H), 7.51 (t, 1H), 7.31 (d, 1H), 7.23 (t, 1H), 6.44 (s, 1H), 4.96-4.91 (m, 1H), 3.52 (dd, 1H), 3.21 (q, 1H), 3.00 (br-s, 2H), 2.87 (br-s, 2H), 2.51 (br-s, 2H), 0.99 (d, 12H)

Example 123

Preparation of S-(2-Dimethylamino)propyl 2-(4-chlorobenzoylamino)-3-(2-oxo-1,2-dihydroquinolin-4-yl)thiopropionate

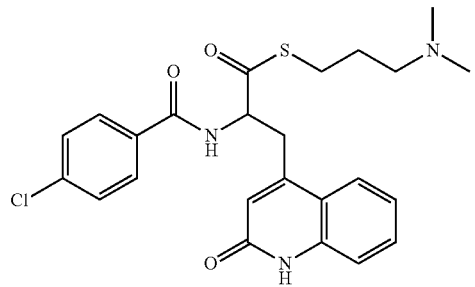

According to Experiment Prototocol C, 2.0 g (5.17 mmol) of 2-(4-chlorobenzoylamino)-3-(2-oxo-1,2-dihydroquinolin-4-yl)thiopropionic acid and 1.22 g (1.5 eq, 7.76 mmol) of 3-dimethylamino-1-propyl chloride HCl were reacted to afford the title compound as a white solid (0.9 g).

$^1$H NMR (400 MHz, DMSO-$d_6$): δ 11.65 (s, 1H), 9.22 (d, 1H), 7.86 (t, 1H), 7.84 (t, 1H), 7.79 (d, 1H), 7.60 (t, 1H), 7.58 (t, 1H), 7.53-7.49 (m, 1H), 7.30 (dd, 1H), 7.23-7.20 (m, 1H), 6.43 (s, 1H), 4.95-4.90 (m, 1H), 3.52 (dd, 1H), 3.20 (q, 1H), 2.88 (t, 2H), 2.25 (t, 2H), 2.09 (s, 6H), 1.68 (m, 2H)

Example 124

Preparation of S-(2-Benzoylamino)ethyl 2-(4-chlorobenzoylamino)-3-(2-oxo-1,2-dihydroquinolin-4-yl) propionate oxalate

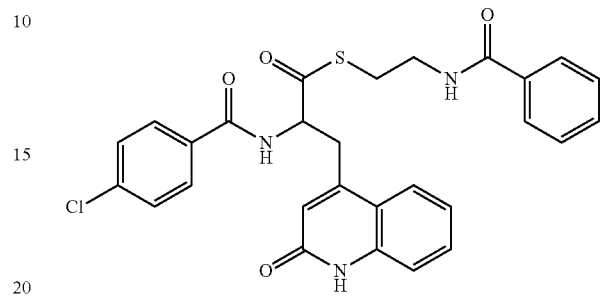

According to Experiment Prototocol C, 2.0 g (5.17 mmol) of 2-(4-chlorobenzoylamino)-3-(2-oxo-1,2-dihydroquinolin-4-yl)thiopropionic acid and 1.42 g (1.5 eq, 7.76 mmol) of N-(2-chloroethyl)benzamide were reacted to afford the title compound as a white solid (0.5 g).

$^1$H NMR (400 MHz, DMSO-$d_6$): δ 11.64 (s, 1H), 9.24 (d, 1H), 8.66 (t, 1H), 7.85-7.83 (m, 4H), 7.77 (d, 1H), 7.58 (s, 1H), 7.56 (s, 1H), 7.51-7.44 (m, 3H), 7.30 (d, 1H), 7.22 (t, 1H), 6.43 (s, 1H), 4.97-4.91 (m, 1H), 3.55-3.42 (m, 3H), 3.20 (q, 1H), 3.11 (t, 2H)

Example 125

Preparation of S-Methoxymethyl 2-(4-chlorobenzoylamino)-3-(2-oxo-1,2-dihydroquinolin-4-yl)thiopropionate

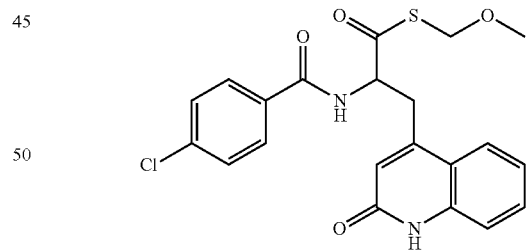

According to Experiment Prototocol C, 2.0 g (5.17 mmol) of 2-(4-chlorobenzoylamino)-3-(2-oxo-1,2-dihydroquinolin-4-yl)thiopropionic acid and 0.62 g (1.5 eq, 7.76 mmol) of chloromethyl methyl ether were reacted to afford the title compound as a white solid (1.2 g).

$^1$H NMR (400 MHz, DMSO-$d_6$): δ 11.67 (s, 1H), 9.29 (d, 1H), 7.86-7.80 (m, 3H), 7.60-7.58 (dd, 2H), 7.53-7.49 (m, 1H), 7.30 (d, 1H), 7.25-7.21 (m, 1H), 6.43 (s, 1H), 5.08 (s, 2H), 4.99-4.93 (m, 1H), 3.54 (dd, 1H), 3.24 (q, 2H), 3.22 (s, 3H)

Example 126

Preparation of S-(2-Benzoyloxyl)ethyl 2-(4-chlorobenzoylamino)-3-(2-oxo-1,2-dihydroquinolin-4-yl)thiopropionate

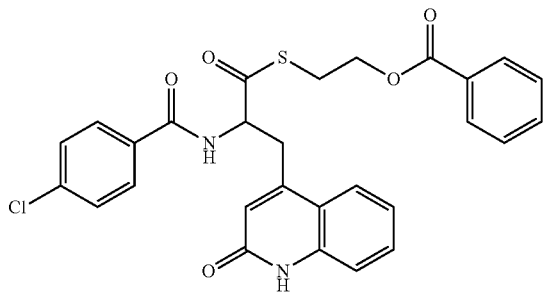 [SMILES: O=C(NC(Cc1cc(=O)[nH]c2ccccc12)C(=O)SCCOC(=O)c1ccccc1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.43 g (1.5 eq, 7.76 mmol) of 2-chloroethyl benzoate were reacted to afford the title compound as a white solid (0.9 g).

$^1$H NMR (400 MHz, DMSO-$d_6$): δ 11.66 (s, 1H), 9.27 (d, 1H), 7.96 (s, 1H), 7.94 (d, 1H), 7.84 (s, 1H), 7.82 (s, 1H), 7.72 (d, 1H), 7.66 (t, 1H), 7.58 (s, 1H), 7.56 (s, 1H), 7.50 (q, 3H), 7.30 (d, 1H), 7.21 (t, 1H), 6.42 (s, 1H), 4.95 (m, 1H), 4.41 (t, 2H), 3.49 (dd, 1H), 3.34-3.30 (m, 2H), 3.19 (q, 1H)

Example 127

Preparation of S-(2-Methylsufanyl)ethyl 2-(4-chlorobenzoylamino)-3-(2-oxo-1,2-dihydroquinolin-4-yl)propionate

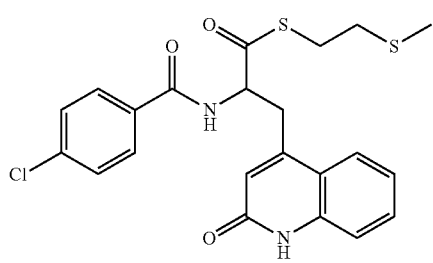 [SMILES: CSCCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 0.86 g (1.5 eq, 7.76 mmol) of 2-chloroethyl methyl sulfide were reacted to afford the title compound as a white solid (0.8 g).

$^1$H NMR (400 MHz, DMSO-$d_6$): δ 11.65 (s, 1H), 9.25 (d, 1H), 7.86 (t, 1H), 7.84 (t, 1H), 7.79 (d, 1H), 7.60 (t, 1H), 7.58 (t, 1H), 7.53-7.49 (m, 1H), 7.31 (dd, 1H), 7.25-7.21 (m, 1H), 6.43 (s, 1H), 4.97-4.92 (m, 1H), 3.53 (dd, 1H), 3.21 (q, 1H), 3.12-3.08 (m, 2H), 2.65-2.49 (m, 2H), 2.11 (s, 3H)

Example 128

Preparation of S-(2-Phenylsufanyl)ethyl 2-(4-chlorobenzoylamino)-3-(2-oxo-1,2-dihydroquinolin-4-yl)propionate

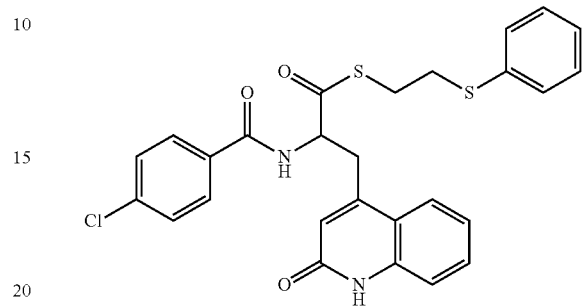

According to Experiment Prototocol C, 2.0 g (5.17 mmol) of 2-(4-chlorobenzoylamino)-3-(2-oxo-1,2-dihydroquinolin-4-yl)thiopropionic acid and 1.68 g (1.5 eq, 7.76 mmol) of 2-bromoethyl phenyl sulfide were reacted to afford the title compound as a white solid (0.6 g).

$^1$H NMR (400 MHz, DMSO-$d_6$): δ 11.66 (s, 1H), 9.26 (d, 1H), 7.86 (s, 1H), 7.84 (s, 1H), 7.79 (d, 1H), 7.60 (s, 1H), 7.58 (s, 1H), 7.51 (t, 1H), 7.39 (dd, 2H), 7.33 (q, 3H), 7.25-7.21 (m, 2H), 6.43 (s, 1H), 4.98-4.93 (m, 1H), 3.52 (dd, 1H), 3.22 (q, 1H), 3.15-3.07 (m, 4H)

Example 129

Preparation of S-(2-Benzenesulfonyl)ethyl 2-(4-chlorobenzoylamino)-3-(2-oxo-1,2-dihydroquinolin-4-yl)propionate

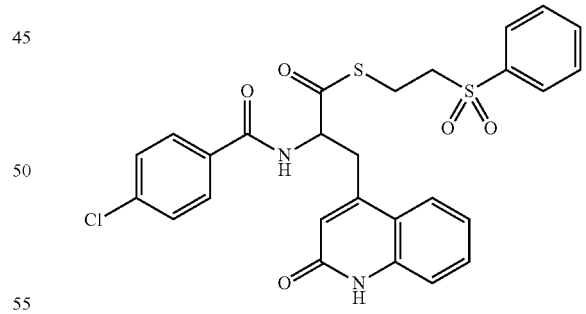

According to Experiment Prototocol C, 2.0 g (5.17 mmol) of 2-(4-chlorobenzoylamino)-3-(2-oxo-1,2-dihydroquinolin-4-yl)thiopropionic acid and 1.68 g (1.5 eq, 7.76 mmol) of 2-chloroethyl phenyl sulfone were reacted to afford the title compound as a white solid (0.6 g).

$^1$H NMR (400 MHz, DMSO-$d_6$): δ 11.65 (s, 1H), 9.22 (d, 1H), 7.92 (t, 2H), 7.83-7.79 (m, 2H), 7.76 (d, 2H), 7.70-7.64 (m, 2H), 7.62-7.58 (m, 2H), 7.53-7.47 (m, 1H), 7.31 (d, 1H), 7.21 (t, 1H), 6.39 (s, 1H), 4.92-4.86 (m, 1H), 3.57-3.47 (m, 3H), 3.17 (q, 1H), 3.07-3.02 (m, 2H)

Example 130

Preparation of S-(2-Oxobutyl)2-(4-chlorobenzoylamino)-3-(2-oxo-1,2-dihydroquinolin-4-yl)thiopropionate

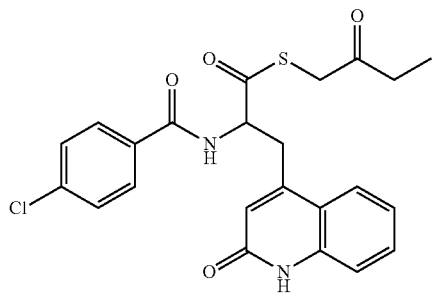

According to Experiment Prototocol C, 2.0 g (5.17 mmol) of 2-(4-chlorobenzoylamino)-3-(2-oxo-1,2-dihydroquinolin-4-yl)thiopropionic acid and 0.82 g (1.5 eq, 7.76 mmol) of 1-chloro-2-butanone were reacted to afford the title compound as a white solid (1.1 g).

$^1$H NMR (400 MHz, DMSO-$d_6$): δ 11.65 (s, 1H), 9.32 (d, 1H), 7.87 (s, 1H), 7.85 (s, 1H), 7.77 (d, 1H), 7.61 (s, 1H), 7.59 (s, 1H), 7.51 (t, 1H), 7.30 (d, 1H), 7.23 (t, 1H), 6.44 (s, 1H), 4.96-4.93 (m, 1H), 3.91 (d, 2H), 3.52 (dd, 1H), 3.20 (q, 1H), 2.58 (q, 2H), 0.96 (t, 3H)

Example 131

Preparation of S-(2-Ureido)ethyl 2-(4-chlorobenzoylamino)-3-(2-oxo-1,2-dihydroquinolin-4-yl)thiopropionate

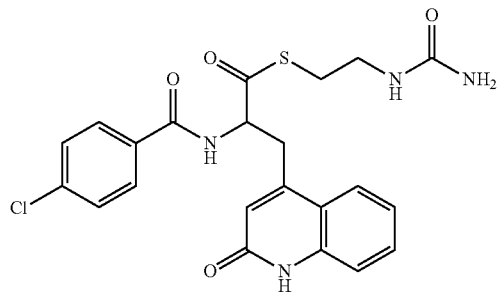 [SMILES: NC(=O)NCCSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 0.95 g (1.5 eq, 7.76 mmol) of 2-chloroethylurea were reacted to afford the title compound as a white solid (1.1 g).

$^1$H NMR (400 MHz, DMSO-$d_6$): δ 11.66 (s, 1H), 9.24 (d, 1H), 7.86 (s, 1H), 7.84 (s, 1H), 7.81 (t, 1H), 7.60 (s, 1H), 7.58 (s, 1H), 7.57 (d, 1H), 7.51 (t, 1H), 7.30 (d, 1H), 7.24 (t, 1H), 6.43 (s, 1H), 6.14 (t, 1H), 5.51 (s, 2H), 4.96-4.92 (m, 1H), 3.54 (dd, 1H), 3.21 (q, 1H), 3.17-3.11 (m, 2H), 2.93 (t, 2H)

Example 132

Preparation of N,N-Dimethyl S-[2-(4-chlorobenzoylamino)-3-(2-oxo-1,2-dihydroquinolin-4-yl)]thiocarbamate

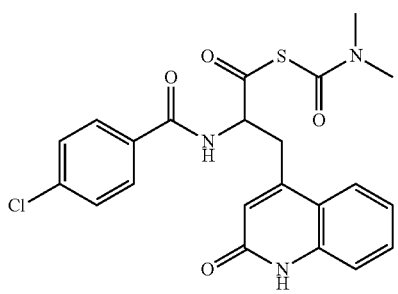 [SMILES: CN(C)C(=O)SC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 0.83 g (1.5 eq, 7.76 mmol) of dimethyl carbamyl chloride were reacted to afford the title compound as a white solid (1.2 g).

$^1$H NMR (400 MHz, DMSO-$d_6$): δ 11.61 (s, 1H), 8.95 (d, 1H), 7.89 (d, 1H), 7.86 (s, 1H), 7.84 (s, 1H), 7.53-7.47 (m, 3H), 7.29 (d, 1H), 7.21 (t, 1H), 6.44 (s, 1H), 5.28-5.22 (m, 1H), 3.28 (dd, 1H), 3.19 (q, 1H), 2.96 (s, 3H), 2.84 (s, 3H)

Example 133

Preparation of S-Allyl 2-(4-chlorobenzoylamino)-3-(2-oxo-1,2-dihydroquinolin-4-yl)thiopropionate

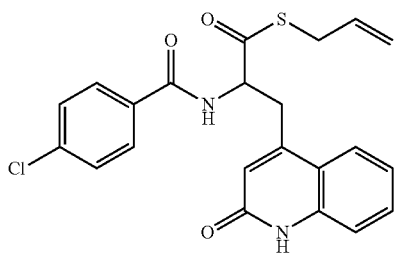

According to Experiment Prototocol C, 2.0 g (5.17 mmol) of 2-(4-chlorobenzoylamino)-3-(2-oxo-1,2-dihydroquinolin-4-yl)thiopropionic acid and 0.94 g (1.5 eq, 7.76 mmol) of allylbromide were reacted to afford the title compound as a white solid (1.2 g).

$^1$H NMR (700 MHz, DMSO-$d_6$): δ 11.67 (s, 1H), 9.26 (d, 1H), 7.86-7.82 (m, 2H), 7.79 (d, 1H), 7.64-7.58 (m, 2H), 7.53-7.49 (m, 1H), 7.32-7.30 (dd, 1H), 7.26-7.22 (m, 1H), 6.43 (s, 1H), 5.84-5.74 (m, 1H), 5.29-5.24 (m, 1H), 5.12-5.09 (tt, 1H), 4.97-4.92 (m, 1H), 3.57-3.52 (m, 3H), 3.21 (q, 2H)

Example 134

Preparation of S-But-2-enyl 2-(4-chlorobenzoylamino)-3-(2-oxo-1,2-dihydroquinolin-4-yl)thiopropionate

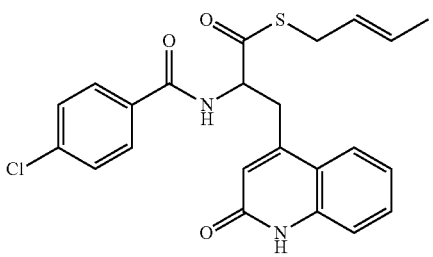 [SMILES: C/C=C/CSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.05 g (1.5 eq, 7.76 mmol) of 1-bromo-2-butene were reacted to afford the title compound as a white solid (1.0 g).

$^1$H NMR (400 MHz, DMSO-$d_6$): δ 11.66 (s, 1H), 9.23 (d, 1H), 7.86-7.79 (m, 3H), 7.60 (t, 1H), 7.58 (t, 1H), 7.53-7.49 (m, 1H), 7.31 (dd, 1H), 7.26-7.22 (m, 1H), 6.42 (s, 1H), 5.71-5.66 (m, 1H), 5.46-5.38 (m, 1H), 4.97-4.91 (m, 1H), 3.58-3.50 (m, 3H), 3.20 (q, 2H), 1.65 (t, 3H)

Example 135

Preparation of S-Prop-2-ynyl 2-(4-chlorobenzoylamino)-3-(2-oxo-1,2-dihydroquinolin-4-yl)thiopropionate

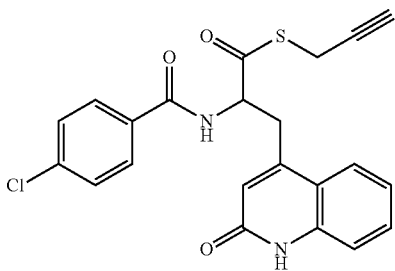

According to Experiment Prototocol C, 2.0 g (5.17 mmol) of 2-(4-chlorobenzoylamino)-3-(2-oxo-1,2-dihydroquinolin-4-yl)thiopropionic acid and 0.92 g (1.5 eq, 7.76 mmol) of progargyl bromide were reacted to afford the title compound as a white solid (1.0 g).

$^1$H NMR (400 MHz, DMSO-$d_6$): δ 11.65 (s, 1H), 9.29 (d, 1H), 7.86 (t, 1H), 7.83 (t, 1H), 7.79 (d, 1H), 7.60 (t, 1H), 7.58 (t, 1H), 7.53-7.49 (m, 1H), 7.30 (d, 1H), 7.25-7.21 (m, 1H), 6.42 (s, 1H), 4.99-4.96 (m, 1H), 3.72 (d, 1H), 3.53 (dd, 3H), 3.32 (s, 2H), 3.21 (q, 2H)

Example 136

Preparation of S-cyclopentyl 2-(4-chlorobenzoylamino)-3-(2-oxo-1,2-dihydroquinolin-4-yl)thiopropionate

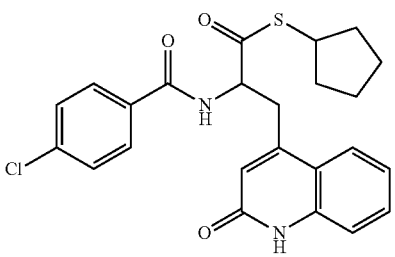

According to Experiment Prototocol C, 2.0 g (5.17 mmol) of 2-(4-chlorobenzoylamino)-3-(2-oxo-1,2-dihydroquinolin-4-yl)thiopropionic acid and 0.81 g (1.5 eq, 7.76 mmol) of chlorocyclopentane were reacted to afford the title compound as a white solid (0.7 g).

$^1$H NMR (400 MHz, DMSO-$d_6$): δ 11.64 (s, 1H), 9.19 (d, 1H), 7.85 (d, 1H), 7.83 (d, 1H), 7.79 (d, 1H), 7.59 (d, 1H), 7.58 (d, 1H), 7.53-7.49 (m, 1H), 7.30 (d, 1H), 7.25-7.21 (m, 1H), 6.42 (s, 1H), 4.94-4.88 (m, 1H), 3.65-3.62 (m, 1H), 3.52 (dd, 1H), 3.19 (q, 2H), 2.09-2.02 (m, 2H), 1.64-1.55 (m, 4H), 1.49 (m, 2H)

Example 137

Preparation of S-Cyclohexyl 2-(4-chlorobenzoylamino)-3-(2-oxo-1,2-dihydroquinolin-4-yl)thiopropionate

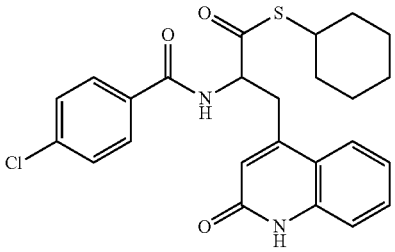

According to Experiment Prototocol C, 2.0 g (5.17 mmol) of 2-(4-chlorobenzoylamino)-3-(2-oxo-1,2-dihydroquinolin-4-yl)thiopropionic acid and 1.26 g (1.5 eq, 7.76 mmol) of bromocyclohexane were reacted to afford the title compound as a white solid (1.3 g).

$^1$H NMR (400 MHz, DMSO-$d_6$): δ 11.65 (s, 1H), 9.20 (d, 1H), 7.86 (s, 1H), 7.84 (s, 1H), 7.60 (s, 1H), 7.58 (s, 1H), 7.51 (t, 1H), 7.30 (d, 1H), 7.24 (t, 1H), 6.42 (s, 1H), 4.93-4.88 (m, 1H), 3.51 (m, 1H), 3.42 (m, 1H), 3.18 (q, 2H), 1.86-1.82 (m, 2H), 1.64-1.52 (m, 3H), 1.45-1.32 (m, 4H), 1.19 (m, 1H)

Example 138

Preparation of S-Cyclopropylmethyl 2-(4-chlorobenzoylamino)-3-(2-oxo-1,2-dihydroquinolin-4-yl)thiopropionate

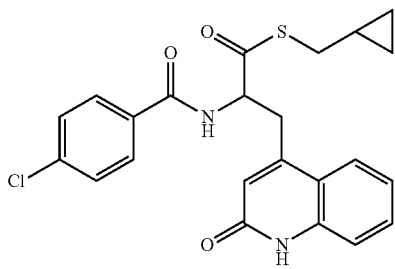 [SMILES: O=C(NC(Cc1cc(=O)[nH]c2ccccc12)C(=O)SCC1CC1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 0.70 g (1.5 eq, 7.76 mmol) of (chloromethyl)cyclopropane were reacted to afford the title compound as a white solid (1.1 g).

$^1$H NMR (400 MHz, DMSO-$d_6$): δ 11.66 (s, 1H), 9.24 (d, 1H), 7.88-7.84 (m, 2H), 7.80 (d, 1H), 7.61-7.58 (m, 2H), 7.53-7.49 (m, 1H), 7.30 (dd, 1H), 7.26-7.22 (m, 1H), 6.43 (s, 1H), 4.95 (m, 1H), 3.54 (dd, 1H), 3.20 (q, 2H), 0.98-0.94 (m, 1H), 0.53-0.48 (m, 2H), 0.25-0.24 (m, 2H)

Example 139

Preparation of S-Cyclobutylmethyl 2-(4-chlorobenzoylamino)-3-(2-oxo-1,2-dihydroquinolin-4-yl)thiopropionate

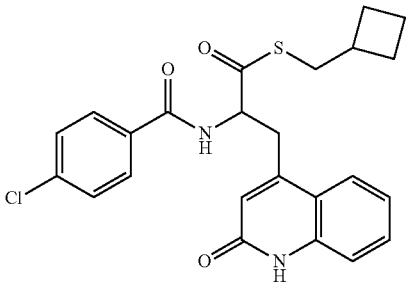 [SMILES: O=C(NC(Cc1cc(=O)[nH]c2ccccc12)C(=O)SCC1CCC1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.12 g (1.5 eq, 7.76 mmol) of (bromomethyl)cyclobutane were reacted to afford the title compound as a white solid (1.4 g).

$^1$H NMR (400 MHz, DMSO-$d_6$): δ 11.66 (s, 1H), 9.23 (d, 1H), 7.86-7.82 (m, 2H), 7.79 (d, 1H), 7.60-7.55 (m, 2H), 7.53-7.49 (m, 1H), 7.35-7.30 (m, 1H), 7.26-7.20 (m, 1H), 6.51 (s, 1H), 4.95-4.90 (m, 1H), 3.51 (dd, 1H), 3.20 (q, 1H), 2.89 (d, 2H), 2.46-2.38 (m, 1H), 2.03-1.96 (m, 2H), 1.83-1.71 (m, 2H), 1.68-1.66 (m, 2H)

Example 140

Preparation of S-Cyclohexylmethyl 2-(4-chlorobenzoylamino)-3-(2-oxo-1,2-dihydroquinolin-4-yl)thiopropionate

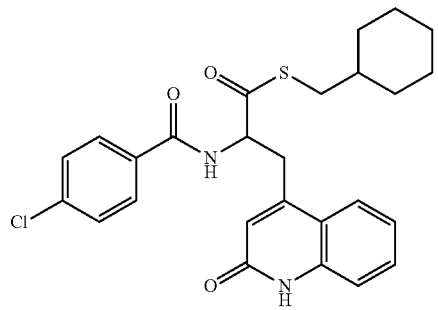

According to Experiment Prototocol C, 2.0 g (5.17 mmol) of 2-(4-chlorobenzoylamino)-3-(2-oxo-1,2-dihydroquinolin-4-yl)thiopropionic acid and 1.37 g (1.5 eq, 7.76 mmol) of (bromomethyl)cyclohexane were reacted to afford the title compound as a white solid (1.3 g).

$^1$H NMR (400 MHz, DMSO-$d_6$): δ 11.66 (s, 1H), 9.22 (d, 1H), 7.86-7.82 (m, 2H), 7.79 (d, 1H), 7.62-7.58 (m, 2H), 7.51 (t, 1H), 7.30 (d, 1H), 7.24 (t, 1H), 6.43 (s, 1H), 4.97-4.91 (m, 1H), 3.52 (dd, 1H), 3.20 (q, 1H), 2.78 (d, 2H), 1.67 (t, 4H), 1.41 (d, 1H), 1.40-1.34 (m, 3H), 1.22-1.16 (m, 2H)

Example 141

Preparation of S-(Cyclopent-3-enyl)methyl 2-(4-chlorobenzoylamino)-3-(2-oxo-1,2-dihydroquinolin-4-yl)thiopropionate

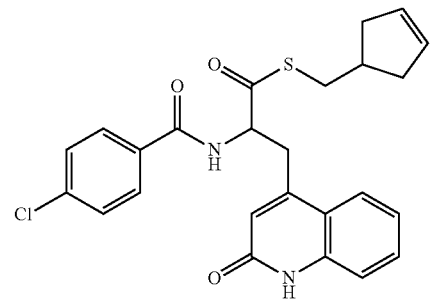

According to Experiment Prototocol D, 2.0 g (5.17 mmol) of 2-(4-chlorobenzoylamino)-3-(2-oxo-1,2-dihydroquinolin-4-yl)thiopropionic acid and 1.96 g (1.5 eq, 7.76 mmol) of (cyclopent-3-enyl)methyl toluenesulfonate were reacted to afford the title compound as a white solid (0.7 g).

$^1$H NMR (400 MHz, DMSO-$d_6$): δ 11.38 (s, 1H), 9.24 (d, 1H), 7.86-7.84 (m, 2H), 7.79 (d, 1H), 7.64-7.62 (m, 2H), 7.50 (t, 1H), 7.32 (d, 1H), 7.24 (t, 1H), 6.50 (s, 1H), 5.63 (s, 2H), 4.95-4.93 (m, 1H), 3.52 (dd, 1H), 3.21 (q, 1H), 2.93 (d, 2H), 2.46-2.43 (m, 3H), 2.00 (dd, 2H)

Example 142

Preparation of S-Oxiranylmethyl 2-(4-chlorobenzoylamino)-3-(2-oxo-1,2-dihydroquinolin-4-yl)thiopropionate

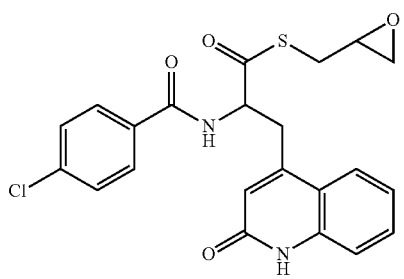

According to Experiment Prototocol C, 2.0 g (5.17 mmol) of 2-(4-chlorobenzoylamino)-3-(2-oxo-1,2-dihydroquinolin-4-yl)thiopropionic acid and 0.72 g (1.5 eq, 7.76 mmol) of 2-(chloromethyl)oxirane were reacted to afford the title compound as a white solid (1.0 g).

$^1$H NMR (400 MHz, DMSO-d$_6$): δ 11.67 (s, 1H), 9.06 (d, 1H), 7.83-7.72 (m, 3H), 7.57-7.41 (m, 3H), 7.31 (dd, 1H), 7.24-7.20 (m, 1H), 6.46 (s, 1H), 5.24-5.20 (m, 1H), 4.96 (m, 1H), 4.81-4.76 (m, 1H), 3.87-3.84 (m, 2H), 3.45 (dd, 1H), 2.86 (q, 2H)

Example 143

Preparation of S-(Tetrahydrofuran-2-yl)methyl 2-(4-chlorobenzoylamino)-3-(2-oxo-1,2-dihydroquinolin-4-yl)thiopropionate

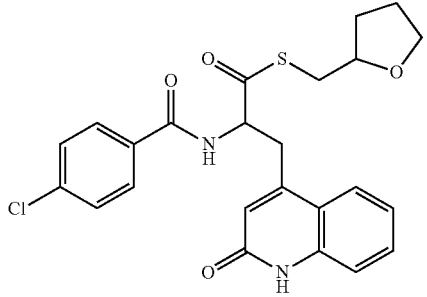 [SMILES: O=C(NC(Cc1cc(=O)[nH]c2ccccc12)C(=O)SCC1CCCO1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 0.94 g (1.5 eq, 7.76 mmol) of tetrahydrofurfuryl chloride were reacted to afford the title compound as a white solid (1.3 g).

$^1$H NMR (400 MHz, DMSO-d$_6$): δ 11.65 (s, 1H), 9.25 (d, 1H), 7.86 (s, 1H), 7.84 (s, 1H), 7.79 (d, 1H), 7.64 (s, 1H), 7.61 (s, 1H), 7.51 (t, 1H), 7.30 (d, 1H), 7.24 (t, 1H), 6.43 (s, 1H), 4.97-4.92 (m, 1H), 3.89 (s, 1H), 3.77 (t, 1H), 3.61 (t, 1H), 3.52 (dd, 1H), 3.18 (q, 2H), 3.09-2.98 (m, 2H), 1.97-1.89 (m, 1H), 1.87-1.78 (m, 2H), 1.54-1.48 (m, 1H)

Example 144

Preparation of S-(2-Pyrrolidin-1-yl)ethyl 2-(4-chlorobenzoylamino)-3-(2-oxo-1,2-dihydroquinolin-4-yl)thiopropionate

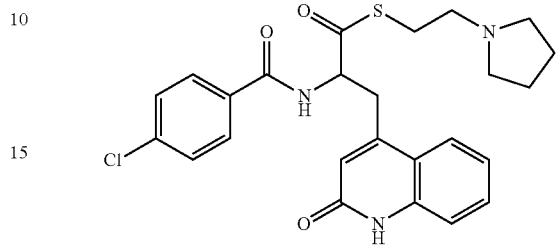

According to Experiment Prototocol D, 2.0 g (5.17 mmol) of 2-(4-chlorobenzoylamino)-3-(2-oxo-1,2-dihydroquinolin-4-yl)thiopropionic acid and 1.50 g (1.5 eq, 7.76 mmol) of 2-pyrrolidine ethylmethanesulfonate were reacted to afford the title compound as a white solid (0.6 g).

$^1$H NMR (400 MHz, DMSO-d$_6$): δ 11.65 (s, 1H), 9.25 (d, 1H), 7.87 (s, 1H), 7.85 (s, 1H), 7.81 (t, 1H), 7.61 (s, 1H), 7.60 (s, 1H), 7.58-7.47 (m, 1H), 7.30 (d, 1H), 7.23 (t, 1H), 6.43 (s, 1H), 4.96-4.91 (m, 1H), 3.53 (dd, 1H), 3.21 (q, 2H), 3.01 (t, 2H), 2.62-2.50 (m, 6H), 1.68 (s, 4H)

Example 145

Preparation of S-[2-(1-Methylpyrrolidin-2-yl)]ethyl 2-(4-chlorobenzoylamino)-3-(2-oxo-1,2-dihydroquinolin-4-yl)thiopropionate

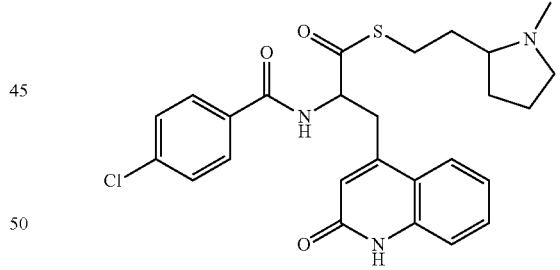

According to Experiment Prototocol D, 2.0 g (5.17 mmol) of 2-(4-chlorobenzoylamino)-3-(2-oxo-1,2-dihydroquinolin-4-yl)thiopropionic acid and 1.61 g (1.5 eq, 7.76 mmol) of 1-methyl-2-pyrrolidine ethylmethanesulfonate were reacted to afford the title compound as a white solid (0.4 g).

$^1$H NMR (400 MHz, DMSO-d$_6$): δ 11.64 (s, 1H), 9.22 (d, 1H), 7.86 (s, 1H), 7.84 (d, 1H), 7.81 (t, 1H), 7.59 (d, 1H), 7.58 (d, 1H), 7.52-7.48 (m, 1H), 7.35-7.30 (m, 1H), 7.25-7.18 (t, 1H), 6.43 (s, 1H), 4.93 (m, 1H), 3.52 (dd, 1H), 3.20 (q, 2H), 2.94-2.80 (m, 2H), 2.19 (s, 3H), 2.09-2.05 (m, 2H), 1.90-1.85 (m, 1H), 1.77-1.75 (m, 1H), 1.64-1.58 (m, 2H), 1.50-1.45 (m, 2H)

Example 146

Preparation of S-([1,3]-Dioxolan-2-yl)methyl 2-(4-chlorobenzoylamino)-3-(2-oxo-1,2-dihydroquinolin-4-yl)thiopropionate

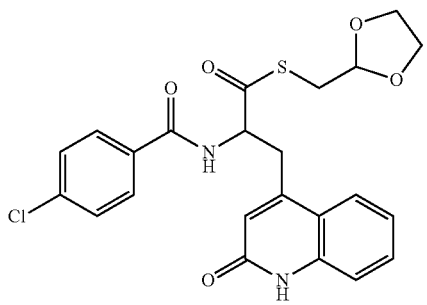 [SMILES: O=C(NC(Cc1cc(=O)[nH]c2ccccc12)C(=O)SCC1OCCO1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.30 g (1.5 eq, 7.76 mmol) of 2-bromomethyl-1,3-dioxolane were reacted to afford the title compound as a white solid (0.8 g).

$^1$H NMR (400 MHz, DMSO-$d_6$): δ 11.65 (s, 1H), 9.27 (d, 1H), 7.86 (s, 1H), 7.84 (s, 1H), 7.68 (d, 1H), 7.61 (s, 1H), 7.59 (s, 1H), 7.53-7.48 (m, 1H), 7.32 (d, 1H), 7.24 (t, 1H), 6.43 (s, 1H), 4.97-4.95 (m, 1H), 4.33 (s, 1H), 3.92-3.89 (m, 2H), 3.82-3.78 (m, 2H), 3.53 (dd, 1H), 3.21 (q, 2H), 3.13 (d, 2H)

Example 147

Preparation of S-(2-[1,3]-Dioxolan-2-yl)ethyl 2-(4-chlorobenzoylamino)-3-(2-oxo-1,2-dihydroquinolin-4-yl)thiopropionate

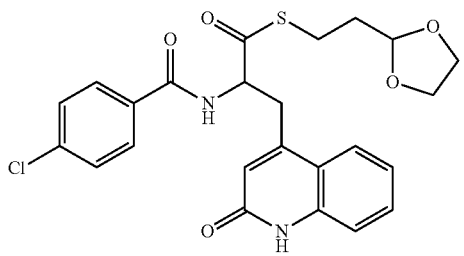

According to Experiment Prototocol C, 2.0 g (5.17 mmol) of 2-(4-chlorobenzoylamino)-3-(2-oxo-1,2-dihydroquinolin-4-yl)thiopropionic acid and 1.40 g (1.5 eq, 7.76 mmol) of 2-(2-bromoethyl)-1,3-dioxolane were reacted to afford the title compound as a white solid (0.8 g).

$^1$H NMR (400 MHz, DMSO-$d_6$): δ 11.65 (s, 1H), 9.23 (d, 1H), 7.86-7.80 (m, 3H), 7.61-7.55 (m, 2H), 7.53-7.49 (m, 1H), 7.31 (dd, 1H), 7.25-7.21 (m, 1H), 6.43 (s, 1H), 4.93-4.91 (m, 1H), 4.84 (t, 1H), 3.91-3.85 (m, 2H), 3.79-3.74 (m, 2H), 3.53 (dd, 1H), 3.20 (q, 2H), 2.91 (t, 2H), 1.86-1.82 (m, 2H)

Example 148

Preparation of S-(2-Piperidin-1-yl)ethyl 2-(4-chlorobenzoylamino)-3-(2-oxo-1,2-dihydroquinolin-4-yl)thiopropionate

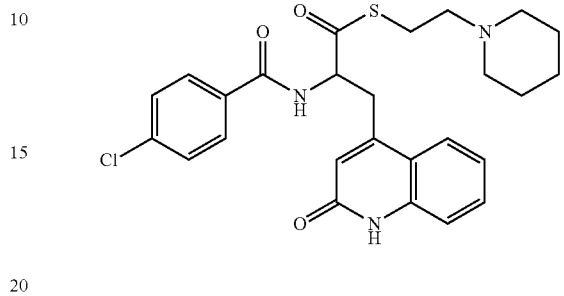

According to Experiment Prototocol D, 2.0 g (5.17 mmol) of 2-(4-chlorobenzoylamino)-3-(2-oxo-1,2-dihydroquinolin-4-yl)thiopropionic acid and 1.43 g (1.5 eq, 7.76 mmol) of 1-(2-chloroethyl)piperidine HCl were reacted to afford the title compound as a white solid (0.9 g).

$^1$H NMR (400 MHz, DMSO-$d_6$): δ 11.64 (s, 1H), 9.27 (d, 1H), 7.87-7.79 (m, 3H), 7.58-7.48 (m, 3H), 7.31 (d, 1H), 7.21 (t, 1H), 6.45 (s, 1H), 4.93 (m, 1H), 3.52 (dd, 1H), 3.21 (q, 2H), 3.05 (t, 2H), 2.74-2.67 (m, 2H), 2.54 (br-s, 4H), 1.52-1.44 (m, 4H), 1.39-1.34 (m, 2H)

Example 149

Preparation of S-(1-Methylpiperidin-2-yl)methyl 2-(4-chlorobenzoylamino)-3-(2-oxo-1,2-dihydroquinolin-4-yl)thiopropionate

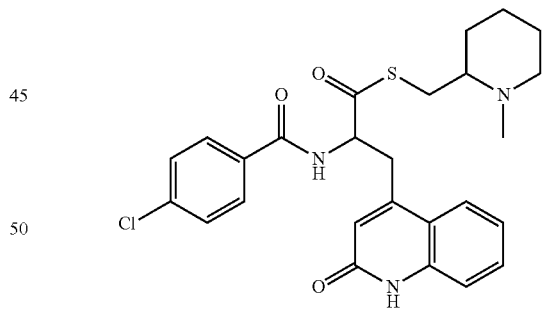

According to Experiment Prototocol D, 2.0 g (5.17 mmol) of 2-(4-chlorobenzoylamino)-3-(2-oxo-1,2-dihydroquinolin-4-yl)thiopropionic acid and 1.61 g (1.5 eq, 7.76 mmol) of 1-methyl-2-piperidinemethyl methanesulfonate were reacted to afford the title compound as a white solid (0.4 g).

$^1$H NMR (400 MHz, DMSO-$d_6$): δ 11.64 (s, 1H), 9.24 (d, 1H), 7.87 (s, 1H), 7.85 (s, 1H), 7.81 (t, 1H), 7.62 (s, 1H), 7.61 (s, 1H), 7.51 (t, 1H), 7.30 (d, 1H), 7.24 (t, 1H), 6.43 (s, 1H), 4.95-4.92 (m, 1H), 3.52 (dd, 1H), 3.32 (br-s, 2H), 3.21 (q, 2H), 3.13-3.06 (m, 1H), 2.74-2.71 (m, 1H), 2.15-2.02 (m, 4H), 2.02-1.97 (m, 1H), 1.65-1.47 (m, 4H), 1.24-1.16 (m, 2H)

Example 150

Preparation of S-{4-[4-(4-Chlorophenyl)piperazin-1-yl]-butyl}2-(4-chlorobenzoylamino)-3-(2-oxo-1,2-dihydroquinolin-4-yl)propionate

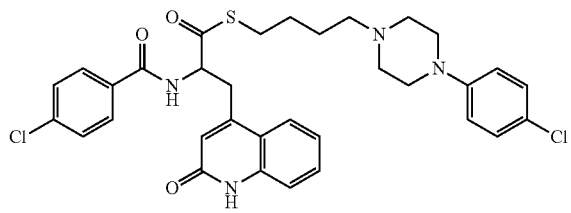 [SMILES: O=C(NC(Cc1cc(=O)[nH]c2ccccc12)C(=O)SCCCCN1CCN(c2ccc(Cl)cc2)CC1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 2.57 g (1.5 eq, 7.76 mmol) of [4-(4-chlorophenyl)piperazin-1-yl]butyl bromide were reacted to afford the title compound as a white solid (0.7 g).

$^1$H NMR (400 MHz, DMSO-d$_6$): δ 11.67 (s, 1H), 9.24 (d, 1H), 7.86 (s, 1H), 7.84 (s, 1H), 7.80 (d, 1H), 7.59 (s, 1H), 7.57 (s, 1H), 7.51 (t, 1H), 7.30 (d, 1H), 7.25-7.18 (m, 2H), 6.92 (s, 1H), 6.86 (d, 1H), 6.77 (d, 1H), 6.43 (s, 1H), 4.96-4.90 (m, 1H), 3.53 (dd, 3H), 3.21 (q, 1H), 3.14 (br-s, 4H), 2.91 (t, 2H), 2.33 (br-s, 2H), 1.73 (br-s, 2H)

Example 151

Preparation of S-(2-Morpholin-4-yl)ethyl 2-(4-chlorobenzoylamino)-3-(2-oxo-1,2-dihydroquinolin-4-yl)propionate

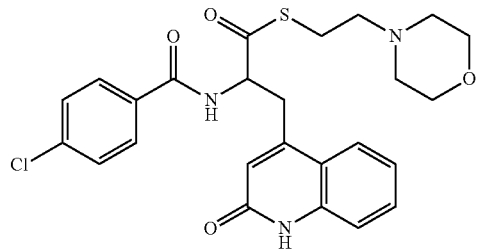 [SMILES: O=C(NC(Cc1cc(=O)[nH]c2ccccc12)C(=O)SCCN1CCOCC1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.44 g (1.5 eq, 7.76 mmol) of 4-(2-chloroethyl)morpholine HCl were reacted to afford the title compound as a white solid (0.9 g).

$^1$H NMR (400 MHz, DMSO-d$_6$): δ 11.65 (s, 1H), 9.24 (d, 1H), 7.87 (t, 1H), 7.84 (t, 1H), 7.79 (d, 1H), 7.60 (t, 1H), 7.58 (t, 1H), 7.53-7.49 (m, 1H), 7.30 (dd, 1H), 7.26-7.22 (m, 1H), 6.43 (s, 1H), 4.96-4.90 (m, 1H), 3.56-3.51 (m, 3H), 3.32 (s, 2H), 3.21 (q, 1H), 2.12 (t, 2H), 2.53 (t, 2H), 2.39 (br-s, 4H)

Example 152

Preparation of S-(Tetrahydropyran 2 yl)methyl 2-(4-chlorobenzoylamino)-3-(2-oxo-1,2-dihydroquinolin-4-yl)thiopropionate

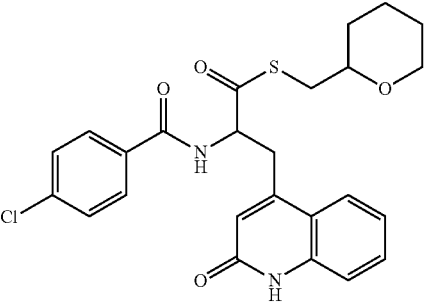

According to Experiment Prototocol C, 2.0 g (5.17 mmol) of 2-(4-chlorobenzoylamino)-3-(2-oxo-1,2-dihydroquinolin-4-yl)thiopropionic acid and 1.04 g (1.5 eq, 7.76 mmol) of 2-(chloromethyl)tetrahydro-2H-pyran were reacted to afford the title compound as a white solid (0.9 g).

$^1$H NMR (400 MHz, DMSO-d$_6$): δ 11.65 (s, 1H), 9.25 (dd, 1H), 7.87 (s, 1H), 7.85 (s, 1H), 7.79 (d, 1H), 7.61 (t, 1H), 7.59 (t, 1H), 7.54-7.49 (m, 1H), 7.29 (d, 1H), 7.24 (t, 1H), 6.43 (s, 1H), 4.97-4.92 (m, 1H), 3.84-2.81 (m, 1H), 3.53 (dd, 1H), 3.33-3.28 (m, 2H), 3.21 (q, 2H), 3.06-3.00 (m, 1H), 2.94-2.86 (m, 1H), 1.74 (br-d, 1H), 1.60 (d, 1H), 1.45-1.40 (m, 3H), 1.23-1.16 (m, 1H)

Example 153

Preparation of S-(2-[1,3]Dioxan-2-yl)ethyl 2-(4-chlorobenzoylamino)-3-(2-oxo-1,2-dihydroquinolin-4-yl)thiopropionate

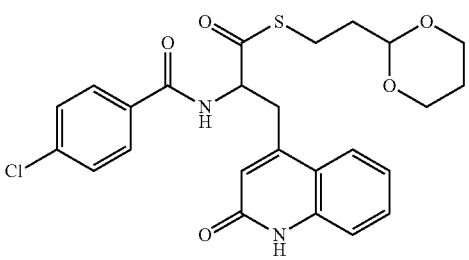 [SMILES: O=C(NC(Cc1cc(=O)[nH]c2ccccc12)C(=O)SCCC1OCCCO1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.51 g (1.5 eq, 7.76 mmol) of 2-(2-bromoethyl)-1,3-dioxane were reacted to afford the title compound as a white solid (0.8 g).

$^1$H NMR (400 MHz, DMSO-d$_6$): δ 11.65 (s, 1H), 9.23 (d, 1H), 7.85 (d, 1H), 7.83 (d, 1H), 7.79 (d, 1H), 7.59 (s, 1H), 7.58 (s, 1H), 7.53-7.49 (m, 1H), 7.30 (d, 1H), 7.23 (t, 1H), 6.42 (s, 1H), 4.93-4.92 (m, 1H), 4.56 (t, 1H), 4.04-3.97 (m, 2H), 3.72-3.66 (m, 2H), 3.52 (dd, 1H), 2.91-2.87 (m, 2H), 1.87-1.72 (m, 4H)

Example 154

Preparation of S-(2-Azepan-1-yl)ethyl 2-(4-chlorobenzoylamino)-3-(2-oxo-1,2-dihydroquinolin-4-yl)thiopropionate

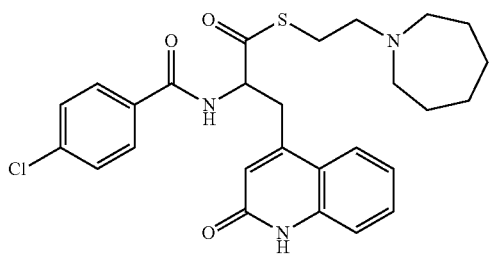 [SMILES: O=C(NC(Cc1cc(=O)[nH]c2ccccc12)C(=O)SCCN1CCCCCC1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.54 g (1.5 eq, 7.76 mmol) of 2-(hexamethyleneimino)ethyl chloride HCl were reacted to afford the title compound as a white solid (0.7 g).

$^1$H NMR (400 MHz, DMSO-$d_6$): δ 11.65 (s, 1H), 9.24 (d, 1H), 7.87 (s, 1H), 7.84 (s, 1H), 7.79 (d, 1H), 7.60 (s, 1H), 7.58 (s, 1H), 7.51 (t, 1H), 7.31 (d, 1H), 7.23 (t, 1H), 6.43 (s, 1H), 4.95-4.90 (m, 1H), 3.52 (dd, 1H), 3.21 (q, 2H), 2.98 (t, 2H), 2.67-2.62 (m, 6H), 1.56-1.51 (d, 8H)

Example 155

Preparation of S-(5-Methyl-2-oxo-[1,3]dioxol-4-yl)methyl 2-(4-chlorobenzoylamino)-3-(2-oxo-1,2-dihydroquinolin-4-yl)thiopropionate

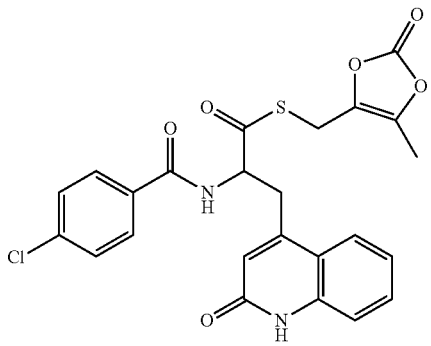

According to Experiment Prototocol C, 2.0 g (5.17 mmol) of 2-(4-chlorobenzoylamino)-3-(2-oxo-1,2-dihydroquinolin-4-yl)thiopropionic acid and 1.15 g (1.5 eq, 7.76 mmol) of 4-chloromethyl-5-methyl-1,3-dioxol-2-one were reacted to afford the title compound as a white solid (0.6 g).

$^1$H NMR (400 MHz, DMSO-$d_6$): δ 11.65 (s, 1H), 9.29 (d, 1H), 7.85 (s, 1H), 7.83 (s, 1H), 7.78 (d, 1H), 7.60 (s, 1H), 7.58 (s, 1H), 7.50 (t, 1H), 7.30 (d, 1H), 7.22 (t, 1H), 6.41 (s, 1H), 5.03-4.98 (m, 1H), 4.06 (s, 2H), 3.55 (dd, 1H), 3.22 (q, 1H), 2.15 (s, 3H)

Example 156

Preparation of S-Benzyl 2-(4-chlorobenzoylamino)-3-(2-oxo-1,2-dihydroquinolin-4-yl)thiopropionate

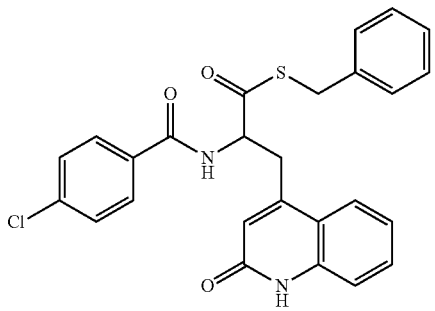 [SMILES: O=C(NC(Cc1cc(=O)[nH]c2ccccc12)C(=O)SCc1ccccc1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.33 g (1.5 eq, 7.76 mmol) of benzyl bromide were reacted to afford the title compound as a white solid (1.3 g).

$^1$H NMR (400 MHz, DMSO-$d_6$): δ 11.67 (s, 1H), 9.26 (d, 1H), 7.84-7.80 (m, 3H), 7.59-7.55 (m, 2H), 7.51 (t, 1H), 7.35-7.29 (m, 5H), 7.28-7.22 (m, 2H), 6.42 (s, 1H), 5.02-4.96 (m, 1H), 4.15 (q, 2H), 3.56 (dd, 1H), 3.20 (q, 2H)

Example 157

Preparation of S-Phenethyl 2-(4-chlorobenzoylamino)-3-(2-oxo-1,2-dihydroquinolin-4-yl)thiopropionate

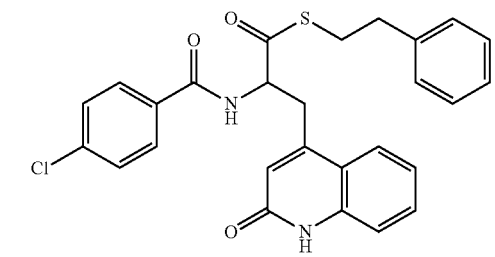 [SMILES: O=C(NC(Cc1cc(=O)[nH]c2ccccc12)C(=O)SCCc1ccccc1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.43 g (1.5 eq, 7.76 mmol) of phenethyl bromide were reacted to afford the title compound as a white solid (1.2 g).

$^1$H NMR (400 MHz, DMSO-$d_6$): δ 11.67 (s, 1H), 9.24 (d, 1H), 7.85-7.79 (m, 3H), 7.62-7.49 (m, 4H), 7.33-7.16 (m, 6H), 6.43 (s, 1H), 4.96-4.87 (m, 1H), 4.34 (s, 1H), 3.50 (dd, 1H), 3.21 (q, 2H), 3.13 (t, 1H), 2.90-2.73 (m, 2H)

Example 158

Preparation of S-(2-Methylbenzyl) 2-(4-chlorobenzoylamino)-3-(2-oxo-1,2-dihydroquinolin-4-yl)thiopropionate

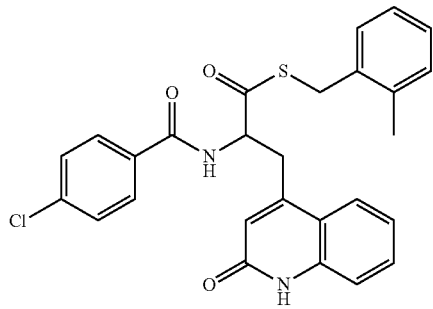 [SMILES: Cc1ccccc1CSC(=O)C(Cc1cc(=O)[nH]c2ccccc12)NC(=O)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.44 g (1.5 eq, 7.76 mmol) of 2-methylbenzyl bromide were reacted to afford the title compound as a white solid (1.2 g).

$^1$H NMR (400 MHz, DMSO-$d_6$): δ 11.65 (s, 1H), 9.23 (d, 1H), 7.83-7.79 (m, 3H), 7.58-7.54 (m, 2H), 7.51 (t, 1H), 7.30 (t, 2H), 7.26-7.19 (m, 1H), 7.17-7.12 (m, 3H), 6.42 (s, 1H), 5.02-4.96 (m, 1H), 4.16 (q, 2H), 3.56 (dd, 1H), 3.21 (q, 2H), 2.27 (s, 3H)

Example 159

Preparation of S-(3-Methylbenzyl) 2-(4-chlorobenzoylamino)-3-(2-oxo-1,2-dihydroquinolin-4-yl)thiopropionate

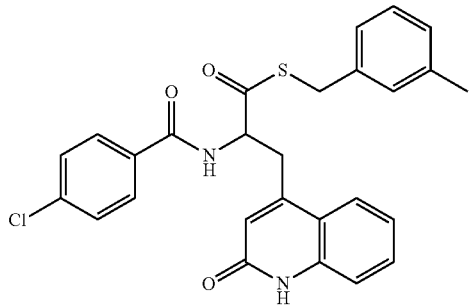 [SMILES: Cc1cccc(CSC(=O)C(Cc2cc(=O)[nH]c3ccccc23)NC(=O)c2ccc(Cl)cc2)c1]

According to Experiment Prototocol C, 2.0 g (5.17 mmol) of 2-(4-chlorobenzoylamino)-3-(2-oxo-1,2-dihydroquinolin-4-yl)thiopropionic acid and 1.44 g (1.5 eq, 7.76 mmol) of 3-methylbenzyl bromide were reacted to afford the title compound as a white solid (1.2 g).

$^1$H NMR (400 MHz, DMSO-$d_6$): δ 11.65 (s, 1H), 9.24 (d, 1H), 7.83-7.80 (m, 3H), 7.58-7.55 (m, 2H), 7.51 (t, 1H), 7.30 (d, 1H), 7.25-7.18 (m, 2H), 7.12-7.05 (m, 3H), 6.43 (s, 1H), 5.02-4.96 (m, 1H), 4.11 (q, 2H), 3.56 (dd, 1H), 3.20 (q, 2H), 2.27 (s, 3H)

Example 160

Preparation of S-(3,4-Dimethylbenzyl) 2-(4-chlorobenzoylamino)-3-(2-oxo-1,2-dihydroquinolin-4-yl)thiopropionate

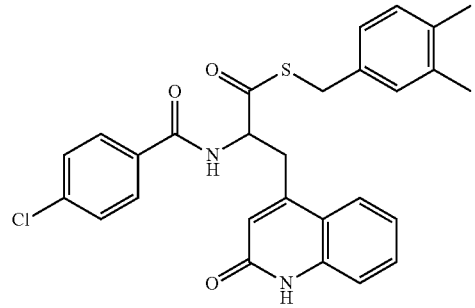

According to Experiment Prototocol C, 2.0 g (5.17 mmol) of 2-(4-chlorobenzoylamino)-3-(2-oxo-1,2-dihydroquinolin-4-yl)thiopropionic acid and 1.20 g (1.5 eq, 7.76 mmol) of 3,4-dimethylbenzyl chloride were reacted to afford the title compound as a white solid (0.9 g).

$^1$H NMR (400 MHz, DMSO-$d_6$): δ 11.65 (s, 1H), 9.23 (d, 1H), 7.87-7.79 (m, 3H), 7.58-7.55 (m, 2H), 7.51 (t, 1H), 7.30 (d, 1H), 7.24 (t, 1H), 7.13 (d, 1H), 7.08-7.02 (m, 2H), 6.42 (s, 1H), 5.00-4.96 (m, 1H), 4.17 (d, 1H), 4.08 (d, 1H), 3.56 (d, 1H), 3.20 (t, 1H), 2.22-2.09 (m, 6H)

Example 161

Preparation of S-(4-Fluorobenzyl) 2-(4-chlorobenzoylamino)-3-(2-oxo-1,2-dihydroquinolin-4-yl)thiopropionate

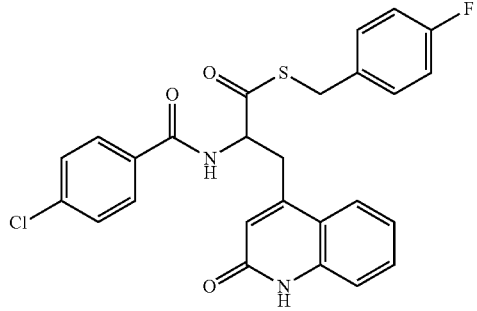 [SMILES: O=C(NC(Cc1cc(=O)[nH]c2ccccc12)C(=O)SCc1ccc(F)cc1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.47 g (1.5 eq, 7.76 mmol) of 4-fluorobenzyl bromide were reacted to afford the title compound as a white solid (1.1 g).

$^1$H NMR (400 MHz, DMSO-$d_6$): δ 11.64 (s, 1H), 9.25 (d, 1H), 7.84-7.72 (m, 3H), 7.74-7.72 (m, 2H), 7.68-7.64 (q, 1H), 7.59-7.48 (m, 4H), 7.33-7.30 (m, 1H), 7.24-7.19 (m, 1H), 6.41 (s, 1H), 5.03-4.97 (m, 1H), 4.21 (d, 2H), 3.55 (dd, 1H), 3.21 (q, 2H)

Example 162

Preparation of S-(2,5-Difluorobenzyl) 2-(4-chlorobenzoylamino)-3-(2-oxo-1,2-dihydroquinolin-4-yl)thiopropionate

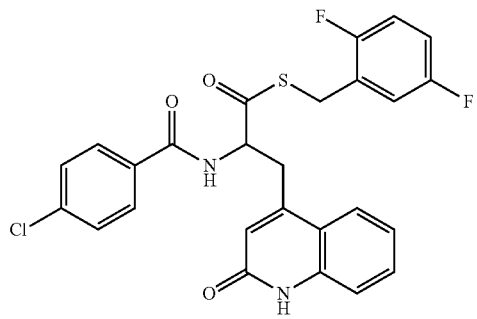

According to Experiment Prototocol C, 2.0 g (5.17 mmol) of 2-(4-chlorobenzoylamino)-3-(2-oxo-1,2-dihydroquinolin-4-yl)thiopropionic acid and 1.61 g (1.5 eq, 7.76 mmol) of 2,5-difluorobenzyl bromide were reacted to afford the title compound as a white solid (0.9 g).

$^1$H NMR (400 MHz, DMSO-$d_6$): δ 11.64 (s, 1H), 9.26 (d, 1H), 7.84-7.79 (m, 3H), 7.59-7.55 (m, 1H), 7.52-7.48 (m, 1H), 7.35-7.15 (m, 5H), 6.41 (s, 1H), 5.03-4.97 (m, 1H), 4.16 (q, 2H), 3.56 (dd, 1H), 3.20 (q, 1H)

Example 163

Preparation of S-(3-Chlorobenzyl) 2-(4-chlorobenzoylamino)-3-(2-oxo-1,2-dihydroquinolin-4-yl)thiopropionate

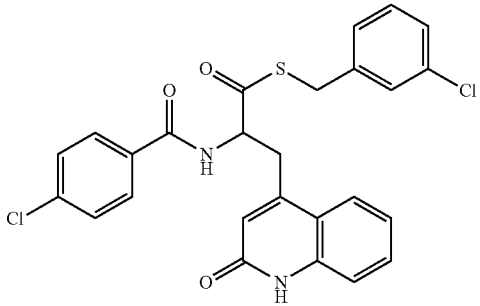 [SMILES: O=C(NC(Cc1cc(=O)[nH]c2ccccc12)C(=O)SCc1cccc(Cl)c1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.59 g (1.5 eq, 7.76 mmol) of 3-chlorobenzyl bromide were reacted to afford the title compound as a white solid (1.5 g).

$^1$H NMR (400 MHz, DMSO-$d_6$): δ 11.65 (s, 1H), 9.26 (d, 1H), 7.84-7.79 (m, 3H), 7.59 (s, 1H), 7.56 (s, 1H), 7.50 (t, 1H), 7.40 (s, 1H), 7.38-7.28 (m, 4H), 7.23 (t, 1H), 6.42 (s, 1H), 5.00 (m, 1H), 4.16 (d, 2H), 3.56 (dd, 1H), 3.20 (q, 1H)

Example 164

Preparation of S-(3,5-Dibromobenzyl) 2-(4-chlorobenzoylamino)-3-(2-oxo-1,2-dihydroquinolin-4-yl)thiopropionate

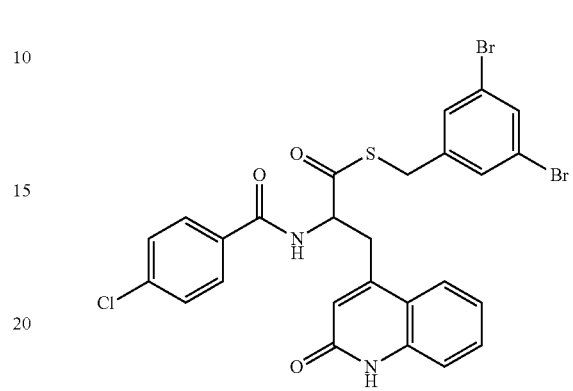

According to Experiment Prototocol C, 2.0 g (5.17 mmol) of 2-(4-chlorobenzoylamino)-3-(2-oxo-1,2-dihydroquinolin-4-yl)thiopropionic acid and 2.55 g (1.5 eq, 7.76 mmol) of 3,5-dibromobenzyl bromide were reacted to afford the title compound as a white solid (1.5 g).

$^1$H NMR (400 MHz, DMSO-$d_6$): δ 11.65 (s, 1H), 9.26 (d, 1H), 7.84-7.78 (m, 4H), 7.59-7.55 (m, 4H), 7.50 (t, 1H), 7.31 (t, 1H), 7.22 (t, 1H), 6.42 (s, 1H), 5.02-4.97 (m, 1H), 4.14 (q, 2H), 3.56 (dd, 1H), 3.20 (q, 1H)

Example 165

Preparation of S-(3-Cyanobenzyl) 2-(4-chlorobenzoylamino)-3-(2-oxo-1,2-dihydroquinolin-4-yl)thiopropionate

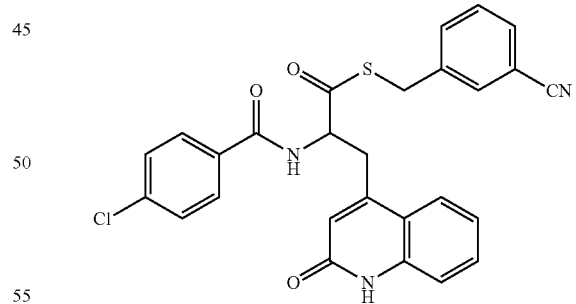

According to Experiment Prototocol C, 2.0 g (5.17 mmol) of 2-(4-chlorobenzoylamino)-3-(2-oxo-1,2-dihydroquinolin-4-yl)thiopropionic acid and 1.28 g (1.5 eq, 7.76 mmol) of 3-cyanobenzyl chloride were reacted to afford the title compound as a white solid (0.9 g).

$^1$H NMR (400 MHz, DMSO-$d_6$): δ 11.64 (s, 1H), 9.24 (d, 1H), 7.84-7.79 (m, 3H), 7.59-7.55 (m, 2H), 7.53-7.49 (m, 1H), 7.38-7.30 (m, 3H), 7.25 (t, 1H), 7.21-7.12 (m, 2H), 6.42 (s, 1H), 5.00-4.96 (m, 1H), 4.15 (d, 2H), 3.55 (dd, 1H), 3.20 (q, 2H)

Example 166

Preparation of S-(4-Cyanobenzyl)2-(4-chlorobenzoylamino)-3-(2-oxo-1,2-dihydroquinolin-4-yl)thiopropionate

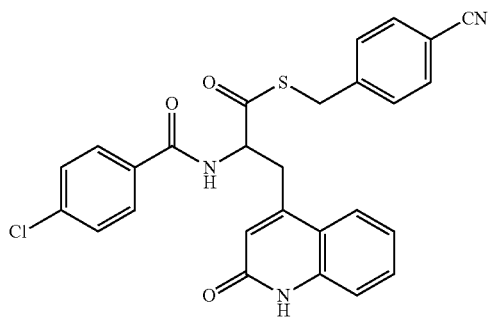 [SMILES: N#Cc1ccc(CSC(=O)C(Cc2cc(=O)[nH]c3ccccc23)NC(=O)c2ccc(Cl)cc2)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.28 g (1.5 eq, 7.76 mmol) of 4-cyanobenzyl chloride were reacted to afford the title compound as a white solid (1.0 g).

$^1$H NMR (400 MHz, DMSO-$d_6$): δ 11.65 (s, 1H), 9.27 (d, 1H), 7.84-7.78 (m, 5H), 7.59-7.55 (m, 2H), 7.53-7.49 (m, 3H), 7.30 (d, 1H), 7.22 (t, 1H), 6.40 (s, 1H), 5.02-4.96 (m, 1H), 4.23 (s, 2H), 3.54 (dd, 1H), 3.21 (q, 2H)

Example 167

Preparation of S-(3-Methoxybenzyl)2-(4-chlorobenzoylamino)-3-(2-oxo-1,2-dihydroquinolin-4-yl)thiopropionate

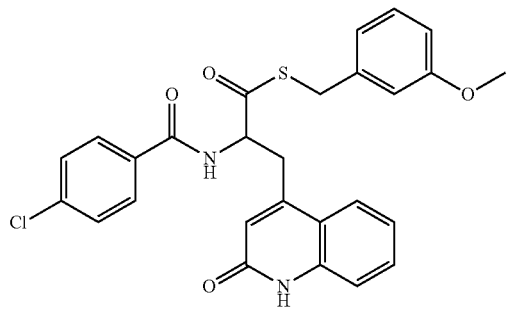 [SMILES: COc1cccc(CSC(=O)C(Cc2cc(=O)[nH]c3ccccc23)NC(=O)c2ccc(Cl)cc2)c1]

According to Experiment Prototocol C, 2.0 g (5.17 mmol) of 2-(4-chlorobenzoylamino)-3-(2-oxo-1,2-dihydroquinolin-4-yl)thiopropionic acid and 1.21 g (1.5 eq, 7.76 mmol) of 3-methoxybenzyl chloride were reacted to afford the title compound as a white solid (1.2 g).

$^1$H NMR (400 MHz, DMSO-$d_6$): δ 11.66 (s, 1H), 9.25 (d, 1H), 7.83-7.80 (m, 3H), 7.59 (s, 1H), 7.58 (s, 1H), 7.51 (t, 1H), 7.30 (d, 1H), 7.26-7.21 (m, 2H), 6.88 (d, 2H), 6.81 (d, 1H), 6.43 (s, 1H), 5.01-4.97 (m, 1H), 4.13 (q, 2H), 3.71 (s, 3H), 3.50 (dd, 1H), 3.21 (q, 2H)

Example 168

Preparation of S-(4-Methoxybenzyl)2-(4-chlorobenzoylamino)-3-(2-oxo-1,2-dihydroquinolin-4-yl)thiopropionate

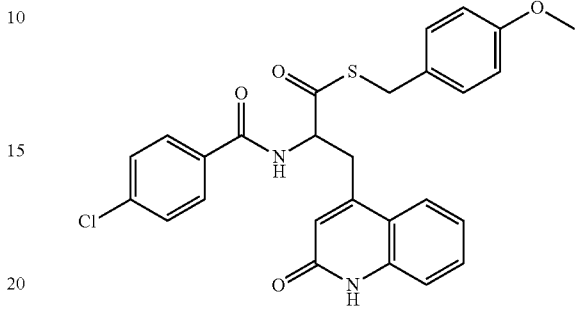

According to Experiment Prototocol C, 2.0 g (5.17 mmol) of 2-(4-chlorobenzoylamino)-3-(2-oxo-1,2-dihydroquinolin-4-yl)thiopropionic acid and 1.21 g (1.5 eq, 7.76 mmol) of 4-methoxybenzyl chloride were reacted to afford the title compound as a white solid (1.2 g).

$^1$H NMR (400 MHz, DMSO-$d_6$): δ 11.66 (s, 1H), 9.24 (d, 1H), 7.84-7.79 (m, 3H), 7.59-7.55 (m, 2H), 7.51 (t, 1H), 7.53-7.48 (m, 1H), 7.35-7.30 (m, 1H), 7.25-7.18 (m, 3H), 6.87-6.51 (dd, 2H), 6.42 (s, 1H), 5.00-4.94 (m, 1H), 4.10 (d, 2H), 3.73 (s, 3H), 3.56 (dd, 1H), 3.19 (q, 2H)

Example 169

Preparation of S-(3-Phenoxybenzyl) 2-(4-chlorobenzoylamino)-3-(2-oxo-1,2-dihydroquinolin-4-yl)thiopropionate

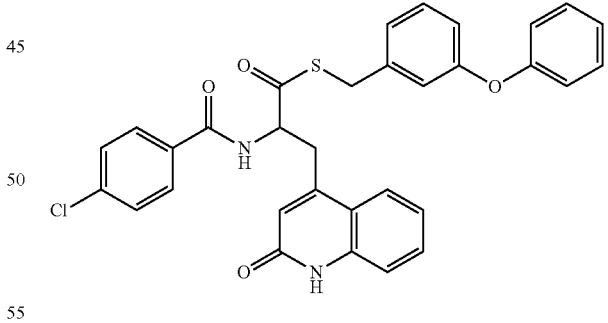

According to Experiment Prototocol C, 2.0 g (5.17 mmol) of 2-(4-chlorobenzoylamino)-3-(2-oxo-1,2-dihydroquinolin-4-yl)thiopropionic acid and 1.70 g (1.5 eq, 7.76 mmol) of 3-phenoxybenzyl chloride were reacted to afford the title compound as a white solid (1.2 g).

$^1$H NMR (400 MHz, DMSO-$d_6$): δ 11.66 (s, 1H), 9.28 (d, 1H), 7.84 (t, 1H), 7.82 (t, 1H), 7.78 (d, 1H), 7.59 (t, 1H), 7.56 (t, 1H), 7.53-7.48 (m, 1H), 7.40-7.36 (m, 2H), 7.32 (t, 2H), 7.25-7.21 (m, 1H), 7.16-7.11 (m, 1H), 7.10 (t, 1H), 7.02 (t, 1H), 6.99 (t, 2H), 6.89-6.86 (m, 1H), 6.43 (s, 1H), 5.01-4.95 (m, 1H), 4.14 (q, 2H), 3.53 (dd, 1H), 3.20 (q, 1H)

Example 170

Preparation of S-(3-Methoxycarbonyl)benzyl 2-(4-chlorobenzoylamino)-3-(2-oxo-1,2-dihydroquinolin-4-yl)thiopropionate

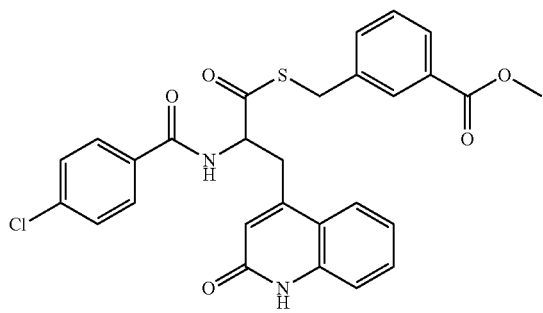 [SMILES: COC(=O)c1cccc(CSC(=O)C(Cc2cc(=O)[nH]c3ccccc23)NC(=O)c2ccc(Cl)cc2)c1]

According to Experiment Prototocol C, 2.0 g (5.17 mmol) of 2-(4-chlorobenzoylamino)-3-(2-oxo-1,2-dihydroquinolin-4-yl)thiopropionic acid and 1.78 g (1.5 eq, 7.76 mmol) of methyl(3-bromomethyl)benzoate were reacted to afford the title compound as a white solid (0.8 g).

$^1$H NMR (400 MHz, DMSO-$d_6$): δ 11.64 (s, 1H), 9.25 (d, 1H), 7.94 (t, 1H), 7.86-7.79 (m, 4H), 7.64-7.56 (m, 3H), 7.54-7.51 (m, 2H), 7.32-7.29 (m, 1H), 7.25-7.21 (m, 1H), 6.41 (s, 1H), 5.02-4.96 (m, 1H), 4.23 (d, 2H), 3.85 (s, 3H), 3.55 (dd, 1H), 3.32 (s, 2H), 3.20 (q, 2H)

Example 171

Preparation of S-(3-Phenyloxycarbonyl)benzyl 2-(4-chlorobenzoylamino)-3-(2-oxo-1,2-dihydroquinolin-4-yl)propionate

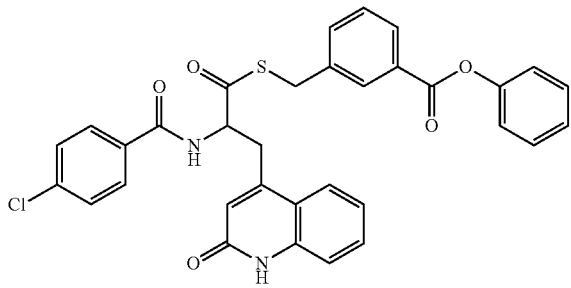

According to Experiment Prototocol A, 2.0 g (5.17 mmol) of 2-(4-chlorobenzoylamino)-3-(2-oxo-1,2-dihydroquinolin-4-yl)thiopropionic acid and 1.33 g (1.2 eq, 6.20 mmol) of phenyl 2-hydroxybenzoate were reacted to afford the title compound as a white solid (0.4 g).

$^1$H NMR (400 MHz, DMSO-$d_6$): δ 11.65 (s, 1H), 9.27 (d, 1H), 8.11 (s, 1H), 8.01 (d, 1H), 7.94 (t, 1H), 7.84-7.79 (m, 3H), 7.69 (d, 1H), 7.59-7.55 (m, 3H), 7.52-7.46 (m, 3H), 7.34-7.28 (m, 4H), 7.22 (t, 1H), 6.41 (s, 1H), 5.02-4.99 (m, 1H), 4.29 (s, 2H), 3.56 (dd, 1H), 3.21 (s, 1H)

Example 172

Preparation of S-[2-(4-Methylthiazol-5yl)ethyl]2-(4-chlorobenzoylamino)-3-(2-oxo-1,2-dihydroquinolin-4-yl)thiopropionate

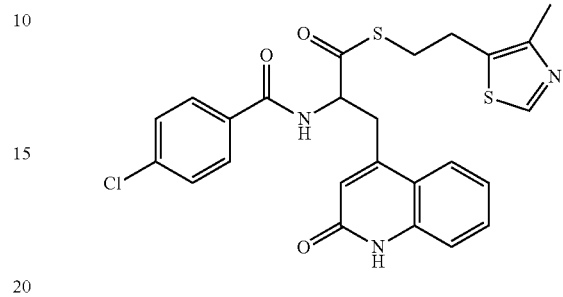

According to Experiment Prototocol B, 2.0 g (5.17 mmol) of 2-(4-chlorobenzoylamino)-3-(2-oxo-1,2-dihydroquinolin-4-yl)thiopropionic acid and 0.89 g (1.2 eq, 6.20 mmol) of 4-methyl-5-thiazole ethanol were reacted to afford the title compound as a white solid (0.5 g).

$^1$H NMR (400 MHz, DMSO-$d_6$): δ 11.67 (s, 1H), 9.25 (d, 1H), 8.84 (s, 1H), 7.83 (d, 2H), 7.79 (d, 1H), 7.64-7.55 (m, 2H), 7.51 (t, 1H), 7.30 (d, 1H), 7.24 (t, 1H), 6.43 (s, 1H), 4.95-4.90 (m, 1H), 3.50 (dd, 1H), 3.20 (q, 2H), 3.11-2.99 (m, 4H), 2.32 (s, 3H)

Example 173

Preparation of S-(Pyrimidin-2-yl)methyl 2-(4-chlorobenzoylamino)-3-(2-oxo-1,2-dihydroquinolin-4-yl)thiopropionate

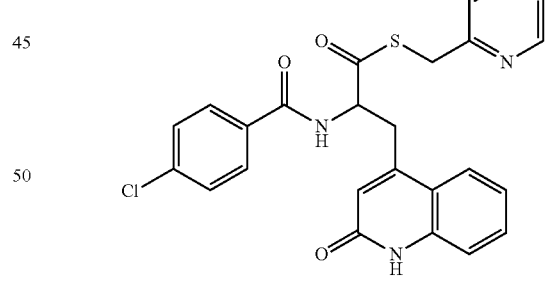

According to Experiment Prototocol C, 2.0 g (5.17 mmol) of 2-(4-chlorobenzoylamino)-3-(2-oxo-1,2-dihydroquinolin-4-yl)thiopropionic acid and 1.27 g (1.5 eq, 7.76 mmol) of 2-(chloromethyl)pyridine HCl are reacted to afford the title compound as a white solid (0.8 g).

$^1$H NMR (400 MHz, DMSO-$d_6$): δ 11.65 (s, 1H), 9.28 (d, 1H), 8.48 (d, 1H), 7.82-7.79 (dd, 2H), 7.78-7.74 (m, 1H), 7.59 (s, 1H), 7.57 (s, 1H), 7.51 (t, 1H), 7.40 (d, 1H), 7.32-7.21 (m, 3H), 6.42 (s, 1H), 5.02-4.97 (m, 1H), 4.26 (q, 2H), 3.56 (dd, 1H), 3.20 (q, 1H)

Example 174

Preparation of S-(Pyrimidin-3-yl)methyl 2-(4-chlorobenzoylamino)-3-(2-oxo-1,2-dihydroquinolin-4-yl)thiopropionate

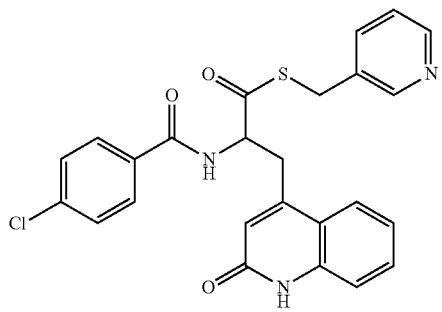

According to Experiment Prototocol C, 2.0 g (5.17 mmol) of 2-(4-chlorobenzoylamino)-3-(2-oxo-1,2-dihydroquinolin-4-yl)thiopropionic acid and 1.27 g (1.5 eq, 7.76 mmol) of 3-(chloromethyl)pyridine HCl were reacted to afford the title compound as a white solid (0.9 g).

$^1$H NMR (400 MHz, DMSO-d$_6$): δ 11.64 (s, 1H), 9.25 (d, 1H), 8.55 (d, 1H), 8.45 (dd, 1H), 7.83-7.79 (m, 3H), 7.73-7.70 (m, 1H), 7.59 (s, 1H), 7.56 (s, 1H), 7.50 (t, 1H), 7.36-7.30 (m, 3H), 7.25-7.21 (m, 1H), 6.42 (s, 1H), 5.02-4.97 (m, 1H), 4.18 (q, 2H), 3.55 (dd, 1H), 3.20 (q, 1H)

Example 175

Preparation of S-(3-Phenylallyl) 2-(4-chlorobenzoylamino)-3-(2-oxo-1,2-dihydroquinolin-4-yl)thiopropionate

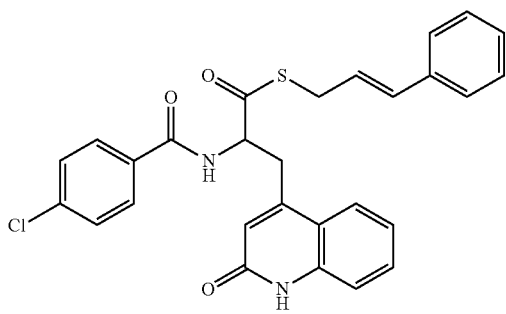 [SMILES: O=C(NC(Cc1cc(=O)[nH]c2ccccc12)C(=O)SC/C=C/c1ccccc1)c1ccc(Cl)cc1]

According to Experiment Prototocol C, 2.0 g (5.17 mmol) of 2-(4-chlorobenzoylamino)-3-(2-oxo-1,2-dihydroquinolin-4-yl)thiopropionic acid and 1.52 g (1.5 eq, 7.76 mmol) of cinnamyl bromide were reacted to afford the title compound as a white solid (1.3 g).

$^1$H NMR (400 MHz, DMSO-d$_6$): δ 11.66 (s, 1H), 9.26 (d, 1H), 7.86-7.80 (m, 3H), 7.59 (s, 1H), 7.55 (d, 1H), 7.51 (m, 1H), 7.42-7.40 (m, 2H), 7.34-7.31 (m, 3H), 7.26-7.21 (m, 2H), 6.62 (d, 1H), 6.44 (s, 1H), 6.28-6.23 (m, 1H), 4.99-4.98 (m, 1H), 3.74 (d, 2H), 3.57 (dd, 1H), 3.23 (q, 1H)

Example 176

Preparation of S-Ethoxy-3-oxopropyl 2-(4-chlorobenzoylamino)-3-(2-oxo-1,2-dihydroquinolin-4-yl)thiopropionate

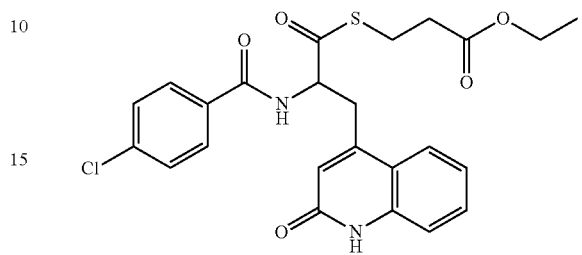

According to Experiment Prototocol C, 2.0 g (5.17 mmol) of 2-(4-chlorobenzoylamino)-3-(2-oxo-1,2-dihydroquinolin-4-yl)thiopropionic acid and 1.06 g (1.5 eq, 7.76 mmol) of ethyl 3-chloropropionate were reacted to afford the title compound as a white solid (0.7 g).

$^1$H NMR (400 MHz, DMSO-d$_6$): δ 11.66 (s, 1H), 9.24 (d, 1H), 7.85-7.82 (m, 2H), 7.79 (d, 1H), 7.60-7.58 (dd, 2H), 7.51 (t, 1H), 7.30 (d, 1H), 7.23 (t, 1H), 6.42 (s, 1H), 4.93 (m, 1H), 4.06 (q, 2H), 3.52 (dd, 1H), 3.19 (q, 1H), 3.06 (t, 2H), 2.61 (t, 2H), 1.17 (t, 3H)

Example 177

Preparation of Ethyl[2-(4-chlorobenzoylamino)-3-(2-oxo-1,2-dihydroquinolin-4-yl)propionylamino]acetate

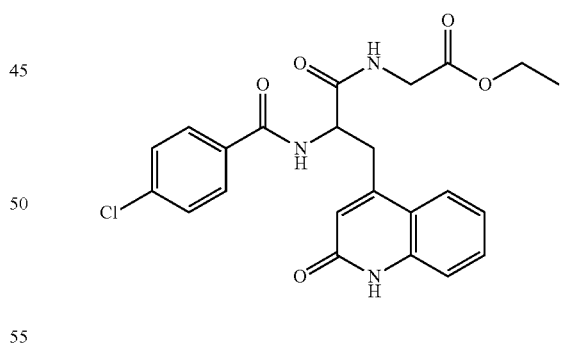

According to Experiment Prototocol B, 2.0 g (5.17 mmol) of 2-(4-chlorobenzoylamino)-3-(2-oxo-1,2-dihydroquinolin-4-yl)propionic acid and 0.87 g (1.2 eq, 6.20 mmol) of glycine ethyl ester HCl were reacted to afford the title compound as a white solid (1.4 g).

$^1$H NMR (400 MHz, DMSO-d$_6$): δ 11.63 (s, 1H), 8.88 (d, 1H), 8.67 (t, 1H), 7.91 (d, 1H), 7.87 (t, 1H), 7.85 (t, 1H), 7.55 (t, 1H), 7.53 (t, 1H), 7.49 (m, 1H), 7.31 (dd, 1H), 7.24 (m, 1H), 6.50 (s, 1H), 4.89 (m, 1H), 4.10 (q, 2H), 3.89 (t, 2H), 3.44 (dd, 1H), 3.16 (q, 1H), 1.19 (t, 3H)

Example 178

Preparation of [2-(4-Chlorobenzoylamino)-3-(2-oxo-1,2-dihydroquinolin-4-yl)propionylamino]acetic acid

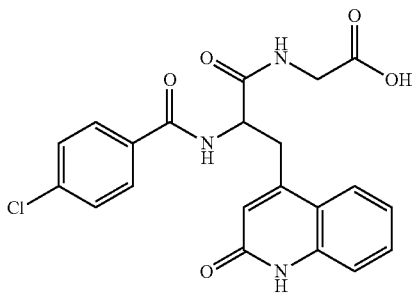 [SMILES: O=C(O)CNC(=O)C(Cc1cc(=O)[nH]c2ccccc12)NC(=O)c1ccc(Cl)cc1]

To a solution of 1.0 g (2.19 mmol) of ethyl[2-(4-chlorobenzoylamino)-3-(2-oxo-1,2-dihydroquinolin-4-yl)propionylamino]acetate in 10 mL of dimethylformamide was added 0.5 mL of trifluoroacetic acid, followed by stirring the solution at room temperature for 30 min. The resulting reaction mixture was added with 20 mL of water, and extracted three times with 20 mL of ethyl acetate. The organic layers thus formed were pooled, dried over anhydrous magnesium sulfate, and concentrated by filtration. The concentrate was crystallized in ethyl acetate to afford the title compound as a pale yellowish solid (0.4 g).

$^1$H NMR (400 MHz, DMSO-$d_6$): δ 11.61 (s, 1H), 8.86 (d, 1H), 8.49 (t, 1H), 7.92 (d, 1H), 7.87 (s, 1H), 7.85 (s, 1H), 7.55 (s, 1H), 7.53 (s, 1H), 7.50 (t, 1H), 7.29 (d, 1H), 7.23 (t, 1H), 6.49 (s, 1H), 4.89 (m, 1H), 3.79 (d, 2H), 3.46 (dd, 1H), 3.14 (q, 1H)

Example 179

Preparation of Ethyl 4-[2-(4-chlorobenzoylamino)-3-(2-oxo-1,2-dihydroquinolin-4-yl)propionylamino]butyrate

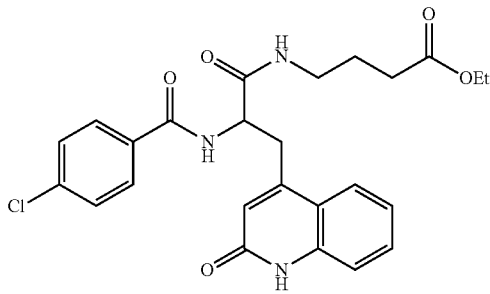 [SMILES: CCOC(=O)CCCNC(=O)C(Cc1cc(=O)[nH]c2ccccc12)NC(=O)c1ccc(Cl)cc1]

According to Experiment Prototocol B, 2.0 g (5.17 mmol) of 2-(4-chlorobenzoylamino)-3-(2-oxo-1,2-dihydroquinolin-4-yl)propionic acid and 1.04 g (1.2 eq, 6.20 mmol) of ethyl 4-aminobutyrate HCl were reacted to afford the title compound as a white solid (1.0 g).

$^1$H NMR (400 MHz, DMSO-$d_6$): δ 11.61 (s, 1H), 8.77 (d, 1H), 8.23 (t, 1H), 7.92 (d, 1H), 7.86 (t, 1H), 7.85 (t, 1H), 7.55 (t, 1H), 7.53 (t, 1H), 7.48 (m, 1H), 7.31 (dd, 1H), 7.23 (m, 1H), 6.47 (s, 1H), 4.78 (m, 1H), 4.04 (q, 2H), 3.42 (dd, 1H), 3.13 (m, 3H), 2.29 (t, 2H), 1.67 (m, 2H), 1.17 (t, 3H)

Example 180

Preparation of Ethyl 2-[2-(4-chlorobenzoylamino)-3-(2-oxo-1,2-dihydroquinolin-4-yl)propionylamino]-4-methyl pentanoate

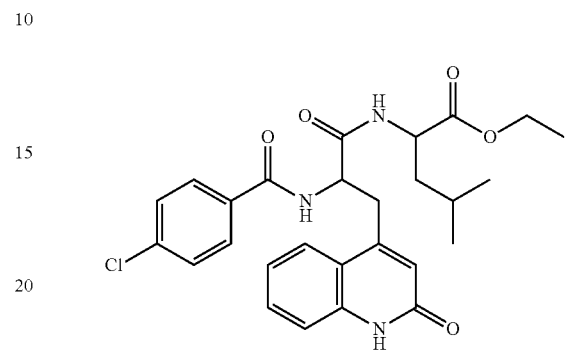

According to Experiment Prototocol B, 2.0 g (5.17 mmol) of 2-(4-chlorobenzoylamino)-3-(2-oxo-1,2-dihydroquinolin-4-yl)propionic acid and 1.18 g (1.2 eq, 6.20 mmol) of L-leucine ethyl ester HCl were reacted to afford the title compound as a white solid (1.5 g).

$^1$H NMR (400 MHz, DMSO-$d_6$): δ 11.62 (d, 1H), 8.77 (t, 1H), 8.59 (dd, 1H), 7.94 (t, 1H), 7.85 (t, 2H), 7.54-7.48 (m, 3H), 7.29 (dd, 1H), 7.22 (q, 1H), 6.50 (d, 1H), 4.95-4.92 (m, 1H), 4.34-4.28 (m, 1H), 4.12-4.05 (m, 2H), 3.29 (dd, 1H), 3.18 (t, 1H), 1.68-1.48 (m, 3H), 1.16 (q, 3H), 0.92-0.87 (m, 6H)

Example 181

Preparation of ethyl 2-[2-(4-Chlorobenzoylamino)-3-(2-oxo-1,2-dihydroquinolin-4-yl)propionylamino]-3-phenyl propionate

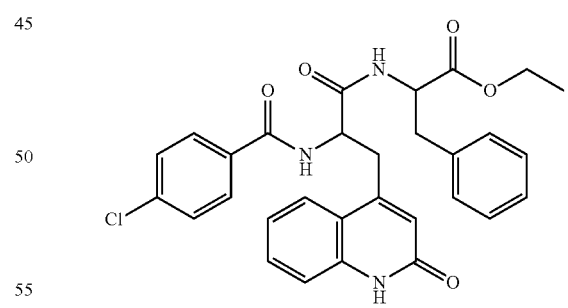

According to Experiment Prototocol B, 2.0 g (5.17 mmol) of 2-(4-chlorobenzoylamino)-3-(2-oxo-1,2-dihydroquinolin-4-yl)propionic acid and 1.38 g (1.2 eq, 6.20 mmol) of phenylalanine ethyl ester HCl were reacted to afford the title compound as a white solid (1.4 g).

$^1$H NMR (400 MHz, DMSO-$d_6$): δ 11.61 (d, 1H), 8.75 (dd, 1H), 7.84 (t, 2H), 7.55-7.49 (m, 3H), 7.31-7.14 (m, 8H), 6.46 (s, 1H), 4.91-4.87 (m, 1H), 4.60-4.57 (m, 1H), 4.06 (q, 2H), 3.34 (m, 1H), 3.09 (q, 1H), 2.936-2.90 (m, 2H), 1.13 (t, 3H)

Example 182

Preparation of Ethyl 2-[2-(4-chlorobenzoylamino)-3-(2-oxo-1,2-dihydroquinolin-4-yl)propionylamino]-3-(1H-indol-3-yl)propionate

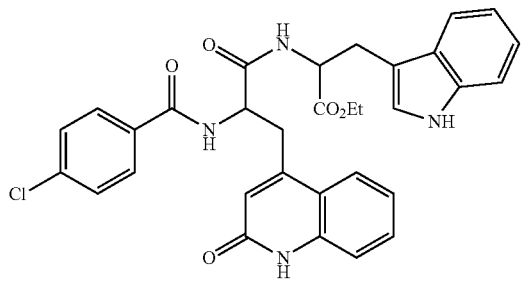 [SMILES: CCOC(=O)C(Cc1c[nH]c2ccccc12)NC(=O)C(Cc1cc(=O)[nH]c2ccccc12)NC(=O)c1ccc(Cl)cc1]

According to Experiment Prototocol B, 2.0 g (5.17 mmol) of 2-(4-chlorobenzoylamino)-3-(2-oxo-1,2-dihydroquinolin-4-yl)propionic acid and 1.67 g (1.2 eq, 6.20 mmol) of L-tryptophan ethyl ester HCl were reacted to afford the title compound as a white solid (1.1 g).

$^1$H NMR (400 MHz, DMSO-$d_6$): δ 11.60 (d, 1H), 9.22 (s, 1H), 8.77-8.67 (m, 2H), 7.90-7.81 (m, 3H), 7.53-7.48 (m, 3H), 7.31-7.23 (m, 2H), 7.02 (t, 2H), 6.62 (t, 2H), 6.45 (s, 1H), 4.89-4.87 (m, 1H), 4.51-4.48 (m, 1H), 4.12-4.02 (m, 2H), 3.16 (dd, 1H), 2.99-2.89 (m, 2H), 2.81 (q, 1H), 1.16 (t, 3H)

Example 183

Preparation of Diethyl 2-[2-(4-chlorobenzoylamino)-3-(2-oxo-1,2-dihydroquinolin-4-yl)propionylamino]pentane-1,5-dioate

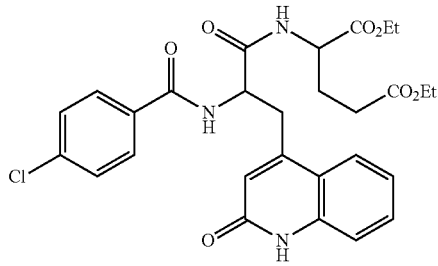 [SMILES: CCOC(=O)CCC(NC(=O)C(Cc1cc(=O)[nH]c2ccccc12)NC(=O)c1ccc(Cl)cc1)C(=O)OCC]

According to Experiment Prototocol B, 2.0 g (5.17 mmol) of 2-(4-chlorobenzoylamino)-3-(2-oxo-1,2-dihydroquinolin-4-yl)propionic acid and 1.49 g (1.2 eq, 6.20 mmol) of L-glutamic acid diethylester HCl were reacted to afford the title compound as a white solid (1.2 g).

$^1$H NMR (400 MHz, DMSO-$d_6$): δ 11.61 (d, 1H), 8.79 (t, 1H), 8.64 (dd, 1H), 7.93 (t, 1H), 7.84 (m, 2H), 7.50 (m, 3H), 7.31 (dd, 1H), 7.23 (m, 1H), 6.51 (s, 1H), 4.92 (m, 1H), 4.31 (m, 1H), 4.08 (m, 4H), 3.38 (m, 1H), 3.18 (m, 1H), 2.43 (t, 1H), 2.35 (t, 1H), 2.03 (m, 1H), 1.88 (m, 1H), 1.18 (m, 6H)

Example 184

Preparation of Diethyl 2-[2-(4-chlorobenzoylamino)-3-(2-oxo-1,2-dihydroquinolin-4-yl)propionylamino]pentane-1,5-dioic acid

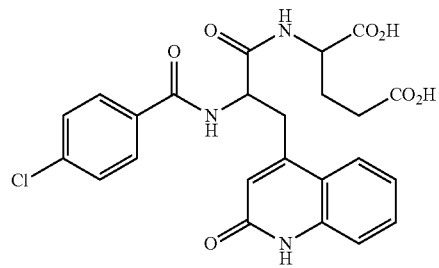 [SMILES: O=C(O)CCC(NC(=O)C(Cc1cc(=O)[nH]c2ccccc12)NC(=O)c1ccc(Cl)cc1)C(=O)O]

From 1.0 g (1.80 mmol) of diethyl 2-[2-(4-chlorobenzoylamino)-3-(2-oxo-1,2-dihydroquinolin-4-yl)propionylamino]pentane-1,5-dioate, the title compound was synthesized as a pale yellow solid in the same manner as in Example 164 (0.4 g).

$^1$H NMR (400 MHz, DMSO-$d_6$): δ 11.62 (s, 1H), 8.84 (t, 1H), 8.44 (dd, 1H), 7.92 (q, 1H), 7.84 (m, 2H), 7.52 (m, 3H), 7.32 (m, 1H), 7.25 (m, 1H), 6.51 (d, 1H), 4.92 (m, 1H), 4.27 (m, 1H), 4.08 (m, 4H), 3.40 (m, 1H), 3.18 (m, 1H), 2.29 (m, 2H), 2.00 (m, 1H), 1.86 (m, 1H)

Example 185

Preparation of 4-Chloro-N-[1-[2-(3H-imidazol-4-yl)ethylcarbamoyl]-2-(2-oxo-1,2-dihydroquinolin-4-yl)ethyl]benzamide

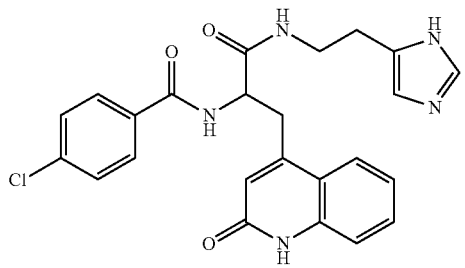 [SMILES: O=C(NC(Cc1cc(=O)[nH]c2ccccc12)C(=O)NCCc1cnc[nH]1)c1ccc(Cl)cc1]

According to Experiment Prototocol B, 2.0 g (5.17 mmol) of 2-(4-chlorobenzoylamino)-3-(2-oxo-1,2-dihydroquinolin-4-yl)propionic acid and 0.69 g (1.2 eq, 6.20 mmol) of histamine were reacted to afford the title compound as a white solid (0.9 g).

$^1$H NMR (400 MHz, DMSO-$d_6$): δ 11.64 (d, 1H), 8.83 (d, 1H), 8.729 (t, 1H), 7.93 (d, 1H), 7.86 (d, 2H), 7.71 (s, 2H), 7.55-7.48 (m, 3H), 7.30 (d, 1H), 7.23 (d, 1H), 7.20 (s, 1H), 6.94 (s, 1H), 6.62 (t, 2H), 6.48 (s, 1H), 4.81-4.75 (m, 1H), 3.40 (dd, 1H), 3.18 (q, 1H), 3.11-3.00 (m, 2H), 1.87-1.80 (m, 2H)

Example 186

Preparation of 4-Chloro-N-[2-(2-oxo-1,2-dihydroquinolin-4-yl)-1-(2-pyrrolidin-1-yl-ethylcarbamoyl)ethyl]benzamide

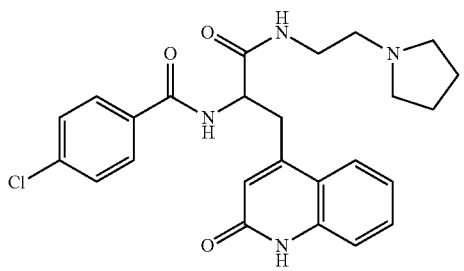 [SMILES: O=C(NC(Cc1cc(=O)[nH]c2ccccc12)C(=O)NCCN1CCCC1)c1ccc(Cl)cc1]

According to Experiment Protocol B, 2.0 g (5.17 mmol) of 2-(4-chlorobenzoylamino)-3-(2-oxo-1,2-dihydroquinolin-4-yl)propionic acid and 0.71 g (1.2 eq, 6.20 mmol) of 1-(2-aminoethyl)pyrrolidine were reacted to afford the title compound as a white solid (0.6 g).

$^1$H NMR (400 MHz, DMSO-$d_6$): δ 11.63 (s, 1H), 8.80 (d, 1H), 8.15 (t, 1H), 7.91 (d, 1H), 7.87 (t, 1H), 7.85 (t, 1H), 7.55 (t, 1H), 7.54 (t, 1H), 7.48 (t, 1H), 7.29 (dd, 1H), 7.24 (m, 1H), 6.46 (s, 1H), 4.79 (m, 1H), 3.41 (m, 1H), 3.21 (m, 3H), 2.42 (m, 6H), 1.64 (m, 4H)

Example 187

Preparation of 4-Chloro-N-[1-(2-morpholin-4-yl-ethylcarbamoyl)-2-(2-oxo-1,2-dihydroquinolin-4-yl)ethyl]benzamide

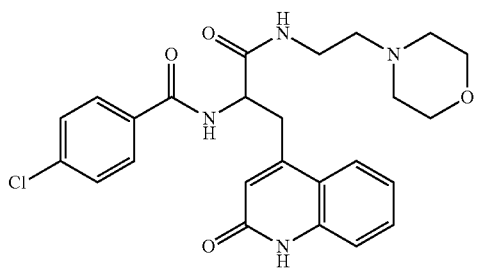 [SMILES: O=C(NC(Cc1cc(=O)[nH]c2ccccc12)C(=O)NCCN1CCOCC1)c1ccc(Cl)cc1]

According to Experiment Protocol B, 2.0 g (5.17 mmol) of 2-(4-chlorobenzoylamino)-3-(2-oxo-1,2-dihydroquinolin-4-yl)propionic acid and 0.81 g (1.2 eq, 6.20 mmol) of 4-(2-aminoethyl)morpholine were reacted to afford the title compound as a white solid (0.5 g).

$^1$H NMR (400 MHz, DMSO-$d_6$): δ 11.63 (s, 1H), 8.81 (d, 1H), 8.09 (t, 1H), 7.91 (d, 1H), 7.87 (t, 1H), 7.86 (t, 1H), 7.56 (t, 1H), 7.54 (t, 1H), 7.48 (t, 1H), 7.29 (dd, 1H), 7.23 (m, 1H), 6.47 (s, 1H), 4.78 (m, 1H), 3.52 (t, 4H), 3.39 (m, 1H), 3.19 (m, 3H), 2.31 (m, 6H)

Example 188

Preparation of 2-(Morpholin-4-yl)ethyl 2-(4-chlorobenzoylamino)-3-(2-oxo-1,2-dihydroquinolin-4-yl)propionate glycolate

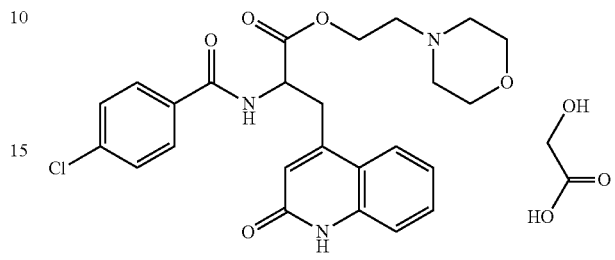

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.16 g (2.07 mmol) of glycolic acid were reacted to afford the title compound as a white solid (0.8 g).

$^1$H NMR (400 MHz, DMSO-$d_6$): δ 11.71 (s, 1H), 9.06 (d, 1H), 7.83 (t, 3H), 7.59 (s, 1H), 7.57 (s, 1H), 7.52 (t, 1H), 7.32 (d, 1H), 7.24 (t, 1H), 6.47 (s, 1H), 4.76 (m, 1H), 4.26-4.15 (m, 2H), 3.50-3.45 (m, 5H), 3.35 (s, 2H), 3.29 (q, 1H), 2.57-2.47 (m, 4H), 2.35 (br-s, 4H)

Example 189

Preparation of 2-(Morpholin-4-yl)ethyl 2-(4-chlorobenzoylamino)-3-(2-oxo-1,2-dihydroquinolin-4-yl)propionate lactate

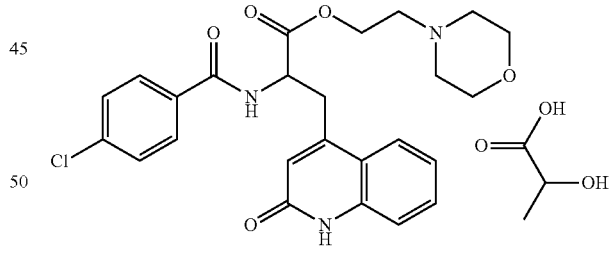

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.19 g (2.07 mmol) of lactic acid were reacted to afford the title compound as a white solid (0.9 g).

$^1$H NMR (400 MHz, DMSO-$d_6$): δ 11.71 (s, 1H), 9.06 (d, 1H), 7.83 (t, 3H), 7.59 (s, 1H), 7.57 (s, 1H), 7.52 (t, 1H), 7.32 (d, 1H), 7.24 (t, 1H), 6.46 (s, 1H), 4.75 (m, 1H), 4.27-4.14 (m, 2H), 3.50-3.45 (m, 2H), 3.35-3.26 (m, 5H), 2.58-2.46 (m, 5H), 2.35 (br-s, 4H)

Example 190

Preparation of 2-(Morpholin-4-yl)ethyl 2-(4-chlorobenzoylamino)-3-(2-oxo-1,2-dihydroquinolin-4-yl)propionate salicylate

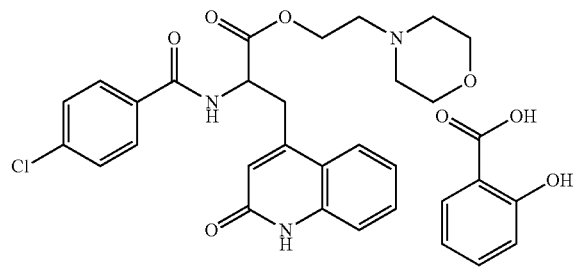

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.29 g (2.07 mmol) of salicylic acid were reacted to afford the title compound as a white solid (0.8 g).

$^1$H NMR (400 MHz, DMSO-$d_6$): δ 11.71 (s, 1H), 9.08 (d, 1H), 7.83 (t, 3H), 7.76 (dd, 1H), 7.59 (s, 1H), 7.56 (s, 1H), 7.52 (t, 1H), 7.42 (m, 1H), 7.32 (d, 1H), 7.23 (t, 1H), 6.85 (q, 1H), 6.46 (s, 1H), 4.78 (m, 1H), 4.32-4.21 (m, 2H), 3.54-3.47 (m, 5H), 3.29 (q, 2H), 2.78-2.67 (m, 2H), 2.54 (br-s, 4H)

Example 191

Preparation of 2-(Morpholin-4-yl)ethyl 2-(4-chlorobenzoylamino)-3-(2-oxo-1,2-dihydroquinolin-4-yl)propionate oxalate

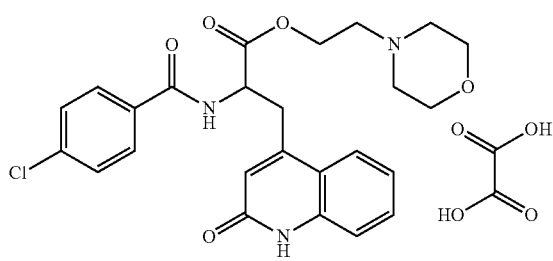

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.19 g (2.07 mmol) of oxalic acid were reacted to afford the title compound as a white solid (1.0 g).

$^1$H NMR (400 MHz, DMSO-$d_6$): δ 11.71 (s, 1H), 9.09 (d, 1H), 7.83 (t, 3H), 7.58 (s, 1H), 7.56 (s, 1H), 7.52 (t, 1H), 7.32 (d, 1H), 7.23 (t, 1H), 6.46 (s, 1H), 4.79 (m, 1H), 4.34-4.25 (m, 2H), 3.56 (t, 4H), 3.49 (dd, 1H), 3.29 (q, 1H), 2.87-2.78 (m, 2H), 2.65 (br-s, 4H)

Example 192

Preparation of 2-(Morpholin-4-yl)ethyl 2-(4-chlorobenzoylamino)-3-(2-oxo-1,2-dihydroquinolin-4-yl)propionate malonate

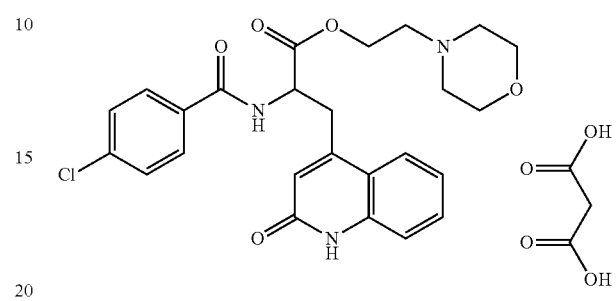

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.22 g (2.07 mmol) of malonic acid were reacted to afford the title compound as a white solid (1.1 g).

$^1$H NMR (400 MHz, DMSO-$d_6$): δ 11.71 (s, 1H), 9.06 (d, 1H), 7.83 (t, 3H), 7.59 (s, 1H), 7.56 (s, 1H), 7.52 (t, 1H), 7.32 (d, 1H), 7.24 (t, 1H), 6.46 (s, 1H), 4.77 (m, 1H), 4.24 (m, 2H), 3.51-3.46 (m, 5H), 3.29 (q, 1H), 3.19 (s, 2H), 2.70-2.61 (m, 2H), 2.51 (t, 2H), 2.47 (br-s, 4H)

Example 193

Preparation of 2-(Morpholin-4-yl)ethyl 2-(4-chlorobenzoylamino)-3-(2-oxo-1,2-dihydroquinolin-4-yl)propionate malate

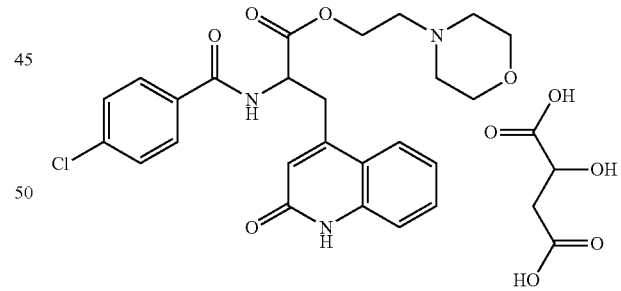

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.28 g (2.07 mmol) of malic acid were reacted to afford the title compound as a white solid (0.6 g).

$^1$H NMR (700 MHz, DMSO-$d_6$): δ 11.70 (s, 1H), 9.06 (d, 1H), 7.85-7.82 (m, 3H), 7.59-7.57 (m, 2H), 7.52 (t, 1H), 7.32 (q, 1H), 7.23 (t, 1H), 6.47 (s, 1H), 4.78-4.75 (m, 1H), 4.26-4.16 (m, 3H), 3.49-3.47 (m, 5H), 3.29 (q, 2H), 2.63-2.51 (m, 2H), 2.45-2.38 (m, 5H)

Example 194

Preparation of 2-(Morpholin-4-yl)ethyl 2-(4-chlorobenzoylamino)-3-(2-oxo-1,2-dihydroquinolin-4-yl) propionate tartarate

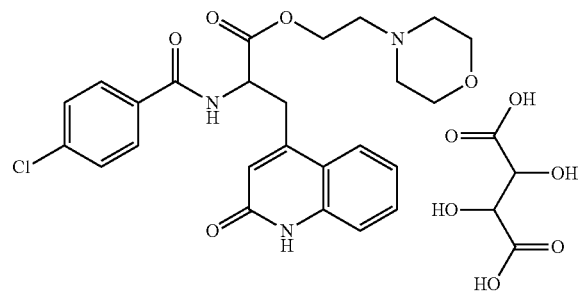

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.31 g (2.07 mmol) of tartaric acid were reacted to afford the title compound as a white solid (0.4 g).

$^1$H NMR (400 MHz, DMSO-$d_6$): δ 11.71 (s, 1H), 9.06 (d, 1H), 7.83 (t, 3H), 7.58 (s, 1H), 7.56 (s, 1H), 7.52 (t, 1H), 7.32 (d, 1H), 7.23 (t, 1H), 6.47 (s, 1H), 4.75 (m, 1H), 4.29-4.15 (m, 4H), 3.51-3.46 (m, 5H), 3.29 (q, 1H), 2.60-2.48 (m, 2H), 2.37 (br-s, 4H)

Example 195

Preparation of 2-(Morpholin-4-yl)ethyl 2-(4-chlorobenzoylamino)-3-(2-oxo-1,2-dihydroquinolin-4-yl) propionate maleate

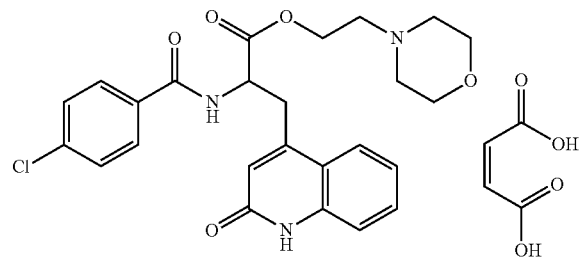

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.24 g (2.07 mmol) of maleic acid were reacted to afford the title compound as a white solid (0.8 g).

$^1$H NMR (400 MHz, DMSO-$d_6$): δ 11.71 (s, 1H), 9.09 (d, 1H), 7.83 (m, 3H), 7.59 (s, 1H), 7.57 (s, 1H), 7.52 (t, 1H), 7.32 (d, 1H), 7.23 (t, 1H), 6.45 (s, 1H), 6.11 (s, 2H), 4.82 (m, 1H), 4.37 (m, 2H), 3.65 (br-s, 4H), 3.49 (dd, 1H), 3.31 (q, 1H), 3.14 (br-s, 2H), 2.95 (br-s, 4H), 2.51 (t, 2H)

Example 196

Preparation of 2-(Morpholin-4-yl)ethyl 2-(4-chlorobenzoylamino)-3-(2-oxo-1,2-dihydroquinolin-4-yl) propionate fumarate

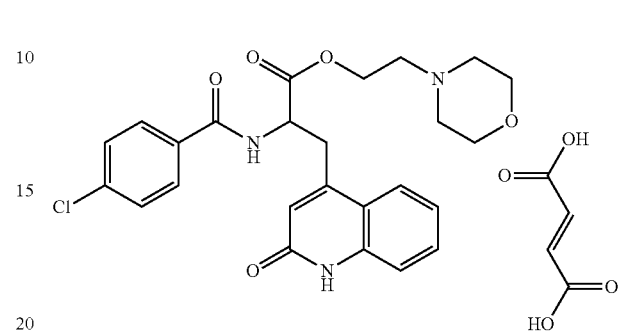

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.16 g (2.07 mmol) of fumaric acid were reacted to afford the title compound as a white solid (0.9 g).

$^1$H NMR (400 MHz, DMSO-$d_6$): δ 11.71 (s, 1H), 9.08 (d, 1H), 7.83 (m, 3H), 7.59 (s, 1H), 7.56 (s, 1H), 7.52 (t, 1H), 7.32 (d, 1H), 7.24 (t, 1H), 6.46 (s, 1H), 6.12 (s, 2H), 4.82 (m, 1H), 4.37 (m, 2H), 3.65 (br-s, 4H), 3.48 (dd, 1H), 3.32 (q, 1H), 3.15 (br-s, 2H), 2.96 (br-s, 4H), 2.52 (t, 2H)

Example 197

Preparation of 2-(Morpholin-4-yl)ethyl 2-(4-chlorobenzoylamino)-3-(2-oxo-1,2-dihydroquinolin-4-yl) propionate citrate

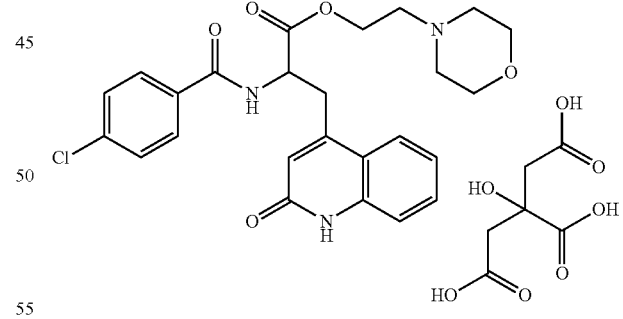

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.40 g (2.07 mmol) of citric acid were reacted to afford the title compound as a white solid (0.7 g).

$^1$H NMR (400 MHz, DMSO-$d_6$): δ 11.71 (s, 1H), 9.06 (d, 1H), 7.83 (t, 3H), 7.59 (s, 1H), 7.56 (s, 1H), 7.52 (t, 1H), 7.32 (d, 1H), 7.24 (t, 1H), 6.47 (s, 1H), 4.77 (m, 1H), 4.28-4.18 (m, 2H), 3.50-3.46 (m, 5H), 3.29 (q, 1H), 2.65 (dd, 2H), 2.64-2.57 (m, 2H), 2.51 (t, 2H), 2.43 (br-s, 4H)

Example 198

Preparation of 2-(Morpholin-4-yl)ethyl 2-(4-chlorobenzoylamino)-3-(2-oxo-1,2-dihydroquinolin-4-yl)propionate benzene sulfonate

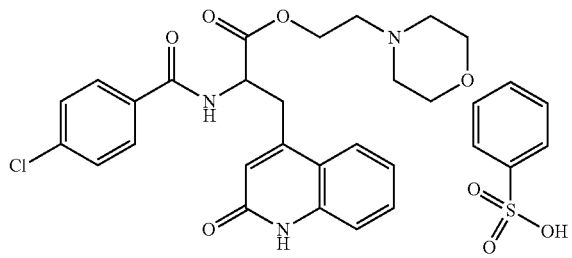

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.33 g (2.07 mmol) of benzenesulfonic acid were reacted to afford the title compound as a white solid (1.0 g).

$^1$H NMR (700 MHz, DMSO-$d_6$): δ 11.71 (s, 1H), 9.80 (br-s, 1H), 9.11 (d, 1H), 7.84-7.81 (m, 3H), 7.62-7.61 (m, 2H), 7.60-7.57 (m, 2H), 7.52 (t, 1H), 7.35-7.30 (m, 4H), 7.23 (t, 1H), 6.45 (s, 1H), 6.11 (s, 2H), 4.89-4.85 (m, 1H), 4.52-4.42 (m, 2H), 3.89 (t, 2H), 3.62 (t, 2H), 3.54-3.52 (m, 3H), 3.44 (t, 2H), 3.33 (q, 1H), 3.15 (br-s, 2H)

Example 199

Preparation of 2-(Morpholin-4-yl)ethyl 2-(4-chlorobenzoylamino)-3-(2-oxo-1,2-dihydroquinolin-4-yl)propionate tosylate

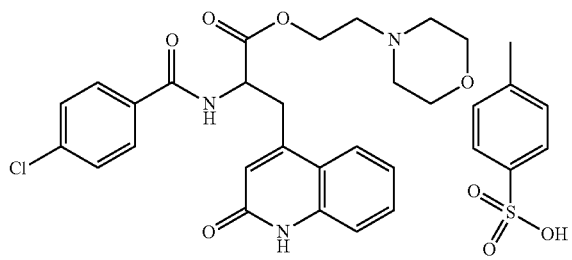

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.39 g (2.07 mmol) of toluene sulfonic acid monohydrate were reacted to afford the title compound as a white solid (0.9 g).

$^1$H NMR (400 MHz, DMSO-$d_6$): δ 11.71 (s, 1H), 9.78 (br-s, 1H), 9.10 (d, 1H), 7.84-7.81 (m, 3H), 7.59-7.47 (m, 5H), 7.32 (d, 1H), 7.23 (t, 1H), 7.11 (d, 2H), 6.45 (s, 1H), 6.11 (s, 2H), 4.86 (m, 1H), 4.52-4.40 (m, 2H), 4.02 (m, 2H), 3.62 (t, 2H), 3.55-3.29 (m, 6H), 3.14 (m, 2H), 2.29 (s, 3H)

Example 200

Preparation of 2-(Morpholin-4-yl)ethyl 2-(4-chlorobenzoylamino)-3-(2-oxo-1,2-dihydroquinolin-4-yl)propionate hydrochlorate

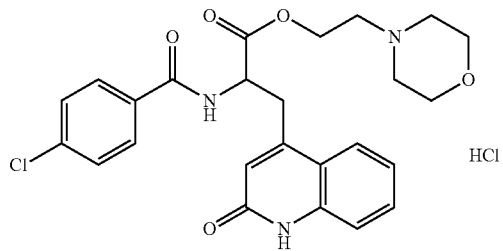 [SMILES: O=C(NC(Cc1cc(=O)[nH]c2ccccc12)C(=O)OCCN1CCOCC1)c1ccc(Cl)cc1 ; Cl]

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.19 mL (2.07 mmol) of HCl were reacted to afford the title compound as a white solid (0.4 g).

$^1$H NMR (400 MHz, DMSO-$d_6$): δ 11.69 (s, 1H), 11.52 (br-s, 1H), 9.24 (d, 1H), 7.89-7.86 (m, 3H), 7.57 (t, 1H), 7.55 (t, 1H), 7.51 (m, 1H), 7.32 (dd, 1H), 7.22 (m, 1H), 6.46 (s, 1H), 4.93 (m, 1H), 4.60-4.47 (m, 2H), 3.87-3.82 (m, 4H), 3.57 (dd, 1H), 3.60-3.33 (m, 5H), 3.12 (m, 2H)

Example 201

Preparation of 2-(Morpholin-4-yl)ethyl 2-(4-chlorobenzoylamino)-3-(2-oxo-1,2-dihydroquinolin-4-yl)propionate sulfate

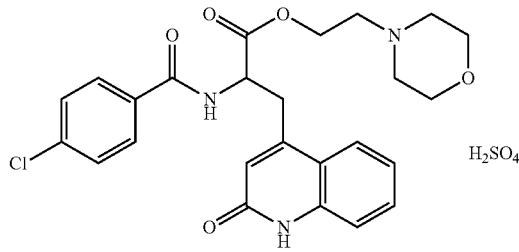

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.20 g (2.07 mmol) of sulfuric acid were reacted to afford the title compound as a white solid (0.4 g).

$^1$H NMR (400 MHz, DMSO-$d_6$): δ 11.71 (s, 1H), 9.09 (d, 1H), 7.83 (t, 3H), 7.59 (s, 1H), 7.56 (s, 1H), 7.52 (t, 1H), 7.32 (d, 1H), 7.23 (t, 1H), 6.46 (s, 1H), 4.82 (m, 1H), 4.35 (t, 2H), 3.63 (s, 4H), 3.50 (dd, 1H), 3.1 (q, 1H), 3.05 (br-s, 2H), 2.86 (br-s, 4H), 2.55 (s, 1H), 2.51 (s, 1H)

Example 202

Preparation of 2-(Morpholin-4-yl)ethyl 2-(4-chlorobenzoylamino)-3-(2-oxo-1,2-dihydroquinolin-4-yl)propionate phosphorate

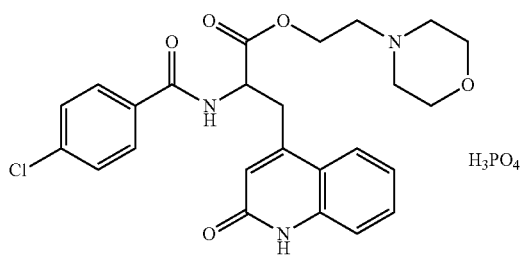

According to Experiment Prototocol E, 1 g (2.07 mmol) of 2-morpholin-4-ylethyl 2-(4-chlorobenzoylamino)-3-(2-oxo-1,2-dihydroquinolin-4-yl)propionate and 0.17 g (2.07 mmol) of phosphoric acid were reacted to afford the title compound as a white solid (0.6 g).

$^1$H NMR (700 MHz, DMSO-$d_6$): δ 11.72 (br-s, 1H), 9.08 (d, 1H), 7.86-7.82 (m, 3H), 7.58-7.57 (m, 2H), 7.52 (t, 1H), 7.33 (dd, 1H), 7.24 (m, 1H), 6.47 (s, 1H), 4.77-4.75 (m, 1H), 4.27-4.17 (m, 2H), 3.50-3.47 (m, 5H), 3.30 (dd, 1H), 2.60-2.57 (m, 2H), 2.56-2.50 (m, 1H), 2.39 (br-s, 4H)

The substitutents X and Y established in Examples 1 to 202, based on the backbone of Chemical Formula I, are summarized in Table 1, below.

[Chemical Formula I]

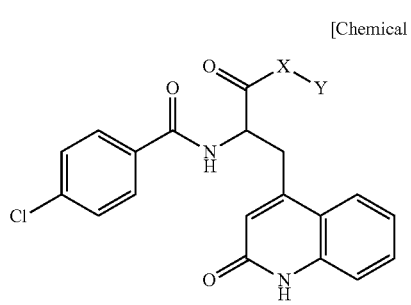

TABLE 1

| Ex. | X | Y |
|-----|---|---|
| 1 | O | —CH₃ |
| 2 | O | ethyl |
| 3 | O | isobutyl with two CH₃ |
| 4 | O | hexyl-CH₃ |
| 5 | O | propyl-Br |
| 6 | O | propyl-OH |
| 7 | O | ethyl-O-CH₃ |
| 8 | O | propyl-O-CH₃ |
| 9 | O | propyl-O-CH=CH₂ |
| 10 | O | propyl-O-C(O)-CH₃ |
| 11 | O | propyl-S-CH₃ |
| 12 | O | propyl-S-phenyl |
| 13 | O | propyl-NH-CH₃ |
| 14 | O | propyl-N(CH₃)₂ |
| 15 | O | isobutyl-N(CH₃)₂ |
| 16 | O | propyl-N(ethyl)₂ |
| 17 | O | propyl-N(isopropyl)₂ |
| 18 | O | butyl-N(CH₃)₂ |
| 19 | O | propyl-N(CH₃)phenyl |
| 20 | O | propyl-N(ethyl)benzyl |
| 21 | O | propyl-N(CH₃)-benzoxazolyl |

TABLE 1-continued

| Ex. | X | Y |
|-----|---|---|
| 22 | O | N-propyl benzamide |
| 23 | O | but-2-enyl |
| 24 | O | pent-2-enyl (CH3 terminal) |
| 25 | O | 2,3-dimethylpent-2-enyl |
| 26 | O | but-1-ynyl |
| 27 | O | butan-2-one (propyl methyl ketone) |
| 28 | O | pentan-3-one |
| 29 | O | methylcyclopentane |
| 30 | O | methylcyclohexane |
| 31 | O | ethylcyclopropane |
| 32 | O | ethylcyclobutane |
| 33 | O | ethylcyclohexane |
| 34 | O | ethylcyclopent-2-ene |
| 35 | O | ethyloxirane |
| 36 | O | 3-ethyl-3-methyloxetane |
| 37 | O | 1-methyl-2-propylpyrrolidine |

TABLE 1-continued

| Ex. | X | Y |
|-----|---|---|
| 38 | O | 1-propylpyrrolidine |
| 39 | O | 2-ethyltetrahydrofuran |
| 40 | O | 2-ethyl-1,3-dioxolane |
| 41 | O | 2-propyl-1,3-dioxolane |
| 42 | O | 2-ethyl-1-methylpiperidine |
| 43 | O | 3-ethyl-1-methylpiperidine |
| 44 | O | 1-propylpiperidine |
| 45 | O | 2-ethyltetrahydropyran |
| 46 | O | 2-propyl-1,3-dioxane |
| 47 | O | 4-propylmorpholine |
| 48 | O | 4-butylmorpholine |
| 49 | O | 4-pentylmorpholine |
| 50 | O | 4-heptylmorpholine |
| 51 | O | 1-ethyl-4-methylpiperazine |

TABLE 1-continued
| Ex. | X | Y |
|---|---|---|
| 52 | O | 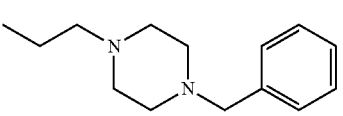 |
| 53 | O | 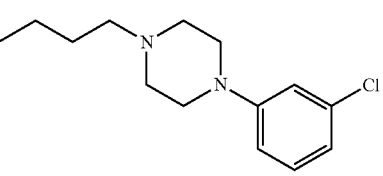 |
| 54 | O | 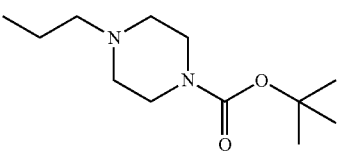 |
| 55 | O | 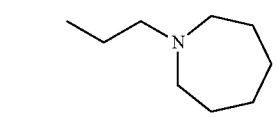 |
| 56 | O | 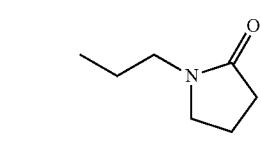 |
| 57 | O | 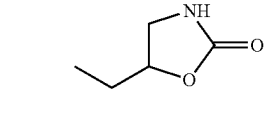 |
| 58 | O | 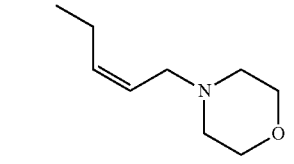 |
| 59 | O | 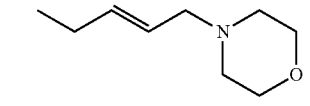 |
| 60 | O | 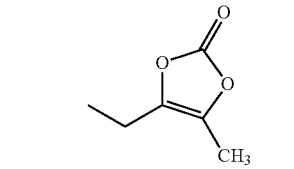 |
| 61 | O | 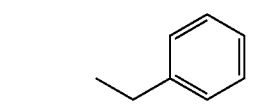 |
| 62 | O | 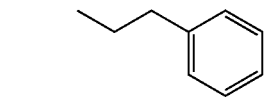 |
TABLE 1-continued
| Ex. | X | Y |
|---|---|---|
| 63 | O | 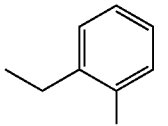 |
| 64 | O | 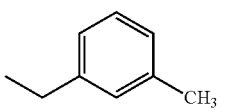 |
| 65 | O | 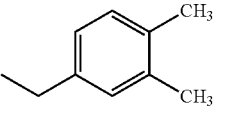 |
| 66 | O | 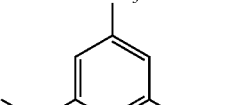 |
| 67 | O | 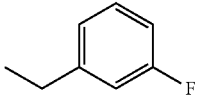 |
| 68 | O | 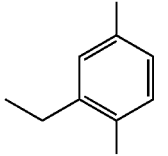 |
| 69 | O | 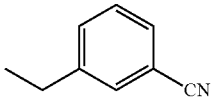 |
| 70 | O | 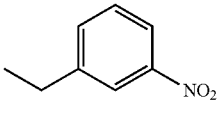 |
| 71 | O | 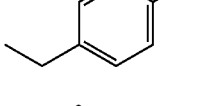 |
| 72 | O | 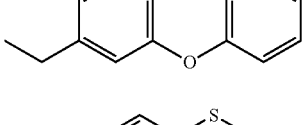 |
| 73 | O | 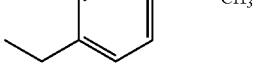 |

TABLE 1-continued
| Ex. | X | Y |
|---|---|---|
| 74 | O | 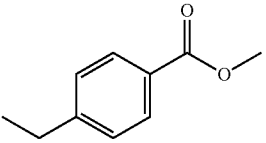 |
| 75 | O | 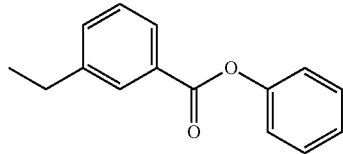 |
| 76 | O | 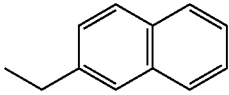 |
| 77 | O | 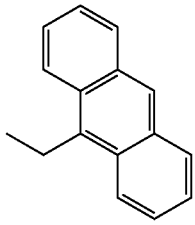 |
| 78 | O | 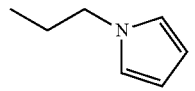 |
| 79 | O | 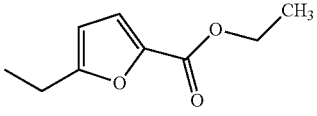 |
| 80 | O |  |
| 81 | O | 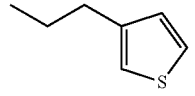 |
| 82 | O | 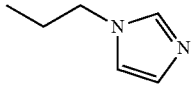 |
| 83 | O | 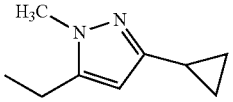 |
| 84 | O | 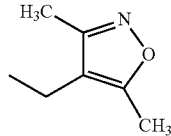 |
| 85 | O | 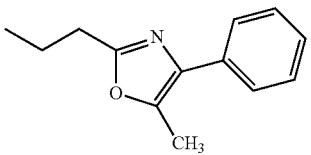 |
| 86 | O | 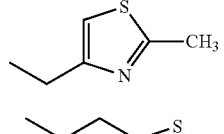 |
| 87 | O | 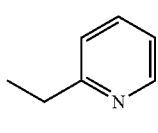 |
| 88 | O | 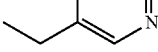 |
| 89 | O | |
| 90 | O | |
| 91 | O | |
| 92 | O | 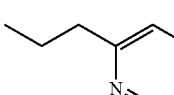 |
| 93 | O | |
| 94 | O | 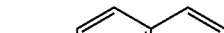 |
| 95 | O | 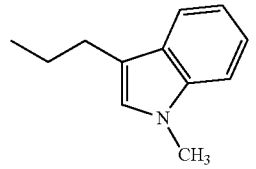 |
| 96 | O | 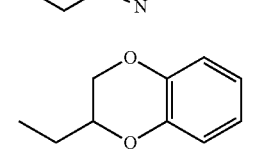 |

TABLE 1-continued

| Ex. | X | Y |
|---|---|---|
| 97 | O | 9-ethylcarbazole |
| 98 | O | N-methylpropanamide |
| 99 | O | 1-(4-methylpiperazin-1-yl)propan-1-one |
| 100 | O | 1-(4-methylpiperazin-1-yl)-2-methylbutan-1-one |
| 101 | O | 1-morpholinopropan-1-one |
| 102 | O | N-methoxy-N-methylpropanamide |
| 103 | O | ethyl propanoate |
| 104 | O | ethyl butanoate |
| 105 | O | 2-morpholinoethyl propanoate |
| 106 | O | 2-morpholinoethyl 2-methylbutanoate |
| 107 | O | 2-propylisoindoline-1,3-dione |
| 108 | O | cyclohexyl ethyl carbonate |
| 109 | O | ethyl 2-morpholinoethyl carbonate |
| 110 | O | 1-propylurea |
| 111 | O | 1-phenyl-3-propylurea |
| 112 | O | 1-benzyl-3-propylurea |
| 113 | S | H |
| 114 | S | —CH$_3$ |
| 115 | S | propyl (CH$_3$) |
| 116 | S | butyl (CH$_3$) |
| 117 | S | pentyl (CH$_3$) |
| 118 | S | isohexyl (CH$_3$/CH$_3$) |
| 119 | S | heptyl (CH$_3$) |
| 120 | S | N,N-dimethylpropylamine |
| 121 | S | N,N-diethylpropylamine |
| 122 | S | N,N-diisopropylpropylamine |
| 123 | S | N,N-dimethylbutylamine |

TABLE 1-continued
| Ex. | X | Y |
|---|---|---|
| 124 | S | 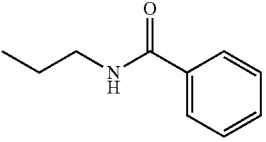 |
| 125 | S | 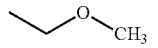 |
| 126 | S | 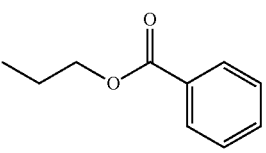 |
| 127 | S | 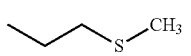 |
| 128 | S | 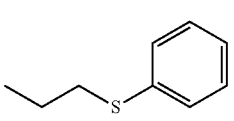 |
| 129 | S | 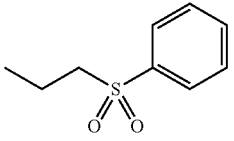 |
| 130 | S | 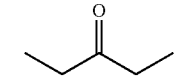 |
| 131 | S | 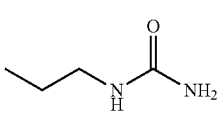 |
| 132 | S | 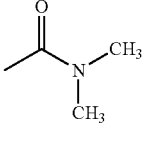 |
| 133 | S | 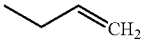 |
| 134 | S | 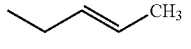 |
| 135 | S |  |
| 136 | S | 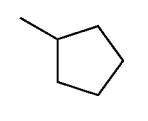 |
| 137 | S | 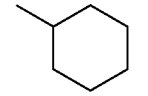 |
| 138 | S | 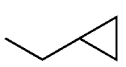 |
| 139 | S | |
| 140 | S | |
| 141 | S | |
| 142 | S | |
| 143 | S | |
| 144 | S | |
| 145 | S | |
| 146 | S | |
| 147 | S | |
| 148 | S | |
| 149 | S | |
| 150 | S | |
| 151 | S | |
| 152 | S | |

TABLE 1-continued
| Ex. | X | Y |
|---|---|---|
| 153 | S | 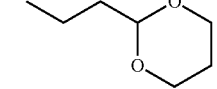 |
| 154 | S | 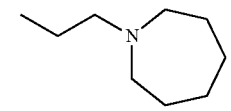 |
| 155 | S | 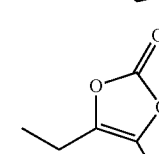 |
| 156 | S | 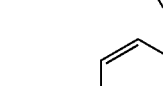 |
| 157 | S | 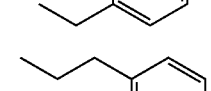 |
| 158 | S | 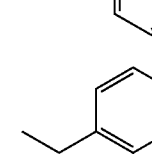 |
| 159 | S | 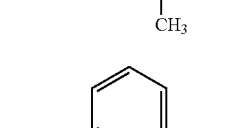 |
| 160 | S | 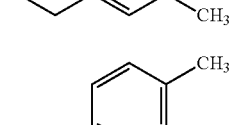 |
| 161 | S | 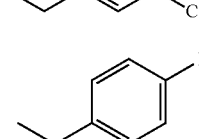 |
| 162 | S | 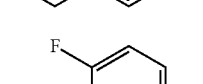 |
| 163 | S | 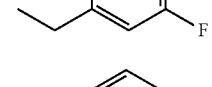 |
| 164 | S | 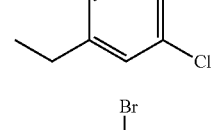 |
| 165 | S | 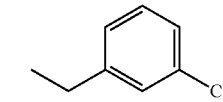 |
| 166 | S | 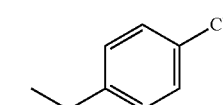 |
| 167 | S | 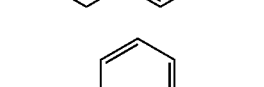 |
| 168 | S | 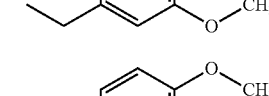 |
| 169 | S | 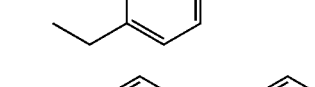 |
| 170 | S | 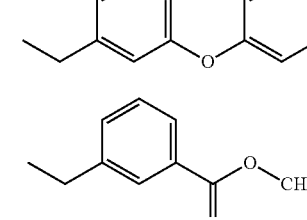 |
| 171 | S | 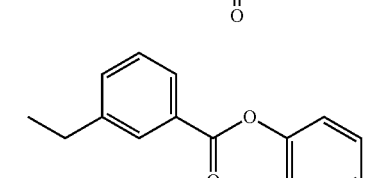 |
| 172 | S | 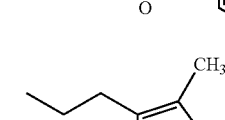 |
| 173 | S | 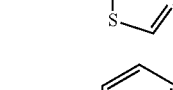 |
| 174 | S | 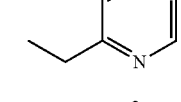 |
| 175 | S | 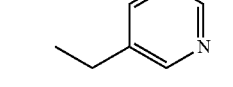 |
| 176 | S | 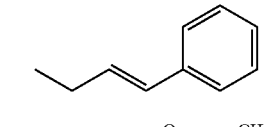 |
| 177 | NH | 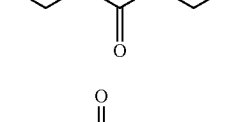 |

TABLE 1-continued
| Ex. | X | Y |
|---|---|---|
| 178 | NH | 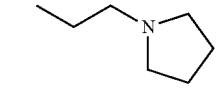 |
| 179 | NH | 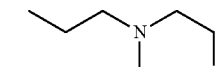 |
| 180 | NH | 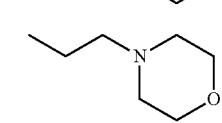 |
| 181 | NH |  |
| 182 | NH |  |
| 183 | NH | 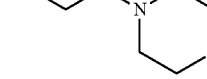 |
| 184 | NH | 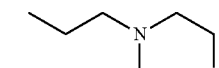 |
| 185 | NH | 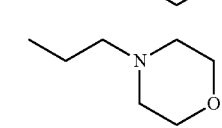 |
| 186 | NH |  |
| 187 | NH |  |
| 188 | O | 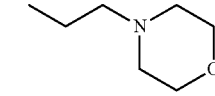 |
| 189 | O | 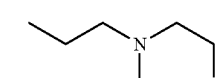 |
| 190 | O | |
| 191 | O | |
| 192 | O | |
| 193 | O | |
| 194 | O | |
| 195 | O | |
| 196 | O | |
| 197 | O | |
| 198 | O | |
| 199 | O |  |
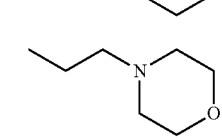

TABLE 1-continued

| Ex. | X | Y |
|-----|---|---|
| 200 | O | [propyl-morpholine structure] |
| 201 | O | [propyl-morpholine structure] |
| 202 | O | [propyl-morpholine structure] |

Experimental Example 1

Assay for Body Absorption Rates of Rebamipide Prodrugs

1. Preparation of Standard Solutions for Calibration Curve
   1) Preparation of MeOH Rebamipide Solutions
   Rebamipide weighing about 5 mg was dissolved in 250 mL of methanol (MeOH) to give a stock solution (20000 ng/mL) from which 1000 ng/mL, 500 ng/mL, 200 ng/mL, and 100 ng/mL MeOH-rebamipide solutions were prepared.
   2) Preparation of Standard Solutions
   In a 1.5 mL tube, 100 μL of each of the MeOH-rebamipide solutions was shaken, together with 100 μL of blank plasma, and 300 μL of methanol (MeOH), for 5 min, and centrifuged for 5 min at 10,000 rpm. To establish standard solutions, 200 μL was taken from each of the supernatants.
   (For a blank, MeOH was used, instead of the MeOH rebamipide solution, and a vial with 250 μL insert was employed.)
2. Preparation of Specimen Solutions
   In a 1.5 mL tube, 100 μL of each blood specimen, and 400 μL of MeOH were shaken together for 5 min, and centrifuged at 10,000 rpm for 5 min. The supernatant was taken in a volume of 200 μL for use as a specimen solution.
3. Information on Specimen
   SD (Sprague Dawley) rats were employed as experimental animals. The dose of the control drug rebamipide administered to the subject was 100 mg/kg while the prodrugs prepared in the above Examples were administered in amounts corresponding to 100 mg/kg of rebamipide.
   Blood samples were taken from the subject 2 hr after administration, and sera were separated therefrom and stored at −24° C.
   The separated sera were monitored for rebamipide concentration with time.
4. Test Result

TABLE 2

| Example No. | Concentration of Stock |
|-------------|------------------------|
| Rebamipide | 128.69 ng/mL |
| 1, 2, 4, 6, 8, 24, 26, 30, 33, 34, 39, 61, 62, 67, 71, 74, 89, 117, 134, 137,177, 178 | 100~500 ng/mL |
| 11, 13, 21, 31, 36, 40, 50, 78, 83, 86, 90, 94, 95, 110, 115, 130, 153, 157, 161, 168, 175 | 500~1,000 ng/mL |
| 15, 19, 38, 48, 51, 55, 58, 82, 95, 103, 108, 120, 125, 154 | 1,000~2,000 ng/mL |
| 14, 16, 44, 47, 99, 100, 102, 105, 106, 109, 121, 144, 151, 155 | >2,000 ng/mL |

Sera taken from the animals to which rebamipide or rebamipid prodrugs peppered in the above Examples were administered were measured for a change in rebamipid level with time. The results are summarized in Table 2. As apparent from the data of Table 2, the serum level of rebamipide was significantly lower at 2 hrs after rebamipide was administered as a free acid than in the form of the prodrugs of the Examples, indicating that the prodrugs according to the present invention are absorbed at higher rates in animal bodies than is remipide, and are completely converted into the acting drug remipide.

Experimental Example 2

Hydrolysis of Prodrug into Acting Drug in Whole Blood of Rat

1. Experiment Procedure
   Frozen rat blood was thawed for about 1 hr in a 37° C. water bath and homogenized.
   A stock solution was prepared by dissolving 10 mg of the compound of each Example in 1 mL of CAN. Optionally, a buffer (prepared by mixing 750 mL of a solution of $Na_2HPO_4$ 0.58 g and $KH_2PO_4$ 2 g in 1 L of $H_2O$ with 250 mL of CAN) was added. In a 4 mL tube, 40 μL of the stock solution was uniformly mixed with 2 mL of blood by shaking, followed by storage at 30 rpm in a water bath.
   At 0, 2, 4, 6, 8, 10, 15, 30, 45, 60, 90, and 120 min after storage, a sample was taken in a volume of 200 μL, diluted in 400 μL of CAN, vortexed for 1 min, and centrifuged for 1 min. The supernatant was analyzed by HPLC (but, for the compound of Example 47, sampling was performed at 0, 1, 3, 5, 7, and 10 min after storage). In addition, measurement was made of the time that it took for the prodrugs to be converted into the acting drug (rebamipide).
2. Result
   The results of the experiment are given in Table 3 and FIG. 1. The conversion times (half lives) taken for the prodrugs to be converted to rebamipide are listed in Table 3. In FIG. 1, conversion rates of the rebamipide prodrug of Example 47 to rebamipide are plotted as area ratios versus time.
   As is understood from the data of FIG. 1, the rebamipide prodrug was converted into rebamipide by half after 2.57 min of storage, and completely after about 10 min of storage, with the conversion rate rapidly increasing from 3 min after storage onwards.

TABLE 3

| Conversion Time (Half Life) from Rebamipide Prodrugs to Rebamipide | |
|---|---|
| Cpd. | Conversion Time in Whole Rat Blood ($t_{1/2}$) |
| Example 14 | <2 min |
| Example 16 | <2 min |

TABLE 3-continued

Conversion Time (Half Life)
from Rebamipide Prodrugs to Rebamipide

| Cpd. | Conversion Time in Whole Rat Blood ($t_{1/2}$) |
|---|---|
| Example 44 | <2 min |
| Example 47 | 2.57 min |
| Example 99 | <2 min |
| Example 100 | <2 min |
| Example 102 | <2 min |
| Example 105 | <2 min |
| Example 106 | <2 min |
| Example 109 | <2 min |
| Example 121 | <2 min |
| Example 144 | <2 min |
| Example 151 | <2 min |
| Example 155 | <2 min |

As can be seen in Table 3, it took 2.57 min for the rebamipide prodrug of Example 47 to be converted into rebamipide by half while the rebamipide prodrugs of the other Examples were converted by half into rebamipide within less than 2 min. Accordingly, the rebamipide prodrugs according to the present invention are highly prone to conversion into rabamipide in vivo, thus guaranteeing a high pharmaceutical efficacy.

The invention claimed is:

1. A compound, selected from among a compound represented by the following Chemical Formula 1, a pharmaceutically acceptable salt thereof, a hydrate thereof, or a solvate thereof:

[Chemical Formula I]

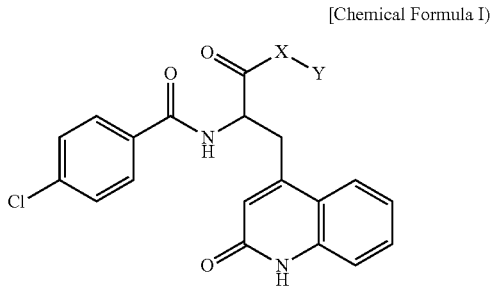

wherein,

X is an oxygen atom, a nitrogen atom, or a sulfur atom; and

Y is a radical selected from the group consisting of $C_1$-$C_6$ alkyl substituted with at least one substituent selected from the group consisting of with fluoro, chloro, bromo, oxo, nitro, and cyano, $C_1$-$C_6$ haloalkyl, ($C_1$-$C_3$ alkyloxy)$C_1$-$C_6$ alkyl, ($C_2$-$C_6$ alkenyloxy)$C_1$-$C_6$ alkyl, ($C_1$-$C_6$ alkylsufanyl)$C_1$-$C_6$ alkyl, (arylsufanyl)$C_1$-$C_6$ alkyl, (arylsulfonyl)$C_1$-$C_6$ alkyl, ($C_1$-$C_6$ alkylamino) $C_1$-$C_6$ alkyl, [($C_1$-$C_3$ alkyl)(aryl)amino]$C_1$-$C_6$ alkyl, {[($C_1$-$C_3$ alkyl)(aryl)$C_1$-$C_3$ alkyl]amino}$C_1$-$C_6$ alkyl, [($C_1$-$C_3$ alkyl)(heteroaryl)amino]$C_1$-$C_6$ alkyl, (arylcarbonylamino)$C_1$-$C_6$ alkyl, $C_2$-$C_6$ alkenyl, $C_2$-$C_6$ alkynyl, $C_2$-$C_6$ oxoalkyl, $C_3$-$C_8$ cycloalkyl, ($C_3$-$C_8$ cycloalkyl) $C_1$-$C_6$ alkyl, ($C_3$-$C_8$ cycloalkenyl)$C_1$-$C_6$ alkyl, ($C_3$-$C_8$ heterocycloalkyl)$C_1$-$C_6$ alkyl, [($C_1$-$C_3$ alkyl)$C_3$-$C_8$ heterocycloalkyl]$C_1$-$C_6$ alkyl, {[(aryl)$C_1$-$C_3$ alkyl]$C_3$-$C_8$ heterocycloalkyl}$C_1$-$C_6$ alkyl, [($C_1$-$C_6$ alkyloxycarbonyl)$C_3$-$C_8$ heterocycloalkyl]$C_1$-$C_6$ alkyl, [($C_1$-$C_3$ alkyloxycarbonyl)$C_3$-$C_8$ heterocycloalkyl]$C_1$-$C_6$ alkyl, ($C_3$-$C_8$ heterocycloalkyl)$C_1$-$C_6$ alkenyl, [($C_1$-$C_3$ alkyl)$C_3$-$C_8$ heterocycloalkenyl]$C_1$-$C_6$ alkyl, (aryl)$C_1$-$C_6$ alkyl, [($C_1$-$C_3$ alkyl)aryl]$C_1$-$C_6$ alkyl, [($C_1$-$C_3$ alkyloxy)aryl] $C_1$-$C_6$ alkyl, [(aryloxy)aryl]$C_1$-$C_6$ alkyl, [($C_1$-$C_3$ alkylsufanyl)aryl]$C_1$-$C_6$ alkyl, [($C_1$-$C_3$ alkyloxycarbonyl)aryl]$C_1$-$C_6$ alkyl, [(aryloxycarbonyl)aryl]$C_1$-$C_6$ alkyl, (aryl)$C_3$-$C_6$ alkenyl, (heteroaryl)$C_1$-$C_6$ alkyl, [(alkyloxycarbonyl)heteroaryl]$C_1$-$C_6$ alkyl, [($C_1$-$C_3$ alkyl)$C_3$-$C_8$ heteroaryl]$C_1$-$C_6$ alkyl, [($C_3$-$C_8$ cycloalkyl)heteroaryl]$C_1$-$C_6$ alkyl, [(aryl)heteroaryl]$C_1$-$C_6$ alkyl, [($C_1$-$C_3$ alkyl)heteroaryl]$C_1$-$C_6$ alkyl, {[(aryl)$C_1$-$C_3$ alkyl]heteroaryl}$C_1$-$C_6$ alkyl, ($C_1$-$C_6$ alkyloxycarbonyl)$C_1$-$C_6$ alkyl, [($C_3$-$C_8$ heterocycloalkyl)$C_1$-$C_6$ alkyloxycarbonyl]$C_1$-$C_6$ alkyl, ($C_3$-$C_8$ heterocycloalkylcarbonyl)$C_1$-$C_6$ alkyl, [($C_1$-$C_3$ alkyl)$C_3$-$C_8$ heterocycloalkylcarbonyl]$C_1$-$C_6$ alkyl, [($C_1$-$C_3$ alkyl)$C_3$-$C_8$ heterocycloalkylcarbonyl]$C_1$-$C_6$ alkyl, [($C_3$-$C_8$ cycloalkyl)oxycarbonyloxy]$C_1$-$C_6$ alkyl, [($C_3$-$C_8$ heterocycloalkyl)oxycarbonyloxy]$C_1$-$C_6$ alkyl, (ureido) $C_1$-$C_6$ alkyl, (arylureido)$C_1$-$C_6$ alkyl, [(aryl)($C_1$-$C_3$ alkylureido]$C_1$-$C_6$ alkyl, ($C_1$-$C_6$ alkylaminocarbonyl) $C_1$-$C_6$ alkyl, [($C_3$-$C_8$ heterocycloalkyl)aminocarbonyl] $C_1$-$C_6$ alkyl, {[($C_1$-$C_3$ alkyl)$C_3$-$C_8$ heterocycloalkyl] aminocarbonyl}$C_1$-$C_6$ alkyl, [($C_1$-$C_3$ alkyl)($C_1$-$C_3$ alkyloxy)aminocarbonyl]$C_1$-$C_6$ alkyl, and (oxo$C_3$-$C_8$ heterocycloalkyl)$C_1$-$C_6$ alkyl, with a proviso that the $C_2$-$C_6$ alkenyl radical, the $C_2$-$C_6$ alkynyl radical, the $C_2$-$C_6$ oxoalkyl radical, the $C_3$-$C_8$ cycloalkyl radical, the $C_3$-$C_8$ cycloalkenyl radical, the $C_3$-$C_8$ heterocycloalkenyl radical, the aryl radical or the heteroaryl radical is optionally substituted with at least one substituent selected from the group consisting of $C_1$-$C_3$ alkyl, fluoro, chloro, bromo, hydroxy, oxo, nitro, and cyano.

2. The compound, pharmaceutically acceptable salt, hydrate, or solvate of claim 1, wherein the compound is selected from the group consisting of:

5) 2-bromoethyl 2-(4-chlorobenzoylamino)-3-(2-oxo-1,2-dihydroquinolin-4-yl)propionate;

7) methoxymethyl 2-(4-chlorobenzoylamino)-3-(2-oxo-1,2-dihydroquinolin-4-yl)propionate;

8) 2-methoxyethyl 2-(4-chlorobenzoylamino)-3-(2-oxo-1,2-dihydroquinolin-4-yl)propionate;

9) 2-vinyloxyethyl 2-(4-chlorobenzoylamino)-3-(2-oxo-1,2-dihydroquinolin-4-yl)propionate;

11) 2-methylsulfanylethyl 2-(4-chlorobenzoylamino)-3-(2-oxo-1,2-dihydroquinolin-4-yl)propionate;

12) 2-phenylsulfanylethyl 2-(4-chlorobenzoylamino)-3-(2-oxo-1,2-dihydroquinolin-4-yl)propionate;

13) 2-methylamino ethyl 2-(4-chlorobenzoylamino)-3-(2-oxo-1,2-dihydroquinolin-4-yl)propionate;

15) 2-dimethylamino-1-methyl-ethyl 2-(4-chlorobenzoylamino)-3-(2-oxo-1,2-dihydroquinolin-4-yl)propionate;

16) 2-diethylamino ethyl 2-(4-chlorobenzoylamino)-3-(2-oxo-1,2-dihydroquinolin-4-yl)propionate;

17) 2-diisopropylaminoethyl 2-(4-chlorobenzoylamino)-3-(2-oxo-1,2-dihydroquinolin-4-yl)propionate;

19) 2-(methyl phenyl amino)ethyl 2-(4-chlorobenzoylamino)-3-(2-oxo-1,2-dihydroquinolin-4-yl)propionate;

20) 2-(benzyl ethyl amino)ethyl 2-(4-chlorobenzoylamino)-3-(2-oxo-1,2-dihydroquinolin-4-yl)propionate;

21) 2-(benzoxazol-2-ylmethyl amino)ethyl 2-(4-chlorobenzoylamino)-3-(2-oxo-1,2-dihydroquinolin-4-yl) propionate;

22) 2-benzoylaminoethyl 2-(4-chlorobenzoylamino)-3-(2-oxo-1,2-dihydroquinolin-4-yl)propionate;
23) allyl 2-(4-chlorobenzoylamino)-3-(2-oxo-1,2-dihydroquinolin-4-yl)propionate;
24) but-2-enyl 2-(4-chlorobenzoylamino)-3-(2-oxo-1,2-dihydroquinolin-4-yl)propionate;
25) 3-methylbut-2-enyl 2-(4-chlorobenzoylamino)-3-(2-oxo-1,2-dihydroquinolin-4-yl)propionate;
26) 3-prop-2-ynyl 2-(4-chlorobenzoylamino)-3-(2-oxo-1,2-dihydroquinolin-4-yl)propionate 27) 2-oxopropyl 2-(4-chlorobenzoylamino)-3-(2-oxo-1,2-dihydroquinolin-4-yl)propionate;
28) 2-oxobutyl 2-(4-chlorobenzoylamino)-3-(2-oxo-1,2-dihydroquinolin-4-yl)propionate;
29) cyclopentyl 2-(4-chlorobenzoylamino)-3-(2-oxo-1,2-dihydroquinolin-4-yl)propionate;
30) cyclohexyl 2-(4-chlorobenzoylamino)-3-(2-oxo-1,2-dihydroquinolin-4-yl)propionate;
31) cyclomethyl 2-(4-chlorobenzoylamino)-3-(2-oxo-1,2-dihydroquinolin-4-yl)propionate;
32) cyclobutylmethyl 2-(4-chlorobenzoylamino)-3-(2-oxo-1,2-dihydroquinolin-4-yl)propionate;
33) cyclohexylmethyl 2-(4-chlorobenzoylamino)-3-(2-oxo-1,2-dihydroquinolin-4-yl)propionate;
34) cyclopent-3-enylmethyl 2-(4-chlorobenzoylamino)-3-(2-oxo-1,2-dihydroquinolin-4-yl)propionate;
35) oxiranylmethyl 2-(4-chlorobenzoylamino)-3-(2-oxo-1,2-dihydroquinolin-4-yl)propionate;
36) 3-methyloxetan-3-ylmethyl 2-(4-chlorobenzoylamino)-3-(2-oxo-1,2-dihydroquinolin-4-yl)propionate;
37) 2-(1-methylpyrrolidin-2-yl)ethyl 2-(4-chlorobenzoylamino)-3-(2-oxo-1,2-dihydroquinolin-4-yl)propionate;
38) 2-pyrrolidin-1-yl-ethyl 2-(4-chlorobenzoylamino)-3-(2-oxo-1,2-dihydroquinolin-4-yl)propionate;
39) tetrahydrofuran-2-ylmethyl 2-(4-chlorobenzoylamino)-3-(2-oxo-1,2-dihydroquinolin-4-yl)propionate;
40) [1,3]dioxolan-2-ylmethyl 2-(4-chlorobenzoylamino)-3-(2-oxo-1,2-dihydroquinolin-4-yl)propionate;
41) 2-[1,3]-dioxolan-2-ylethyl 2-(4-chlorobenzoylamino)-3-(2-oxo-1,2-dihydroquinolin-4-yl)propionate;
42) 1-methylpiperidin-2-ylmethyl 2-(4-chlorobenzoylamino)-3-(2-oxo-1,2-dihydroquinolin-4-yl)propionate;
43) 1-methylpiperidin-3-ylmethyl 2-(4-chlorobenzoylamino)-3-(2-oxo-1,2-dihydroquinolin-4-yl)propionate;
44) 2-piperidin-1-ylethyl 2-(4-chlorobenzoylamino)-3-(2-oxo-1,2-dihydroquinolin-4-yl)propionate;
45) tetrahydropyran-2-ylmethyl 2-(4-chlorobenzoylamino)-3-(2-oxo-1,2-dihydroquinolin-4-yl)propionate;
46) 2-[1,3]dioxan-2-ylethyl 2-(4-chlorobenzoylamino)-3-(2-oxo-1,2-dihydroquinolin-4-yl)propionate;
47) 2-morpholin-4-ylethyl 2-(4-chlorobenzoylamino)-3-(2-oxo-1,2-dihydroquinolin-4-yl)propionate;
48) 3-morpholin-4-ylpropyl 2-(4-chlorobenzoylamino)-3-(2-oxo-1,2-dihydroquinolin-4-yl)propionate;
49) 4-morpholin-4-ylbutyl 2-(4-chlorobenzoylamino)-3-(2-oxo-1,2-dihydroquinolin-4-yl)propionate;
50) 6-morpholin-4-ylhexyl 2-(4-chlorobenzoylamino)-3-(2-oxo-1,2-dihydroquinolin-4-yl)propionate;
51) (4-methylpiperazin-1-yl)methyl 2-(4-chlorobenzoylamino)-3-(2-oxo-1,2-dihydroquinolin-4-yl)propionate;
52) 2-(4-benzylpiperazin-1-yl)ethyl 2-(4-chlorobenzoylamino)-3-(2-oxo-1,2-dihydroquinolin-4-yl)propionate;
53) 4-[4-(3-chlorophenyl)piperazin-1-yl]butyl 2-(4-chlorobenzoylamino)-3-(2-oxo-1,2-dihydroquinolin-4-yl)propionate;
54) (4-tert-butyloxycarbonylpiperazin-1-yl)ethyl 2-(4-chlorobenzoylamino)-3-(2-oxo-1,2-dihydroquinolin-4-yl)propionate;
55) 2-azepan-1-ylethyl 2-(4-chlorobenzoylamino)-3-(2-oxo-1,2-dihydroquinolin-4-yl)propionate;
56) 2-(2-oxopyrrolidin-1-yl)ethyl 2-(4-chlorobenzoylamino)-3-(2-oxo-1,2-dihydroquinolin-4-yl)propionate;
57) (2-oxooxazolidin-5-yl)methyl 2-(4-chlorobenzoylamino)-3-(2-oxo-1,2-dihydroquinolin-4-yl)propionate;
58) 4-morpholin-4-yl-cis-but-2-enyl 2-(4-chlorobenzoylamino)-3-(2-oxo-1,2-dihydroquinolin-4-yl)propionate;
59) 4-morpholin-4-yl-trans-but-2-enyl 2-(4-chlorobenzoylamino)-3-(2-oxo-1,2-dihydroquinolin-4-yl)propionate;
60) 5-methyl-2-oxo-[1,3]dioxol-4-ylmethyl 2-(4-chlorobenzoylamino)-3-(2-oxo-1,2-dihydroquinolin-4-yl)propionate;
61) benzyl 2-(4-chlorobenzoylamino)-3-(2-oxo-1,2-dihydroquinolin-4-yl)propionate;
62) phenethyl 2-(4-chlorobenzoylamino)-3-(2-oxo-1,2-dihydroquinolin-4-yl)propionate;
63) 2-methylbenzyl 2-(4-chlorobenzoylamino)-3-(2-oxo-1,2-dihydroquinolin-4-yl)propionate;
64) 3-methylbenzyl 2-(4-chlorobenzoylamino)-3-(2-oxo-1,2-dihydroquinolin-4-yl)propionate;
65) 3,4-dimethylbenzyl 2-(4-chlorobenzoylamino)-3-(2-oxo-1,2-dihydroquinolin-4-yl)propionate;
66) 3,5-dimethylbenzyl 2-(4-chlorobenzoylamino)-3-(2-oxo-1,2-dihydroquinolin-4-yl)propionate;
67) 3-fluorobenzyl 2-(4-chlorobenzoylamino)-3-(2-oxo-1,2-dihydroquinolin-4-yl)propionate;
68) 2,5-difluorobenzyl 2-(4-chlorobenzoylamino)-3-(2-oxo-1,2-dihydroquinolin-4-yl)propionate;
69) 3-cyanobenzyl 2-(4-chlorobenzoylamino)-3-(2-oxo-1,2-dihydroquinolin-4-yl)propionate;
70) 3-nitrobenzyl 2-(4-chlorobenzoylamino)-3-(2-oxo-1,2-dihydroquinolin-4-yl)propionate;
71) 4-methoxybenzyl 2-(4-chlorobenzoylamino)-3-(2-oxo-1,2-dihydroquinolin-4-yl)propionate;
72) 3-phenoxybenzyl 2-(4-chlorobenzoylamino)-3-(2-oxo-1,2-dihydroquinolin-4-yl)propionate;
73) 4-methylsulfanylbenzyl 2-(4-chlorobenzoylamino)-3-(2-oxo-1,2-dihydroquinolin-4-yl)propionate;
74) (4-methyloxycarbonyl)benzyl 4-[2-(4-chlorobenzoylamino)-3-(2-oxo-1,2-dihydroquinolin-4-yl)propionate;
75) (3-phenyloxycarbonyl)benzyl 2-(4-chlorobenzoylamino)-3-(2-oxo-1,2-dihydroquinolin-4-yl)propionate;
76) naphthalen-2-ylmethyl 2-(4-chlorobenzoylamino)-3-(2-oxo-1,2-dihydroquinolin-4-yl)propionate;
77) anthracen-9-ylmethyl 2-(4-chlorobenzoylamino)-3-(2-oxo-1,2-dihydroquinolin-4-yl)propionate;
78) 2-pyrrol-1-ylethyl 2-(4-chlorobenzoylamino)-3-(2-oxo-1,2-dihydroquinolin-4-yl)propionate;

79) (2-ethoxycarbonyl)furan-4-ylmethyl 2-(4-chlorobenzoylamino)-3-(2-oxo-1,2-dihydroquinolin-4-yl)propionate;
80) 2-thiophen-2-ylethyl 2-(4-chlorobenzoylamino)-3-(2-oxo-1,2-dihydroquinolin-4-yl)propionate;
81) 2-thiophen-3-ylethyl 2-(4-chlorobenzoylamino)-3-(2-oxo-1,2-dihydroquinolin-4-yl)propionate;
82) 2-imidazol-1-ylethyl 2-(4-chlorobenzoylamino)-3-(2-oxo-1,2-dihydroquinolin-4-yl)propionate;
83) 5-cyclopropyl-2-methyl-2H-pyrazol-3-ylmethyl 2-(4-chlorobenzoylamino)-3-(2-oxo-1,2-dihydroquinolin-4-yl)propionate;
84) 3,5-dimethylisoxazol-4-ylmethyl 2-(4-chlorobenzoylamino)-3-(2-oxo-1,2-dihydroquinolin-4-yl)propionate;
85) 2-(5-methyl-4-phenyloxazol-2-yl)ethyl 2-(4-chlorobenzoylamino)-3-(2-oxo-1,2-dihydroquinolin-4-yl)propionate;
86) 2-methylthiazol-4-ylmethyl 2-(4-chlorobenzoylamino)-3-(2-oxo-1,2-dihydroquinolin-4-yl)propionate;
87) 2-(4-methylthiazol-5-yl)ethyl 2-(4-chlorobenzoylamino)-3-(2-oxo-1,2-dihydroquinolin-4-yl)propionate;
88) pyrimidin-2-ylmethyl 2-(4-chlorobenzoylamino)-3-(2-oxo-1,2-dihydroquinolin-4-yl)propionate;
89) pyrimidin-3-ylmethyl 2-(4-chlorobenzoylamino)-3-(2-oxo-1,2-dihydroquinolin-4-yl)propionate;
90) pyrimidin-4-ylmethyl 2-(4-chlorobenzoylamino)-3-(2-oxo-1,2-dihydroquinolin-4-yl)propionate;
91) 2-(pyrimidin-2-yl)ethyl 2-(4-chlorobenzoylamino)-3-(2-oxo-1,2-dihydroquinolin-4-yl)propionate;
92) quinolin-2-ylmethyl 2-(4-chlorobenzoylamino)-3-(2-oxo-1,2-dihydroquinolin-4-yl)propionate;
93) quinolin-3-ylmethyl 2-(4-chlorobenzoylamino)-3-(2-oxo-1,2-dihydroquinolin-4-yl)propionate;
94) 2-(1-methyl-1H-indol-3-yl)ethyl 2-(4-chlorobenzoylamino)-3-(2-oxo-1,2-dihydroquinolin-4-yl)propionate;
95) benzothiazol-2-ylmethyl 2-(4-chlorobenzoylamino)-3-(2-oxo-1,2-dihydroquinolin-4-yl)propionate;
96) 2,3-dihydrobenzo[1,4]dioxin-2-ylmethyl 2-(4-chlorobenzoylamino)-3-(2-oxo-1,2-dihydroquinolin-4-yl)propionate;
97) carbazol-9-ylmethyl 2-(4-chlorobenzoylamino)-3-(2-oxo-1,2-dihydroquinolin-4-yl)propionate;
98) methylcarbamoylmethyl 2-(4-chlorobenzoylamino)-3-(2-oxo-1,2-dihydroquinolin-4-yl)propionate;
99) 2-(4-methylpiperazin-1-yl)-2-oxo ethyl 2-(4-chlorobenzoylamino)-3-(2-oxo-1,2-dihydroquinolin-4-yl)propionate;
100) 1-(4-methylpiperazine-1-carbonyl)propyl 2-(4-chlorobenzoylamino)-3-(2-oxo-1,2-dihydroquinolin-4-yl)propionate;
101) 2-morpholin-4-yl-2-oxoethyl 2-(4-chlorobenzoylamino)-3-(2-oxo-1,2-dihydroquinolin-4-yl)propionate;
102) (methoxymethylcarbamoyl)methyl 2-(4-chlorobenzoylamino)-3-(2-oxo-1,2-dihydroquinolin-4-yl)propionate;
103) 2-ethoxycarbonylethyl 2-(4-chlorobenzoylamino)-3-(2-oxo-1,2-dihydroquinolin-4-yl)propionate;
104) 2-ethoxycarbonylethyl 2-(4-chlorobenzoylamino)-3-(2-oxo-1,2-dihydroquinolin-4-yl)propionate;
105) 2-morpholin-4-yl-ethoxycarbonylmethyl 2-(4-chlorobenzoylamino)-3-(2-oxo-1,2-dihydroquinolin-4-yl)propionate;
106) 2-morpholin-4-ylethyl 2-[2-(4-chlorobenzoylamino)-3-(2-oxo-1,2-dihydroquinolin-4-yl)propionyloxy]butyrate;
107) 2-(1,3-dioxo-1,3-dihydroisoindol-2-yl)ethyl 2-(4-chlorobenzoylamino)-3-(2-oxo-1,2-dihydroquinolin-4-yl)propionate;
108) cyclohexyloxycarbonyloxymethyl 2-(4-chlorobenzoylamino)-3-(2-oxo-1,2-dihydroquinolin-4-yl)propionate;
109) 2-morpholin-4-yl-ethoxycarbonyloxymethyl 2-(4-chlorobenzoylamino)-3-(2-oxo-1,2-dihydroquinolin-4-yl)propionate;
110) 2-ureidoethyl 2-(4-chlorobenzoylamino)-3-(2-oxo-1,2-dihydroquinolin-4-yl)propionate;
111) 2-(3-phenyl-ureido)ethyl 2-(4-chlorobenzoylamino)-3-(2-oxo-1,2-dihydroquinolin-4-yl)propionate;
112) 2-(3-benzyl-ureido)ethyl 2-(4-chlorobenzoylamino)-3-(2-oxo-1,2-dihydroquinolin-4-yl)propionate;
120) S-(2-dimethylamino)ethyl 2-(4-chlorobenzoylamino)-3-(2-oxo-1,2-dihydroquinolin-4-yl)thiopropionate;
121) S-(2-diethylamino)ethyl 2-(4-chlorobenzoylamino)-3-(2-oxo-1,2-dihydroquinolin-4-yl)thiopropionate;
122) S-(2-diisopropylamino)ethyl 2-(4-chlorobenzoylamino)-3-(2-oxo-1,2-dihydroquinolin-4-yl)thiopropionate;
123) S-(2-dimethylamino)propyl 2-(4-chlorobenzoylamino)-3-(2-oxo-1,2-dihydroquinolin-4-yl)thiopropionate;
124) S-(2-benzoylamino)ethyl 2-(4-chlorobenzoylamino)-3-(2-oxo-1,2-dihydroquinolin-4-yl)propionate oxalate;
126) S-(2-benzoyloxyl)ethyl 2-(4-chlorobenzoylamino)-3-(2-oxo-1,2-dihydroquinolin-4-yl)thiopropionate;
127) S-(2-methylsufanyl)ethyl 2-(4-chlorobenzoylamino)-3-(2-oxo-1,2-dihydroquinolin-4-yl)thiopropionate;
128) S-(2-phenylsufanyl)ethyl 2-(4-chlorobenzoylamino)-3-(2-oxo-1,2-dihydroquinolin-4-yl)propionate;
129) S-(2-benzenesulfonyl)ethyl 2-(4-chlorobenzoylamino)-3-(2-oxo-1,2-dihydroquinolin-4-yl)propionate;
130) S-(2-oxobutyl) 2-(4-chlorobenzoylamino)-3-(2-oxo-1,2-dihydroquinolin-4-yl)thiopropionate;
131) S-(2-ureido)ethyl 2-(4-chlorobenzoylamino)-3-(2-oxo-1,2-dihydroquinolin-4-yl)thiopropionate;
132) N,N-dimethyl S-[2-(4-chlorobenzoylamino)-3-(2-oxo-1,2-dihydroquinolin-4-yl)]thiocarbamate;
133) S-allyl 2-(4-chlorobenzoylamino)-3-(2-oxo-1,2-dihydroquinolin-4-yl)thiopropionate;
134) S-but-2-enyl 2-(4-chlorobenzoylamino)-3-(2-oxo-1,2-dihydroquinolin-4-yl)thiopropionate;
135) S-prop-2-ynyl 2-(4-chlorobenzoylamino)-3-(2-oxo-1,2-dihydroquinolin-4-yl)thiopropionate;
136) S-cyclopentyl 2-(4-chlorobenzoylamino)-3-(2-oxo-1,2-dihydroquinolin-4-yl)thiopropionate;
137) S-cyclohexyl 2-(4-chlorobenzoylamino)-3-(2-oxo-1,2-dihydroquinolin-4-yl)thiopropionate;
138) S-cyclopropylmethyl 2-(4-chlorobenzoylamino)-3-(2-oxo-1,2-dihydroquinolin-4-yl)thiopropionate;
139) S-cyclobutylmethyl 2-(4-chlorobenzoylamino)-3-(2-oxo-1,2-dihydroquinolin-4-yl)thiopropionate;
140) S-cyclohexylmethyl 2-(4-chlorobenzoylamino)-3-(2-oxo-1,2-dihydroquinolin-4-yl)thiopropionate;

141) S-(cyclopent-3-enyl)methyl 2-(4-chlorobenzoylamino)-3-(2-oxo-1,2-dihydroquinolin-4-yl)thiopropionate;
142) S-oxiranylmethyl 2-(4-chlorobenzoylamino)-3-(2-oxo-1,2-dihydroquinolin-4-yl)thiopropionate;
143) S-(tetrahydrofuran-2-yl)methyl 2-(4-chlorobenzoylamino)-3-(2-oxo-1,2-dihydroquinolin-4-yl)thiopropionate;
144) S-(2-pyrrolidin-1-yl)ethyl 2-(4-chlorobenzoylamino)-3-(2-oxo-1,2-dihydroquinolin-4-yl)thiopropionate;
145) S-[2-(1-methylpyrrolidin-2-yl)]ethyl 2-(4-chlorobenzoylamino)-3-(2-oxo-1,2-dihydroquinolin-4-yl)thiopropionate;
146) S-([1,3]dioxolan-2-yl)methyl 2-(4-chlorobenzoylamino)-3-(2-oxo-1,2-dihydroquinolin-4-yl)thiopropionate;
147) S-(2-[1,3]dioxolan-2-yl)ethyl 2-(4-chlorobenzoylamino)-3-(2-oxo-1,2-dihydroquinolin-4-yl)thiopropionate;
148) S-(2-piperidin-1-yl)ethyl 2-(4-chlorobenzoylamino)-3-(2-oxo-1,2-dihydroquinolin-4-yl)thiopropionate;
149) S-(1-methylpiperidin-2-yl)methyl 2-(4-chlorobenzoylamino)-3-(2-oxo-1,2-dihydroquinolin-4-yl)thiopropionate;
150) S-{4-[4-(4-chlorophenyl)piperazin-1-yl]-butyl}2-(4-chlorobenzoylamino)-3-(2-oxo-1,2-dihydroquinolin-4-yl)propionate;
151) S-(2-morpholin-4-yl)ethyl 2-(4-chlorobenzoylamino)-3-(2-oxo-1,2-dihydroquinolin-4-yl)propionate;
152) S-(tetrahydropyran 2 yl)methyl 2-(4-chlorobenzoylamino)-3-(2-oxo-1,2-dihydroquinolin-4-yl)thiopropionate;
153) S-(2-[1,3]-dioxan-2-yl)ethyl 2-(4-chlorobenzoylamino)-3-(2-oxo-1,2-dihydroquinolin-4-yl)thiopropionate;
154) S-(2-azepan-1-yl)ethyl 2-(4-chlorobenzoylamino)-3-(2-oxo-1,2-dihydroquinolin-4-yl)thiopropionate;
155) S-(5-methyl-2-oxo-[1,3]dioxol-4-yl)methyl 2-(4-chlorobenzoylamino)-3-(2-oxo-1,2-dihydroquinolin-4-yl)thiopropionate;
156) S-benzyl 2-(4-chlorobenzoylamino)-3-(2-oxo-1,2-dihydroquinolin-4-yl)thiopropionate;
157) S-phenethyl 2-(4-chlorobenzoylamino)-3-(2-oxo-1,2-dihydroquinolin-4-yl)thiopropionate;
158) S-(2-methylbenzyl) 2-(4-chlorobenzoylamino)-3-(2-oxo-1,2-dihydroquinolin-4-yl)thiopropionate;
159) S-(3-methylbenzyl) 2-(4-chlorobenzoylamino)-3-(2-oxo-1,2-dihydroquinolin-4-yl)thiopropionate;
160) S-(3,4-dimethylbenzyl) 2-(4-chlorobenzoylamino)-3-(2-oxo-1,2-dihydroquinolin-4-yl)thiopropionate;
161) S-(4-fluorobenzyl) 2-(4-chlorobenzoylamino)-3-(2-oxo-1,2-dihydroquinolin-4-yl)thiopropionate;
162) S-(2,5-difluorobenzyl) 2-(4-chlorobenzoylamino)-3-(2-oxo-1,2-dihydroquinolin-4-yl)thiopropionate;
163) S-(3-chlorobenzyl) 2-(4-chlorobenzoylamino)-3-(2-oxo-1,2-dihydroquinolin-4-yl)thiopropionate;
164) S-(3,5-dibromobenzyl) 2-(4-chlorobenzoylamino)-3-(2-oxo-1,2-dihydroquinolin-4-yl)thiopropionate;
165) S-(3-cyanobenzyl) 2-(4-chlorobenzoylamino)-3-(2-oxo-1,2-dihydroquinolin-4-yl)thiopropionate;
166) S-(4-cyanobenzyl) 2-(4-chlorobenzoylamino)-3-(2-oxo-1,2-dihydroquinolin-4-yl)thiopropionate;
167) S-(3-methoxybenzyl) 2-(4-chlorobenzoylamino)-3-(2-oxo-1,2-dihydroquinolin-4-yl)thiopropionate;
168) S-(4-methoxybenzyl) 2-(4-chlorobenzoylamino)-3-(2-oxo-1,2-dihydroquinolin-4-yl)thiopropionate;
169) S-(3-phenoxybenzyl) 2-(4-chlorobenzoylamino)-3-(2-oxo-1,2-dihydroquinolin-4-yl)thiopropionate;
170) S-(3-methoxycarbonyl)benzyl 2-(4-chlorobenzoylamino)-3-(2-oxo-1,2-dihydroquinolin-4-yl)thiopropionate;
171) S-(3-phenyloxycarbonyl)benzyl 2-(4-chlorobenzoylamino)-3-(2-oxo-1,2-dihydroquinolin-4-yl)propionate;
172) S-[2-(4-methylthiazol-5yl)ethyl]2-(4-chlorobenzoylamino)-3-(2-oxo-1,2-dihydroquinolin-4-yl)thiopropionate;
173) S-(pyrimidin-2-yl)methyl 2-(4-chlorobenzoylamino)-3-(2-oxo-1,2-dihydroquinolin-4-yl)thiopropionate;
174) S-(pyrimidin-3-yl)methyl 2-(4-chlorobenzoylamino)-3-(2-oxo-1,2-dihydroquinolin-4-yl)thiopropionate;
175) S-(3-phenylallyl)2-(4-chlorobenzoylamino)-3-(2-oxo-1,2-dihydroquinolin-4-yl)thiopropionate;
176) S-ethoxy-3-oxopropyl 2-(4-chlorobenzoylamino)-3-(2-oxo-1,2-dihydroquinolin-4-yl)thiopropionate;
177) ethyl[2-(4-chlorobenzoylamino)-3-(2-oxo-1,2-dihydroquinolin-4-yl)propionylamino]acetate;
178) [2-(4-chlorobenzoylamino)-3-(2-oxo-1,2-dihydroquinolin-4-yl)propionylamino]acetic acid;
179) ethyl 4-[2-(4-chlorobenzoylamino)-3-(2-oxo-1,2-dihydroquinolin-4-yl)propionylamino]butyrate;
180) ethyl 2-[2-(4-chlorobenzoylamino)-3-(2-oxo-1,2-dihydroquinolin-4-yl)propionylamino]-4-methyl pentanoate;
181) ethyl 2-[2-(4-chlorobenzoylamino)-3-(2-oxo-1,2-dihydroquinolin-4-yl)propionylamino]-3-phenyl propionate;
182) ethyl 2-[2-(4-chlorobenzoylamino)-3-(2-oxo-1,2-dihydroquinolin-4-yl)propionylamino]-3-(1H-indol-3-yl)propionate;
183) diethyl 2-[2-(4-chlorobenzoylamino)-3-(2-oxo-1,2-dihydroquinolin-4-yl)propionylamino]pentane-1,5-dioate;
184) diethyl 2-[2-(4-chlorobenzoylamino)-3-(2-oxo-1,2-dihydroquinolin-4-yl)propionylamino]pentane-1,5-dioic acid;
185) 4-chloro-N-[1-[2-(3H-imidazol-4-yl)ethylcarbamoyl]-2-(2-oxo-1,2-dihydroquinolin-4-yl)ethyl]benzamide;
186) 4-chloro-N-[2-(2-oxo-1,2-dihydroquinolin-4-yl)-1-(2-pyrrolidin-1-yl-ethylcarbamoyl)ethyl]benzamide; and
187) 4-chloro-N-[1-(2-morpholin-4-yl-ethylcarbamoyl)-2-(2-oxo-1,2-dihydroquinolin-4-yl)ethyl]benzamide.

3. The compound of claim 1, wherein the salt is an acid addition salt formed with a pharmaceutically acceptable free acid.

4. The compound of claim 3, wherein the free acid is an organic acid or an inorganic acid.

5. The compound of claim 4, wherein the organic acid is selected from the group consisting of citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, camphorsulfonic acid, glutamic acid, aspartic acid, salicylic acid, malonic acid, malic acid, and benzosulfonic acid, and the inorganic acid is selected from the group consisting of hydrochloric acid, bromic acid, sulfuric acid, and phosphoric acid.

6. A method for preparing the compound represented by Chemical Formula I of claim 1, comprising reacting a compound represented by the following Chemical Formula II with a compound represented by the following Chemical Formula III:

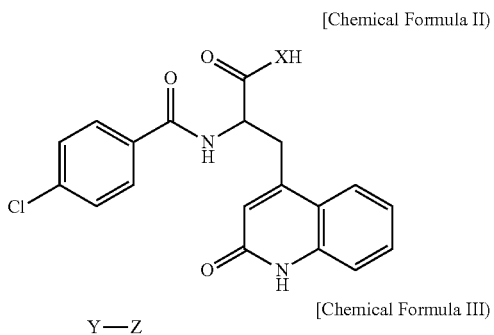

[Chemical Formula II]

Y—Z  [Chemical Formula III]

wherein,

X and Y are as defined in claim 1, and Z is hydroxy, amino, amine, halogen or a leaving group.

7. The method of claim 6, wherein Z is hydroxy, —$NH_2$, Cl, Br, alkylsulfonyl, or arylsulfonyl.

8. A pharmaceutical composition for therapy of a disease, comprising the compound of claim 1 as an active ingredient, said disease being selected from among gastric ulcer, acute gastritis, chronic gastritis, xerophthalmia, cancer, osteoarthritis, rheumatoid arthritis, hyperlipidemia, hypertriglyceridemia, diabetes, irritable bowel syndrome, and obesity.

9. A method for treating a disease, comprising administering the compound of claim 1 to a subject in need thereof, said disease being selected from among gastric ulcer, acute gastritis, chronic gastritis, xerophthalmia, cancer, osteoarthritis, rheumatoid arthritis, hyperlipidemia, hypertriglyceridemia, diabetes, irritable bowel syndrome, and obesity.

10. The compound of claim 2, wherein the salt is an acid addition salt formed with a pharmaceutically acceptable free acid.

11. A pharmaceutical composition for therapy of a disease, comprising the compound of claim 2 as an active ingredient, said disease being selected from among gastric ulcer, acute gastritis, chronic gastritis, xerophthalmia, cancer, osteoarthritis, rheumatoid arthritis, hyperlipidemia, hypertriglyceridemia, diabetes, irritable bowel syndrome, and obesity.

12. A method for treating a disease, comprising administering the compound of claim 2 to a subject in need thereof, said disease being selected from among gastric ulcer, acute gastritis, chronic gastritis, xerophthalmia, cancer, osteoarthritis, rheumatoid arthritis, hyperlipidemia, hypertriglyceridemia, diabetes, irritable bowel syndrome, and obesity.

* * * * *